United States Patent
Boyle et al.

(10) Patent No.: US 11,884,656 B2
(45) Date of Patent: Jan. 30, 2024

(54) PYRROLE DERIVATIVES AS PLK1 INHIBITORS

(71) Applicant: SENTINEL ONCOLOGY LIMITED, Cambridge (GB)

(72) Inventors: Robert George Boyle, Cambridge (GB); David Winter Walker, Linton (GB); Richard Justin Boyce, Newmarket (GB)

(73) Assignee: SENTINEL ONCOLOGY LIMITED, Cambridge (GB)

( * ) Notice: Subject to any disclaimer, the term of this patent is extended or adjusted under 35 U.S.C. 154(b) by 0 days.

(21) Appl. No.: 17/453,959

(22) Filed: Nov. 8, 2021

(65) Prior Publication Data

US 2022/0135552 A1   May 5, 2022

Related U.S. Application Data

(63) Continuation of application No. 16/606,934, filed as application No. PCT/EP2018/060984 on Apr. 27, 2018, now Pat. No. 11,208,405.

(30) Foreign Application Priority Data

Apr. 28, 2017 (GB) .................................. 1706806.5

(51) Int. Cl.
*C07D 413/14* (2006.01)
*C07D 207/32* (2006.01)
(Continued)

(52) U.S. Cl.
CPC ............ *C07D 413/14* (2013.01); *A61P 35/00* (2018.01); *C07D 207/325* (2013.01); (Continued)

(58) Field of Classification Search
CPC .......................... C07D 413/14; C07D 207/325; C07D 231/12; C07D 261/08; C07D 401/04;
(Continued)

(56) References Cited

U.S. PATENT DOCUMENTS

| | | | |
|---|---|---|---|
| 5,792,778 | A | 8/1998 | De Laszlo et al. |
| 11,208,405 | B2 | 12/2021 | Boyle et al. |

(Continued)

FOREIGN PATENT DOCUMENTS

| | | |
|---|---|---|
| CA | 2938547 A1 | 4/2012 |
| CN | 102190625 A | 9/2011 |

(Continued)

OTHER PUBLICATIONS

Noureen, S., et al., "Strong π-delocalization and substitution effect on electronic properties of dithienylpyrrole-containing bupyridine ligands and corresponding ruthenium complexes", Dalton Trans., (2012), 41, pp. 4833-4844.

Kim, K-S., et al., "Highly Efficient Photocurrent Generation from a Self-Assembled Monolayer Film of a Novel $C_{60}$-Tethered 2,5-Dithienylpyrrole Triad", Chem. Mater., (2004), 16(24), pp. 5058-5062.

Comrie, A. M., "3,4,5-Triphenylpyrazoles", J. Chem. Soc., (1971), pp. 2807-2810.

Zhou, Z., et al., "Nonvolatile electrical switching behavior and mechanism of functional polyimides bearing a pyrrole unit: influence of different side groups", RSC Adv., (2016), 6, pp. 52798-52809.

(Continued)

*Primary Examiner* — Shawquia Jackson
(74) *Attorney, Agent, or Firm* — Heslin Rothenberg Farley & Mesiti P.C.

(57) ABSTRACT

The invention provides compounds of the formula (3):

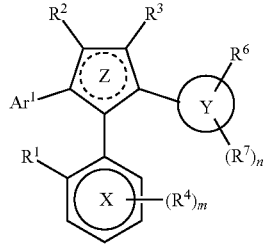

(3)

or a pharmaceutically acceptable salt or tautomer thereof, wherein:

Z is a 5-membered heteroaryl ring containing one or two nitrogen ring members and optionally one further heteroatom ring member selected from N and O;
ring X is a benzene or pyridine ring;
ring Y is a benzene, pyridine, thiophene or furan ring;
$Ar^1$ is an optionally substituted benzene, pyridine, thiophene or furan ring;
m is 0, 1 or 2;
n is 0, 1 or 2;
$R^1$ is selected from various substituents:
$R^2$ is selected from hydrogen and a $C_{1-4}$ hydrocarbon group;
$R^3$ is selected from hydrogen and a $C_{1-4}$ hydrocarbon group;
$R^4$ is selected from various substituents;
$R^5$ is selected from various substituents;
$Ar^2$ is an optionally substituted phenyl, pyridyl or pyridone group;
$R^6$ is a group $Q^1$-$R^a$—$R^b$;
$Q^1$ is absent or is a $C_{1-3}$ saturated hydrocarbon linker;
$R^a$ is selected from O; C(O); C(O)O; $CONR^c$; $N(R^c)CO$; $N(R^c)CONR^c$, $NR^c$; and $SO_2NR^c$;
$R^b$ is selected from hydrogen and various substituents; and $R^b$ is selected from $R^4$.

The compounds are useful in the treatment of cancers.

20 Claims, 2 Drawing Sheets

(51) Int. Cl.

| | |
|---|---|
| C07D 231/12 | (2006.01) |
| C07D 261/08 | (2006.01) |
| C07D 401/04 | (2006.01) |
| C07D 403/10 | (2006.01) |
| C07D 405/14 | (2006.01) |
| C07D 409/04 | (2006.01) |
| A61P 35/00 | (2006.01) |
| C07D 207/325 | (2006.01) |
| C07D 401/14 | (2006.01) |
| C07D 403/12 | (2006.01) |
| C07D 413/12 | (2006.01) |

(52) U.S. Cl.
CPC ......... *C07D 231/12* (2013.01); *C07D 261/08* (2013.01); *C07D 401/04* (2013.01); *C07D 401/14* (2013.01); *C07D 403/10* (2013.01); *C07D 403/12* (2013.01); *C07D 405/14* (2013.01); *C07D 409/04* (2013.01); *C07D 413/12* (2013.01)

(58) Field of Classification Search
CPC .. C07D 403/10; C07D 405/14; C07D 409/04; C07D 413/12; A61P 35/00
See application file for complete search history.

(56) References Cited

U.S. PATENT DOCUMENTS

| | | |
|---|---|---|
| 2003/0144338 A1 | 7/2003 | Matsumoto et al. |
| 2004/0248896 A1 | 12/2004 | Dean et al. |
| 2006/0128759 A1 | 6/2006 | Laufer et al. |
| 2015/0079154 A1 | 3/2015 | Zender et al. |

FOREIGN PATENT DOCUMENTS

| | | |
|---|---|---|
| CN | 103922989 A | 7/2014 |
| DE | 10237883 A1 | 3/2004 |
| EP | 1389626 A1 | 2/2004 |
| EP | 1813613 A1 | 8/2007 |
| EP | 2730565 A1 | 5/2014 |
| EP | 3040330 A1 | 7/2016 |
| JP | H10237442 A | 9/1998 |
| JP | 2000260567 A | 9/2000 |
| JP | 2002/121186 A | 4/2002 |
| JP | 2016106075 A | 6/2016 |
| WO | 00/08001 A1 | 2/2000 |
| WO | 03/055860 A1 | 7/2003 |
| WO | 2005/012298 A1 | 2/2005 |
| WO | 2005012298 A1 | 2/2005 |
| WO | 2010/019909 A1 | 2/2010 |
| WO | 2011/049274 A1 | 4/2011 |
| WO | 2012/051361 A1 | 4/2012 |
| WO | 2012/052395 A1 | 4/2012 |
| WO | 2012/084711 A1 | 6/2012 |
| WO | 2012/143248 A1 | 10/2012 |
| WO | 2013152206 A1 | 10/2013 |
| WO | 2016/022465 A1 | 2/2016 |
| WO | 2018/197714 A1 | 11/2018 |

OTHER PUBLICATIONS

Shi et al., "A highly sensitive, single selective, real-time and "turn-on" fluorescent sensor for $Al^{3+}$ detection in aqueous media", J. Mater. Chem, (2012), 22, pp. 19296-19302.

Tamilavan, V., et al., "Structural optimization of thiophene-(N-aryl)pyrrole-thiophene-based metal-free organic sensitizers for the enhanced dye-sensitized solar cell performance", Tetrahedron, (2014), 70, pp. 371-379.

Kim, T., et al., "A Novel Method for the Synthesis of 2,3-Benzo-1,3a,6a-triazapentalenes through Pummer Type Reactions of γ-(Benzotriazol-1-yl)allylic Sulfoxides", Eur. J. Chem., (2002), 3, pp. 493-502.

Yanai, H, et al., "Novel Emitting Materials of Organic Electroluminescent Device: 1-Aryl-2,5-di(2-thienyl)pyrrole Derivates Having an Electron-withdrawing Group", Chemistry Letters, (2000), 29(3), pp. 238-239.

CAS registry No. 952009-27-7, Entry date Oct. 30, 2007, 2, 2'-[1-(4-methylphenyl)-1Hpyrrole-2,5-diyl]bis-benzoic acid.

CAS registry No. 952009-23-3, Entry date Oct. 30, 2007, 2, 2'-[1-phenyl-1H-pyrrole-2,5-diyl]bisbenzoic acid.

CAS registry No. 952009-19-7, Entry date Oct. 30, 2007, 2, 2'-[1-phenyl-1H-pyrrole-2,5-diyl]bis-(1,1'-diethyl benzoate).

CAS registry No. 1349999-41-2, Entry date Dec. 7, 2011, 4-[5-(4-chlorophenyl)-4-(3-hydroxyphenyl)-1H-pyrazol-1-yl-benzenesulfonamide.

Marsili et al., "Rearrangements of phthalimidine derivatives formation of a pyrrole and a benzazepine from 3-(α-bromobenzylidene)-2-(β-phenethyl) phthalimidine", Tetrahedron Lett. (1969), 10(11), pp. 887-890.

International Search Report and Written Opinion of the International Searching Authority for International Application No. PCT/EP2018/060984 dated Jul. 24, 2018.

Great Britain Search Report for GB1706806.5 dated Feb. 6, 2018.

Balbi, A., et al., "Synthesis and biological evaluation of novel pyrazole derivatives with anticancer activity", European Journal of Medicinal Chemistry, vol. 46, pp. 5293-5309 (2011).

Bechara, W.S., et al., "One-Pot Synthesis of 3,4,5-Trisubstituted 1,2,4-Triazoles via the Addition of Hydrazides to Activated Secondary Amides", Organic Letters, vol. 17, pp. 1184-1187 (2015).

Howe, R.K., et al., "3',4'-Diarylspiro[isobenzofuran-1(3H),5'(4'H)-isoxazol]-3-ones. Reaction of Nitrile Oxides with 3-Benzylidenephthalides", J. Org. Chem., vol. 50, pp. 903-904 (1985).

Sharshira, E.M., et al., "Synthesis and Antimicrobial Evaluation of Some Pyrazole Derivatives", Molecules, vol. 17, pp. 4962-4671 (2012).

Nun et al., "Gold(I)-catalyzed synthesis of furans and pyrroles via alkyne hydration", Catal. Sci. Technol., (2011), 1, pp. 58-61.

Cao et al., "Synthesis of 3,4,5-trisubstituted isoxazoles via 1,3-dipolar cycloaddition/$SO_2$ extrusion of benzoisothiazole-2,2-dioxide-3-ylidenes with nitrile oxides", RSC Adv., (2016), 6, pp. 22516-22525.

Levai et al., "Synthesis of 4-Aryl-3(5)-(2-hydroxyphenyl)pyrazoles by Reaction of Isoflavones and their 4-Thio Analogues with Hydrazine Derivatives", Aust. J. Chem., (2007), 60, pp. 905-914.

Cui et al., "Diversity-oriented synthesis of pyrazoles derivatives from flavones and isoflavones leads to the discovery of promising reversal agents of fluconazole resistance in Candida albicans", Bioorg. Med. Chem., (2018), 28, pp. 1545-1549.

Feldman et al., "Highly Quantum Efficient Phosphorescent Sky Blue Emitters Based on Diasteromeric Iridium(III) Complexes of Atropisomeric 5-Aryl-4H-1,2,4-triazole ligands", Organometallics, (2015), 34, pp. 3665-3669.

GB 2015187.4 UKIPO Search Report dated Mar. 3, 2021.

Eistert et al. Document No. 70:37375, retrieved from STN, entered in STN on May 12, 1984.

Cancer and Metastasis Reviews ( 1998), 17 ( 1), 91-106.

Science (1999), vol. 286, 531-537.

Cancer [online], [retrieved on Jul. 6, 2007]. Retrieved from the internet, URL http://www.nlm.nih.gov/medlineplus/cancer.html>.

Kong Kai-lai et al., "Research progress of antitumor Polo-like kinase 1 inhibitors", Journal of China Pharmaceutical University, (2011), 42(1), pp. 9-15 (with English Translation).

PYRROLE DERIVATIVES AS PLK1 INHIBITORS

This application is a continuation of U.S. application Ser. No. 16/606,934 filed Oct. 21, 2019 and published as US 2020-0247796 A1 on Aug. 6, 2020, which is a § 371 national phase entry of International Patent Application No. PCT/EP2018/060984, filed Apr. 27, 2018 and published as WO/2018/197714 on Nov. 1, 2018, which claims priority to GB Patent Application No. 1706806.5 filed Apr. 28, 2017. The entire contents of WO/2018/197714 and US 2020-0247796 A1 are hereby incorporated herein by reference.

This invention relates to tri-aryl pyrrole derivatives and their analogues, methods for their preparation, pharmaceutical compositions containing them and their use in treating diseases such as cancer.

BACKGROUND OF THE INVENTION

The protein expressed by the normal KRAS gene performs an essential function in normal tissue signalling. The mutation of a KRAS gene by a single amino acid substitution, and in particular a single nucleotide substitution, is responsible for an activating mutation which is an essential step in the development of many cancers. The mutated protein that results is implicated in various malignancies, including lung adenocarcinoma, mucinous adenoma, ductal carcinoma of the pancreas and colorectal carcinoma. Like other members of the Ras family, the KRAS protein is a GTPase and is involved in many signal transduction pathways.

KRAS acts as a molecular on/off switch. Once it is turned on, it recruits and activates proteins necessary for the propagation of growth factor and other receptors' signal such as c-Raf and PI-3 Kinase. Normal KRAS binds to GTP in the active state and possesses an intrinsic enzymatic activity which cleaves the terminal phosphate of the nucleotide converting it to GDP. Upon conversion of GTP to GDP, KRAS is turned off. The rate of conversion is usually slow but can be sped up dramatically by an accessory protein of the GTPase-activating protein (GAP) class, for example RasGAP. In turn KRAS can bind to proteins of the Guanine Nucleotide Exchange Factor (GEF) class, for example SOS1, which forces the release of bound nucleotide. Subsequently, KRAS binds GTP present in the cytosol and the GEF is released from ras-GTP. In mutant KRAS, its GTPase activity is directly removed, rendering KRAS constitutively in the active state. Mutant KRAS is often characterised by mutations in codons 12, 13, 61 or mixtures thereof.

The viability of cancer cells carrying a mutant KRAS is known to be dependent on Polo-Like Kinase 1 (PLK1) and it has been shown that silencing PLK1 leads to the death of cells containing mutant KRAS (see Luo et al., *Cell*. 2009 May 29; 137(5): 835-848). Compounds that inhibit PLK1 should therefore be useful in treating cancers that arise from KRAS mutations, but current kinase inhibitors designed to bind to the conserved ATP-binding domain of PLK1 may be too unselective versus other kinases to access this mode-of-action.

PLK1 is a serine/threonine kinase consisting of 603 amino acids and having a molecular weight of 66 kDa and is an important regulator of the cell cycle. In particular, PLK1 is important to mitosis and is involved in the formation of and the changes in the mitotic spindle and in the activation of CDK/cyclin complexes during the M-phase of the cell cycle.

All Polo-like kinases contain an N-terminal Serine/Threonine kinase catalytic domain and a C-terminal region that contains one or two Polo-boxes (Lowery et al., *Oncogene*, (2005), 24, 248-259). For Polo-like kinases 1, 2, and 3, the entire C-terminal region, including both Polo-boxes, functions as a single modular phosphoserine/threonine-binding domain known as the Polo-box domain (PBD). In the absence of a bound substrate, the PBD inhibits the basal activity of the kinase domain. Phosphorylation-dependent binding of the PBD to its ligands releases the kinase domain, while simultaneously localizing Polo-like kinases to specific subcellular structures.

It has been shown (Reindl et al., *Chemistry & Biology*, 15, 459-466, May 2008 that, because PLKL1 localizes to its intracellular anchoring sites via its polo-box domain, the action of PLK1 can be inhibited by small molecules which interfere with its intracellular localization by inhibiting the function of the PBD.

Tumour protein p53 functions as a tumour suppressor and plays a role in apoptosis, genomic stability and inhibition of angiogenesis. It is known that tumours with both p53-deficiency and high PLK1 expression may be particularly sensitive to PLK1 inhibitors (Yim et al., *Mutat Res Rev Mutat Res*, (2014). 761, 31-39).

The evidence in the literature thus suggests that small molecules that bind to and inhibit the function of the PBD should be effective inhibitors of PLK1 kinase and therefore should also be useful in the treatment of cancers arising from KRAS mutations. In particular, since PBD domains only reside in PLKs, the potential for inhibitors designed to this domain to have greater selectivity over previous ATP-competitive inhibitors, may enable a greater ability to target KRAS mutant and p53 deficient cancers.

The identification and development of drugs for treating primary brain cancers has proved to be particularly challenging. Targeted cancer therapies, and in particular therapies using protein kinase inhibitors, have been a major focus for pharmaceutical and biotechnology companies (Nature Reviews Clinical Oncology 2016, 13, 209-227). However, although over thirty kinase inhibitors have been approved for use in oncology, none of these have been for the treatment of primary brain cancer. A particular problem has been that most of the approved kinase inhibitor oncology drugs lack the necessary drug substance qualities to achieve the brain exposure needed if they are to be of use in the treatment of brain cancer [JMC 2016, 59(22), 10030-10066].

The alkylating agent temozolomide (Temodar®, Temodal®) is currently the first line treatment for the brain cancer glioblastoma multiforme and is frequently used in combination with radiation therapy. However, drug resistance is a major problem in the management of glioblastoma and therefore limits the usefulness of temozolomide. At the present time, therefore, malignant glioblastoma remains incurable.

Polo like kinase 1 (PLK1) is overexpressed in a range of tumour types including glioblastoma multiforme (Translational Oncology 2017, 10, 22-32). Furthermore, recent studies have shown that PLK1 drives checkpoint adaptation and resistance to temozolomide in glioblastoma multiforme [Oncotarget 2017, 8, 15827-15837].

Thus, compounds that inhibit PLKL1, but without inducing drug resistance, and which exhibit good brain exposure would be expected to be useful in the treatment of glioblastoma multiforme and other brain cancers.

THE INVENTION

The present invention provides compounds that have anti-cancer activity and have good brain exposure after oral dosing, making them good candidates for the treatment of brain cancers. The compounds are active against glioblastoma cell lines and are believed to act as inhibitors of the Polo Box Domain of PLK1 kinase. The compounds are also active against mutant-RAS cancer cell lines (such as HCT116) and should also be useful in the treatment of cancers arising from KRAS mutations.

According to a first Embodiment (Embodiment 1.1), the invention provides a compound of formula (1):

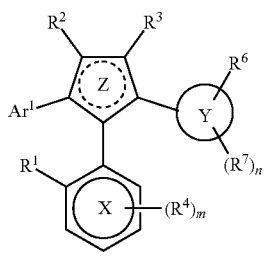

(1)

or a pharmaceutically acceptable salt or tautomer thereof, wherein

Z is a 5-membered heteroaryl ring containing one or two nitrogen ring members and optionally one further heteroatom ring member selected from N and O;

ring X is 6 membered carbocyclic or heterocyclic aromatic ring containing 0, 1 or 2 nitrogen heteroatom ring members;

ring Y is a 6 membered carbocyclic ring or a 5- or 6-membered heterocyclic aromatic ring containing 1 or 2 heteroatom ring members selected from N, O and S;

$Ar^1$ is a monocyclic 5- or 6-membered aromatic ring, optionally containing 0, 1 or 2 heteroatom ring members selected from N, O and S and being optionally substituted with one or more substituents $R^5$;

m is 0, 1 or 2;

n is 0, 1 or 2;

$R^1$ is selected from:
chlorine;
bromine;
hydroxyl;
cyano;
carboxyl;
$C(O)O(Hyd^1)$;
$CONH_2$;
amino;
$(Hyd^2)NH$;
$(Hyd^2)_2N$; and
a $C_{1-5}$ hydrocarbon group where 0, 1 or 2 of the carbons in the hydrocarbon group are replaced with a heteroatom selected from N, O and S, the hydrocarbon group being optionally substituted with one or more fluorine atoms;

provided that when a substituent $R^4$ is present at the meta or para-position of the ring X, and/or when an atom or group other than hydrogen is present at the ortho-position of the ring Y, then $R^1$ is additionally selected from hydrogen and fluorine;

$Hyd^1$ and $Hyd^2$ are the same or different and are $C_{1-4}$ hydrocarbon groups;

$R^2$ is selected from hydrogen and a $C_{1-4}$ hydrocarbon group;

$R^3$ is selected from hydrogen and a $C_{1-4}$ hydrocarbon group;

$R^4$ is selected from:
fluorine;
chlorine;
bromine;
hydroxyl;
cyano;
carboxyl;
$C(O)O(Hyd^1)$;
$CONH_2$;
amino;
$(Hyd^2)NH$;
$(Hyd^2)_2N$; and
a $C_{1-5}$ hydrocarbon group where 0, 1 or 2 of the carbons in the hydrocarbon group are replaced with a heteroatom selected from N, O and S, the hydrocarbon group being optionally substituted with one or more fluorine atoms;

$R^5$ is selected from halogen; $O-Ar^2$; cyano, hydroxy; amino; $Hyd^1-SO_2-$ and a non-aromatic $C_{1-3}$ hydrocarbon group where 0, 1 or 2 but not all of the carbons in the hydrocarbon group are optionally replaced with a heteroatom selected from N, O and S and where the hydrocarbon group is optionally substituted with one or more fluorine atoms;

$Ar^2$ is a phenyl, pyridyl or pyridone group optionally substituted with 1 or 2 substituents selected from halogen; cyano and a $C_{1-4}$ hydrocarbon group optionally substituted with one or more fluorine atoms;

$R^6$ is selected from halogen, cyano, nitro and a group $Q^1-R^a-R^b$;

$Q^1$ is absent or is a $C_{1-6}$ saturated hydrocarbon linker;

$R^a$ is absent or is selected from O; C(O); C(O)O; $CONR^c$; $N(R^c)CO$; $N(R^c)CONR^c$, $NR^c$; S; SO; $SO_2$; $SO_2NR^c$; and $NR^cSO_2$;

$R^b$ is selected from:
hydrogen;
a $C_{1-3}$ non-aromatic hydrocarbon group where 0, 1 or 2 of the carbon atoms in the hydrocarbon group are replaced with a heteroatom selected from N and O, the $C_{1-8}$ non-aromatic hydrocarbon group being optionally substituted with one or more substituents selected from fluorine and a group $Cyc^1$; and
a group $Cyc^1$;

$Cyc^1$ is a non-aromatic 4-7 membered carbocyclic or heterocyclic ring group containing 0, 1 or 2 heteroatom ring members selected from N, O and S and being optionally substituted with one or more substituents selected from hydroxyl; amino; $(Hyd^2)NH$; $(Hyd^2)_2N$; and a $C_{1-5}$ hydrocarbon group where 0, 1 or 2 of the carbons in the hydrocarbon group are replaced with a heteroatom selected from N, O and S, the hydrocarbon group being optionally substituted with one or more fluorine atoms or by a 5- or 6-membered heteroaryl group containing 1 or 2 heteroatom ring members selected from N and O; $R^c$ is selected from hydrogen and a $C_{1-4}$ non-aromatic hydrocarbon group; and $R^7$ is selected from $R^4$.

In formula (1), Z is a 5-membered heteroaryl ring containing one or two nitrogen ring members and optionally one further heteroatom ring member selected from N and O.

It will be appreciated that when the 5-membered heteroaryl ring Z contains a second heteroatom ring member, for example when it is a pyrazole or isoxazole, one or both of $R^2$ and $R^3$ will be absent. Accordingly, in each of the above and following aspects and embodiments where the 5-membered heteroaryl ring is other than a pyrrole, the definitions are to be taken as including compounds wherein one or both of $R^2$ and $R^3$ are absent.

Particular and preferred aspects and embodiments of the invention are set out below in Embodiments 1.1A to 1.183.

1.1A A compound according to Embodiment 1.1 provided that the compound is other than:
(i) a compound wherein $R^1$ is methyl, and $R^4$ is a 4-cyano or 4-carbamoyl group;
(ii) a compound wherein $R^6$ is hydroxy, methoxymethyl or unsubstituted or fluoro-substituted $C_{1-8}$ alkoxy (e.g. trifluoromethoxy);
(iii) a compound wherein the ring Z is a (2H)-pyrazole ring; $Ar^1$ is unsubstituted phenyl; $R^2$ is methyl; $R^3$ is absent; the ring Y is phenyl; n is 0; $R^6$ is $SO_2NH_2$; the ring X is phenyl; $R^1$ is hydrogen; m is 0 or 1; and $R^4$ is 4-methoxy, 4-chloro or 4-bromo;
(iv) the compounds 3-phenyl-4-(3-trifluoromethylphenyl)-5-(2-methoxycarbonylphenyl)-isoxazole, 3-(4-chlorophenyl)-4-(4-chlorophenyl)-5-(2-methoxycarbonylphenyl)-isoxazole;
(v) a compound wherein the ring Z is an isoxazole ring; $Ar^1$ is an unsubstituted 4-pyridyl group attached to the isoxazole 3-position; $R^2$ and $R^3$ are both absent; the ring X is phenyl; $R^1$ is hydrogen; m is 1; $R^4$ is 4-fluoro; and either Y is phenyl, n is 0 and $R^6$ is 4-methoxy, ethoxy or 4-dimethylamino, or Y is 4-pyridyl, n is 0 and $R^6$ is 2-acetylamino (acetylamino ortho with respect to the pyridine nitrogen atom);
(vi) a compound wherein the ring Z is an isoxazole ring and $Ar^1$ is an unsubstituted 4-pyridyl group attached to the isoxazole 3-position; and $R^2$ and $R^3$ are both absent;
(vii) a compound wherein the ring Z is a pyrrole ring; $Ar^1$ is unsubstituted 2-thienyl or phenyl group attached to the 2-position of the pyrrole ring; $R^2$ and $R^3$ are both hydrogen; Y is a 2-thienyl group; n is 0; $R^6$ is a CHO or $CO_2Me$ group attached to the 5-position of the 2-thienyl group; X is phenyl; $R^1$ is hydrogen; m is 1; and $R^4$ is 4-fluoro or 4-methoxy;
(viii) a compound wherein Z is an isoxazole ring and $R^4$ is an azetidin-4-yloxy group; or
(ix) the compounds 4-{4-(4-hydroxyphenyl)-3-[4-(2-piperidylethoxy)phenyl]isoxazol-5-yl}phenol; 4-methoxy-1-{4-(4-methoxyphenyl)-5-[4-(2-piperidylethoxy)phenyl]isoxazol-3-yl}benzene; and 4-methoxy-1-[4-(4-methoxyphenyl)-5-[4-prop-2-enyloxyphenyl)-isoxazol-3-yl]benzene.

1.1B A compound according to Embodiment 1.1 or Embodiment 1.1A which is other than a pyrrole substituted at each of the 1, 2 and 3 positions thereof with a substituted phenyl or pyridyl ring.

1.1C A compound according to any one of Embodiments 1.1 to 1.1B wherein the ring Z is other than a 1,2,3-trisubstituted pyrrole ring.

1.1D A compound according to any one of Embodiments 1.1 to 1.1B wherein the ring Z is other than an imidazole ring.

1.1E A compound according to any one of Embodiments 1.1 to 1.1D wherein the ring Z is other than a 1,2,4 triazole ring.

1.2 A compound according to any one of Embodiments 1.1 to Embodiment 1.1E wherein Z is a heteroaryl ring containing a nitrogen ring member and optionally one further heteroatom ring member selected from N and O.

1.3 A compound according to any one of Embodiments 1.1 to 1.1E wherein Z is selected from pyrrole, isoxazole, imidazole, pyrazole and triazole rings.

1.4 A compound according to Embodiment 1.3 wherein Z is selected from pyrrole, pyrazole and isoxazole rings.

1.5 A compound according to Embodiment 1.4 wherein Z is a pyrrole ring.

1.6 A compound according to Embodiment 1.5 wherein ring X is attached to the nitrogen atom of the pyrrole ring.

1.7 A compound according to Embodiment 1.4 wherein Z is a pyrazole ring.

1.8 A compound according Embodiment 1.7 wherein ring X is attached to a carbon atom of the pyrazole ring.

1.9 A compound according to Embodiment 1.7 or Embodiment 1.8 wherein ring Y is attached to a carbon atom of the pyrazole ring.

1.10 A compound according to Embodiment 1.7 or Embodiment 1.8 wherein ring Y is attached to a nitrogen atom of the pyrazole ring.

1.11 A compound according to any one of Embodiments 1.7 to 1.9 wherein $Ar^1$ is attached to a carbon atom of the pyrazole ring.

1.12 A compound according to Embodiment 1.4 wherein Z is an isoxazole ring.

1.13 A compound according to Embodiment 1.12 wherein ring X is attached to the 4-position of the isoxazole ring.

1.14 A compound according to Embodiment 1.12 or Embodiment 1.13 wherein ring Y is attached to the 5-position of the isoxazole ring.

1.15 A compound according to any one of Embodiments 1.12 to 1.14 wherein $Ar^1$ is attached to the 3-position of the isoxazole ring.

1.16 A compound according to any one of Embodiments 1.1 to 1.15 wherein the ring X is a benzene, pyridine or pyrimidine ring.

1.17 A compound according to Embodiment 1.16 wherein the ring X is a benzene ring or pyridine ring.

1.18 A compound according to Embodiment 1.17 wherein the ring X is a benzene ring.

1.19 A compound according to Embodiment 1.17 wherein the ring X is a pyridine ring.

1.20 A compound according to any one of Embodiments 1.16 to 1.17 and 1.19 wherein the pyridine ring is a 2-pyridine ring.

1.21 A compound according to any one of Embodiments 1.16 to 1.17 and 1.19 wherein the pyridine ring is a 3-pyridine ring.

1.22 A compound according to any one of Embodiments 1.16 to 1.17 and 1.19 wherein the pyridine ring is a 4-pyridine ring.

1.23 A compound according to any one of Embodiments 1.16 to 1.17 and 1.19 wherein the pyridine ring is a 2-pyridine or 3-pyridine ring.

1.24 A compound according to any one of Embodiments 1.1 to 1.23 wherein $R^1$ is selected from:
chlorine;
bromine;
hydroxyl;
cyano;
carboxyl;
amino;
$(Hyd^2)NH$;
$(Hyd^2)_2N$;
a $C_{1-5}$ hydrocarbon group where 0, 1 or 2 of the carbons in the hydrocarbon group are replaced with a heteroatom selected from N, O and S, the hydrocarbon group being optionally substituted with one or more fluorine atoms;

provided that when a substituent $R^4$ is present at the meta or para-position of the ring X, and/or when an atom or group other than hydrogen is present at the ortho-position of the ring Y, then $R^1$ is additionally selected from hydrogen.

1.25 A compound according to Embodiment 1.24 wherein $R^1$ is selected from:
chlorine;
bromine;
hydroxyl;
carboxyl;
amino;
methylamino;
dimethylamino;
a $C_{1-5}$ hydrocarbon group where 0, 1 or 2 of the carbons in the hydrocarbon group are replaced with a heteroatom selected from N, O and S, the hydrocarbon group being optionally substituted with one or more fluorine atoms;
provided that when a substituent $R^4$ is present at the meta or para-position of the ring X, and/or when an atom or group other than hydrogen is present at the ortho-position of the ring Y, then $R^1$ is additionally selected from hydrogen.

1.26 A compound according to Embodiment 1.25 wherein $R^1$ is selected from:
chlorine;
bromine;
hydroxyl;
amino;
a $C_{1-5}$ hydrocarbon group where 0, 1 or 2 of the carbons in the hydrocarbon group are replaced with a heteroatom selected from N, O and S, the hydrocarbon group being optionally substituted with one or more fluorine atoms;
provided that when a substituent $R^4$ is present at the meta or para-position of the ring X, and/or when an atom or group other than hydrogen is present at the ortho-position of the ring Y, then $R^1$ is additionally selected from hydrogen.

1.27 A compound according to Embodiment 1.26 wherein $R^1$ is selected from:
hydroxyl;
amino; and
a $C_{1-5}$ hydrocarbon group where 0, 1 or 2 of the carbons in the hydrocarbon group are replaced with a heteroatom selected from N, O and S, the hydrocarbon group being optionally substituted with one or more fluorine atoms;
provided that when a substituent $R^4$ is present at the meta or para-position of the ring X, and/or when an atom or group other than hydrogen is present at the ortho-position of the ring Y, then $R^1$ is additionally selected from hydrogen.

1.28 A compound according to Embodiment 1.27 wherein $R^1$ is selected from:
hydroxyl;
amino; and
a $C_{1-4}$ hydrocarbon group where 0, 1 or 2 of the carbons in the hydrocarbon group are replaced with a heteroatom selected from N and O, the hydrocarbon group being optionally substituted with one or more fluorine atoms;
provided that when a substituent $R^4$ is present at the para-position of the ring X, and/or when an atom or group other than hydrogen is present at the ortho-position of the ring Y, then $R^1$ is additionally selected from hydrogen.

1.29 A compound according to Embodiment 1.28 wherein $R^1$ is selected from a saturated $C_{1-4}$ hydrocarbon group where 0 or 1 or 2 of the carbons in the hydrocarbon group are replaced with a heteroatom selected from N and O, the hydrocarbon group being optionally substituted with one or more fluorine atoms.

1.30 A compound according to Embodiment 1.29 wherein $R^1$ is selected from a saturated $C_{1-4}$ hydrocarbon group where 0 or 1 of the carbons in the hydrocarbon group are replaced with a heteroatom selected from N and O, the hydrocarbon group being optionally substituted with one or more fluorine atoms.

1.31 A compound according to Embodiment 1.30 wherein $R^1$ is selected from a $C_{1-4}$ alkyl group where 0 or 1 of the carbons in the alkyl group are replaced with a heteroatom selected from N and O, the hydrocarbon group being optionally substituted with one or more fluorine atoms.

1.32 A compound according to Embodiment 1.24 wherein $R^1$ is selected from hydroxyl; carboxyl; amino; a $C_{1-4}$ alkyl group which is optionally substituted with one or more fluorine atoms; a $C_{1-3}$ alkoxy group which is optionally substituted with one or more fluorine atoms; (dimethylamino)methyl and (methoxy)methyl; provided that when a substituent $R^4$ is present at the para-position of the ring X, and/or when an atom or group other than hydrogen is present at the ortho-position of the ring Y, then $R^1$ is additionally selected from hydrogen.

1.33 A compound according to Embodiment 1.32 wherein $R^1$ is selected from hydroxyl; carboxyl; amino; trifluoromethyl; (dimethylamino)methyl and (methoxy)methyl; provided that when m is 0 or 1 and a fluorine substituent $R^4$ is present at the para-position of the ring X; and/or a trifluoromethyl substituent $R^4$ is present at the meta-position of the ring X; and/or when a methoxy or chlorine substituent is present at the ortho-position of the ring Y, then $R^1$ is additionally selected from hydrogen.

1.34 A compound according Embodiment 1.28 wherein $R^1$ is a $C_{1-4}$ alkyl group optionally substituted with one or more fluorine atoms; or a $C_{1-3}$ alkoxy group optionally substituted with one or more fluorine atoms.

1.35 A compound according Embodiment 1.34 wherein $R^1$ is a $C_{1-4}$ alkyl group substituted with one or more fluorine atoms.

1.36 A compound according Embodiment 1.35 wherein $R^1$ is a $C_{1-2}$ alkyl group substituted with one or more fluorine atoms.

1.37 A compound according Embodiment 1.36 wherein $R^1$ is a methyl group substituted with two or three fluorine atoms.

1.38 A compound according to Embodiment 1.37 wherein $R^1$ is trifluoromethyl.

1.39 A compound according to Embodiment 1.33 wherein $R^1$ is selected from hydrogen, trifluoromethyl, trifluoromethoxy, difluoromethyl or difluoromethoxy, hydroxyl, amino, carboxyl, (dimethylamino)methyl and (methoxy)methyl.

1.40 A compound according to Embodiment 1.39 wherein $R^1$ is selected from trifluoromethyl; hydroxyl; amino; (dimethylamino)methyl and (methoxy)methyl.

1.41 A compound according to any one of Embodiments 1.1 to 1.40 wherein m is 0 or 1.

1.42 A compound according to any one of Embodiments 1.1 to 1.40 wherein m is 0.

1.43 A compound according to any one of Embodiments 1.1 to 1.40 wherein m is 1.

1.44 A compound according to any one of Embodiments 1.1 to 1.40 wherein m is 2.

1.45 A compound according to any one of Embodiments 1.1 to 1.41, 1.43 and 1.44 wherein $R^4$ is selected from:
fluorine;
chlorine;
bromine;
cyano; and
a $C_{1-5}$ hydrocarbon group where 0, 1 or 2 of the carbons in the hydrocarbon group are replaced with a heteroatom selected from N, O and S, the hydrocarbon group being optionally substituted with one or more fluorine atoms.

1.46 A compound according to Embodiment 1.45 wherein $R^4$ is selected from:
fluorine;
chlorine;
bromine;
cyano; and
a $C_{1-4}$ hydrocarbon group where 0 or 1 of the carbons in the hydrocarbon group are replaced with a heteroatom selected from N, O and S, the hydrocarbon group being optionally substituted with one or more fluorine atoms.

1.47 A compound according to Embodiment 1.46 wherein $R^4$ is selected from:
fluorine;
chlorine;
bromine;
cyano; and
a $C_{1-4}$ alkyl group where 0 or 1 of the carbons in the alkyl group are replaced with a heteroatom selected from N and O, the alkyl group being optionally substituted with one or more fluorine atoms.

1.48 A compound according to Embodiment 1.47 wherein $R^4$ is selected from:
fluorine;
chlorine;
bromine; and
a $C_{1-4}$ alkyl group where 0 or 1 of the carbons in the alkyl group are replaced with a heteroatom O, the alkyl group being optionally substituted with one or more fluorine atoms.

1.49 A compound according to Embodiment 1.48 wherein $R^4$ is selected from fluorine; chlorine; bromine and $C_{1-4}$ alkyl.

1.50 A compound according to Embodiment 1.49 wherein $R^4$ is selected from fluorine; chlorine; and $C_{1-4}$ alkyl.

1.51 A compound according to any one of Embodiments 1.1 to 1.50 wherein $R^2$ is selected from hydrogen and a saturated $C_{1-4}$ hydrocarbon group.

1.52 A compound according to Embodiment 1.51 wherein $R^2$ is selected from hydrogen; $C_{1-4}$ alkyl; cyclopropyl and cyclopropylmethyl.

1.53 A compound according to Embodiment 1.52 wherein $R^2$ is selected from hydrogen; $C_{1-3}$ alkyl and cyclopropyl.

1.54 A compound according to Embodiment 1.53 wherein $R^2$ is selected from hydrogen; methyl and ethyl.

1.55 A compound according to Embodiment 1.54 wherein $R^2$ is hydrogen or methyl.

1.56 A compound according to Embodiment 1.55 wherein $R^2$ is hydrogen.

1.57 A compound according to any one of Embodiments 1.1 to 1.56 wherein $R^3$ is selected from hydrogen and a saturated $C_{1-4}$ hydrocarbon group.

1.58 A compound according to Embodiment 1.57 wherein $R^3$ is selected from hydrogen; $C_{1-4}$ alkyl; cyclopropyl and cyclopropylmethyl.

1.59 A compound according to Embodiment 1.58 wherein $R^3$ is selected from hydrogen; $C_{1-3}$ alkyl and cyclopropyl.

1.60 A compound according to Embodiment 1.59 wherein $R^3$ is selected from hydrogen; methyl and ethyl.

1.61 A compound according to Embodiment 1.60 wherein $R^3$ is hydrogen or methyl.

1.62 A compound according to Embodiment 1.61 wherein $R^3$ is hydrogen.

1.63 A compound according to any one of Embodiments 1.1 to 1.62 wherein $Ar^1$ is a monocyclic aromatic ring selected from benzene; pyridine; pyrimidine; thiophene; and furan; each of the monocyclic aromatic rings being optionally substituted with one or more substituent $R^5$.

1.64 A compound according to Embodiment 1.63 wherein $Ar^1$ is a monocyclic aromatic ring selected from benzene; pyridine and pyrimidine; each of the monocyclic aromatic rings being optionally substituted with one or more substituent $R^5$.

1.65 A compound according to Embodiment 1.64 wherein $Ar^1$ is a monocyclic aromatic ring selected from benzene and pyridine; each of the monocyclic aromatic rings being optionally substituted with one or more substituent $R^5$.

1.66 A compound according to Embodiment 1.65 wherein $Ar^1$ is a benzene ring optionally substituted with one or more substituent $R^5$.

1.67 A compound according to Embodiment 1.65 wherein $Ar^1$ is a pyridine ring optionally substituted with one or more substituent $R^5$.

1.68 A compound according to any one of Embodiments 1.1 to 1.67 wherein the monocyclic aromatic ring $Ar^1$ is unsubstituted or is substituted with 1, 2, or 3 substituents $R^5$.

1.69 A compound according to Embodiment 1.68 wherein the monocyclic aromatic ring $Ar^1$ is unsubstituted or is substituted with 1 or 2 substituents $R^5$.

1.70 A compound according to Embodiment 1.69 wherein the monocyclic aromatic ring $Ar^1$ is unsubstituted or is substituted with 1 substituent $R^5$.

1.71 A compound according to Embodiment 1.70 wherein the monocyclic aromatic ring $Ar^1$ is substituted with 1 substituent $R^5$.

1.72 A compound according to Embodiment 1.70 wherein the monocyclic aromatic ring $Ar^1$ is unsubstituted.

1.73 A compound according to Embodiment 1.69 wherein the monocyclic aromatic ring $Ar^1$ is substituted with 2 substituents $R^5$.

1.74 A compound according to any one of Embodiments 1.1 to 1.71 and 1.73 wherein $R^5$ is selected from halogen; O—$Ar^2$; cyano, $Hyd^1$-$SO_2$— and a $C_{1-8}$ hydrocarbon group where 0, 1 or 2 but not all of the carbons in the hydrocarbon group are optionally replaced with a heteroatom selected from N, O and S and where the hydrocarbon group is optionally substituted with one or more fluorine atoms.

1.75 A compound according to any one of Embodiments 1.1 to 1.71, 1.73 and 1.74 wherein $Ar^2$ is a phenyl or pyridyl group optionally substituted with 1 or 2 substituents selected from fluorine, chlorine, cyano and trifluoromethyl.

1.76 A compound according to Embodiment 1.75 wherein $Ar^2$ is a phenyl group optionally substituted with 1 or 2 substituents selected from fluorine, chlorine, cyano and trifluoromethyl.

1.77 A compound according to any one of Embodiments 1.1 to 1.71, 1.73 and 1.74 wherein $Hyd^1$ is a saturated $C_{1-4}$ hydrocarbon group.

1.78 A compound according to Embodiment 1.77 wherein $Hyd^1$ is selected from $C_{1-4}$ alkyl; cyclopropyl and cyclopropylmethyl.

1.79 A compound according to Embodiment 1.78 wherein $Hyd^1$ is selected from methyl; ethyl; propyl; cyclopropyl and cyclopropylmethyl.

1.80 A compound according to Embodiment 1.79 wherein $Hyd^1$ is selected from methyl; ethyl; propyl and cyclopropyl.

1.81 A compound according to Embodiment 1.80 wherein $Hyd^1$ is selected from methyl and ethyl.

1.82 A compound according to Embodiment 1.81 wherein $Hyd^1$ is methyl.

1.83 A compound according to any one of Embodiments 1.1 to 1.71 and 1.73 wherein $R^5$ is selected from bromine; fluorine; chlorine; cyano; phenoxy; $C_{1-4}$ alkylsulphonyl; $C_{1-4}$ alkoxy and $C_{1-4}$ alkyl wherein the $C_{1-4}$ alkoxy and $C_{1-4}$ alkyl are each optionally substituted with one or more fluorine atoms.

1.84 A compound according to Embodiment 1.83 wherein $R^5$ is selected from bromine; fluorine; chlorine; cyano; phenoxy; methylsulphonyl; methyl; ethyl; isopropyl; difluoromethyl; trifluoromethyl; methoxy; difluoromethoxy; and trifluoromethoxy.

1.85 A compound according to Embodiment 1.84 wherein $R^5$ is selected from bromine; fluorine; chlorine; cyano; phenoxy; methylsulphonyl; and isopropyl.

1.86 A compound according to Embodiment 1.85 wherein $R^5$ is selected from bromine; fluorine; chlorine; cyano; phenoxy; and isopropyl.

1.87 A compound according to Embodiment 1.86 wherein $R^5$ is selected from bromine; fluorine and chlorine.

1.88 A compound according to Embodiment 1.87 wherein $R^5$ is bromine.

1.89 A compound according to Embodiment 1.88 wherein $Ar^1$ is 4-bromophenyl.

1.90 A compound according to Embodiment 1.87 wherein $R^5$ is chlorine.

1.91 A compound according to Embodiment 1.90 wherein $Ar^1$ is 4-chlorophenyl.

1.92 A compound according to any one of Embodiments 1.1 to 1.91 wherein the ring Y is a benzene, pyridine, pyrimidine, furan, thiophene or pyrrole ring.

1.93 A compound according to Embodiment 1.92 wherein the ring Y is either a) a benzene ring, b) a pyridine ring or c) a thiophene ring.

1.94 A compound according to Embodiment 1.93 wherein the ring Y is a benzene ring.

1.95 A compound according to Embodiment 1.93 wherein the ring Y is a pyridine ring.

1.96 A compound according to any one of Embodiments 1.1 to 1.95 wherein $R^6$ is a group Q1-$R^a$—$R^b$.

1.97 A compound according to any one of Embodiments 1.1 to 1.96 wherein $Q^1$ has the formula $(CR^pR^q)_r$ wherein r is 0, 1, 2, 3 or 4 and $R^p$ and $R^q$ are independently selected from hydrogen and methyl or $R^p$ and $R^q$ together with the carbon atom to which they are attached form a 3- or 4-membered saturated cyclic hydrocarbon ring, provided that the total number of carbons in $Q^1$ does not exceed 6.

1.98 A compound according any one of Embodiments 1.1 to 1.97 wherein $Q^1$ is absent or is selected from $CH_2$, $CH(CH_3)$, $C(CH_3)_2$, cyclopropane-1,1-diyl and cyclobutane-1,1-diyl.

1.99 A compound according any Embodiment 1.98 wherein $Q^1$ is absent.

1.100 A compound according to Embodiment 1.98 wherein $Q^1$ is a —$CH_2$— group.

1.101 A compound according to any one of Embodiments 1.1 to 1.100 wherein $R^a$ is absent or is selected from O; C(O); C(O)O; $CONR^c$; $N(R^c)CO$; $N(R^c)CONR^c$; $NR^c$; and $SO_2$.

1.102 A compound according to Embodiment 1.101 wherein $R^a$ is absent or is selected from O; $CONR^c$; $N(R^c)CO$; $N(R^c)CONR^c$, $NR^c$ and $SO_2$.

1.103 A compound according to Embodiment 1.101 wherein $R^a$ is $CONR^c$.

1.104 A compound according to Embodiment 1.101 wherein $R^a$ is $N(R^c)CO$.

1.105 A compound according to Embodiment 1.101 wherein $R^a$ is $NR^c$.

1.106 A compound according to Embodiment 1.101 wherein $R^a$ is absent.

1.107 A compound according to Embodiment 1.101 wherein $R^a$ is O.

1.108 A compound according to Embodiment 1.101 wherein $R^a$ is C(O).

1.109 A compound according to Embodiment 1.101 wherein $R^a$ is C(O)O.

1.110 A compound according to Embodiment 1.101 wherein $R^a$ is $SO_2$.

1.111 A compound according to any one of Embodiments 1.1 to 1.110 wherein $R^b$ is selected from:
a $C_{1-8}$ non-aromatic hydrocarbon group where 0, 1 or 2 but not all of the carbon atoms in the hydrocarbon group are replaced with a heteroatom selected from N and O, the $C_{1-8}$ non-aromatic hydrocarbon group being optionally substituted with one or more substituents selected from fluorine and a group $Cyc^1$; and
a group $Cyc^1$;
provided that when $R^a$ is C(O)O or $CONR^c$; then $R^b$ is additionally selected from hydrogen.

1.112 A compound according to Embodiment 1.111 wherein $R^b$ is selected from:
a $C_{1-3}$ non-aromatic hydrocarbon group where 0, 1 or 2 of the carbon atoms in the hydrocarbon group are replaced with a heteroatom selected from N and O, the $C_{1-8}$ non-aromatic hydrocarbon group being optionally substituted with one or more substituents selected from fluorine and a group $Cyc^1$; and
a group $Cyc^1$.

1.113 A compound according to Embodiment 1.112 wherein $R^b$ is selected from:
a $C_{1-3}$ non-aromatic hydrocarbon group where 0 or 1 but not all of the carbon atoms in the hydrocarbon group are replaced with a heteroatom selected from N and O, the $C_{1-3}$ non-aromatic hydrocarbon group being optionally substituted with one or more substituents selected from fluorine and a group $Cyc^1$; and
a group $Cyc^1$.

1.114 A compound according to Embodiment 1.113 wherein $R^b$ is selected from:
   a $C_{1-3}$ non-aromatic hydrocarbon group where 0 or 1 but not all of the carbon atoms in the hydrocarbon group are replaced with a heteroatom selected from N and O, the $C_{1-8}$ non-aromatic hydrocarbon group being optionally substituted with a group $Cyc^1$; and
   a group $Cyc^1$.
1.115 A compound according to Embodiment 1.114 wherein $R^b$ is selected from:
   a $C_{1-8}$ non-aromatic hydrocarbon group wherein 1 of the carbon atoms in the hydrocarbon group is replaced with a heteroatom selected from N and O; and
   a group $Cyc^1$.
1.116 A compound according to Embodiment 1.115 wherein $R^b$ is selected from:
   a $C_{1-8}$ non-aromatic hydrocarbon group wherein 1 of the carbon atoms in the hydrocarbon group is replaced with a heteroatom N; and
   a group $Cyc^1$.
1.117 A compound according to any one of Embodiments 1.1 to 1.110 wherein $R^b$ is a $C_{1-8}$ non-aromatic hydrocarbon group where 0, 1 or 2 but not all of the carbon atoms in the hydrocarbon group are replaced with a heteroatom selected from N and O, the $C_{1-3}$ non-aromatic hydrocarbon group being optionally substituted with one or more substituents selected from fluorine and a group $Cyc^1$.
1.118 A compound according to Embodiment 1.117 wherein $R^b$ is selected from:
   a $C_{1-3}$ non-aromatic hydrocarbon group where 0 or 1 but not all of the carbon atoms in the hydrocarbon group are replaced with a heteroatom selected from N and O, the $C_{1-3}$ non-aromatic hydrocarbon group being optionally substituted with one or more substituents selected from fluorine and a group $Cyc^1$.
1.119 A compound according to Embodiment 1.118 wherein $R^b$ is selected from:
   a $C_{1-3}$ non-aromatic hydrocarbon group where 0 or 1 but not all of the carbon atoms in the hydrocarbon group are replaced with a heteroatom selected from N and O, the $C_{1-3}$ non-aromatic hydrocarbon group being optionally substituted with a group $Cyc^1$.
1.120 A compound according to Embodiment 1.119 wherein $R^b$ is selected from:
   a $C_{1-3}$ non-aromatic hydrocarbon group wherein 1 of the carbon atoms in the hydrocarbon group is replaced with a heteroatom selected from N and O.
1.121 A compound according to any one of Embodiments 1.1 to 1.120 wherein $R^b$ is selected from:
   a $C_{1-8}$ non-aromatic hydrocarbon group wherein 1 of the carbon atoms in the hydrocarbon group is replaced with a nitrogen heteroatom.
1.122 A compound according to any one of Embodiments 1.111 to 1.121 wherein $R^b$ is selected from:
   a $C_{1-8}$ non-aromatic hydrocarbon group wherein a carbon atom in the hydrocarbon group is replaced with a nitrogen heteroatom so as to form a terminal dimethylamino group.
1.123 A compound according to any one of Embodiments 1.111 to 1.122 wherein the non-aromatic hydrocarbon group is acyclic.
1.124 A compound according to any one of Embodiments 1.111 to 1.123 wherein the non-aromatic hydrocarbon group is saturated.
1.125 A compound according to any one of Embodiments 1.111 to 1.124 wherein the non-aromatic hydrocarbon group contains 1 to 6 carbon atoms.
1.126 A compound according to any one of Embodiments 1.111 to 1.125 wherein the non-aromatic hydrocarbon group contains 1 to 5 carbon atoms.
1.127 A compound according to any one of Embodiments 1.111 to 1.125 wherein the non-aromatic hydrocarbon group contains 3 to 5 carbon atoms.
1.128 A compound according to any one of Embodiments 1.1 to 1.119 wherein $R^b$ is or contains a group $Cyc^1$.
1.129 A compound according to Embodiment 1.128 wherein $R^b$ is a group $Cyc^1$.
1.130 A compound according to any one of Embodiments 1.1 to 1.119, 1.128 and 1.129 wherein $Cyc^1$ is a non-aromatic 4-7 membered carbocyclic or heterocyclic ring group containing 0, 1 or 2 heteroatom ring members selected from N and O and being optionally substituted with one or more substituents selected from hydroxyl; amino; mono-$C_{1-4}$ alkylamino; di-$C_{1-4}$ alkylamino; and a $C_{1-5}$ saturated hydrocarbon group where 0 or 1 but not all of the carbons in the hydrocarbon group are replaced with a heteroatom selected from N and O.
1.131 A compound according to any one of Embodiments 1.1 to 1.119, 1.128 and 1.129 wherein $Cyc^1$ is a non-aromatic 4-7 membered heterocyclic ring group containing a nitrogen ring member and optionally second heteroatom ring member selected from N and O; the non-aromatic 4-7 membered heterocyclic ring group being optionally substituted with one or more substituents selected from hydroxyl; amino; mono-$C_{1-4}$ alkylamino; di-$C_{1-4}$ alkylamino; and a $C_{1-4}$ saturated hydrocarbon group where 0 or 1 but not all of the carbons in the hydrocarbon group are replaced with a heteroatom selected from N and O.
1.132 A compound according to any one of Embodiments 1.1 to 1.119, 1.128 and 1.129 wherein $Cyc^1$ is a non-aromatic 5-6 membered heterocyclic ring group containing a nitrogen ring member and optionally second heteroatom ring member selected from N and O; the non-aromatic 5-6 membered heterocyclic ring group being optionally substituted with one or more substituents selected from hydroxyl; amino; mono-$C_{1-4}$ alkylamino; di-$C_{1-4}$ alkylamino; and a $C_{1-4}$ saturated hydrocarbon group where 0 or 1 but not all of the carbons in the hydrocarbon group are replaced with a heteroatom selected from N and O.
1.133 A compound according to any one of Embodiments 1.1 to 1.119, 1.128 and 1.129 wherein $Cyc^1$ is a non-aromatic 5-6 membered heterocyclic ring group containing a nitrogen ring member and optionally second heteroatom ring member selected from N and O; the non-aromatic 5-6 membered heterocyclic ring group being optionally substituted with one or more substituents selected from hydroxyl; amino; mono-$C_{1-2}$ alkylamino; di-$C_{1-2}$ alkylamino; and a $C_{1-4}$ alkyl group where 0 or 1 but not all of the carbons in the alkyl group are replaced with a heteroatom selected from N and O.
1.134 A compound according to any one of Embodiments 1.1 to 1.119, and 1.128 to 1.133 wherein $Cyc^1$ is a saturated ring.
1.135 A compound according to Embodiment 1.134 wherein $Cyc^1$ is selected from pyrrolidine; piperidine; and piperazine; each of which is optionally substituted with one or more substituents selected from hydroxyl; amino; mono-$C_{1-2}$ alkylamino; di-$C_{1-2}$ alkylamino; and a C$_{1-4}$ alkyl group where 0 or 1 but not all of the carbons in the alkyl group are replaced with a heteroatom selected from N and O.

1.136 A compound according to any one of Embodiments 1.1 to 1.105 and 1.111 to 1.135 wherein R$^c$ is selected from hydrogen; methyl; ethyl; propyl; iso-propyl; cyclopropyl; cyclopropylmethyl; butyl; iso-butyl and cyclobutyl.

1.137 A compound according to Embodiment 1.136 wherein R$^c$ is selected from hydrogen and methyl.

1.138 A compound according to Embodiment 1.137 wherein R$^c$ is hydrogen.

1.139 A compound according to Embodiment 1.137 wherein, R$^c$ is methyl.

1.140 A compound according to any one of Embodiments 1.1 to 1.95 wherein R$^6$ is selected from groups A to AM in Table 1 below.

TABLE 1

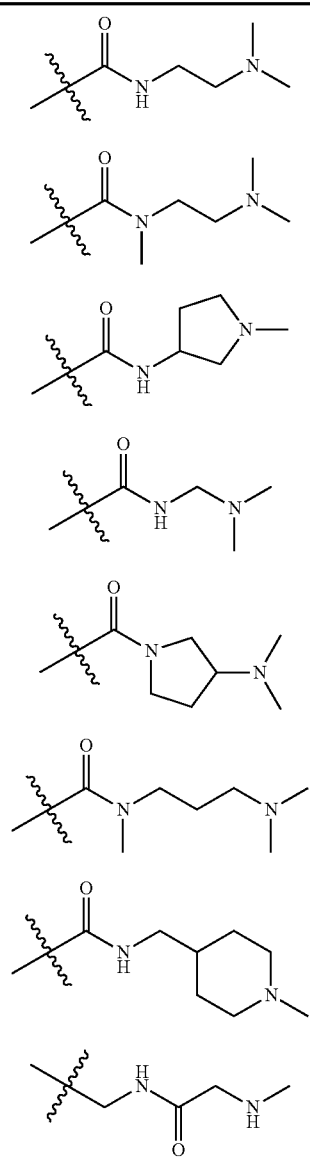

TABLE 1-continued

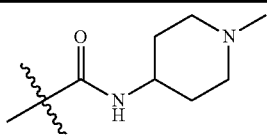  I

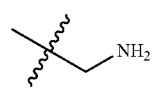  J

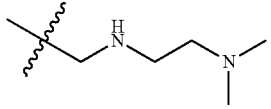 [SMILES: *CNCCN(C)C]  K

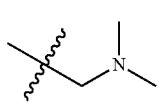 [SMILES: *CN(C)C]  L

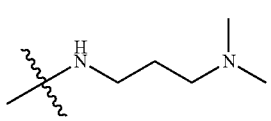 [SMILES: *NCCCN(C)C]  M

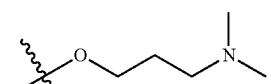  N

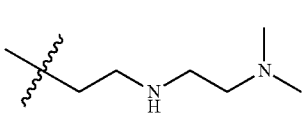 [SMILES: *CCNCCN(C)C]  O

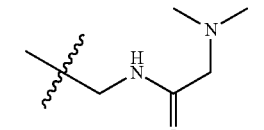  P

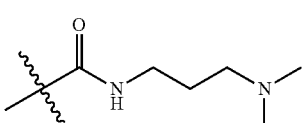  Q

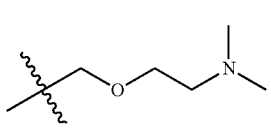 [SMILES: *COCCN(C)C]  R

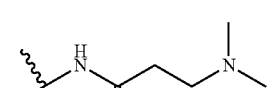  S

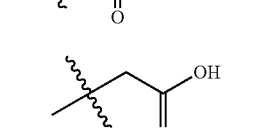  T

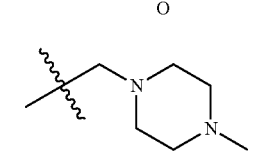  U

TABLE 1-continued

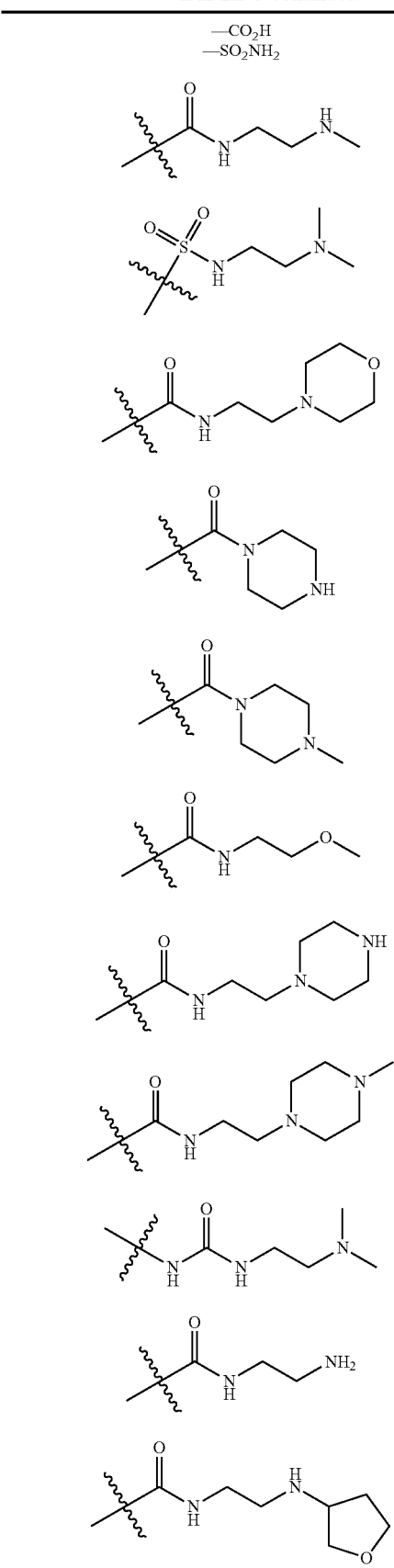

| | |
|---|---|
| —CO₂H | V |
| —SO₂NH₂ | W |
| | X |
| | Y |
| | Z |
| | AA |
| | AB |
| | AC |
| | AD |
| | AE |
| | AF |
| | AG |
| | AH |

TABLE 1-continued

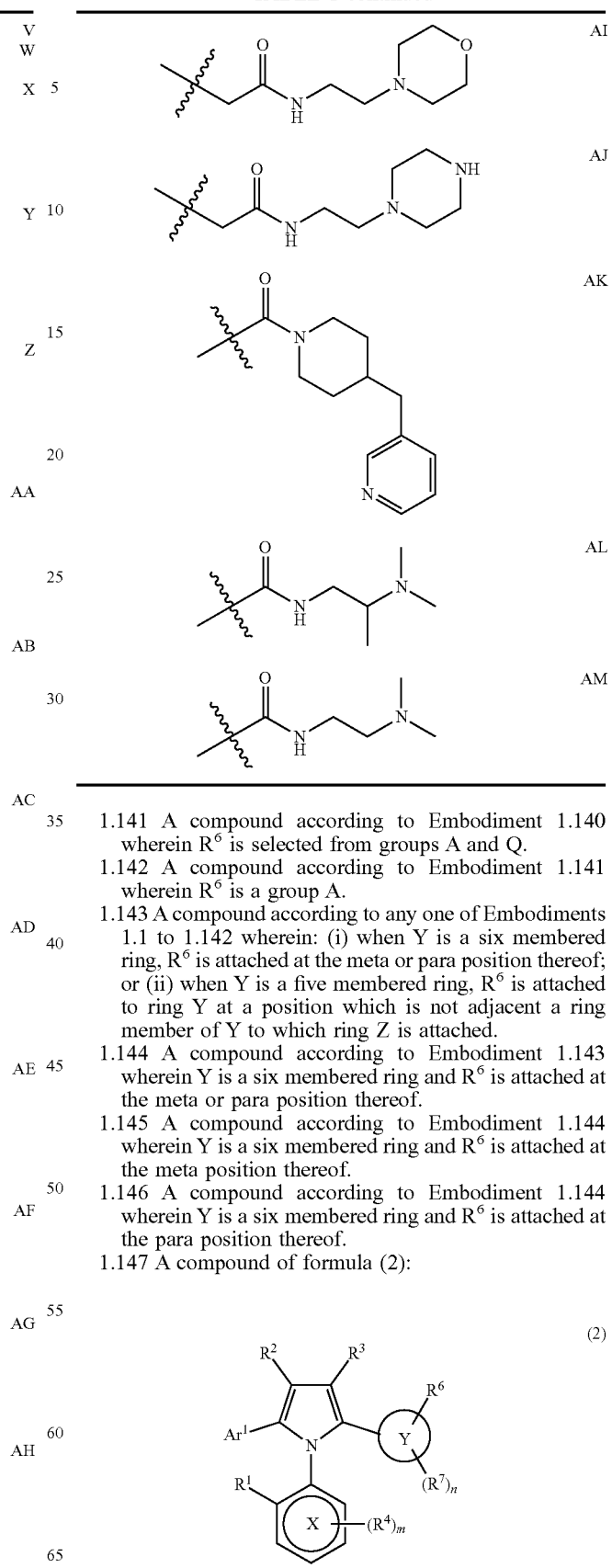

| | |
|---|---|
| | AI |
| | AJ |
| | AK |
| | AL |
| | AM |

1.141 A compound according to Embodiment 1.140 wherein $R^6$ is selected from groups A and Q.

1.142 A compound according to Embodiment 1.141 wherein $R^6$ is a group A.

1.143 A compound according to any one of Embodiments 1.1 to 1.142 wherein: (i) when Y is a six membered ring, $R^6$ is attached at the meta or para position thereof; or (ii) when Y is a five membered ring, $R^6$ is attached to ring Y at a position which is not adjacent a ring member of Y to which ring Z is attached.

1.144 A compound according to Embodiment 1.143 wherein Y is a six membered ring and $R^6$ is attached at the meta or para position thereof.

1.145 A compound according to Embodiment 1.144 wherein Y is a six membered ring and $R^6$ is attached at the meta position thereof.

1.146 A compound according to Embodiment 1.144 wherein Y is a six membered ring and $R^6$ is attached at the para position thereof.

1.147 A compound of formula (2):

or a pharmaceutically acceptable salt or tautomer thereof; wherein $R^1$, $R^2$, $R^3$, $R^4$, $R^6$, $R^7$, $Ar^1$, X and Y are as defined in any one of Embodiments 1.1 to 1.6 and 1.16 to 1.146.

1.148 A compound according to Embodiment 1.147 wherein
$R^1$ is selected from trifluoromethyl, hydroxyl, amino, carboxyl, (dimethylamino)methyl and (methoxy)methyl;
$R^2$ is hydrogen;
$R^3$ is hydrogen;
$R^4$ is absent or is selected from chlorine and fluorine;
$Ar^1$ is phenyl or pyridyl optionally substituted with one or two substituents $R^5$ selected from bromine, fluorine, chlorine, phenoxy, iso-propyl, methanesulphonyl and cyano;
X is selected from phenyl and pyridyl;
m is 0 or 1;
Y is selected from phenyl, pyridyl and thienyl;
n is 0 or 1;
$R^6$ is selected from groups A to AM in Table 1 above; and
$R^7$ is selected from chlorine, fluorine and methoxy.

1.149 A compound of formula (3):

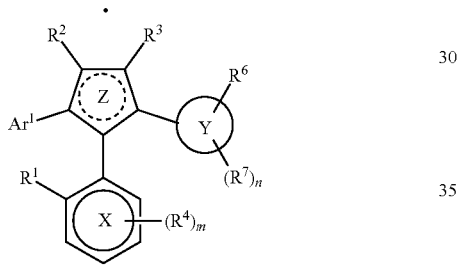

(3)

or a pharmaceutically acceptable salt or tautomer thereof, wherein:
Z is a 5-membered heteroaryl ring containing one or two nitrogen ring members and optionally one further heteroatom ring member selected from N and O;
ring X is a benzene or pyridine ring;
ring Y is a benzene, pyridine, thiophene or furan ring;
$Ar^1$ is a benzene, pyridine, thiophene or furan ring optionally substituted with one or more substituent $R^5$;
m is 0, 1 or 2;
n is 0, 1 or 2;
$R^1$ is selected from:
  chlorine;
  bromine;
  hydroxyl;
  cyano;
  $CONH_2$;
  amino;
  $(Hyd^2)NH$;
  $(Hyd^2)_2N$; and
  a $C_{1-5}$ hydrocarbon group where 0, 1 or 2 of the carbons in the hydrocarbon group are replaced with a heteroatom selected from N, O and S, the hydrocarbon group being optionally substituted with one or more fluorine atoms;
provided that when a substituent $R^4$ is present at the meta or para-position of the ring X, and/or when an atom or group other than hydrogen is present at the ortho-position of the ring Y, then $R^1$ is additionally selected from hydrogen and fluorine;
$Hyd^1$ and $Hyd^2$ are the same or different and are $C_{1-4}$ hydrocarbon groups;
$R^2$ is selected from hydrogen and a $C_{1-4}$ hydrocarbon group;
$R^3$ is selected from hydrogen and a $C_{1-4}$ hydrocarbon group;
$R^4$ is selected from:
  fluorine;
  chlorine;
  bromine;
  hydroxyl;
  cyano;
  carboxyl;
  $C(O)O(Hyd^1)$;
  amino;
  $(Hyd^2)NH$;
  $(Hyd^2)_2N$; and
  a $C_{1-5}$ hydrocarbon group where 0, 1 or 2 of the carbons in the hydrocarbon group are replaced with a heteroatom selected from N, O and S, the hydrocarbon group being optionally substituted with one or more fluorine atoms;
$R^5$ is selected from halogen; $O-Ar^2$; cyano, hydroxy; amino; $Hyd^1-SO_2-$ and a non-aromatic $C_{1-3}$ hydrocarbon group where 0, 1 or 2 but not all of the carbons in the hydrocarbon group are optionally replaced with a heteroatom selected from N, O and S and where the hydrocarbon group is optionally substituted with one or more fluorine atoms;
$Ar^2$ is a phenyl, pyridyl or pyridone group optionally substituted with 1 or 2 substituents selected from halogen; cyano and a $C_{1-4}$ hydrocarbon group optionally substituted with one or more fluorine atoms;
$R^6$ is a group $Q1-R^a-R^b$;
$Q^1$ is absent or is a $C_{1-3}$ saturated hydrocarbon linker;
$R^a$ is selected from O; C(O); C(O)O; $CONR^c$; $N(R^c)$ CO; $N(R^c)CONR^c$, $NR^c$; and $SO_2NR^c$;
$R^b$ is selected from:
hydrogen;
  a $C_{1-3}$ non-aromatic hydrocarbon group where 0, 1 or 2 of the carbon atoms in the hydrocarbon group are replaced with a heteroatom selected from N and O, the $C_{1-3}$ non-aromatic hydrocarbon group being optionally substituted with one or more substituents selected from fluorine and a group $Cyc^1$; and
  a group $Cyc^1$;
$Cyc^1$ is a non-aromatic 4-7 membered carbocyclic or heterocyclic ring group containing 0, 1 or 2 heteroatom ring members selected from N, O and S and being optionally substituted with one or more substituents selected from hydroxyl; amino; $(Hyd^2)NH$; $(Hyd^2)_2N$; and a $C_{1-5}$ hydrocarbon group where 0, 1 or 2 of the carbons in the hydrocarbon group are replaced with a heteroatom selected from N, O and S, the hydrocarbon group being optionally substituted with one or more fluorine atoms or by a 5- or 6-membered heteroaryl group containing 1 or 2 heteroatom ring members selected from N and O;
$R^c$ is selected from hydrogen and a $C_{1-4}$ non-aromatic hydrocarbon group; and
$R^7$ is selected from $R^4$ with the proviso that when n is 2 and both occurrences of $R^7$ are —$OCH_3$, $R^6$ is not —$NH_2$ or —$NHCH_3$; and with the proviso that when $R^1$ is methyl, $R^4$ is other than a 4-cyano or 4-carbamoyl group; and excluding compounds where $R^6$ is hydroxy, methoxymethyl or unsubstituted or fluoro-substituted $C_{1-8}$ alkoxy.

1.150 A compound according to Embodiment 1.149 wherein Z, X, Y and $Ar^1$ are as defined in any one of Embodiments 1.1A to 1.15.

1.151 A compound according to Embodiment 1.149 or Embodiment 1.150 wherein Z is other than a 1,2,3-trisubstituted pyrrole.

1.152 A compound according to any one of Embodiments 1.149 to 1.151 wherein Z is other than a 1,4,5-trisubstituted imidazole.

1.153 A compound according to any one of Embodiments 1.149 to 1.152 wherein Z is other than an imidazole ring.

1.154 A compound according to any one of Embodiments 1.149 to 1.153 wherein X is as defined in any one of Embodiments 1.18 to 1.23.

1.155 A compound according to any one of Embodiments 1.149 to 1.154 where $R^1$ is as defined in any one of Embodiments 1.26 to 1.31, 1.34 to 1.38 or 1.40.

1.156 A compound according to any one of Embodiments 1.149 to 1.155 wherein m is as defined in any one of Embodiments 1.41 to 1.44.

1.157 A compound according to any one of Embodiments 1.149 to 1.155 wherein $R^4$ is as defined in any one of Embodiments 1.45 to 1.50.

1.158 A compound according to any one of Embodiments 1.149 to 1.157 wherein $R^2$ and $R^3$ are as defined in any one of Embodiments 1.51 to 1.62.

1.159 A compound according to any one of Embodiments 1.149 to 1.158 wherein $Ar^1$ is selected from a benzene or pyridine ring optionally substituted with one or more substituents $R^5$.

1.160 A compound according to any one of Embodiments 1.149 to 1.159 wherein $Ar^1$, $R^5$, $Ar^2$ and $Hyd^1$ are as defined in any one of Embodiments 1.65 to 1.91.

1.161 A compound according to any one of Embodiments 1.149 to 1.160 wherein Y is as defined in any one of Embodiments 1.93 to 1.95.

1.162 A compound according to any one of Embodiments 1.149 to 1.161 wherein $Q^1$ has the formula $(CR^pR^q)_r$ wherein r is 0, 1 or 2 and $R^p$ and $R^q$ are independently selected from hydrogen and methyl or $R^p$ and $R^q$ together with the carbon atom to which they are attached form a 3-membered saturated cyclic hydrocarbon ring, provided that the total number of carbons in $Q^1$ does not exceed 3.

1.163 A compound according any one of Embodiments 1.149 to 1.162 wherein $Q^1$ is absent or is selected from $CH_2$, $CH(CH_3)$, $C(CH_3)_2$ and cyclopropane-1,1-diyl.

1.164 A compound according to Embodiment 1.163 wherein $Q^1$ is absent or selected from $CH_2$ and $C(CH_3)_2$.

1.165 A compound according any Embodiment 1.164 wherein $Q^1$ is absent.

1.166 A compound according to Embodiment 1.164 wherein $Q^1$ is $CH_2$.

1.167 A compound according to any one of Embodiments 1.149 to 1.166 wherein $R^a$ is selected from O; C(O); C(O)O; $CONR^c$; $N(R^c)CO$; $N(R^c)CONR^c$ and $NR^c$.

1.168 A compound according to Embodiment 1.167 wherein $R^a$ is O;

1.169 A compound according to Embodiment 1.167 wherein $R^a$ is $CONR^c$.

1.170 A compound according to Embodiment 1.167 wherein $R^a$ is $N(R^c)CO$.

1.171 A compound according to Embodiment 1.167 wherein $R^a$ is $NR^c$.

1.172 A compound according to Embodiment 1.167 wherein $R^a$ is C(O).

1.173 A compound according to Embodiment 1.167 wherein $R^a$ is C(O)O.

1.174 A compound according to Embodiment 1.173 wherein $R^b$ is other than hydrogen.

1.175 A compound according to any one of Embodiments 1.149 to 1.174 wherein $R^b$, $R^c$ and $Cyc^1$ are as defined in any one of Embodiments 1.111 to 1.139.

1.176 A compound according to any one of Embodiment 1.149 to 1.162 wherein:
$Q^1$ is absent or is a $CH_2$ or $C(CH_3)_2$ linker;
$R^a$ is selected from O; C(O); C(O)O; $CONR^c$; $N(R^c)CO$; $N(R^c)CONR^c$, $NR^c$; and $SO_2NR^c$;
$R^b$ is selected from:
hydrogen;
a $C_{1-3}$ non-aromatic hydrocarbon group where 0, 1 or 2 of the carbon atoms in the hydrocarbon group are replaced with a heteroatom selected from N and O, the $C_{1-3}$ non-aromatic hydrocarbon group being optionally substituted with a substituent $Cyc^1$; and
a group $Cyc^1$;
$Cyc^1$ is a non-aromatic 5-6 membered carbocyclic or heterocyclic ring group containing 0, 1 or 2 heteroatom ring members selected from N and O and being optionally substituted with one or more substituents selected from methyl and (dimethyl)amino; and
$R^c$ is selected from hydrogen and methyl.

1.177 A compound according to any one of Embodiments 1.149 to 1.175 wherein $R^6$ is selected from groups A to AM in Table 1 above.

1.178 A compound according to any one of Embodiments 1.149 to 1.175 wherein $R^6$ is selected from the groups A to M, O to Q, S, U, X, Z and AA to AJ in Table 1 above.

1.179 A compound according to Embodiment 1.178 wherein $R^6$ is selected from groups A and Q.

1.180 A compound according to Embodiment 1.178 wherein $R^6$ is a group A.

1.180A A compound of formula (4):

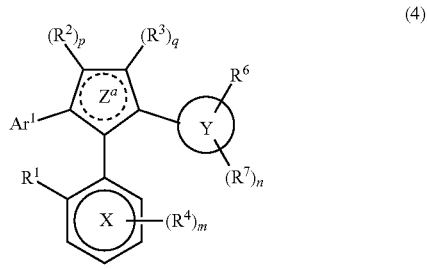

or a pharmaceutically acceptable salt or tautomer thereof, wherein $Z^a$ is a 5-membered heteroaryl ring containing one or two nitrogen ring members and one further heteroatom ring member selected from N and O;

ring X is 6 membered carbocyclic or heterocyclic aromatic ring containing 0, 1 or 2 nitrogen heteroatom ring members;

ring Y is a 6 membered carbocyclic ring or a 5- or 6-membered heterocyclic aromatic ring containing 1 or 2 heteroatom ring members selected from N, O and S;

$Ar^1$ is a monocyclic 5- or 6-membered aromatic ring, optionally containing 0, 1 or 2 heteroatom ring members selected from N, O and S and being optionally substituted with one or more substituents $R^5$;

m is 0, 1 or 2;

n is 0, 1 or 2;

one of p and q is 0 and the other of p and q is 0 or 1;

$R^1$ is selected from:
chlorine;
bromine;
hydroxyl;
cyano;
carboxyl;
$C(O)O(Hyd^1)$;
$CONH_2$;
amino;
$(Hyd^2)NH$;
$(Hyd^2)_2N$; and
a $C_{1-5}$ hydrocarbon group where 0, 1 or 2 of the carbons in the hydrocarbon group are replaced with a heteroatom selected from N, O and S, the hydrocarbon group being optionally substituted with one or more fluorine atoms;

provided that when a substituent $R^4$ is present at the meta or para-position of the ring X, and/or when an atom or group other than hydrogen is present at the ortho-position of the ring Y, then $R^1$ is additionally selected from hydrogen and fluorine;

$Hyd^1$ and $Hyd^2$ are the same or different and are $C_{1-4}$ hydrocarbon groups;

$R^2$ is selected from hydrogen and a $C_{1-4}$ hydrocarbon group;

$R^3$ is selected from hydrogen and a $C_{1-4}$ hydrocarbon group;

$R^4$ is selected from:
fluorine;
chlorine;
bromine;
hydroxyl;
cyano;
carboxyl;
$C(O)O(Hyd^1)$;
$CONH_2$;
amino;
$(Hyd^2)NH$;
$(Hyd^2)_2N$; and
a $C_{1-5}$ hydrocarbon group where 0, 1 or 2 of the carbons in the hydrocarbon group are replaced with a heteroatom selected from N, O and S, the hydrocarbon group being optionally substituted with one or more fluorine atoms;

$R^5$ is selected from halogen; $O$—$Ar^2$; cyano, hydroxy; amino; $Hyd^1$-$SO_2$— and a non-aromatic $C_{1-3}$ hydrocarbon group where 0, 1 or 2 but not all of the carbons in the hydrocarbon group are optionally replaced with a heteroatom selected from N, O and S and where the hydrocarbon group is optionally substituted with one or more fluorine atoms;

$Ar^2$ is a phenyl, pyridyl or pyridone group optionally substituted with 1 or 2 substituents selected from halogen; cyano and a $C_{1-4}$ hydrocarbon group optionally substituted with one or more fluorine atoms;

$R^6$ is selected from halogen, cyano, nitro and a group $Q^1$-$R^a$—$R^b$;

$Q^1$ is absent or is a $C_{1-6}$ saturated hydrocarbon linker;

$R^a$ is absent or is selected from O; C(O); C(O)O; $CONR^c$; $N(R^c)CO$; $N(R^c)CONR^c$, $NR^c$; S; SO; $SO_2$; $SO_2NR^c$; and $NR^cSO_2$;

$R^b$ is selected from:
hydrogen;
a $C_{1-3}$ non-aromatic hydrocarbon group where 0, 1 or 2 of the carbon atoms in the hydrocarbon group are replaced with a heteroatom selected from N and O, the $C_{1-8}$ non-aromatic hydrocarbon group being optionally substituted with one or more substituents selected from fluorine and a group $Cyc^1$; and
a group $Cyc^1$;

$Cyc^1$ is a non-aromatic 4-7 membered carbocyclic or heterocyclic ring group containing 0, 1 or 2 heteroatom ring members selected from N, O and S and being optionally substituted with one or more substituents selected from hydroxyl; amino; $(Hyd^2)NH$; $(Hyd^2)_2N$; and a $C_{1-5}$ hydrocarbon group where 0, 1 or 2 of the carbons in the hydrocarbon group are replaced with a heteroatom selected from N, O and S, the hydrocarbon group being optionally substituted with one or more fluorine atoms or by a 5- or 6-membered heteroaryl group containing 1 or 2 heteroatom ring members selected from N and O;

$R^c$ is selected from hydrogen and a $C_{1-4}$ non-aromatic hydrocarbon group; and $R^7$ is selected from $R^4$.

1.180B A compound according to Embodiment 1.180A wherein one of p and q is 0 and the other of p and q is 1.

1.180C A compound according to Embodiment 1.180B wherein $Z^a$ is a pyrazole ring.

1.180D A compound according to Embodiment 1.180A wherein both p and q are 0.

1.180E A compound according to Embodiment 1.180D wherein $Z^a$ is an isoxazole.

1.180F A compound according to any one of Embodiments 1.180A to 1.180E wherein $Ar^1$, $R^1$, $R^2$, $R^3$, $R^4$, $R^6$, $R^7$, m, n, the ring X and the ring Y are as defined in any one of Embodiments 1.1, 1.1A to 1.1E and 1.7 to 1.146 and 1.148 to 1.180.

1.181 A compound which is a title compound of any one of Examples 1 to 107 herein.

1.182 A compound as defined in any one of Embodiments 1.1 to 1.181 in the form of a salt.

1.183 A compound according to Embodiment 1.182 wherein the salt is an acid addition salt.

Definitions

Unless the context indicates otherwise, references to formula (1) in all sections of this document (including the uses, methods and other aspects of the invention) include references to all other sub-formulae (e.g. formulae (2) and (3)), sub-groups, preferences, embodiments and examples as defined herein.

Salts

The compounds of the invention as defined in Embodiments 1.1 to 1.181 may be presented in the form of salts.

The salts referred to above are typically acid addition salts.

The salts can be synthesized from the parent compound by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free base form of the compound with the acid in water or in an organic solvent, or in a mixture of the two; generally, nonaqueous media such as ether, ethyl acetate, ethanol, isopropanol, or acetonitrile are used.

Acid addition salts (as defined in Embodiment 1.183) may be formed with a wide variety of acids, both inorganic and organic. Examples of acid addition salts include salts formed with an acid selected from the group consisting of acetic, 2,2-dichloroacetic, adipic, alginic, ascorbic (e.g. L-ascorbic), L-aspartic, benzenesulphonic, benzoic, 4-acetamidobenzoic, butanoic, (+) camphoric, camphor-sulphonic, (+)-(1S)-camphor-10-sulphonic, capric, caproic, caprylic, cinnamic, citric, cyclamic, dodecylsulphuric, ethane-1,2-disulphonic, ethanesulphonic, 2-hydroxyethanesulphonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrobromic, hydrochloric, hydriodic, isethionic, (+)-L-lactic, (±)-DL-lactic, lactobionic, maleic, malic, (−)-L-malic, malonic, (±)-DL-mandelic, methanesulphonic, naphthalene-2-sulphonic, naphthalene-1,5-disulphonic, 1-hydroxy-2-naphthoic, nicotinic, nitric, oleic, orotic, oxalic, palmitic, pamoic, phosphoric, propionic, L-pyroglutamic, salicylic, 4-amino-salicylic, sebacic, stearic, succinic, sulphuric, tannic, (+)-L-tartaric, thiocyanic, p-toluenesulphonic, undecylenic and valeric acids, as well as acylated amino acids and cation exchange resins.

The salt forms of the compounds of the invention are typically pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

Geometric Isomers and Tautomers

The compounds of the invention may exist in a number of different geometric isomeric, and tautomeric forms and references to the compounds as defined in Embodiments 1.1 to 1.183 include all such forms. For the avoidance of doubt, where a compound can exist in one of several geometric isomeric or tautomeric forms and only one is specifically described or shown, all others are nevertheless embraced by formula (1) or subgroups, subsets, preferences and examples thereof.

Optical Isomers

Where compounds of the formula contain one or more chiral centres, and can exist in the form of two or more optical isomers, references to the compounds include all optical isomeric forms thereof (e.g. enantiomers, epimers and diastereoisomers), either as individual optical isomers, or mixtures (e.g. racemic mixtures) or two or more optical isomers, unless the context requires otherwise.

The optical isomers may be characterised and identified by their optical activity (i.e. as + and − isomers, or d and/isomers) or they may be characterised in terms of their absolute stereochemistry using the "R and S" nomenclature developed by Cahn, Ingold and Prelog, see *Advanced Organic Chemistry* by Jerry March, 4$^{th}$ Edition, John Wiley & Sons, New York, 1992, pages 109-114, and see also Cahn, Ingold & Prelog, *Angew. Chem. Int. Ed. Engl.*, 1966, 5, 385-415.

Optical isomers can be separated by a number of techniques including chiral chromatography (chromatography on a chiral support) and such techniques are well known to the person skilled in the art.

As an alternative to chiral chromatography, optical isomers can be separated by forming diastereoisomeric salts with chiral acids such as (+)-tartaric acid, (−)-pyroglutamic acid, (−)-di-toluoyl-L-tartaric acid, (+)-mandelic acid, (−)-malic acid, and (−)-camphorsulphonic, separating the diastereoisomers by preferential crystallisation, and then dissociating the salts to give the individual enantiomer of the free base.

Where compounds of the invention exist as two or more optical isomeric forms, one enantiomer in a pair of enantiomers may exhibit advantages over the other enantiomer, for example, in terms of biological activity. Thus, in certain circumstances, it may be desirable to use as a therapeutic agent only one of a pair of enantiomers, or only one of a plurality of diastereoisomers. Accordingly, the invention provides compositions containing a compound having one or more chiral centres, wherein at least 55% (e.g. at least 60%, 65%, 70%, 75%, 80%, 85%, 90% or 95%) of the compound of the formula (1) is present as a single optical isomer (e.g. enantiomer or diastereoisomer). In one general embodiment, 99% or more (e.g. substantially all) of the total amount of the compound of the formula (1) may be present as a single optical isomer (e.g. enantiomer or diastereoisomer).

Isotopes

The compounds of the invention as defined in any one of Embodiments 1.1 to 1.183 may contain one or more isotopic substitutions, and a reference to a particular element includes within its scope all isotopes of the element. For example, a reference to hydrogen includes within its scope $^1H$, $^2H$ (D), and $^3H$ (T). Similarly, references to carbon and oxygen include within their scope respectively $^{12}C$, $^{13}C$ and $^{14}C$ and $^{16}O$ and $^{18}O$.

The isotopes may be radioactive or non-radioactive. In one embodiment of the invention, the compounds contain no radioactive isotopes. Such compounds are preferred for therapeutic use. In another embodiment, however, the compound may contain one or more radioisotopes. Compounds containing such radioisotopes may be useful in a diagnostic context.

Solvates

Compounds as defined in any one of Embodiments 1.1 to 1.183 may form solvates.

Preferred solvates are solvates formed by the incorporation into the solid state structure (e.g. crystal structure) of the compounds of the invention of molecules of a non-toxic pharmaceutically acceptable solvent (referred to below as the solvating solvent).

Examples of such solvents include water, alcohols (such as ethanol, isopropanol and butanol) and dimethylsulphoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGE), differential scanning calorimetry (DSC) and X-ray crystallography.

The solvates can be stoichiometric or non-stoichiometric solvates.

Particularly preferred solvates are hydrates, and examples of hydrates include hemihydrates, monohydrates and dihydrates.

For a more detailed discussion of solvates and the methods used to make and characterise them, see Bryn et al., Solid-State Chemistry of Drugs, Second Edition, published by SSCI, Inc of West Lafayette, IN, USA, 1999, ISBN 0-967-06710-3.

Prodrugs

The compounds as defined in any one of Embodiments 1.1 to 1.183 may be presented in the form of a pro-drug.

By "prodrugs" is meant for example any compound that is converted in vivo into a biologically active compound of the formula (1), as defined in any one of Embodiments 1.1 to 1.183.

For example, some prodrugs are esters of the active compound (e.g., a physiologically acceptable metabolically labile ester). During metabolism, the ester group (—C(=O) OR) is cleaved to yield the active drug. Such esters may be formed by esterification, for example, of any hydroxyl groups present in the parent compound with, where appropriate, prior protection of any other reactive groups present in the parent compound, followed by deprotection if required.

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

Methods for the Preparation of Compounds of the Invention

Compounds of the formula (1) and the various sub-groups therefore can be prepared in accordance with synthetic methods well known to the skilled person. Unless stated otherwise, $R^1$-$R^7$, $Ar^1$, X, Y and Z are as hereinbefore defined. In this section, unless indicated to the contrary, references to formula (1) include formulae (2), (3) and (4).

Compounds of the formula (1) wherein Z is a pyrrole can be prepared by reacting a 1,4-dicarbonyl compound of formula (10) with an aminoaryl compound of formula (11) as shown in Scheme 1.

Scheme 1

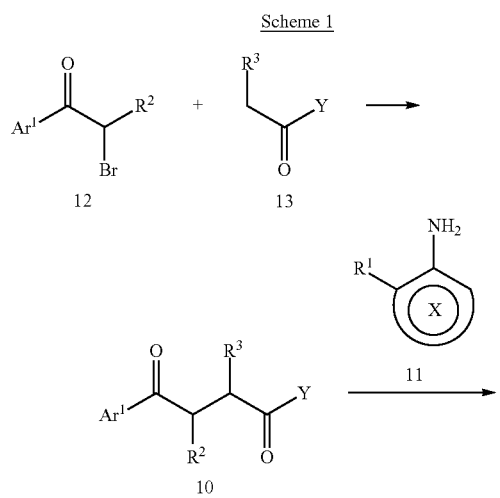

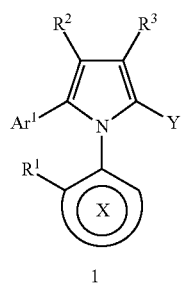

The starting materials for the synthetic route shown in Scheme 1 is the 1-aryl-3-bromopropanone (12) with arylpropanone (13), which can both be obtained commercially.

The 1-aryl-2-bromoethanone (12), is reacted with arylpropanone (13) to give the 1,4-dicarbonyl compound (10). The reaction is preferably carried out in the presence of a zinc (II) salt (for example, zinc chloride) in a non-polar, aprotic solvent (for example, benzene or toluene). Preferably a tertiary alcohol (for example, t-butanol) and a tertiary amine (for example, triethylamine) are also added. The reaction may be carried out at room temperature, for example over a period of 12 to 48 hours.

The 1,4-dicarbonyl compound (10) may then be reacted with aminoarene (11) to form the trisubstituted pyrroles of the present invention (1). The reaction may be carried out in a non-polar, aprotic solvent (for example dioxane). The reaction mixture may be subject to heating (for example between 150 and 170° C.) and/or microwave irradiation. The reaction may be carried out for between 1 and 12 hours, for example between 1 and 6 hours. A strong acid (e.g. p-toluenesulphonic acid) may also be added as a catalyst.

Alternatively, compounds of formula (10) where $R^2$ and $R^3$ are both hydrogen can be prepared by the synthetic route as shown in Scheme 2.

Scheme 2

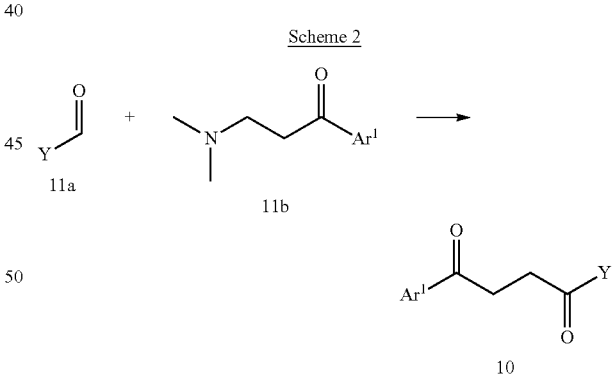

Starting aldehyde (11a) may be prepared from the corresponding acid by reduction with a reducing agent (for example $NaBH_4$), followed by oxidation with a suitable oxidising agent. One such example of an oxidising agent to prepare the aldehyde without further oxidation to the carboxylic acid is Dess-Martin periodinane. Starting amine (11b) may be prepared via a Mannich reaction with dimethylamine hydrochloride and formaldehyde in a polar, protic solvent (for example ethanol) in the presence of an acid catalyst.

Compounds of formula (10) can then be prepared by reacting compound (11a) and (11b) in a polar, aprotic solvent (for example, 1,2-dimethoxyethane) with a suitable catalyst. One such class of suitable catalysts are thiazolium salts (for example, 3-ethyl-5-(2-hydroxyethyl)-4-methylthiazoliumbromide). The reaction is typically carried out at elevated temperatures (for example between 800C and 1200C) for between 1 and 24 hours, even more preferably between 2 and 12 hours.

Once formed, one compound of the formula (1) may be transformed into another compound of the formula (1) using standard chemistry procedures well known in the art. For examples of functional group interconversions, see for example, *March's Advanced Organic Chemistry*, Michael B. Smith & Jerry March, 6$^{th}$ Edition, Wiley-Blackwell (ISBN: 0-471-72091-7), 2007 and Organic Syntheses, Volumes 1-9, John Wiley, edited by Jeremiah P. Freeman (ISBN: 0-471-12429), 1996.

Compounds of the formula (1) where Y is substituted with a substituent $R^6$ wherein $R^6$ is an amide group of the formula $C(O)NHR^3$, wherein $R^3$ is an optionally substituted $C_{1-8}$ hydrocarbon group can be prepared by according to the synthetic route as shown in Scheme 3.

tetrahydrofuran and water. A strong, water-soluble base (for example, lithium hydroxide) is added and the reaction mixture is stirred at room temperature for an extended period, for example between 6 and 48 hours, more usually between 12 and 48 hours.

The acid compound (15) may then be reacted with a corresponding amine ($H_2N—R^8$) under amide-forming conditions, for example in the presence of a reagent of the type commonly used in the formation of amide bonds, to afford a compound of the formula (1) wherein $R^6$ is an amide. Examples of such reagents include carbodiimide-based coupling agents such as 1,3-dicyclohexylcarbo-diimide (DCC) (Sheehan et al, J. Amer. Chem Soc. 1955, 77, 1067) and 1-ethyl-3-(3'-dimethylaminopropyl)-carbodiimide (referred to herein either as EDC or EDCI) (Sheehan et al, J. Org. Chem., 1961, 26, 2525), which are typically used in combination with 1-hydroxy-7-azabenzotriazole (HOAt) (L. A. Carpino, *J. Amer. Chem. Soc.*, 1993, 115, 4397) or 1-hydroxybenzotriazole (HOBt) (Konig et al, *Chem. Ber.*, 103, 708, 2024-2034). Further examples of such reagents are uronium-based coupling agents such as O-(7-azabenzotriazol-1-yl)-N,N,N'N'-tetramethyluronium hexafluorophosphate (HATU). One preferred amide coupling agent is HATU.

The coupling reaction is typically carried out in a non-aqueous, non-protic solvent such as dimethylformamide at room temperature in the presence of a non-interfering base, for example a tertiary amine such as triethylamine or N,N-diisopropylethylamine.

Compounds of formula (15) may alternatively be prepared from the hydrolysis of the corresponding nitrile, using appropriate hydrolysis conditions. Preferably the hydrolysis is carried out with a strong base, for example an alkali metal hydroxide (for example, sodium hydroxide) in a polar protic solvent or a mixture of polar protic solvents. One such example of a suitable solvent system in a mixture of methanol and water. The reaction is preferably carried out at elevated temperature for between 12 and 24 hours.

Compounds of the formula (1) where Y is substituted with a substituent $R^6$ wherein $R^6$ is an amine group having the formula $NHR^9$ can be prepared by according to the synthetic route as shown in Scheme 4.

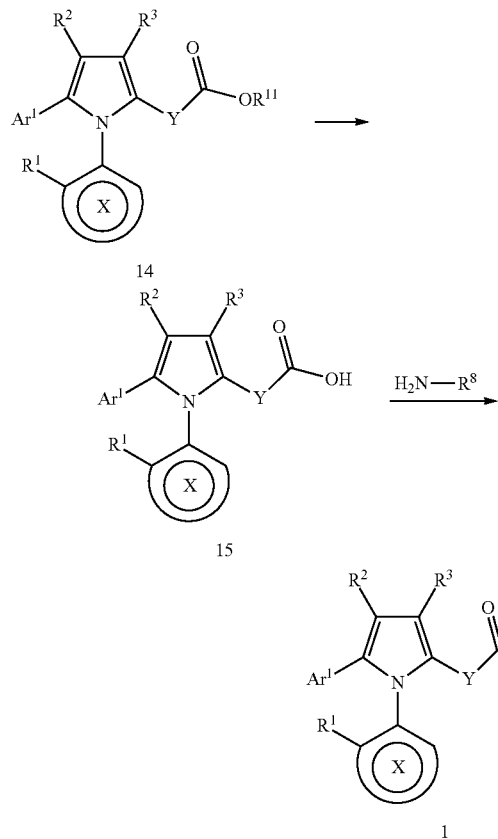

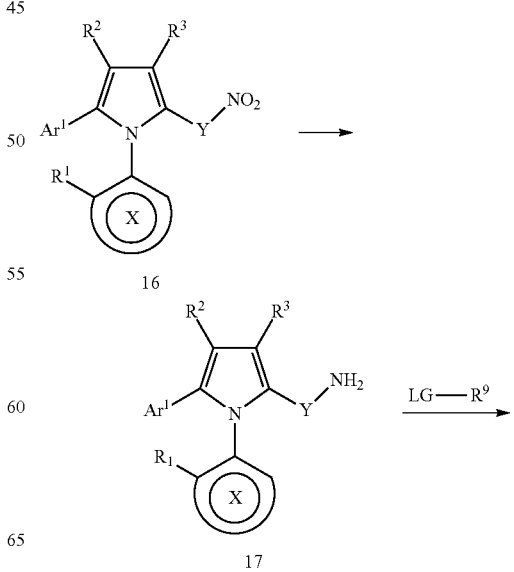

In Scheme 3, Y represents ring Y as defined herein.

A compound of the formula (14) can be prepared in accordance with the synthetic route as shown in Scheme 1 above, wherein $R^{11}$ is a $C_{1-8}$ hydrocarbon group or another carboxylic acid protecting group. Ester (14) can be hydrolysed to give carboxylic acid (15). This is preferably carried out in a mixture of a non-polar, aprotic solvent (for example, tetrahydrofuran) and a polar, protic solvent (for example, water). One such suitable solvent system is a 1:1 mixture of -continued

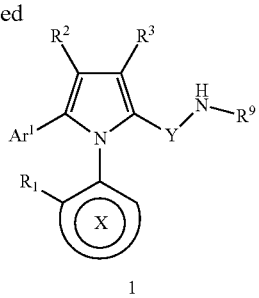

1

In Scheme 4, Y represents ring Y as defined herein.

A compound of formula (16) can be prepared according to the synthetic route as shown in Scheme 1 above. Compound (16) can then be reduced to compound (17) using a suitable reducing agent (for example, sodium borohydride) and optionally with catalytic quantities of a copper (II) salt (for example, copper (II) acetate). The reaction is preferably carried out in an anhydrous, polar, aprotic solvent (for example, methanol).

Compound (17) can then be reacted with a compound of the formula LG-$R^9$, wherein LG is a suitable leaving group (for example, halogen, more preferably chlorine) and $R^9$ is an optionally substituted non-aromatic $C_{1-8}$ hydrocarbon group. The amine compound (17) is first treated with a suitable base (for example, sodium hydride) in a polar, aprotic solvent (for example, dimethylformamide), typically at room temperature and is then reacted with compound LG-$R^9$, typically at an elevated temperature (for example, between 60° C. and 100° C.).

Alternatively, compounds of formula (1) where $R^6$ is an amide in which the nitrogen atom of the amide is bonded to ring Y can be prepared from compounds of formula (17) in an analogous method to the method shown in Scheme 4 and carboxylic acids, or activated derivatives (such as acyl chlorides or acid anhydrides).

Alternatively, the compounds of formula (1) wherein $R^6$ is an amide of the formula NHCO$R^{10}$ where $R^{10}$ is an optionally substituted $C_{1-8}$ hydrocarbon group, can be prepared from intermediate (17), under amide-forming conditions, for example in the presence of a reagent of the type commonly used in the formation of amide bonds, according to Scheme 5.

Scheme 5

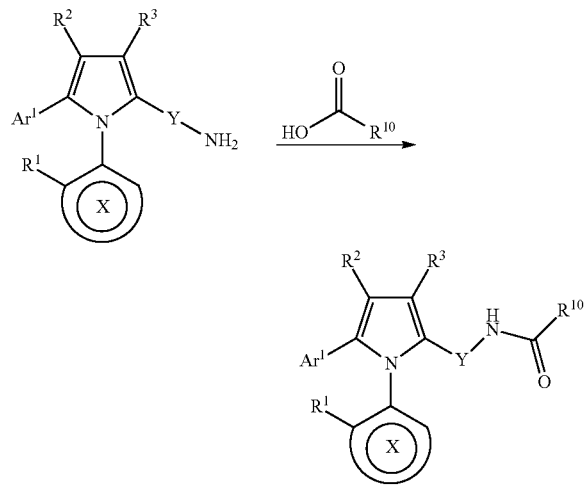

In Scheme 5, Y represents ring Y as defined herein.

Examples of such reagents include carbodiimide-based coupling agents such as 1,3-dicyclohexylcarbo-diimide (DCC) (Sheehan et al, J. Amer. Chem Soc. 1955, 77, 1067) and 1-ethyl-3-(3'-dimethylaminopropyl)-carbodiimide (referred to herein either as EDC or EDCI) (Sheehan et al, J. Org. Chem., 1961, 26, 2525), which are typically used in combination with 1-hydroxy-7-azabenzotriazole (HOAt) (L. A. Carpino, J. Amer. Chem. Soc., 1993, 115, 4397) or 1-hydroxybenzotriazole (HOBt) (Konig et al, Chem. Ber., 103, 708, 2024-2034). Further examples of such reagents are uronium-based coupling agents such as O-(7-azabenzotriazol-1-yl)-N,N,N'N'-tetramethyluronium hexafluorophosphate (HATU). One preferred amide coupling agent is HATU.

The coupling reaction is typically carried out in a non-aqueous, non-protic solvent such as dimethylformamide at room temperature in the presence of a non-interfering base, for example a tertiary amine such as triethylamine or N,N-diisopropylethylamine.

Compounds of the formula (1) where Y is substituted with a substituent $R^6$ wherein $R^6$ is an ether group having the formula O$R^{12}$ where $R^{12}$ is an optionally substituted $C_{1-8}$ hydrocarbon group can be prepared by according to the synthetic route as shown in Scheme 6.

Scheme 6

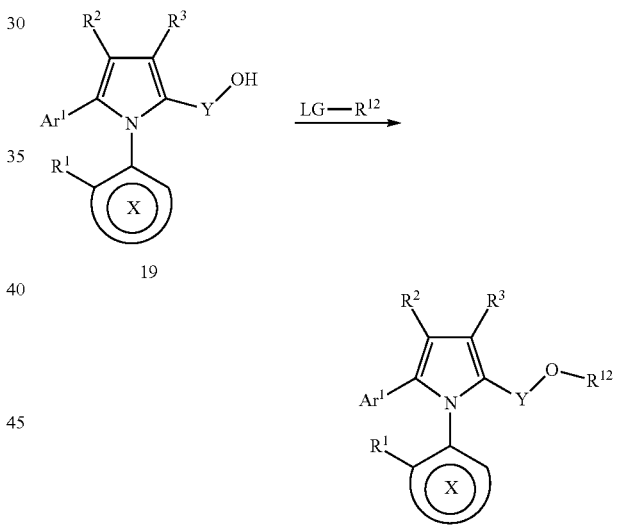

In Scheme 6, Y represents ring Y as defined herein.

A compound of formula (19) can be prepared according to the synthetic route as shown in Scheme 1 above. Compound (19) can then be reacted with a compound of the formula LG-$R^{12}$, wherein LG is a suitable leaving group (for example, halogen, more preferably chlorine) and $R^7$ is an optionally substituted non-aromatic $C_{1-8}$ hydrocarbon group. The alcohol compound (19) is first deprotonated with a suitable base (for example, sodium hydride) in a polar, aprotic solvent (for example, dimethylformamide). This reaction may be carried out at room temperature. The reaction mixture is then treated with compound of the formula LG-$R^{12}$. The second step of this reaction may occur at elevated temperatures, typically between 800C and 100° C.

Compounds of formula (1) wherein $R^6$ is $Q^1$-$R^a$—$R^b$ and $Q^1$ is a methylene group can be prepared according to Scheme 7.

Scheme 7

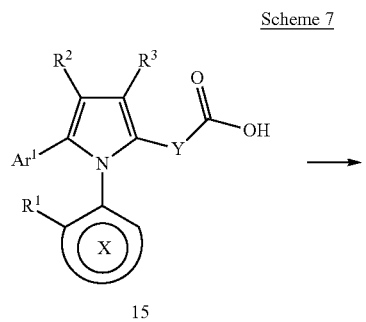

In Scheme 7, Y represents ring Y as defined herein.

Compound (15) (obtainable as described in Scheme 3 above) is treated with a reducing agent (for example sodium borohydride) in an polar aprotic solvent, such as tetrahydrofuran, to afford the primary alcohol (20). Alcohol (20) can then be reacted in the manner described above in Scheme 6 to provide further compounds of formula (1) wherein $R^6$ is an ether.

Alternatively, compound (20) may undergo other standard functional group interconversions to yield further compounds of formula (1), for example via oxidation to an aldehyde and reductive amination to form an amine. Amines produced via this method can be further reacted with carboxylic acids or acid derivatives to yield amide compounds of formula (1) using the method described above in Scheme 5.

Compounds of the formula (1) wherein Z is a 1,4,5-trisubstituted pyrazole can be prepared by reacting an aryl hydrazine (21) with the α,β-unsaturated carbonyl compound (22) as shown in Scheme 8.

Scheme 8

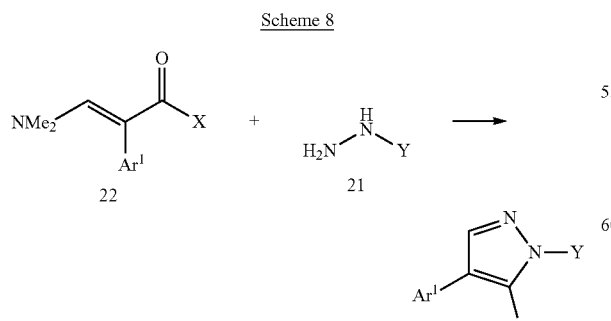

In Scheme 8, X and Y represent rings X and Y respectively as defined herein.

The aryl hydrazine (21) and α,β-unsaturated carbonyl compound (22) are dissolved in a suitable polar, protic solvent system (e.g. 1:1 water:methanol) with a suitable base (e.g. sodium carbonate). The mixture is typically stirred at or about room temperature (e.g. for about 15 minutes) before a weak acid, such as acetic acid, is added. The resulting mixture is then heated (e.g. between 100° C. and 140° C., for an extended period of time, (for example between 6 and 12 hours), for a period of time (e.g. 8 hours) sufficient to afford a compound of formula (1) wherein Z is a 1,4,5-trisubstituted pyrazole.

Scheme 9

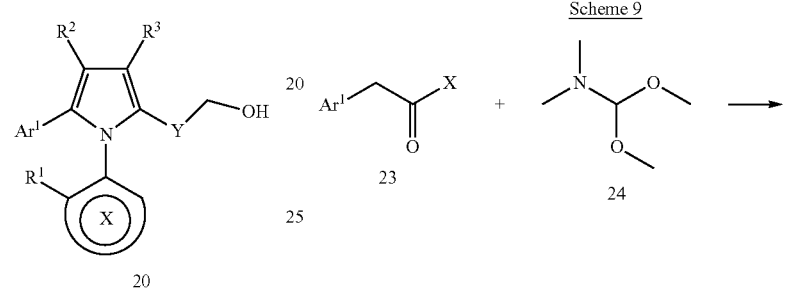

The starting α,β-unsaturated carbonyl compound (22) of Scheme 8 can be prepared from the corresponding ketone (23) and N,N-dimethylformamide dimethyl acetal. A solution of N,N-dimethylformamide dimethyl acetal in a polar aprotic solvent such as DMF, is added to a solution of ketone (23). The mixture is typically heated, for example to a temperature between 70° C. and 110° C. (e.g. approximately 90° C.) to afford compound (22). Compound (23) may be obtained through a Grignard reaction between $Ar^1CH_2CHO$ and Br—X followed by oxidation of the resulting alcohol with a suitable oxidising agent (for example, Dess-Martin periodinane) in a solvent such as DCM to afford ketone (23).

Alternatively, when alternative isomers of formula (1) wherein Z is a 3,4,5-trisubstituted pyrazole, are required, these can be prepared as described in Scheme 10 below.

Scheme 10

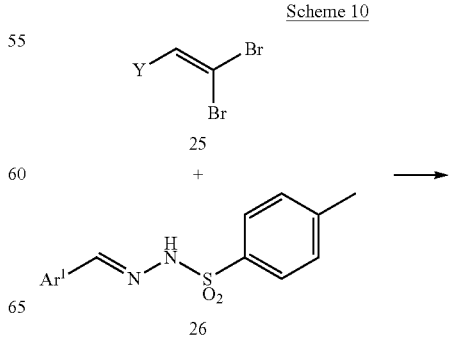

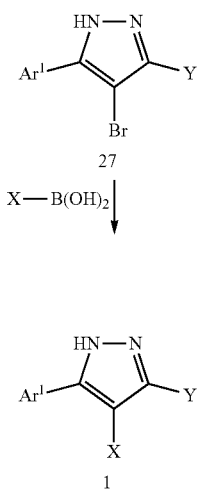

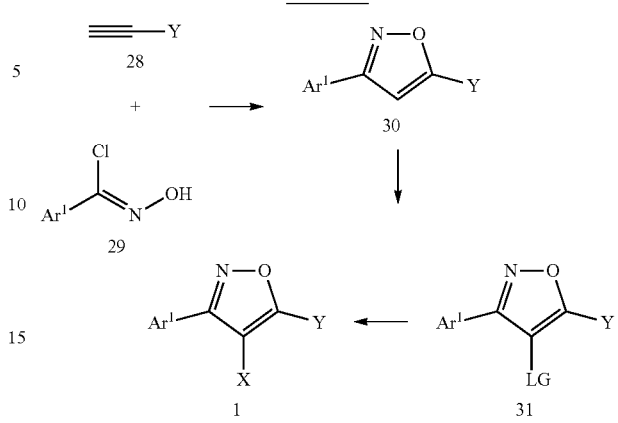

In Scheme 10, X and Y represent rings X and Y respectively as defined herein.

Alkenyl bromide (25) is reacted with diazo compound (26) in a 1,3-dipolar cycloaddition reaction by mixing the two compounds with a strong base (e.g. sodium hydroxide) and heating (e.g. to a temperature of approximately 70° C.) to afford bromo-pyrazole (27).

The bromo-pyrazole (27) is then reacted with a boronic acid having formula X—B(OH)$_2$ (wherein X is a ring as defined herein) in a polar solvent such as dioxane in the presence of a palladium (0) catalyst, such as bis(tri-tert-butylphosphine)palladium (0), and suitable base (such as caesium or potassium carbonate or phosphate) under Suzuki reaction conditions to give the compound of formula (1) wherein Z is a pyrazole or a protected derivative thereof. The bromo-pyrazole (27) may be in a protected form. For example, in the NH group on the pyrazole, a protecting group such as a Boc (tert-butoxycarbonyl) group may be attached to the nitrogen atom, replacing the hydrogen atom. After the reaction between the boronic acid and the pyrazole (27), a deprotection step may be required in order to give the compound of formula (1). In the case of a Boc protecting group, this can be removed by treatment with an acid such as hydrochloric acid.

Boronates and boronic acids are widely available commercially or can be prepared for example as described in the review article by N. Miyaura and A. Suzuki, Chem. Rev. 1995, 95, 2457. Thus, boronates can be prepared by reacting the corresponding bromo-compound with an alkyl lithium such as butyl lithium and then reacting with a borate ester. The resulting boronate ester derivative can, if desired, be hydrolysed to give the corresponding boronic acid.

Starting material (25) can be prepared by treating the aryl aldehyde with carbon tetrabromide and triphenylphosphine in a solvent such as DCM at a reduced temperature (e.g. approximately 0° C.). Starting material (26) can be prepared from the corresponding aryl aldehyde by treating with p-toluenesulfonyl hydrazide in a polar protic solvent such as methanol and heating (e.g. to approximately 60° C.).

Compounds of formula (1) wherein Z is an isoxazole may be prepared according to the synthetic scheme in Scheme 11.

In Scheme 11, X and Y represent rings X and Y respectively as defined herein.

Intermediate (30) can be prepared by reacting alkyne (28) with oxime (29) by mixing in a polar, aprotic solvent (such as diethyl ether) with a base (such as triethylamine), for example at a temperature around room temperature to afford isoxazole (30). Isoxazole (30) can then be brominated, with a suitable brominating agent, such as N-bromosuccinimide as a bromine source, to afford the bromoisoxazole (31). The reaction typically takes place in an acidic solution (e.g. acetic acid) at elevated temperatures (for example between 90° C. and 120° C.).

The bromo-isoxazole (31) is then reacted with a boronic acid having formula X—B(OH)$_2$ (wherein X is a ring as defined herein) in a polar solvent such as dioxane in the presence of a palladium (0) catalyst, such as bis(tri-tert-butylphosphine)palladium (0), and a base (e.g. caesium or potassium carbonate or phosphate) under Suzuki reaction conditions to give the compound of formula (1) wherein Z is a isoxazole or a protected derivative thereof. The bromo-isoxazole (31) may be in a protected form. For example, in a NH group on groups Ar, or Y, a protecting group such as a Boc (tert-butoxycarbonyl) group may be attached to the nitrogen atom, replacing the hydrogen atom. After the reaction between the boronic acid and the isoxazole (31), a deprotection step may be required in order to give the compound of formula (1). In the case of a Boc protecting group, this can be removed by treatment with an acid such as hydrochloric acid.

Boronates and boronic acids are widely available commercially or can be prepared for example as described in the review article by N. Miyaura and A. Suzuki, Chem. Rev. 1995, 95, 2457. Thus, boronates can be prepared by reacting the corresponding bromo-compound with an alkyl lithium such as butyl lithium and then reacting with a borate ester. The resulting boronate ester derivative can, if desired, be hydrolysed to give the corresponding boronic acid.

Starting material (29) can be prepared from the corresponding aryl aldehyde via a two-step process. The first step consists of treating the aldehyde with NH$_2$OH and a strong base (such as sodium hydroxide) in a polar, protic solvent system (such as 1:1 ethanol:water) to afford the aryl oxime. This can then be the chlorinated by mixing with N-chlorosuccinimide in dimethylformamide and stirring for 18 hours to afford starting material (29).

The synthesis of the compounds of formula (1) has been illustrated above with reaction schemes for preparing pyrroles, isoxazoles and pyrazoles. It will readily be appreciated however that analogous methods may be used to prepare compounds of formula (1) containing other five-membered heteroaryl rings.

Protecting Groups

In many of the reactions described above, it may be necessary to protect one or more groups to prevent reaction from taking place at an undesirable location on the molecule. Examples of protecting groups, and methods of protecting and deprotecting functional groups, can be found in Protective Groups in Organic Synthesis (T. Green and P. Wuts; 3rd Edition; John Wiley and Sons, 1999).

A hydroxy group may be protected, for example, as an ether (—OR) or an ester (—OC(=O)R), for example, as: a t-butyl ether; a tetrahydropyranyl (THP) ether; a benzyl, benzhydryl (diphenylmethyl), or trityl (triphenylmethyl) ether; a trimethylsilyl or t-butyldimethylsilyl ether; or an acetyl ester (—OC(=O)CH$_3$, —OAc).

An aldehyde or ketone group may be protected, for example, as an acetal (R—CH(OR)$_2$) or ketal (R$_2$C(OR)$_2$), respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

An amine group may be protected, for example, as an amide (—NRCO—R) or a urethane (—NRCO—OR), for example, as: a methyl amide (—NHCO—CH$_3$); a benzyloxy amide (—NHCO—OCH$_2$C$_6$H$_5$, —NH-Cbz or NH—Z); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH—Nvoc), as a 2-trimethylsilylethyloxy amide (—NH-Teoc), as a 2,2,2-trichloroethyloxy amide (—NH-Troc), as an allyloxy amide (—NH-Alloc), or as a 2(-phenylsulphonyl)ethyloxy amide (—NH-Psec).

For example, in Scheme 1 above, when the moiety R$^3$ in the amine H$_2$N—Y—R$^3$ contains a second amino group, such as a cyclic amino group (e.g. a piperidine or pyrrolidine group), the second amino group can be protected by means of a protecting group as hereinbefore defined, one preferred group being the tert-butyloxycarbonyl (Boc) group.

Where no subsequent modification of the second amino group is required, the protecting group can be carried through the reaction sequence to give an N-protected form of a compound of the formula (1) which can then be de-protected by standard methods (e.g. treatment with acid in the case of the Boc group) to give the compound of formula (1).

Other protecting groups for amines, such as cyclic amines and heterocyclic N—H groups, include toluenesulphonyl (tosyl) and methanesulphonyl (mesyl) groups, benzyl groups such as a para-methoxybenzyl (PMB) group and tetrahydropyranyl (THP) groups.

A carboxylic acid group may be protected as an ester for example, as: an C$_{1-7}$ alkyl ester (e.g., a methyl ester; a t-butyl ester); a C$_{1-7}$ haloalkyl ester (e.g., a C$_{1-7}$ trihaloalkyl ester); a triC$_{1-7}$ alkylsilyl-C$_{1-7}$alkyl ester; or a C$_{5-20}$ aryl-C$_{1-7}$ alkyl ester (e.g., a benzyl ester; a nitrobenzyl ester); or as an amide, for example, as a methyl amide. A thiol group may be protected, for example, as a thioether (—SR), for example, as: a benzyl thioether; an acetamidomethyl ether (—S—CH$_2$NHC(=O)CH$_3$).

Isolation and Purification of the Compounds of the Invention

The compounds of the invention can be isolated and purified according to standard techniques well known to the person skilled in the art. One technique of particular usefulness in purifying the compounds is preparative liquid chromatography using mass spectrometry as a means of detecting the purified compounds emerging from the chromatography column.

Preparative LC-MS is a standard and effective method used for the purification of small organic molecules such as the compounds described herein. The methods for the liquid chromatography (LC) and mass spectrometry (MS) can be varied to provide better separation of the crude materials and improved detection of the samples by MS. Optimisation of the preparative gradient LC method will involve varying columns, volatile eluents and modifiers, and gradients. Methods are well known in the art for optimising preparative LC-MS methods and then using them to purify compounds. Such methods are described in Rosentreter U, Huber U.; Optimal fraction collecting in preparative LC/MS; *J Comb Chem.;* 2004; 6(2), 159-64 and Leister W, Strauss K, Wisnoski D, Zhao Z, Lindsley C., Development of a custom high-throughput preparative liquid chromatography/mass spectrometer platform for the preparative purification and analytical analysis of compound libraries; *J Comb Chem.;* 2003; 5(3); 322-9.

An example of such a system for purifying compounds via preparative LC-MS is described below in the Examples section of this application (under the heading "Mass Directed Purification LC-MS System"). However, it will be appreciated that alternative systems and methods to those described could be used. In particular, normal phase preparative LC based methods might be used in place of the reverse phase methods described here. Most preparative LC-MS systems utilise reverse phase LC and volatile acidic modifiers, since the approach is very effective for the purification of small molecules and because the eluents are compatible with positive ion electrospray mass spectrometry. Employing other chromatographic solutions e.g. normal phase LC, alternatively buffered mobile phase, basic modifiers etc as outlined in the analytical methods described below could alternatively be used to purify the compounds.

Biological Properties and Therapeutic Uses

It is believed that compounds of the invention may be effective in exploiting weaknesses in cellular pathways as a result of constitutively activating KRAS mutants and therefore the compounds of the invention may be useful for the treatment of diseases and conditions mediated by modulation of KRAS.

Mutation of KRAS, resulting from a single nucleotide substitution, has been associated with various forms of cancer. In particular, KRAS mutations are found at high rates in leukemias, colon cancer, pancreatic cancer and lung cancer.

A primary screen for anticancer activity, which makes use of a cancer cell line (HCT116) containing mutant KRAS, is described in the Examples below.

In addition, it is believed that compounds of the invention may be useful in treating cancers characterised by p53 deficiency or mutation in the TP53 gene. PLK1 is believed to inhibit p53 in cancer cells. Therefore, upon treatment with PLK1 inhibitors, p53 in tumour cells should be activated and hence should induce apoptosis.

The activity of the compounds against KRAS mutant and p53 deficient cancers is believed to arise, at least in part, through inhibition of PLK1 kinase and, in particular, the C-terminal polo box domain (PBD) of PLK1 kinase. KRAS is known to be dependent on interaction with PLK1. Compounds of the invention that only inhibit the PBD domain and not the N-terminal catalytic domain of PLK1 are advantageous in that they are selective for PLK1-PBD over other structurally and functionally similar kinases, against which they show negligible inhibitory activity (see Example E below).

Compounds of the invention induce mitotic arrest with non-congressed chromosomes, a property which is believed to arise from the PLK1-PBD inhibiting activity of the compounds (see Example B below).

A further advantage of inhibiting the PBD domain rather than the catalytic domain is that this may result in a reduced tendency to induce drug resistance compared to PLK1 inhibitors that inhibit the catalytic domain (see Example I below).

The activity of compounds of the invention as inhibitors of the PBD domain of PLK1 kinase has been demonstrated using the fluorescence polarization (FP) assay described in Narvaez et al., Cell Chemical Biology, 24, 1017-1028, 2017, see page 1018 and page 1026 (Method Details).

Compounds of the invention have good oral bioavailability (see Example F below) and have good brain exposure when administered orally (see Example G below). Accordingly, the compounds of the invention should be useful in treating brain cancers such as gliomas and glioblastomas.

Examples of cancers (and their benign counterparts) which may be treated include, but are not limited to tumours of epithelial origin (adenomas and carcinomas of various types including adenocarcinomas, squamous carcinomas, transitional cell carcinomas and other carcinomas) such as carcinomas of the bladder and urinary tract, breast, gastrointestinal tract (including the esophagus, stomach (gastric), small intestine, colon, rectum and anus), liver (hepatocellular carcinoma), gall bladder and biliary system, exocrine pancreas, kidney, lung (for example adenocarcinomas, small cell lung carcinomas, non-small cell lung carcinomas, bronchioalveolar carcinomas and mesotheliomas), head and neck (for example cancers of the tongue, buccal cavity, larynx, pharynx, nasopharynx, tonsil, salivary glands, nasal cavity and paranasal sinuses), ovary, fallopian tubes, peritoneum, vagina, vulva, penis, cervix, myometrium, endometrium, thyroid (for example thyroid follicular carcinoma), adrenal, prostate, skin and adnexae (for example melanoma, basal cell carcinoma, squamous cell carcinoma, keratoacanthoma, dysplastic naevus); haematological malignancies (i.e. leukemias, lymphomas) and premalignant haematological disorders and disorders of borderline malignancy including haematological malignancies and related conditions of lymphoid lineage (for example acute lymphocytic leukemia [ALL], chronic lymphocytic leukemia [CLL], B-cell lymphomas such as diffuse large B-cell lymphoma [DLBCL], follicular lymphoma, Burkitt's lymphoma, mantle cell lymphoma, T-cell lymphomas and leukaemias, natural killer [NK] cell lymphomas, Hodgkin's lymphomas, hairy cell leukaemia, monoclonal gammopathy of uncertain significance, plasmacytoma, multiple myeloma, and post-transplant lymphoproliferative disorders), and haematological malignancies and related conditions of myeloid lineage (for example acute myelogenous leukemia [AML], chronic myelogenous leukemia [CML], chronic myelomonocytic leukemia [CMML], hypereosinophilic syndrome, myeloproliferative disorders such as polycythaemia vera, essential thrombocythaemia and primary myelofibrosis, myeloproliferative syndrome, myelodysplastic syndrome, and promyelocytic leukemia); tumours of mesenchymal origin, for example sarcomas of soft tissue, bone or cartilage such as osteosarcomas, fibrosarcomas, chondrosarcomas, rhabdomyosarcomas, leiomyosarcomas, liposarcomas, angiosarcomas, Kaposi's sarcoma, Ewing's sarcoma, synovial sarcomas, epithelioid sarcomas, gastrointestinal stromal tumours, benign and malignant histiocytomas, and dermatofibrosarcoma protuberans; tumours of the central or peripheral nervous system (for example astrocytomas, gliomas and glioblastomas, meningiomas, ependymomas, pineal tumours and schwannomas); endocrine tumours (for example pituitary tumours, adrenal tumours, islet cell tumours, parathyroid tumours, carcinoid tumours and medullary carcinoma of the thyroid); ocular and adnexal tumours (for example retinoblastoma); germ cell and trophoblastic tumours (for example teratomas, seminomas, dysgerminomas, hydatidiform moles and choriocarcinomas); and paediatric and embryonal tumours (for example medulloblastoma, neuroblastoma, Wilms tumour, and primitive neuroectodermal tumours); or syndromes, congenital or otherwise, which leave the patient susceptible to malignancy (for example Xeroderma Pigmentosum).

One subset of cancers that may be treated consists of gliomas and glioblastomas.

Prior to administration of a compound of any one of Embodiments 1.1 to 1.183, a patient may be screened to determine whether a cancer from which the patient is or may be suffering is one which is characterised by the presence of a mutated form of KRAS. Mutant KRAS can have a mutation at any amino acid in the protein, and in particular amino acid glycine 12, glycine 13, glutamine 61, or a combination thereof. PCR kits for detecting the presence of mutated KRAS are commercially available (for example, the Cobas® KRAS Mutation Test from Roche Molecular Systems, Inc and therascreen KRAS RGQ PCR Kit from Qiagen Manchester, Ltd.)

The term 'medicament' as used herein refers to a pharmaceutical formulation that is of use in treating, curing or improving a disease or in treating, ameliorating or alleviating the symptoms of a disease. A pharmaceutical formulation comprises a pharmacologically active ingredient in a form not harmful to the subject it is being administered to and additional constituents designed to stabilise the active ingredient and affect its absorption into the circulation or target tissue.

It will be appreciated that references herein to "treatment" extend to suppression or amelioration of symptoms (whether mild, 20 moderate or severe) as well as the treatment of established conditions.

Accordingly, in further Embodiments (Embodiments 2.1 to 2.19) of the Invention, there is provided:

2.1 A compound according to any one of Embodiments 1.1 to 1.183 or a pharmaceutically acceptable salt thereof for use in medicine or therapy.

2.2 A compound according to any one of Embodiments 1.1 to 1.183 or a pharmaceutically acceptable salt thereof for use in preventing or treating disease states and conditions characterised by abnormal expression of KRAS protein.

2.3 A compound according to any one of Embodiments 1.1 to 1.183 or a pharmaceutically acceptable salt thereof for use as an anti-cancer agent.

2.4 A compound according to any one of Embodiments 1.1 to 1.183 or a pharmaceutically acceptable salt thereof for the manufacture of a medicament for treatment of cancer.

2.5 A method of treating cancer, the method comprising administering to the subject in need thereof a therapeutically effective amount of a compound according to any one of Embodiments 1.1 to 1.183 or a pharmaceutically acceptable salt thereof, optionally together with another anti-cancer agent.

2.6 A compound according to any one of Embodiments 1.1 to 1.183 or a pharmaceutically acceptable salt thereof for use in enhancing a therapeutic effect of radiation therapy or chemotherapy in the treatment of a proliferative disease such as cancer.

2.7 The use of a compound according to any one of Embodiments 1.1 to 1.183 or a pharmaceutically acceptable salt thereof for the manufacture of a medicament for enhancing a therapeutic effect of radiation therapy or chemotherapy in the treatment of a proliferative disease such as cancer.

2.8 A method for the prophylaxis or treatment of a proliferative disease such as cancer, which method comprises administering to a patient in combination with radiotherapy or chemotherapy a compound according to any one of Embodiments 1.1 to 1.183 or a pharmaceutically acceptable salt thereof.

2.9 A method for the diagnosis and treatment of a disease state or condition mediated by KRAS which method comprises (i) screening a patient to determine whether a disease or condition from which the patient is or may be suffering is one which would be susceptible to treatment with a compound having activity against KRAS; and (ii) where it is indicated that the disease or condition from which the patient is thus susceptible, thereafter administering to the patient a compound as defined in any one of Embodiments 1.1 to 1.183 or a pharmaceutically acceptable salt thereof.

2.10 Use of a compound as defined in any one of Embodiments 1.1 to 1.183 or a pharmaceutically acceptable salt thereof for the manufacture of a medicament for the treatment or prophylaxis of a disease state or condition in a patient who has been screened and has been determined as suffering from, or being at risk of suffering from, a disease or condition which would be susceptible to treatment with a compound having activity against KRAS.

2.11 A compound as defined in any one of Embodiments 1.1 to 1.183 or a pharmaceutically acceptable salt thereof for use in the treatment or prophylaxis of a disease state or condition in a patient who has been screened and has been determined as suffering from, or being at risk of suffering from, a disease or condition which would be susceptible to treatment with a compound having activity against KRAS.

2.12 A method for the diagnosis and treatment of a disease state or condition characterised by the presence of a mutated form of KRAS which method comprises (i) screening a patient to determine whether a disease or condition from which the patient is or may be suffering is one which would be susceptible to treatment with a compound having activity against KRAS; and (ii) where it is indicated that the disease or condition from which the patient is thus susceptible, thereafter administering to the patient a compound as defined in any one of Embodiments 1.1 to 1.183 or a pharmaceutically acceptable salt thereof.

2.13 A method for the treatment of a disease state or condition characterised by the presence of a mutated form of KRAS, which method comprises administering a therapeutically effective amount of a compound as defined in any one of Embodiments 1.1 to 1.183 to a patient who has been screened and has been determined as suffering from, or being at risk of suffering from, a disease or condition which would be susceptible to treatment with a compound having activity against KRAS.

2.14 A method of inhibiting PLK1 kinase, which method comprises contacting the PLK1 kinase with a kinase inhibiting amount of a compound as defined in any one of Embodiments 1.1 to 1.183.

2.15 A compound according to any one of Embodiments 1.1 to 1.183 for use in the treatment of a cancer which is characterised by PLK1 overexpression.

2.15 A method for the treatment of a subject (e.g. a human patient) suffering from a cancer characterised by PLK1 overexpression, which method comprises administering to the subject and effective therapeutic amount of a compound of any one of Embodiments 1.1 to 1.183.

2.16 The use of a compound of any one of Embodiments 1.1 to 1.183 for the manufacture of a medicament for the treatment of a subject (e.g. a human patient) suffering from a cancer characterised by PLK1 overexpression.

2.17 A compound as defined in any one of Embodiments 1.1 to 1.183 for use in the treatment of a cancer in a patient who has been screened and has been determined as suffering from a cancer which is characterised by elevated levels of PLK1 kinase.

2.18 The use of a compound as defined in any one of Embodiments 1.1 to 1.183 for the manufacture of a medicament for the treatment of a cancer in a patient who has been screened and has been determined as suffering from a cancer which is characterised by elevated levels of PLK1 kinase.

2.19 A method for the diagnosis and treatment of a cancer which is characterised by elevated levels of PLK1 kinase, which method comprises (i) screening a patient to determine whether a cancer from which the patient is suffering is one which is characterised by elevated levels of PLK1 kinase; and (ii) where it is indicated that the cancer is one which is characterised by elevated levels of PLK1 kinase, thereafter administering to the patient a therapeutically effective amount of a compound as defined in any one of Embodiments 1.1 to 1.183.

Pharmaceutical Formulations

The pharmaceutical compositions of the invention can be in any form suitable for oral, parenteral, topical, intranasal, intrabronchial, ophthalmic, optic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery.

Pharmaceutical dosage forms suitable for oral administration include tablets, capsules, caplets, pills, lozenges, syrups, solutions, sprays, powders, granules, elixirs and suspensions, sublingual tablets, sprays, wafers or patches and buccal patches.

Pharmaceutical compositions containing the compounds according to Embodiments 1.1 to 1.183 of the invention can be formulated in accordance with known techniques, see for example, Remington's Pharmaceutical Sciences, Mack Publishing Company, Easton, PA, USA.

Thus, tablet compositions can contain a unit dosage of active compound together with an inert diluent or carrier such as a sugar or sugar alcohol, e.g.; lactose, sucrose, sorbitol or mannitol; and/or a non-sugar derived diluent such as sodium carbonate, calcium phosphate, talc, calcium carbonate, or a cellulose or derivative thereof such as methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (e.g.; tablets, capsules etc.) can be coated or un-coated, but typically have a coating, for example a protective film coating (e.g. a wax or varnish) or a release controlling coating. The coating (e.g. a Eudragit™ type polymer) can be designed to release the active component at a desired location within the gastro-intestinal tract. Thus, the coating can be selected so as to degrade under certain pH conditions within the gastrointestinal tract, thereby selectively release the compound in the stomach or in the ileum or duodenum.

Instead of, or in addition to, a coating, the drug can be presented in a solid matrix comprising a release controlling agent, for example a release delaying agent which may be adapted to selectively release the compound under conditions of varying acidity or alkalinity in the gastrointestinal tract. Alternatively, the matrix material or release retarding coating can take the form of an erodible polymer (e.g. a maleic anhydride polymer) which is substantially continuously eroded as the dosage form passes through the gastrointestinal tract.

Compositions for topical use include ointments, creams, sprays, patches, gels, liquid drops and inserts (for example intraocular inserts). Such compositions can be formulated in accordance with known methods.

Compositions for parenteral administration are typically presented as sterile aqueous or oily solutions or fine suspensions, or may be provided in finely divided sterile powder form for making up extemporaneously with sterile water for injection.

Examples of formulations for rectal or intra-vaginal administration include pessaries and suppositories which may be, for example, formed from a shaped mouldable or waxy material containing the active compound.

Compositions for administration by inhalation may take the form of inhalable powder compositions or liquid or powder sprays, and can be administered in standard form using powder inhaler devices or aerosol dispensing devices. Such devices are well known. For administration by inhalation, the powdered formulations typically comprise the active compound together with an inert solid powdered diluent such as lactose.

The compounds of the inventions will generally be presented in unit dosage form and, as such, will typically contain sufficient compound to provide a desired level of biological activity. For example, a formulation intended for oral administration may contain from 2 milligrams to 200 milligrams of active ingredient, more usually from 10 milligrams to 100 milligrams, for example, 12.5 milligrams, 25 milligrams and 50 milligrams.

Methods of Treatment

The active compound will be administered to a patient in need thereof (for example a human or animal patient) in an amount sufficient to achieve the desired therapeutic effect.

The compounds will generally be administered to a subject in need of such administration, for example a human or animal patient, preferably a human.

The compounds will typically be administered in amounts that are therapeutically or prophylactically useful and which generally are non-toxic. However, in certain situations, the benefits of administering compounds of the invention may outweigh the disadvantages of any toxic effects or side effects, in which case it may be considered desirable to administer compounds in amounts that are associated with a degree of toxicity.

A typical daily dose of the compound can be in the range from 0.025 milligrams to 5 milligrams per kilogram of body weight, for example up to 3 milligrams per kilogram of bodyweight, and more typically 0.15 milligrams to 5 milligrams per kilogram of bodyweight although higher or lower doses may be administered where required.

By way of example, an initial starting dose of 12.5 mg may be administered 2 to 3 times a day. The dosage can be increased by 12.5 mg a day every 3 to 5 days until the maximal tolerated and effective dose is reached for the individual as determined by the physician. Ultimately, the quantity of compound administered will be commensurate with the nature of the disease or physiological condition being treated and the therapeutic benefits and the presence or absence of side effects produced by a given dosage regimen, and will be at the discretion of the physician.

Methods of Diagnosis and Treatment

Prior to administration of a compound of any one of Embodiments 1.1 to 1.183, a patient may be screened to determine whether a cancer from which the patient is or may be suffering is one which is characterised by elevated levels of PLK1 kinase and which would therefore be would be susceptible to treatment with a compound having activity against PLK1 kinase.

For example, a biological sample taken from a patient may be analysed to determine whether a cancer, that the patient is or may be suffering from is one which is characterised by a genetic abnormality or abnormal protein expression which leads to up-regulation of PLK1 kinase. The term up-regulation includes elevated expression or overexpression, including gene amplification (i.e. multiple gene copies) and increased expression by a transcriptional effect, and hyperactivity and activation, including activation by mutations. Thus, the patient may be subjected to a diagnostic test to detect a marker characteristic of up-regulation of PLK1 kinase. The term diagnosis includes screening. By marker we include genetic markers including, for example, the measurement of DNA composition to identify mutations of PLK1. The term marker also includes markers which are characteristic of up-regulation of PLK1, including enzyme activity, enzyme levels, enzyme state (e.g. phosphorylated or not) and mRNA levels of the aforementioned proteins.

Tumours with upregulation of PLK1 kinase may be particularly sensitive to PLK1 inhibitors. Tumours may preferentially be screened for upregulation of PLK1. Thus, the patient may be subjected to a diagnostic test to detect a marker characteristic of up-regulation of PLK1. The diagnostic tests are typically conducted on a biological sample selected from tumour biopsy samples, blood samples (isolation and enrichment of shed tumour cells), stool biopsies, sputum, chromosome analysis, pleural fluid and peritoneal fluid.

Methods of identification and analysis of mutations and up-regulation of proteins are known to a person skilled in the art. Screening methods could include, but are not limited to, standard methods such as reverse-transcriptase polymerase chain reaction (RT-PCR) or in-situ hybridisation.

In screening by RT-PCR, the level of mRNA in the tumour is assessed by creating a cDNA copy of the mRNA followed by amplification of the cDNA by PCR. Methods of PCR amplification, the selection of primers, and conditions for amplification, are known to a person skilled in the art. Nucleic acid manipulations and PCR are carried out by standard methods, as described for example in Ausubel, F. M. et al., eds. Current Protocols in Molecular Biology, 2004, John Wiley & Sons Inc., or Innis, M. A. et-al., eds. PCR Protocols: a guide to methods and applications, 1990, Academic Press, San Diego. Reactions and manipulations involving nucleic acid techniques are also described in Sambrook et al., 2001, $3^{rd}$ Ed, Molecular Cloning: A Laboratory Manual, Cold Spring Harbor Laboratory Press. Alternatively a commercially available kit for RT-PCR (for example Roche Molecular Biochemicals) may be used, or methodology as set forth in U.S. Pat. Nos. 4,666,828; 4,683,202; 4,801,531; 5,192,659, 5,272,057, 5,882,864, and 6,218,529 and incorporated herein by reference.

An example of an in-situ hybridisation technique for assessing mRNA expression would be fluorescence in-situ hybridisation (FISH) (see Angerer, 1987 Meth. Enzymol., 152: 649).

Generally, in situ hybridization comprises the following major steps: (1) fixation of tissue to be analyzed; (2) pre-hybridization treatment of the sample to increase accessibility of target nucleic acid, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labelled, for example, with radioisotopes or fluorescent reporters. Preferred probes are sufficiently long, for example, from about 50, 100, or 200 nucleotides to about 1000 or more nucleotides, to enable specific hybridization with the target nucleic acid(s) under stringent conditions. Standard methods for carrying out FISH are described in Ausubel, F. M. et al., eds. Current Protocols in Molecular Biology, 2004, John Wiley & Sons Inc and Fluorescence In Situ Hybridization: Technical Overview by John M. S. Bartlett in Molecular Diagnosis of Cancer, Methods and Protocols, 2nd ed.; ISBN: 1-59259-760-2; March 2004, pps. 077-088; Series: Methods in Molecular Medicine.

Alternatively, the protein products expressed from the mRNAs may be assayed by immunohistochemistry of tumour samples, solid phase immunoassay with microtiter plates, Western blotting, 2-dimensional SDS-polyacrylamide gel electrophoresis, ELISA, flow cytometry and other methods known in the art for detection of specific proteins. Detection methods would include the use of site specific antibodies. The skilled person will recognize that all such well-known techniques for detection of up-regulation of PLK1 kinase could be applicable in the present case.

Prior to administration of a compound of any one of Embodiments 1.1 to 1.183, a patient may be screened to determine whether a cancer from which the patient is or may be suffering is one which is characterised by mutated KRAS and which would therefore be would be susceptible to treatment with a compound having activity against cancer cells carrying a mutant KRAS.

For example, a biological sample taken from a patient may be analysed to determine whether a cancer, that the patient is or may be suffering from is one which is characterised by a presence of mutant KRAS. Thus, for example, the patient may be subjected to a diagnostic test to detect mutations in at codons 12, 13, 61 or mixtures thereof in the KRAS protein. Commercially available diagnostic tests for mutant KRAS include the Cobas® KRAS Mutation Test from Roche Molecular Systems, Inc and therascreen KRAS RGQ PCR Kit from Qiagen Manchester, Ltd.

Tumours with mutant KRAS may be particularly sensitive to PLK1 inhibitors. Methods of identification and analysis of mutations and up-regulation of proteins are known to a person skilled in the art. Screening methods could include, but are not limited to, standard methods such as reverse-transcriptase polymerase chain reaction (RT-PCR) or in-situ hybridisation as described above.

Combination Therapy

It is envisaged that the compounds of Embodiments 1.1 to 1.183 will be useful either as sole chemotherapeutic agents or, more usually, in combination therapy with chemotherapeutic agents or radiation therapy in the prophylaxis or treatment of a range of proliferative disease states or conditions. Examples of such disease states and conditions are set out above.

Particular examples of chemotherapeutic agents that may be co-administered with the compounds of Embodiments 1.1 to 1.183 include:

Topoisomerase I inhibitors
Antimetabolites: (e.g. Cytarabine)
Tubulin targeting agents
DNA binder and topoisomerase II inhibitors
EGFR inhibitors (e.g. Gefitinib—see Biochemical Pharmacology 78 2009 460-468)
mTOR inhibitors (e.g. Everolimus)
PI3K pathway inhibitors (e.g. PI3K, PDK1)
Akt inhibitors
Alkylating Agents (e.g. temozolomide)
Monoclonal Antibodies.
Anti-Hormones
Signal Transduction inhibitors
Proteasome Inhibitors
DNA methyl transferase inhibitors
Cytokines and retinoids
Hypoxia triggered DNA damaging agents (e.g. Tirapazamine)
Aromatase inhibitors
Anti Her2 antibodies, (see for example http://www.wipo.int/pctdb/en/wo.jsp?wo=2007056118)
Anti cd20 antibodies
Inhibitors of angiogenesis
HDAC inhibitors
MEK inhibitors
B-Raf inhibitors
ERK inhibitors
HER2 small molecule inhibitors e.g. lapatinib
Bcr-Abl tyrosine-kinase inhibitors e.g. imatinib
CDK4/6 inhibitor e.g. Ibrance
Mps1/TTK inhibitors
Aurora B inhibitors
FLT3 kinase inhibitors
IDH1 or IDH2 inhibitors
BRD4 inhibitors
Inhibitors of immune checkpoint blockade signalling components including PD1, PDL-1 and CTLA4

EXAMPLES

Figure 1:
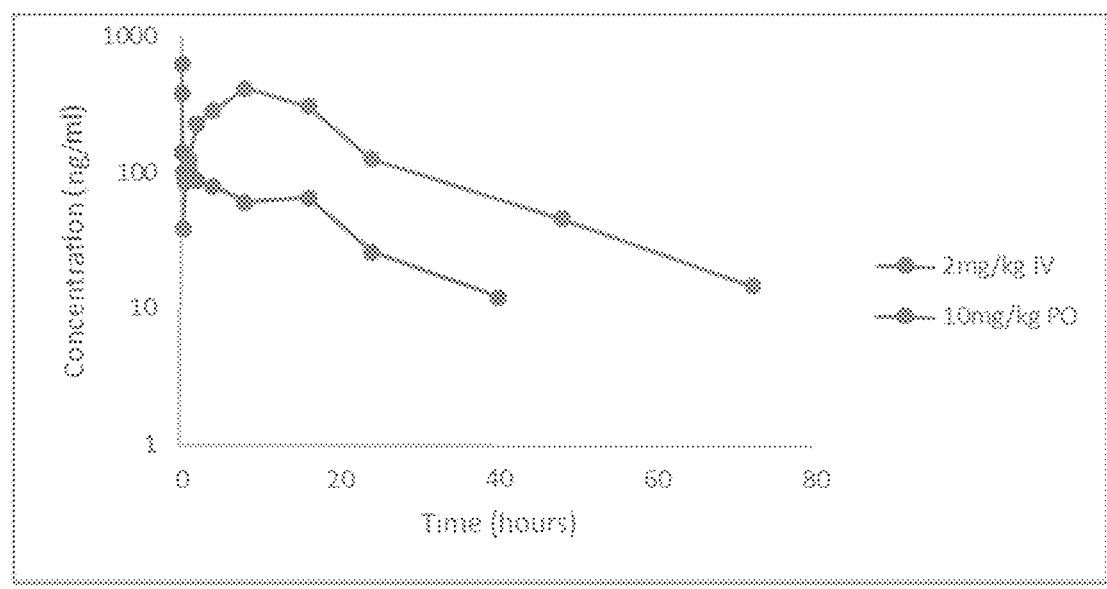
FIG. 1 is a plot of blood plasma concentrations against time following oral and i.v. dosing to mice of the compound of Example 33. The lower line, extending as far as 40 hours, is the line for the 2 mg/kg I.V. dose. The other line is for the 10 mg/kg P.O. dose.

The invention will now be illustrated, but not limited, by reference to the specific embodiments described in the following examples.

In the examples, the following abbreviations are used.
AcCl acetyl chloride
aq aqueous
Boc$_2$O di-tert-butyl dicarbonate
DCM dichloromethane
DIPEA N,N-diisopropylethylamine
DMA N,N-dimethylacetamide
DME dimethoxyethane
DMF dimethylformamide
DMSO dimethylsulfoxide
Et$_3$N triethylamine
Et$_2$O diethyl ether
EtOAc ethyl acetate
EtOH ethanol
HATU (1-[bis(dimethylamino)methylene]-1H-1,2,3-triazolo[4,5-b]pyridinium-3-oxid hexafluorophosphate)
HCl hydrogen chloride
HPLC high performance liquid chromatography
LC liquid chromatography
LCMS liquid chromatography-mass spectrometry
LiOH lithium hydroxide
MeCN acetonitrile
MeOH methanol
MsCl mesyl chloride
NaBH(AcO)$_3$ sodium triacetoxyborohydride
NaH sodium hydride
NaHCO$_3$ sodium hydrogen carbonate
NaOH sodium hydroxide
Na$_2$SO$_4$ sodium sulfate
NBS N-bromosuccinimide
NCS N-chlorosuccinimide
NH$_3$ ammonia
NH$_4$Cl ammonium chloride
NMR nuclear magnetic resonance
Pd(dba)$_2$ bis(dibenzylideneacetone)palladium(0)
PhMe toluene
PTSA p-toluenesulfonic acid
TFA trifluroacetic acid
TH F tetrahydrofuran
UV ultraviolet Proton magnetic resonance ($^1$H NMR) spectra were recorded on a Bruker 400 instrument operating at 400 MHz, in DMSO-d$_6$ or MeOH-d$_4$ (as indicated) at 27° C., unless otherwise stated and are reported as follows: chemical shift b/ppm (multiplicity where s=singlet, d=doublet, dd=double coublet, dt—double triplet, t=triplet, q=quartet, m=multiplet, br=broad, number of protons). The residual protic solvent was used as the internal reference.

Liquid chromatography and mass spectroscopy analyses were carried out using the system and operating conditions set out below. Where atoms with different isotopes are present and a single mass quoted, the mass quoted for the compound is the monoisotopic mass (i.e. $^5$Cl; $^{79}$Br etc.)

LCMS Conditions

The LCMS data given in the following examples were obtained using one of Methods B, C or, where stated, Method A below LCMS Method A Samples were analysed by reverse phase HPLC-MS using a Waters 2795 Alliance HT HPLC, a Micromass ZQ mass spectrometer and a Waters 996 photodiode array UV detector. The LCMS used electrospray ionisation and the chromatography system, as follows:

| Mass Spectrometer: | | |
| --- | --- | --- |
| Ionization mode: | Positive | Negative |
| Capillary Voltage: | 3.20 kV | −3.00 kV |
| Cone Voltage: | 30 V | −30 V |
| Source Temperature: | 110° C. | 110° C. |
| Desolvation Temperature: | 350° C. | 350° C. |
| Cone Gas Flow: | 30 L/Hr | 30 L/Hr |
| Desolvation Gas Flow: | 400 L/Hr | 400 L/Hr |
| Scan duration: | 0.50 seconds | 0.50 seconds |
| Interscan delay: | 0.20 seconds | 0.20 seconds |
| Mass range: | 80 to 1000 AMU | 80 to 1000 AMU |

LCMS was carried using a X-BRIDGE C18 100×4.6 mm, 5 micron column. Column flow was 1.0 mL/min and the mobile phase used were 0.1% formic acid in water (A) and methanol (B), with an injection volume of 10 μL.

The gradient was as described below.

| Time (min) | % A | % B |
| --- | --- | --- |
| 0.01 | 90 | 10 |
| 3.00 | 10 | 90 |
| 6.00 | 0 | 100 |
| 7.00 | 0 | 100 |
| 7.01 | 90 | 10 |
| 10.00 | 90 | 10 |

LCMS Method B

Samples were analysed by reverse phase HPLC-MS using a Waters 2795 Alliance HT HPLC, a Micromass ZQ mass spectrometer and a Waters 996 photodiode array UV detector. The LCMS used electrospray ionisation and the chromatography system, as follows:

| Mass Spectrometer: | | |
| --- | --- | --- |
| Ionization mode: | Positive | Negative |
| Capillary Voltage: | 3.20 kV | −3.00 kV |
| Cone Voltage: | 30 V | −30 V |
| Source Temperature: | 110° C. | 110° C. |
| Desolvation Temperature: | 350° C. | 350° C. |
| Cone Gas Flow: | 30 L/Hr | 30 L/Hr |
| Desolvation Gas Flow: | 400 L/Hr | 400 L/Hr |
| Scan duration: | 0.50 seconds | 0.50 seconds |
| Interscan delay: | 0.20 seconds | 0.20 seconds |
| Mass range: | 80 to 1000 AMU | 80 to 1000 AMU |

LC-MS was carried out on BEH C18 50*2.1 mm 1.7 micron. Column flow was 0.55 mL/min and mobile phase used were: (A) 5 mM ammonium acetate and 0.1% formic acid in water; and (B) 0.1% formic acid in acetonitrile. The injection volume was 2 uL.

The gradient was as described below.

| Time (min) | % A | % B |
|---|---|---|
| 0.01 | 50 | 50 |
| 0.4 | 50 | 50 |
| 0.8 | 65 | 35 |
| 1.2 | 45 | 55 |
| 2.5 | 0 | 100 |
| 3.3 | 0 | 100 |
| 3.31 | 50 | 50 |
| 4.0 | 50 | 50 |

LCMS Method C

Samples were analysed by reverse phase HPLC-MS using a Waters 2795 Alliance HT HPLC, a Micromass ZQ mass spectrometer and a Waters 996 photodiode array UV detector. The LCMS used electrospray ionisation and the chromatography system, as follows:

| Mass Spectrometer: | | |
|---|---|---|
| Ionization mode: | Positive | Negative |
| Capillary Voltage: | 3.20 kV | −3.00 kV |
| Cone Voltage: | 30 V | −30 V |
| Source Temperature: | 110° C. | 110° C. |
| Desolvation Temperature: | 350° C. | 350° C. |
| Cone Gas Flow: | 30 L/Hr | 30 L/Hr |
| Desolvation Gas Flow: | 400 L/Hr | 400 L/Hr |
| Scan duration: | 0.50 seconds | 0.50 seconds |

| Mass Spectrometer: | | |
|---|---|---|
| Ionization mode: | Positive | Negative |
| Interscan delay: | 0.20 seconds | 0.20 seconds |
| Mass range: | 80 to 1000 AMU | 80 to 1000 AMU |

LC-MS was carried out on X-BRIDGE, C18, 5 micron 4.6×100 mm Column. Flow was 1.2 mL/min and mobile phase used were: (A) 0.1% Ammonia in water; and (B) 100% methanol. The injection volume was 10 uL.

Following gradient was used for the elution.

| Time (min) | % A | % B |
|---|---|---|
| 0.0 | 90 | 10 |
| 1.00 | 90 | 10 |
| 5.00 | 0 | 100 |
| 7.00 | 0 | 100 |
| 7.50 | 90 | 10 |
| 8.00 | 90 | 10 |

Examples 1 to 107

The compounds of Examples 1 to 107 shown in Table 2 below have been prepared. Their NMR and LCMS properties are set out in Table 3.

TABLE 2

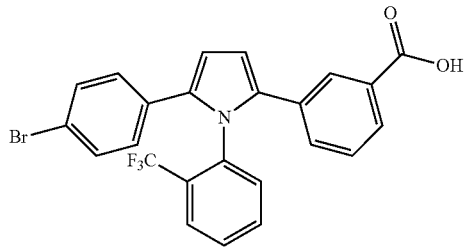 [SMILES: O=C(O)c1cccc(-c2ccc(-c3ccc(Br)cc3)n2-c2ccccc2C(F)(F)F)c1]

Example 1

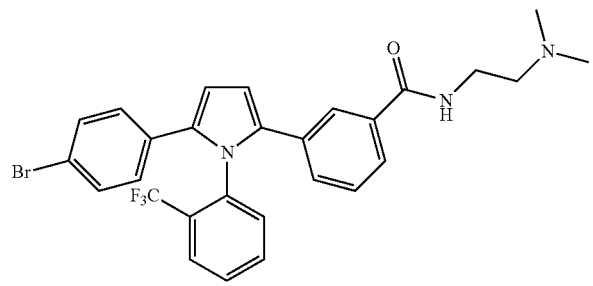 [SMILES: CN(C)CCNC(=O)c1cccc(-c2ccc(-c3ccc(Br)cc3)n2-c2ccccc2C(F)(F)F)c1]

Example 2

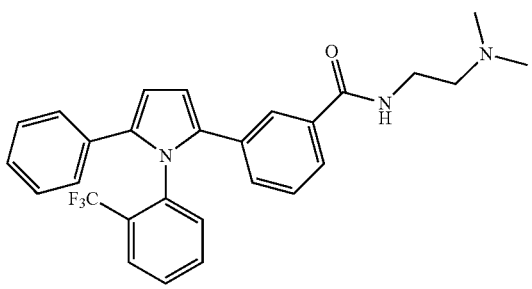 [SMILES: CN(C)CCNC(=O)c1cccc(-c2ccc(-c3ccccc3)n2-c2ccccc2C(F)(F)F)c1]

Example 3

TABLE 2-continued
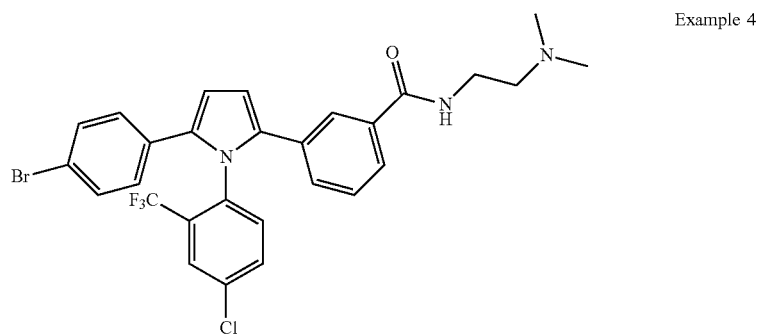
Example 4
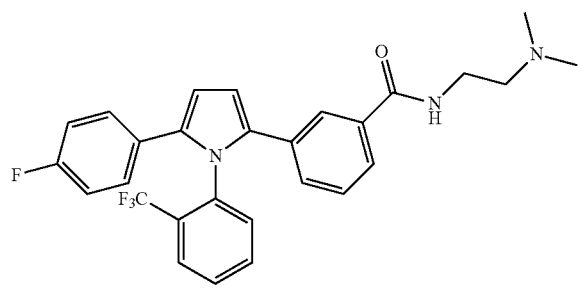 [SMILES: CN(C)CCNC(=O)c1cccc(-c2ccc(-c3ccc(F)cc3)n2-c2ccccc2C(F)(F)F)c1]
Example 5
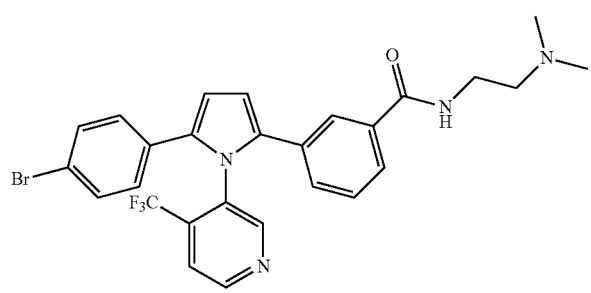 [SMILES: CN(C)CCNC(=O)c1cccc(-c2ccc(-c3ccc(Br)cc3)n2-c2cnccc2C(F)(F)F)c1]
Example 6
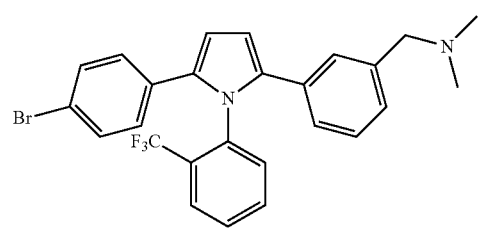 [SMILES: CN(C)Cc1cccc(-c2ccc(-c3ccc(Br)cc3)n2-c2ccccc2C(F)(F)F)c1]
Example 7
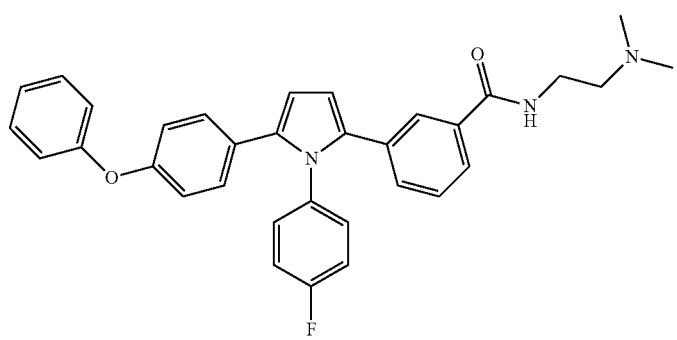 [SMILES: CN(C)CCNC(=O)c1cccc(-c2ccc(-c3ccc(Oc4ccccc4)cc3)n2-c2ccc(F)cc2)c1]
Example 8

TABLE 2-continued
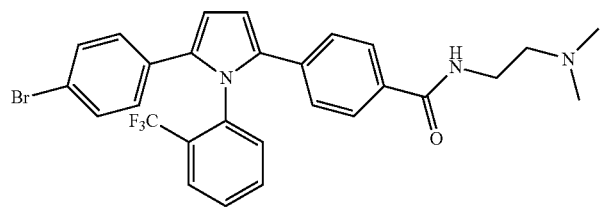
Example 9
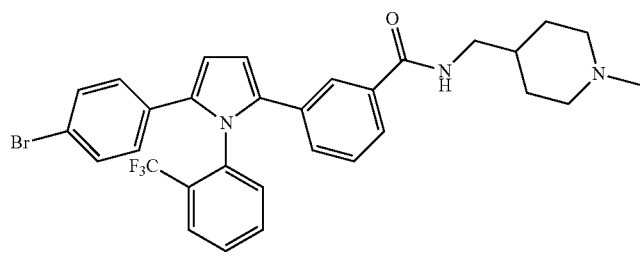 [SMILES: CN1CCC(CNC(=O)c2cccc(-c3ccc(-c4ccc(Br)cc4)n3-c3ccccc3C(F)(F)F)c2)CC1]
Example 10
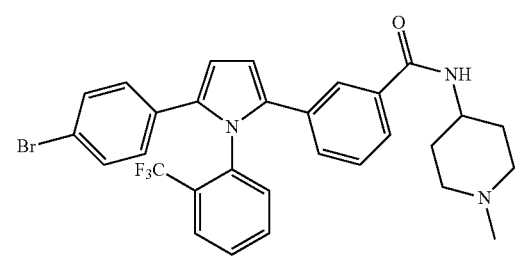 [SMILES: CN1CCC(NC(=O)c2cccc(-c3ccc(-c4ccc(Br)cc4)n3-c3ccccc3C(F)(F)F)c2)CC1]
Example 11
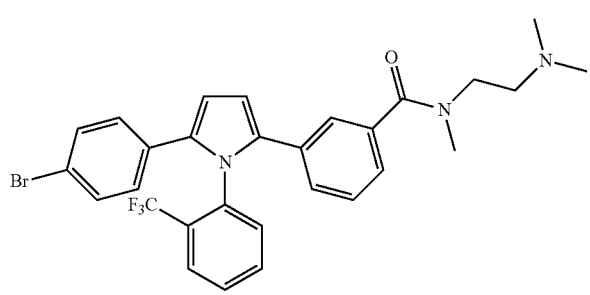 [SMILES: CN(C)CCN(C)C(=O)c1cccc(-c2ccc(-c3ccc(Br)cc3)n2-c2ccccc2C(F)(F)F)c1]
Example 12
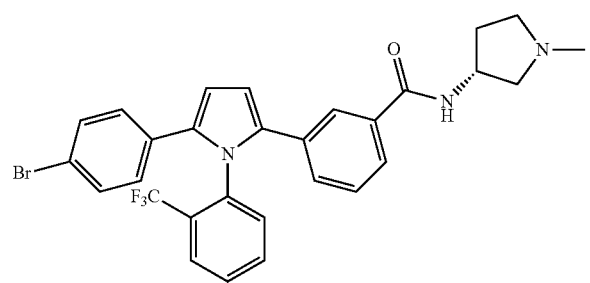 [SMILES: CN1CC[C@@H](NC(=O)c2cccc(-c3ccc(-c4ccc(Br)cc4)n3-c3ccccc3C(F)(F)F)c2)C1]
Example 13
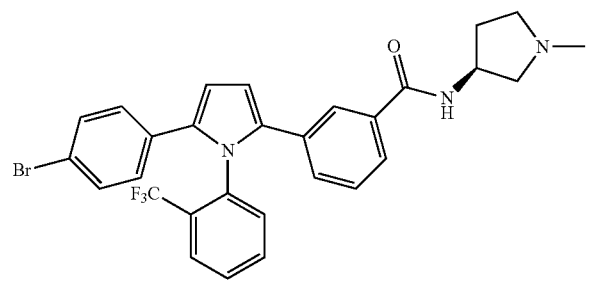 [SMILES: CN1CC[C@H](NC(=O)c2cccc(-c3ccc(-c4ccc(Br)cc4)n3-c3ccccc3C(F)(F)F)c2)C1]
Example 14

TABLE 2-continued
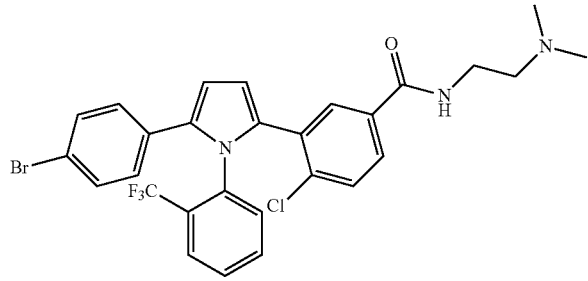 [SMILES: CN(C)CCNC(=O)c1ccc(Cl)c(-c2ccc(-c3ccc(Br)cc3)n2-c2ccccc2C(F)(F)F)c1]
Example 15
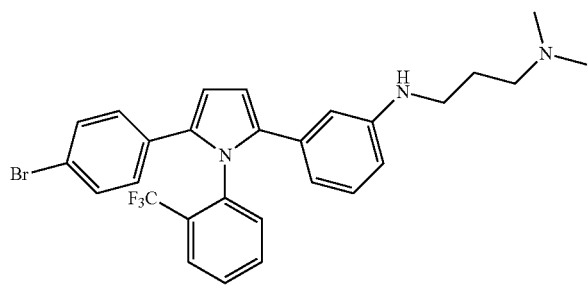 [SMILES: CN(C)CCCNc1cccc(-c2ccc(-c3ccc(Br)cc3)n2-c2ccccc2C(F)(F)F)c1]
Example 16
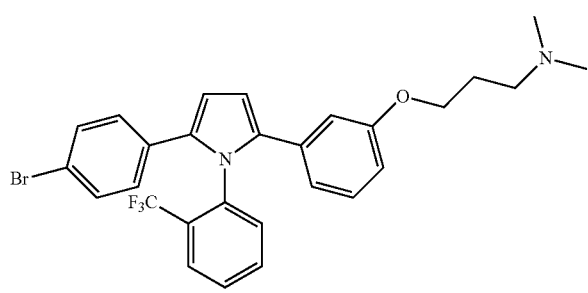 [SMILES: CN(C)CCCOc1cccc(-c2ccc(-c3ccc(Br)cc3)n2-c2ccccc2C(F)(F)F)c1]
Example 17
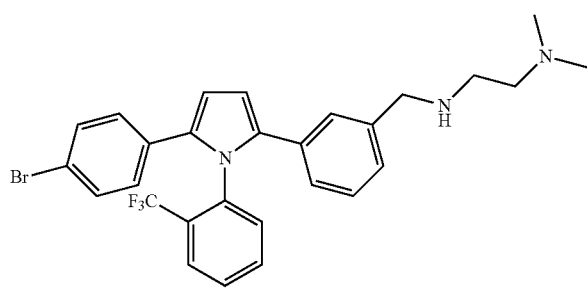 [SMILES: CN(C)CCNCc1cccc(-c2ccc(-c3ccc(Br)cc3)n2-c2ccccc2C(F)(F)F)c1]
Example 18
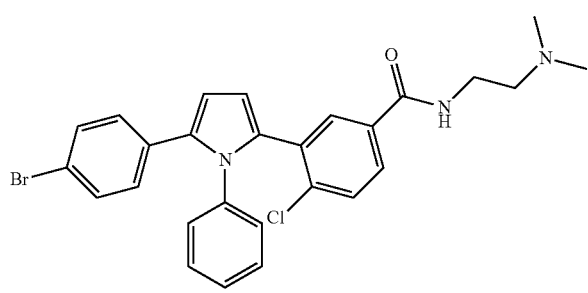 [SMILES: CN(C)CCNC(=O)c1ccc(Cl)c(-c2ccc(-c3ccc(Br)cc3)n2-c2ccccc2)c1]
Example 19

TABLE 2-continued
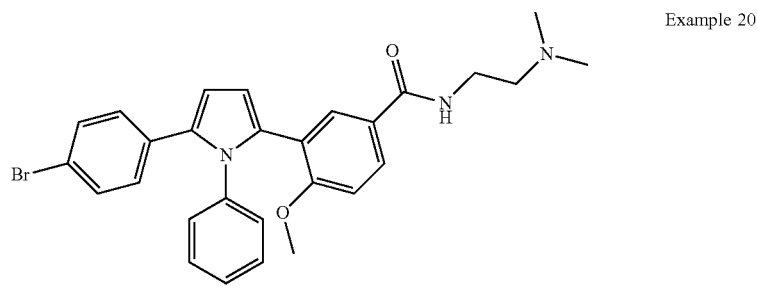
Example 20
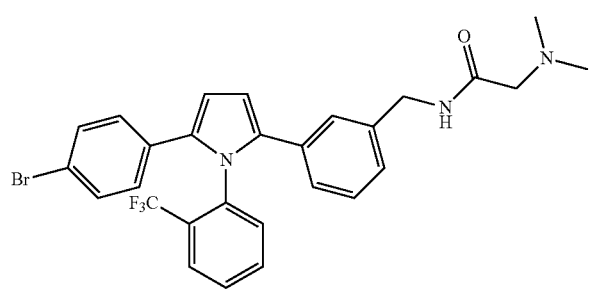 [SMILES: CN(C)CC(=O)NCc1cccc(-c2ccc(-c3ccc(Br)cc3)n2-c2ccccc2C(F)(F)F)c1]
Example 21
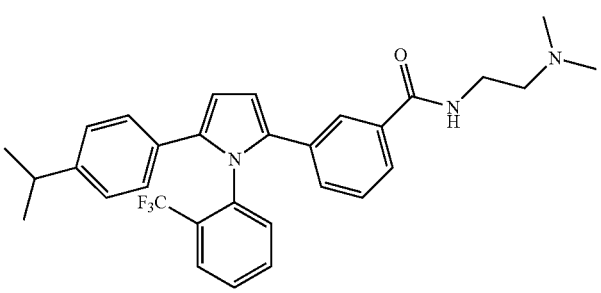 [SMILES: CC(C)c1ccc(-c2ccc(-c3cccc(C(=O)NCCN(C)C)c3)n2-c2ccccc2C(F)(F)F)cc1]
Example 22
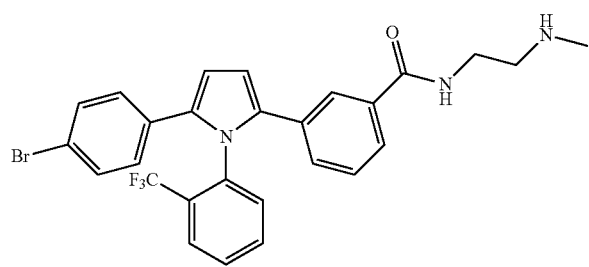 [SMILES: CNCCNC(=O)c1cccc(-c2ccc(-c3ccc(Br)cc3)n2-c2ccccc2C(F)(F)F)c1]
Example 23
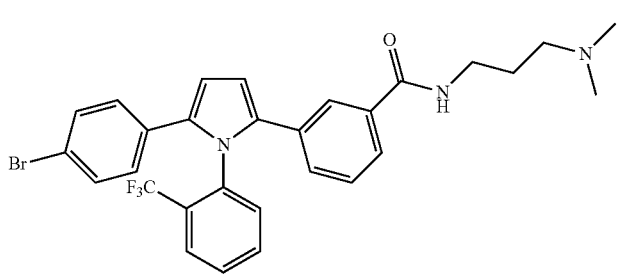 [SMILES: CN(C)CCCNC(=O)c1cccc(-c2ccc(-c3ccc(Br)cc3)n2-c2ccccc2C(F)(F)F)c1]
Example 24

TABLE 2-continued
| | |
|---|---|
| 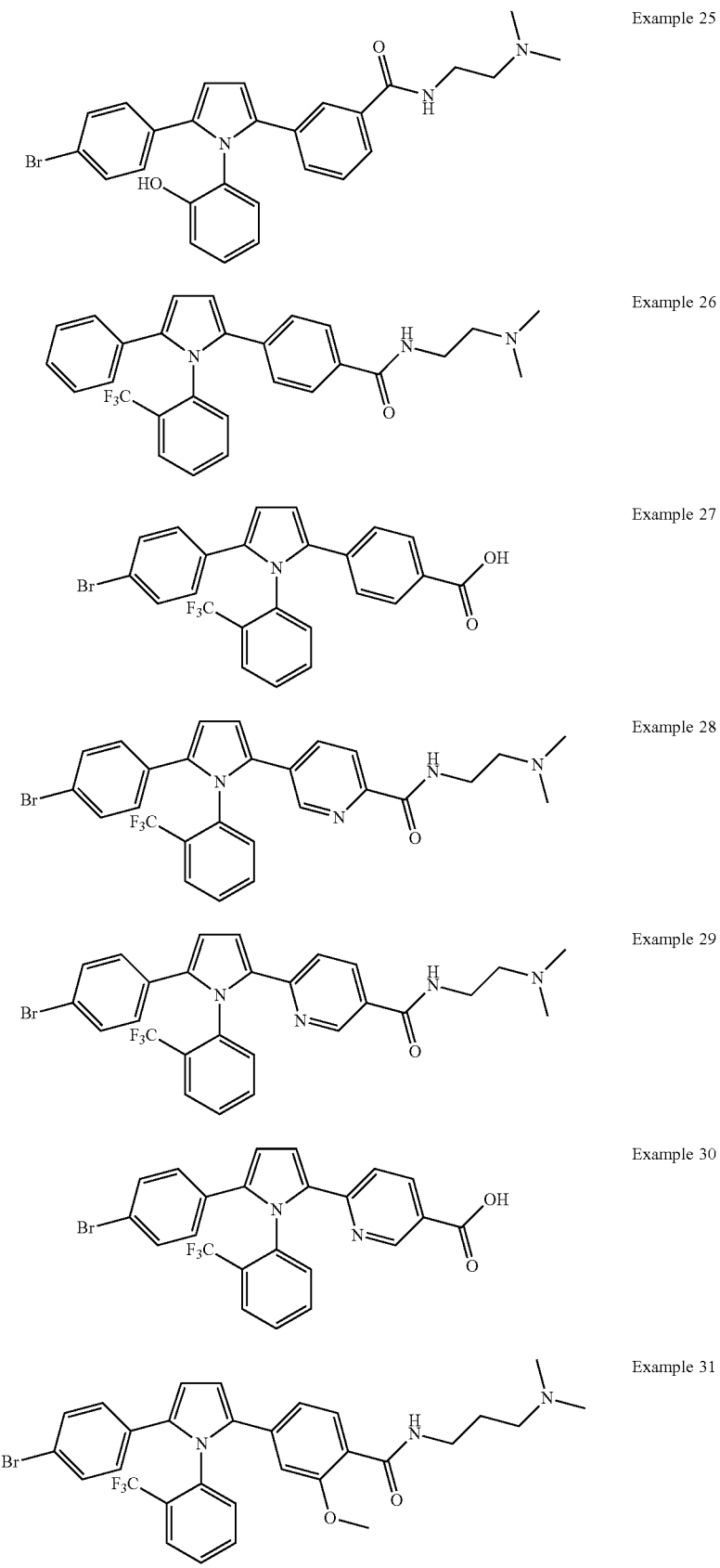 | Example 25 |
| | Example 26 |
| | Example 27 |
| | Example 28 |
| | Example 29 |
| | Example 30 |
| | Example 31 |

TABLE 2-continued
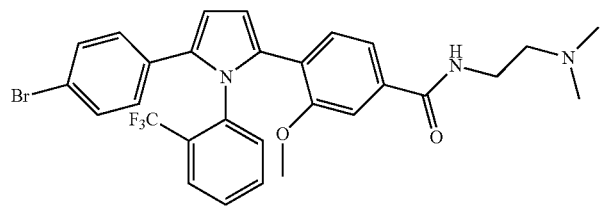 Example 32
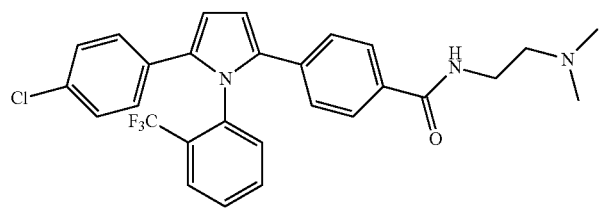 [SMILES: CN(C)CCNC(=O)c1ccc(-c2ccc(-c3ccc(Cl)cc3)n2-c2ccccc2C(F)(F)F)cc1] Example 33
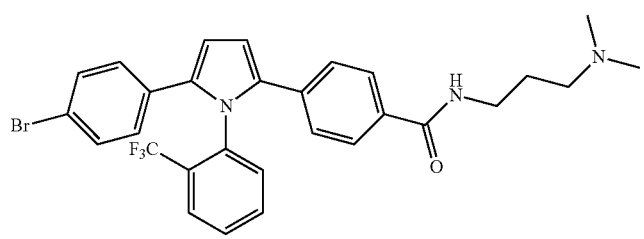 Example 34
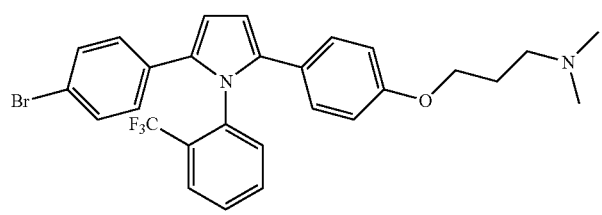 [SMILES: CN(C)CCCOc1ccc(-c2ccc(-c3ccc(Br)cc3)n2-c2ccccc2C(F)(F)F)cc1] Example 35
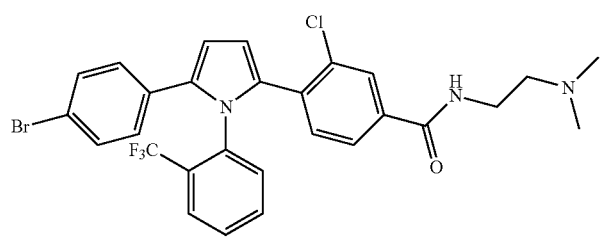 Example 36
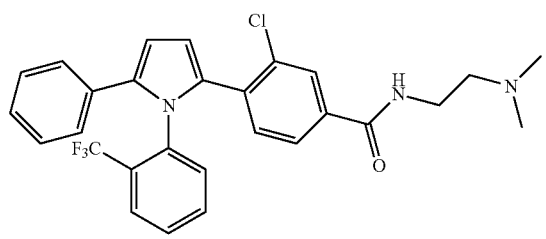 [SMILES: CN(C)CCNC(=O)c1ccc(-c2ccc(-c3ccccc3)n2-c2ccccc2C(F)(F)F)c(Cl)c1] Example 37
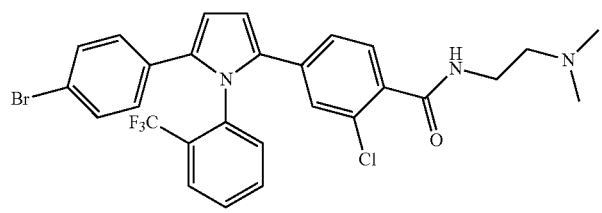 Example 38

TABLE 2-continued
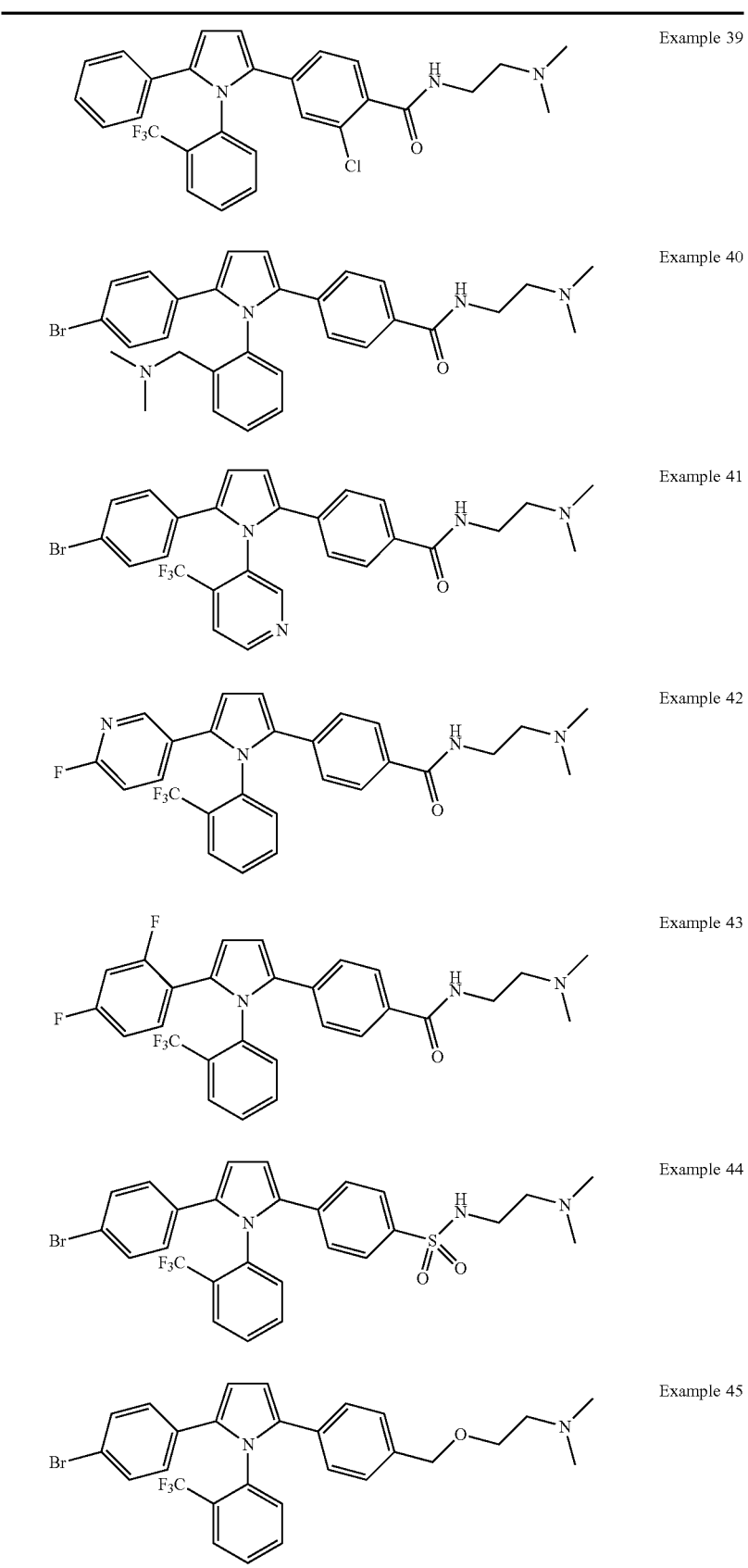
Example 39
Example 40
Example 41
Example 42
Example 43
Example 44
Example 45

TABLE 2-continued
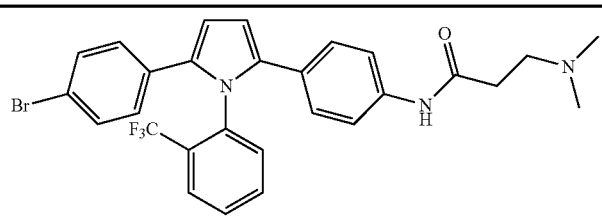 Example 46
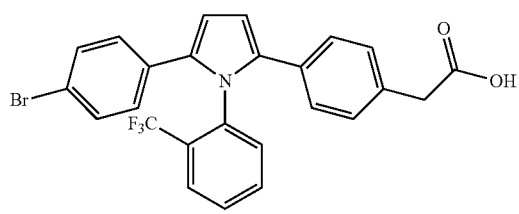 [SMILES: O=C(O)Cc1ccc(-c2ccc(-c3ccc(Br)cc3)n2-c2ccccc2C(F)(F)F)cc1] Example 47
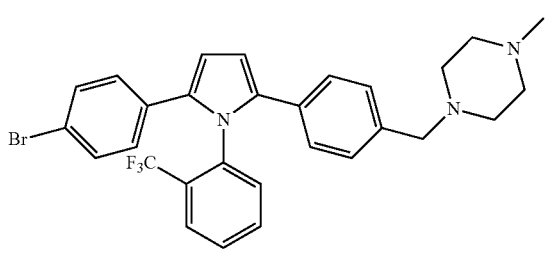 [SMILES: CN1CCN(Cc2ccc(-c3ccc(-c4ccc(Br)cc4)n3-c3ccccc3C(F)(F)F)cc2)CC1] Example 48
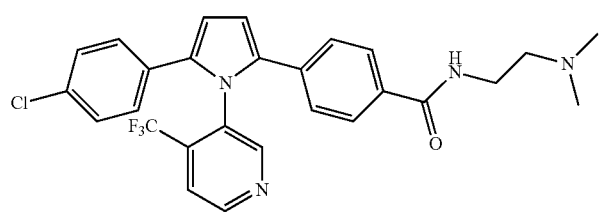 Example 49
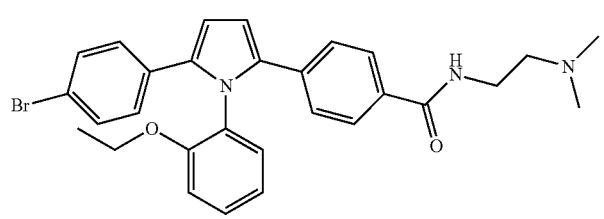 Example 50
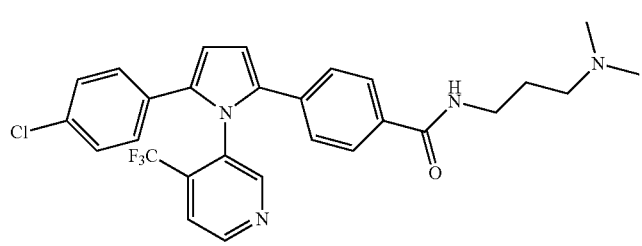 Example 51
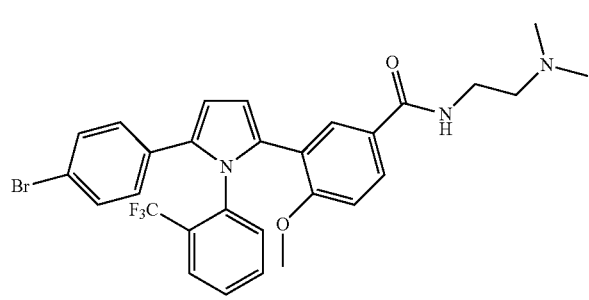 [SMILES: COc1ccc(C(=O)NCCN(C)C)cc1-c1ccc(-c2ccc(Br)cc2)n1-c1ccccc1C(F)(F)F] Example 52

TABLE 2-continued
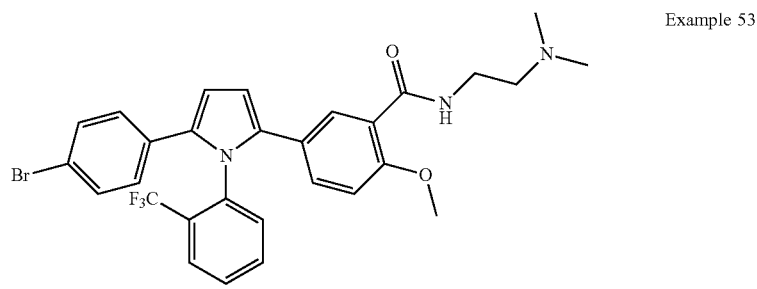
Example 53
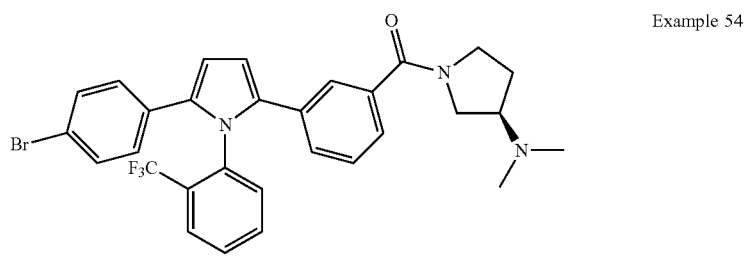
Example 54
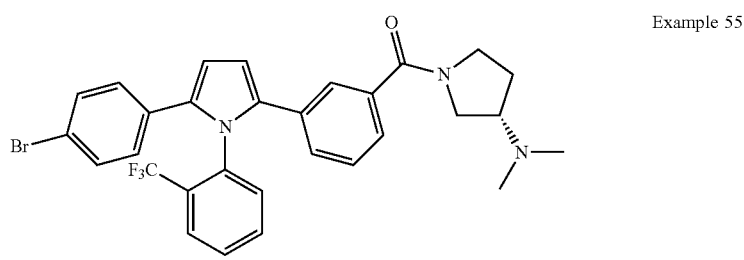
Example 55
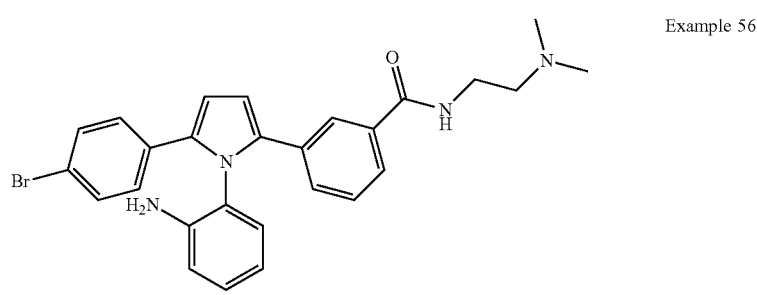
Example 56
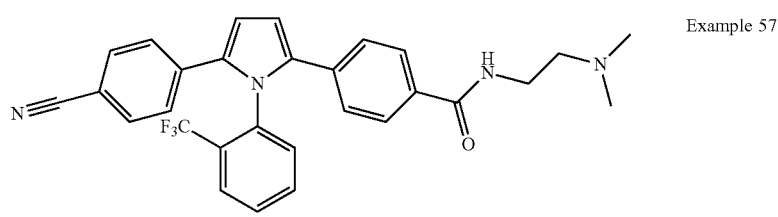
Example 57
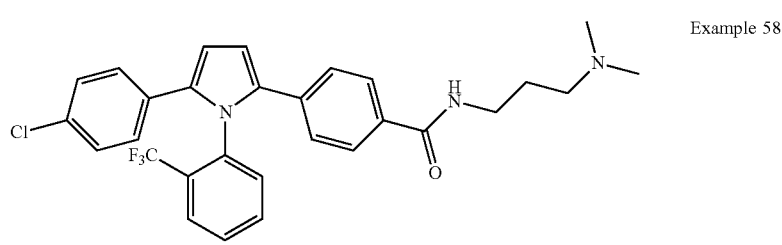
Example 58

TABLE 2-continued
| | |
|---|---|
| 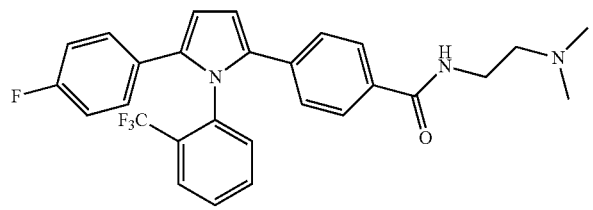 | Example 59 |
| 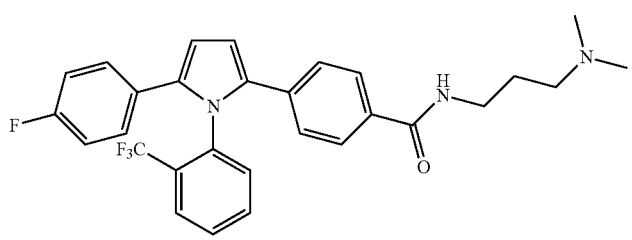 [SMILES: CN(C)CCCNC(=O)c1ccc(-c2ccc(-c3ccc(F)cc3)n2-c2ccccc2C(F)(F)F)cc1] | Example 60 |
| 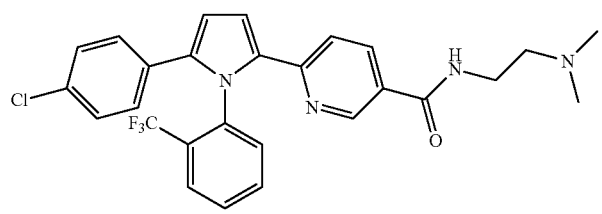 [SMILES: CN(C)CCNC(=O)c1ccc(-c2ccc(-c3ccc(Cl)cc3)n2-c2ccccc2C(F)(F)F)nc1] | Example 61 |
| 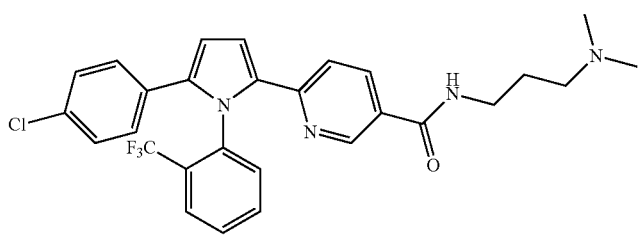 [SMILES: CN(C)CCCNC(=O)c1ccc(-c2ccc(-c3ccc(Cl)cc3)n2-c2ccccc2C(F)(F)F)nc1] | Example 62 |
| 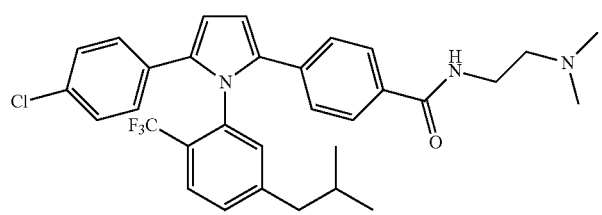 [SMILES: CC(C)Cc1ccc(C(F)(F)F)c(-n2c(-c3ccc(Cl)cc3)ccc2-c2ccc(C(=O)NCCN(C)C)cc2)c1] | Example 63 |
| 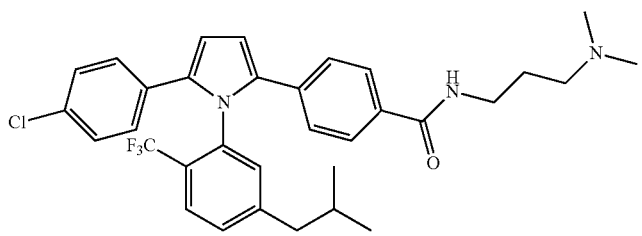 [SMILES: CC(C)Cc1ccc(C(F)(F)F)c(-n2c(-c3ccc(Cl)cc3)ccc2-c2ccc(C(=O)NCCCN(C)C)cc2)c1] | Example 64 |
| 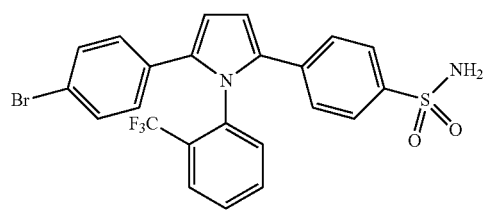 [SMILES: NS(=O)(=O)c1ccc(-c2ccc(-c3ccc(Br)cc3)n2-c2ccccc2C(F)(F)F)cc1] | Example 65 |

TABLE 2-continued
| 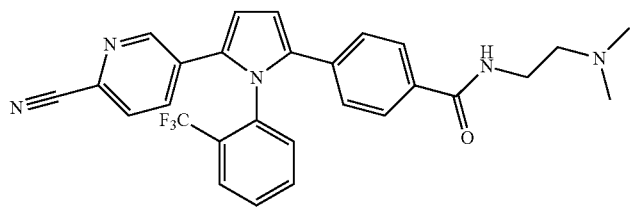 [SMILES: CN(C)CCNC(=O)c1ccc(-c2ccc(-c3ccc(C#N)nc3)n2-c2ccccc2C(F)(F)F)cc1] | Example 66 |
| 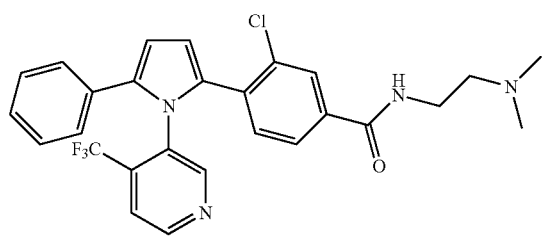 [SMILES: CN(C)CCNC(=O)c1ccc(-c2ccc(-c3ccccc3)n2-c2cnccc2C(F)(F)F)c(Cl)c1] | Example 67 |
| 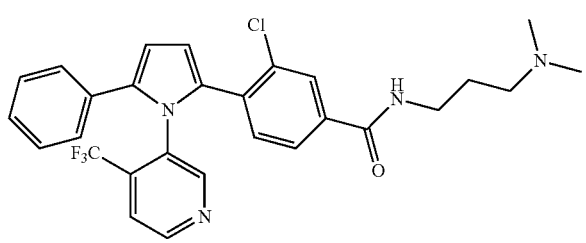 [SMILES: CN(C)CCCNC(=O)c1ccc(-c2ccc(-c3ccccc3)n2-c2cnccc2C(F)(F)F)c(Cl)c1] | Example 68 |
| 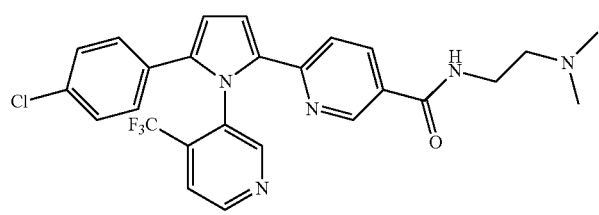 [SMILES: CN(C)CCNC(=O)c1ccc(-c2ccc(-c3ccc(Cl)cc3)n2-c2cnccc2C(F)(F)F)nc1] | Example 69 |
| 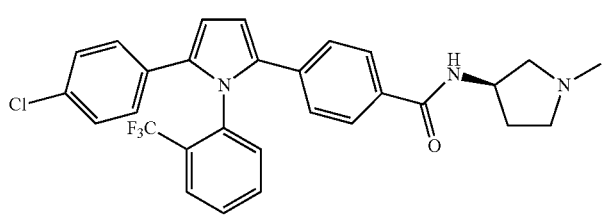 [SMILES: CN1CC[C@@H](NC(=O)c2ccc(-c3ccc(-c4ccc(Cl)cc4)n3-c3ccccc3C(F)(F)F)cc2)C1] | Example 70 |
| 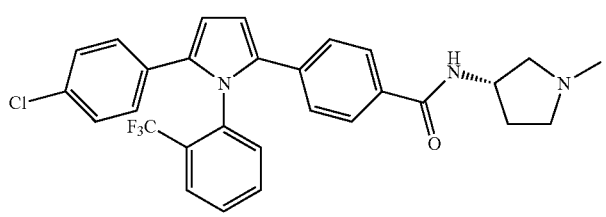 [SMILES: CN1CC[C@H](NC(=O)c2ccc(-c3ccc(-c4ccc(Cl)cc4)n3-c3ccccc3C(F)(F)F)cc2)C1] | Example 71 |
| 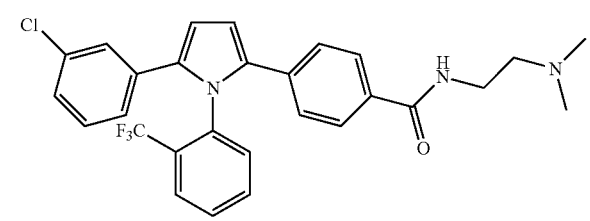 [SMILES: CN(C)CCNC(=O)c1ccc(-c2ccc(-c3cccc(Cl)c3)n2-c2ccccc2C(F)(F)F)cc1] | Example 72 |

TABLE 2-continued
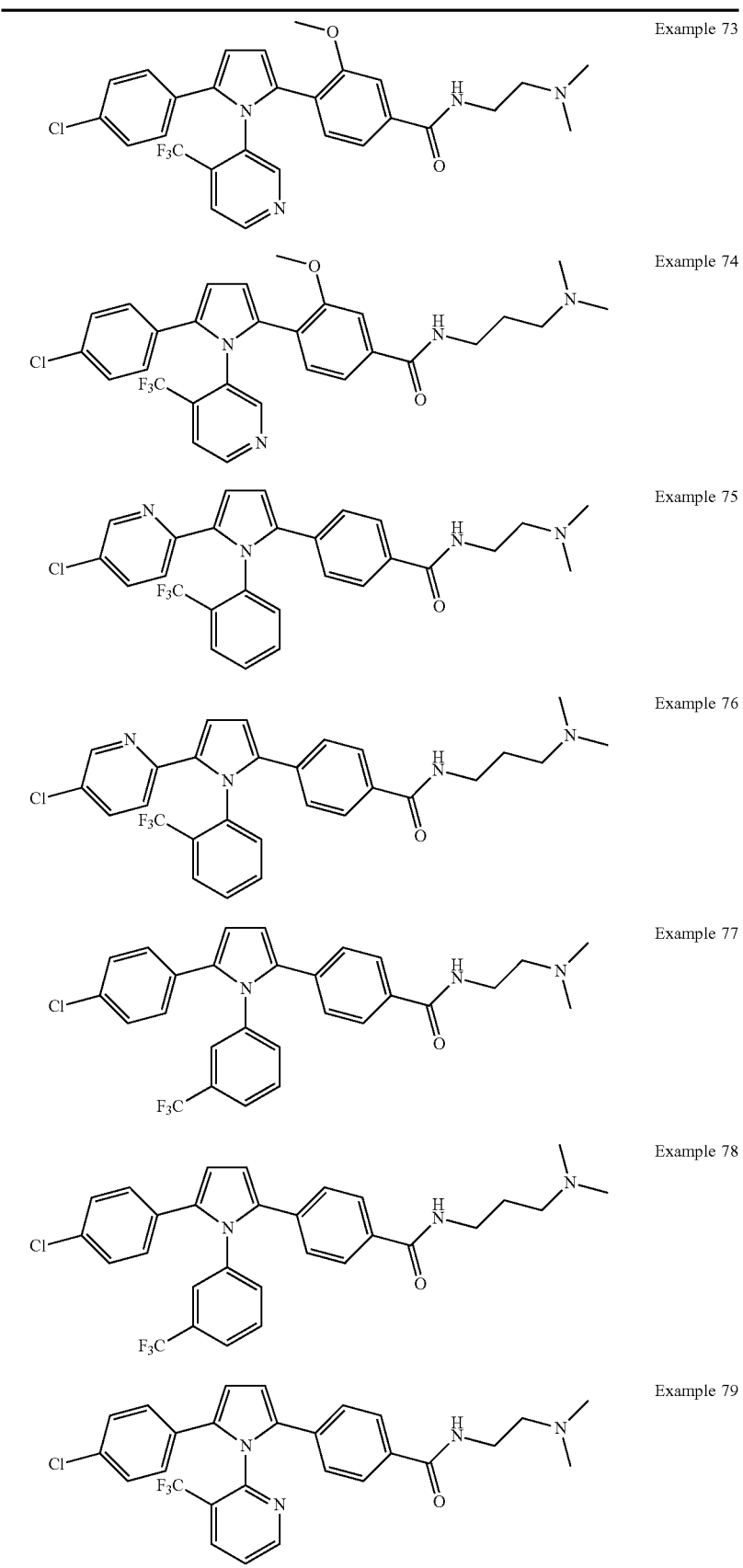
Example 73
Example 74
Example 75
Example 76
Example 77
Example 78
Example 79

TABLE 2-continued
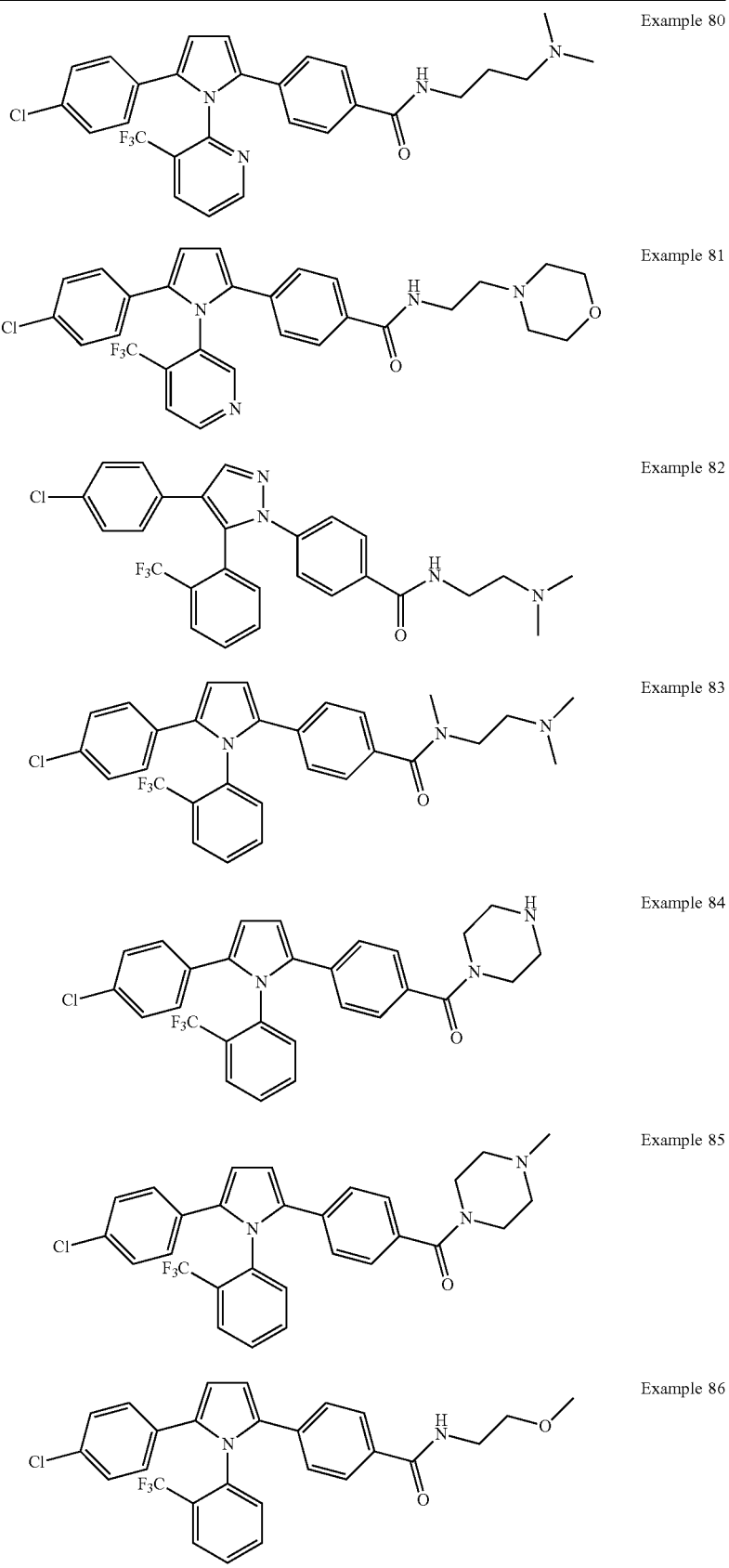
Example 80
Example 81
Example 82
Example 83
Example 84
Example 85
Example 86

TABLE 2-continued
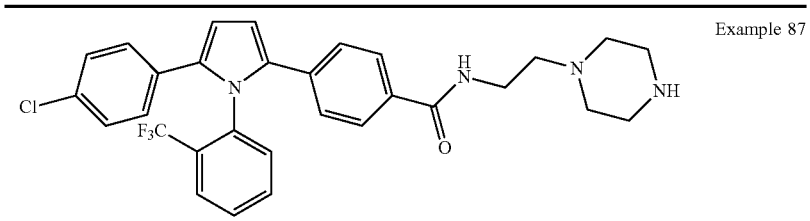
Example 87
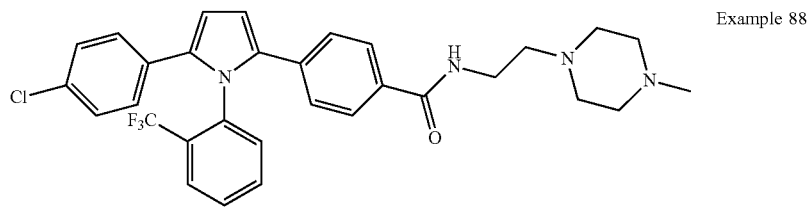
Example 88
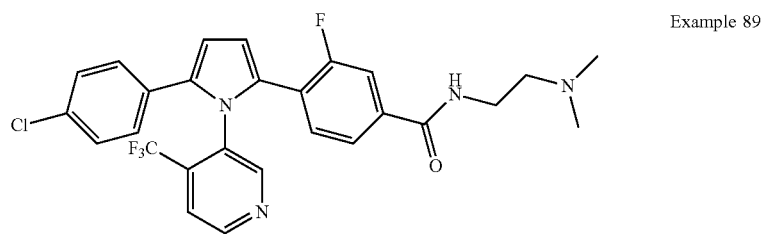
Example 89
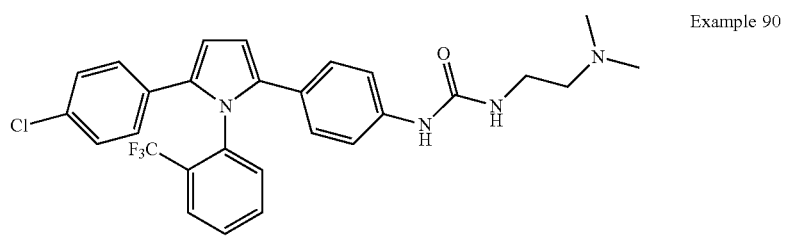
Example 90
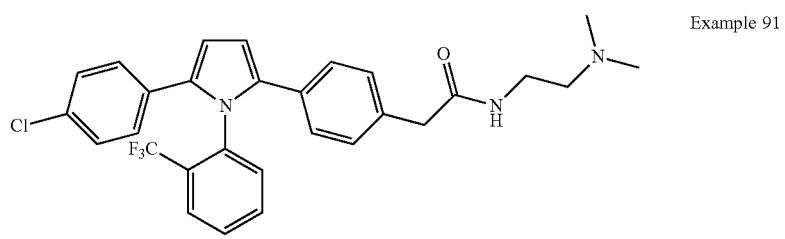
Example 91
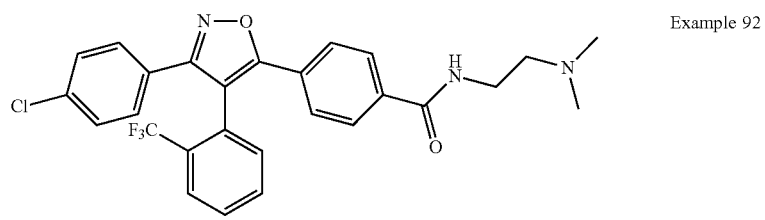
Example 92
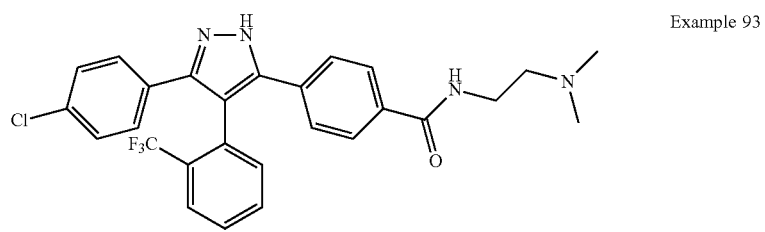
Example 93

TABLE 2-continued
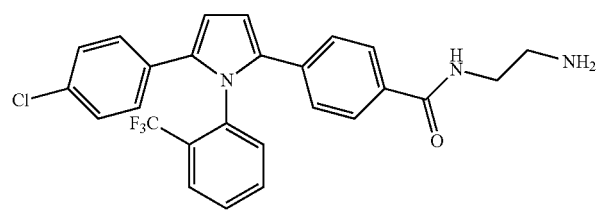 [SMILES: NCCNC(=O)c1ccc(-c2ccc(-c3ccc(Cl)cc3)n2-c2ccccc2C(F)(F)F)cc1]
Example 94
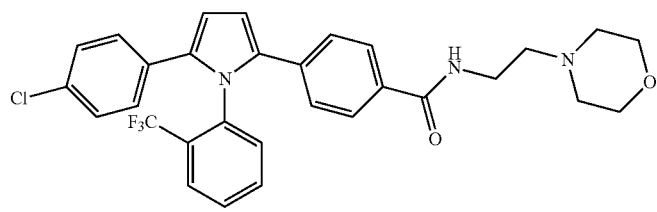 [SMILES: O=C(NCCN1CCOCC1)c1ccc(-c2ccc(-c3ccc(Cl)cc3)n2-c2ccccc2C(F)(F)F)cc1]
Example 95
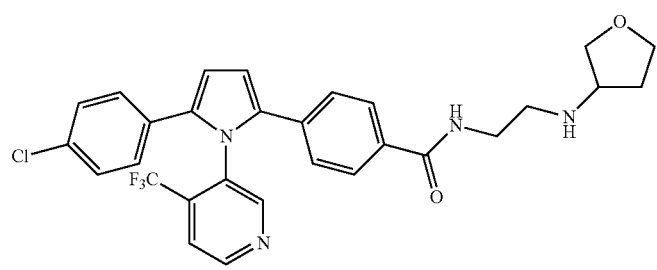 [SMILES: O=C(NCCNC1CCOC1)c1ccc(-c2ccc(-c3ccc(Cl)cc3)n2-c2cnccc2C(F)(F)F)cc1]
Example 96
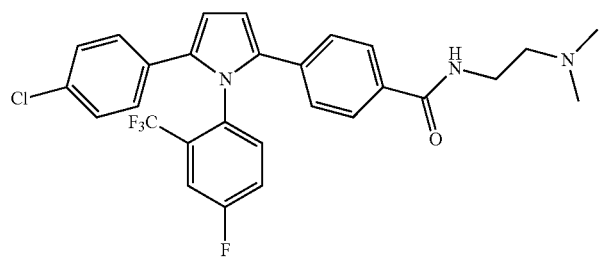 [SMILES: CN(C)CCNC(=O)c1ccc(-c2ccc(-c3ccc(Cl)cc3)n2-c2ccc(F)cc2C(F)(F)F)cc1]
Example 97
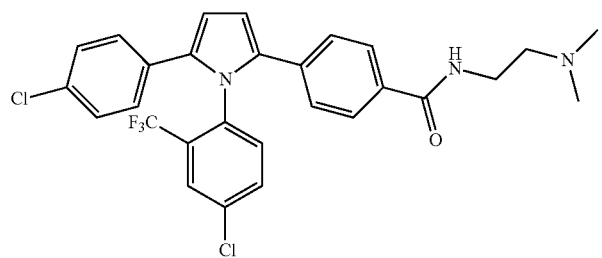
Example 98
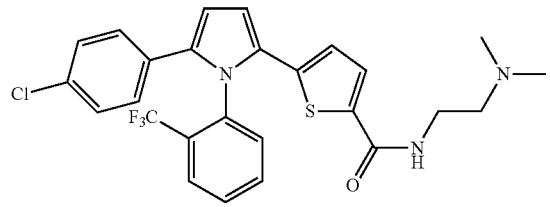 [SMILES: CN(C)CCNC(=O)c1ccc(-c2ccc(-c3ccc(Cl)cc3)n2-c2ccccc2C(F)(F)F)s1]
Example 99

TABLE 2-continued
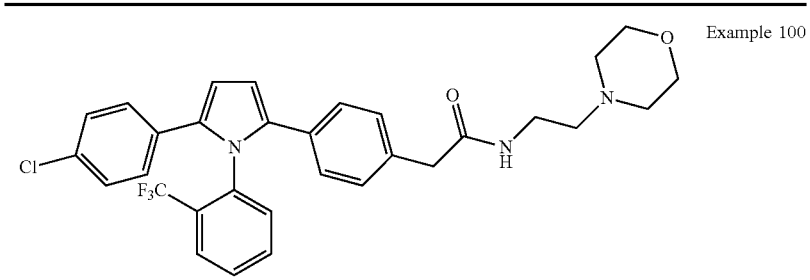
Example 100
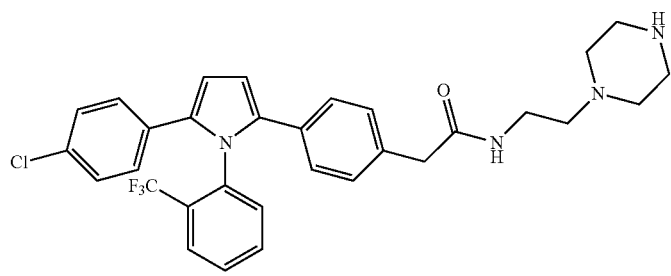 [SMILES: O=C(Cc1ccc(-c2ccc(-c3ccc(Cl)cc3)n2-c2ccccc2C(F)(F)F)cc1)NCCN1CCNCC1]
Example 101
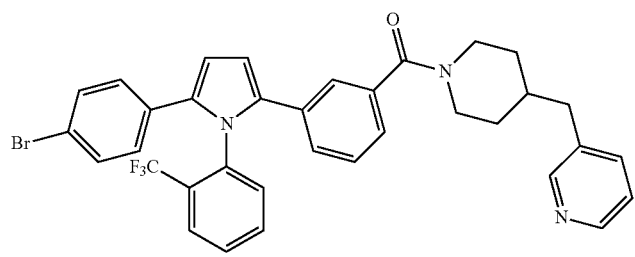 [SMILES: O=C(c1cccc(-c2ccc(-c3ccc(Br)cc3)n2-c2ccccc2C(F)(F)F)c1)N1CCC(Cc2cccnc2)CC1]
Example 102
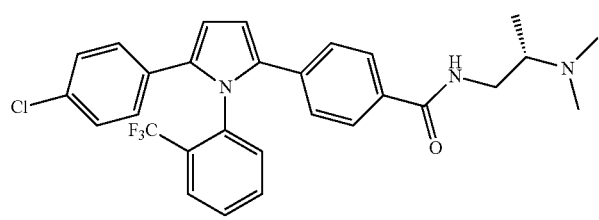 [SMILES: C[C@@H](CNC(=O)c1ccc(-c2ccc(-c3ccc(Cl)cc3)n2-c2ccccc2C(F)(F)F)cc1)N(C)C]
Example 103
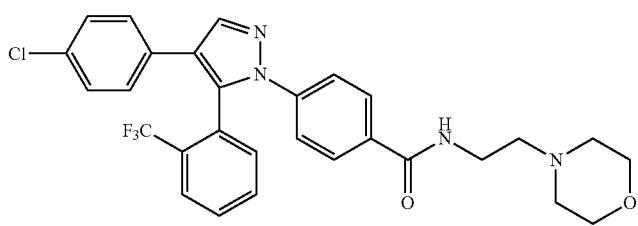 [SMILES: O=C(NCCN1CCOCC1)c1ccc(-n2ncc(-c3ccc(Cl)cc3)c2-c2ccccc2C(F)(F)F)cc1]
Example 104
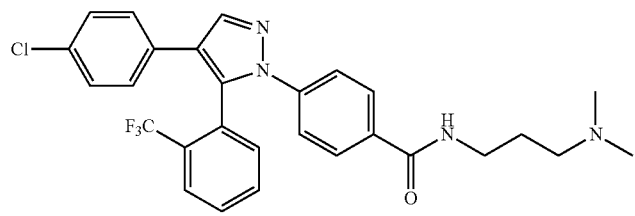 [SMILES: CN(C)CCCNC(=O)c1ccc(-n2ncc(-c3ccc(Cl)cc3)c2-c2ccccc2C(F)(F)F)cc1]
Example 105

TABLE 2-continued

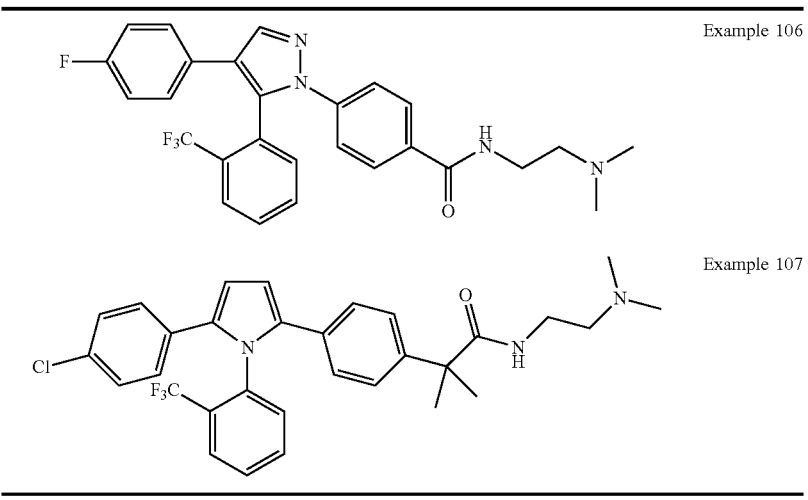

Example 106

Example 107

TABLE 3

| Ex. No. | Name | Synthetic Method | ¹H NMR | LC (RT) | MS (MH⁺) | LCMS Method |
|---|---|---|---|---|---|---|
| 1 | 3-[5-(4-bromophenyl)-1-[2-(trifluoromethyl)phenyl]pyrrol-2-yl]benzoic acid | A | (DMSO-$d_6$) δ 12.91 (s, 1H), 7.79 (m, 3H), 7.70 (m, 2H), 7.61 (s, 1H), 7.39 (d, 2H), 7.32 (m, 2H), 7.01 (d, 2H) and 6.62 (m, 2H). | 2.88 | 486 | A |
| 2 | 3-[5-(4-bromophenyl)-1-[2-(trifluoromethyl)phenyl]pyrrol-2-yl]-N-[2-(dimethylamino)ethyl]benzamide hydrochloride | A | (DMSO-$d_6$) δ 8.82 (br s, 1H), 7.79 (m, 4H), 7.68 (s, 2H), 7.41 (d, 2H), 7.24 (m, 1H), 7.00 (m, 3H), 6.65 (m, 2H), 3.58 (s, 2H), 3.20 (s, 2H) and 2.74 (s, 6H). | 2.10 | 558 | A |
| 3 | N-[2-(dimethylamino)ethyl]-3-[5-phenyl-1-[2-(trifluoromethyl)phenyl]pyrrol-2-yl]benzamide hydrochloride | A | (DMSO-$d_6$) δ 8.75 (t, 1H), 7.85 (s, 1H), 7.70-7.56 (m, 5H), 7.24-7.08 (m, 7H), 6.62 (d, 1H), 6.52 (d, 1H), 3.75 (t, 2H), 3.38 (t, 2H) and 2.99 (s, 6H). | 4.70 | 478 | A |
| 4 | 3-[5-(4-bromophenyl)-1-[4-chloro-2-(trifluoromethyl)phenyl] pyrrol-2-yl]-N-[2-(dimethylamino)ethyl]benzamide hydrochloride | A | (DMSO-$d_6$) δ 7.82 (t, 1H), 7.76-7.74 (m, 2H), 7.72-7.69 (m, 2H), 7.66-7.63 (m, 1H), 7.37 (d, 2H), 7.30 (t, 1H), 7.18-7.16 (m, 1H), 7.03 (d, 2H), 6.63 (d, 1H), 6.57 (d, 1H), 3.77 (t, 2H), 3.40 (t, 2H) and 2.99 (s, 6H). | 5.30 | 592 | A |
| 5 | N-[2-(dimethylamino)ethyl]-3-[5-(4-fluorophenyl)-1-[2-(trifluoromethyl)phenyl]pyrrol-2-yl]benzamide hydrochloride | A | (DMSO-$d_6$) δ 10.29 (br s, 1H), 8.87 (t, 1H), 7.80-7.74 (m, 4H), 7.71-7.64 (m, 2H), 7.24 (t, 1H), 7.11-7.02 (m, 5H), 6.67 (d, 1H), 6.55 (d, 1H), 3.61 (q, 2H), 3.24 (br s, 2H) and 2.81 (br s, 6H). | 5.11 | 496 | A |
| 6 | 3-[5-(4-bromophenyl)-1-[4-(trifluoromethyl)-3-pyridyl]pyrrol-2-yl]-N-[2-(dimethylamino)ethyl]benzamide hydrochloride | A | (DMSO-$d_6$) δ 10.27 (br s, 1H), 9.20 (s, 1H), 8.90-8.89 (m, 2H), 7.81-7.74 (m, 3H), 7.46-7.44 (m, 2H), 7.39-7.26 (m, 2H), 7.14-7.12 (m, 1H), 7.04-7.02 (m, 1H), 6.72-6.71 (d, 1H), 6.65 (d, 1H), 3.61 (br s, 2H), 3.25 (q, 2H) and 2.82 (d, 6H). | 4.85 | 559 | A |
| 7 | 1-[3-[5-(4-bromophenyl)-1-[2-(trifluoromethyl)phenyl]pyrrol-2-yl]phenyl]-N,N-dimethyl-methanamine hydrochloride | B | (DMSO-$d_6$) δ 7.74-7.72 (m, 2H), 7.64 (t, 2H), 7.35-7.29 (m, 5H), 7.14 (dt, 1H), 6.99 (d, 2H), 6.61 (d, 1H), 6.57 (d, 1H), 4.22 (s, 2H) and 2.74 (d, 6H). | 5.06 | 499 | A |
| 8 | N-[2-(dimethylamino)ethyl]-3-[1-(4-fluorophenyl)-5-(4-phenoxyphenyl)pyrrol-2-yl]benzamide hydrochloride | A | (DMSO-$d_6$) δ 9.55 (br s, 1H), 8.73 (t, 1H), 7.79 (s, 1H), 7.67 (d, 1H), 7.40 (q, 2H), 7.30 (t, 1H), 7.22-7.14 (m, 5H), 7.09-7.05 (m, 3H), 7.00 (d, 2H), 6.86 (d, 2H), 6.57 (d, 1H), 6.49 (d, 1H), 3.60 (q, 2H), 3.25 (br d, 2H) and 2.84 (d, 6H). | 5.17 | 520 | A |
| 9 | 4-[5-(4-bromophenyl)-1-[2-(trifluoromethyl)phenyl]pyrrol-2-yl]-N-[2-(dimethylamino)ethyl]benzamide hydrochloride | C | (DMSO-$d_6$) δ 9.60 (br s, 1H), 8.68 (t, 1H), 7.82-7.77 (m, 3H), 7.70-7.68 (m, 3H), 7.39 (d, 2H), 7.12 (d, 2H), 6.99 (d, 2H), 6.69 (d, 1H), 6.61 (d, 1H), 3.56-3.54 (m, 2H), 3.22-3.16 (m, 2H) and 2.80 (s, 6H). | 4.96 | 556 | A |
| 10 | 3-[5-(4-bromophenyl)-1-[2-(trifluoromethyl)phenyl]pyrrol-2-yl]-N-[(1-methyl-4-piperidyl)methyl]benzamide hydrochloride | A | (DMSO-$d_6$) δ 9.72 (br s, 1H), 8.54 (t, 1H), 7.79-7.76 (m, 3H), 7.68-7.66 (m, 2H), 7.61 (d, 1H), 7.41-7.39 (m, 2H), 7.24 (t, 1H), 7.06 (d, 1H), 7.00-6.98 (m, 2H), 6.65-6.61 (m, 2H), 3.41 (d, 2H), 3.17-3.11 (m, 2H), 2.93-2.87 (m, 2H), 2.73 (d, 3H), 1.83-1.74 (m, 3H) and 1.45-1.36 (m, 2H). | 5.09 | 596 | A |
| 11 | 3-[5-(4-bromophenyl)-1-[2-(trifluoromethyl)phenyl]pyrrol-2-yl]-N-(1-methyl-4-piperidyl)benzamide hydrochloride | A | (DMSO-$d_6$) δ 9.75 (br s, 1H), 8.42 (d, 1H), 7.79-7.76 (m, 3H), 7.70-7.62 (m, 3H), 7.42-7.38 (m, 2H), 7.25 (t, 1H), 7.08 (d, 1H), 7.01-6.98 (m, 2H), 6.62 (dd, 2H), 3.97-3.95 (m, 1H), 3.46-3.43 (m, 2H), 3.06-3.02 (m, 2H), 2.76 (s, 3H), 2.00-1.97 (m, 2H) and 1.83-1.74 (m, 2H). | 5.09 | 582 | A |
| 12 | 3-[5-(4-bromophenyl)-1-[2-(trifluoromethyl)phenyl]pyrrol-2-yl]-N-[2-(dimethylamino)ethyl]-N-methyl-benzamide hydrochloride | A | (DMSO-$d_6$) δ 9.95 (br s, 1H), 7.83-7.77 (m, 3H), 7.69 (t, 1H), 7.40 (d, 2H), 7.27 (d, 2H), 7.18 (s, 1H), 7.07 (br s, 1H), 6.99 (d, 2H), 6.61 (t, 2H), 3.76 (q, 2H), 3.30 (t, 2H), 2.84 (s, 6H) and 2.74 (s, 3H). | 5.01 | 570 | A |

TABLE 3-continued

| Ex. No. | Name | Synthetic Method | ¹H NMR | LC (RT) | MS (MH⁺) | LCMS Method |
|---|---|---|---|---|---|---|
| 13 | 3-[5-(4-bromophenyl)-1-[2-(trifluoromethyl)phenyl]pyrrol-2-yl]-N-[(3R)-1-methylpyrrolidin-3-yl]benzamide hydrochloride | A | (DMSO-d$_6$) δ 10.80 (br s, 1H), 8.83 (d, 1H), 7.81-7.76 (m, 4H), 7.70-7.68 (m, 2H), 7.40 (d, 2H), 7.25 (t, 1H), 7.06 (s, 1H), 6.99 (d, 2H), 6.69 (s, 1H), 6.62 (d, 1H), 4.65-4.62 (m, 1H), 3.97-3.57 (m, 1H), 3.51-3.48 (m, 1H), 3.06-3.03 (m, 2H), 2.85 (s, 3H), 2.24-2.33 (m, 1H) and 2.02-1.99 (m, 1H). | 4.98 | 568 | A |
| 14 | 3-[5-(4-bromophenyl)-1-[2-(trifluoromethyl)phenyl]pyrrol-2-yl]-N-[(3S)-1-methylpyrrolidin-3-yl]benzamide hydrochloride | A | (DMSO-d$_6$) δ 8.79 (br s, 1H), 7.81-7.58 (m, 6H), 7.33-7.31 (d, 2H), 7.16 (dt, 2H), 7.00 (d, 2H), 6.63 (d, 1H), 6.57 (d, 1H), 4.61-4.57 (m, 1H), 4.05-3.91 (m, 1H), 3.77 (d, 1H), 3.47-3.42 (m, 1H), 3.24-3.12 (m, 1H), 3.02 (d, 3H), 2.68-2.42 (m, 1H) and 2.29-2.24 (m, 1H). | 4.99 | 568 | A |
| 15 | 3-[5-(4-bromophenyl)-1-[2-(trifluoromethyl)phenyl]pyrrol-2-yl]-4-chloro-N-[2-(dimethylamino)ethyl]benzamide hydrochloride | A | (DMSO-d$_6$) δ 10.00 (br s, 1H), 8.81 (t, 1H), 7.80-7.77 (m, 1H), 7.71-7.66 (m, 4H), 7.58 (d, 2H), 7.41 (d, 2H), 6.99-6.97 (m, 2H), 6.65 (d, 1H), 6.51 (d, 1H), 3.55 (q, 2H), 3.21 (t, 2H) and 2.79 (s, 6H). | 5.10 | 590 | A |
| 16 | N-[3-[5-(4-bromophenyl)-1-[2-(trifluoromethyl)phenyl]pyrrol-2-yl]phenyl]-N',N'-dimethyl-propane-1,3-diamine hydrochloride | D | (DMSO-d$_6$) δ 10.26 (br s, 2H), 7.81-7.76 (m, 3H), 7.70-7.66 (m, 1H), 7.38 (d, 2H), 7.02-6.96 (m, 3H), 6.66 (d, 1H), 6.59 (s, 1H), 6.57 (d, 1H), 6.51 (d, 1H), 6.45 (d, 1H), 3.10-3.06 (m, 2H), 2.97 (t, 2H), 2.73 (s, 6H) and 1.84-1.79 (m, 2H). | 5.12 | 542 | A |
| 17 | 3-[3-[5-(4-bromophenyl)-1-[2-(trifluoromethyl)phenyl]pyrrol-2-yl]phenoxy]-N,N-dimethyl-propan-1-amine hydrochloride | E | (DMSO-d$_6$) δ 10.37 (br s, 1H), 7.81-7.77 (m, 3H), 7.71-7.67 (m, 1H), 7.39 (d, 2H), 7.10 (t, 1H), 6.98 (d, 2H), 6.74-6.72 (m, 1H), 6.63-6.56 (m, 4H), 3.89-3.83 (m, 2H), 3.15-3.12 (m, 2H), 2.76 (s, 6H) and 2.10-2.03 (m, 2H). | 5.22 | 543 | A |
| 18 | N-[[3-[5-(4-bromophenyl)-1-[2-(trifluoromethyl)phenyl]pyrrol-2-yl]phenyl]methyl]-N',N'-dimethyl-ethane-1,2-diamine hydrochloride | B | (DMSO-d$_6$) δ 7.73 (t, 2H), 7.64-7.60 (m, 3H), 7.37 (d, 1H), 7.32 (d, 2H), 7.20 (t, 1H), 6.99 (d, 2H), 6.93 (d, 1H), 6.65 (d, 1H), 6.56 (d, 1H), 4.24 (d, 2H), 3.57 (s, 4H) and 3.00 (s, 6H). | 4.75 | 542 | A |
| 19 | 3-[5-(4-bromophenyl)-1-phenyl-pyrrol-2-yl]-4-chloro-N-[2-(dimethylamino)ethyl]benzamide hydrochloride | A | (DMSO-d$_6$) δ 10.11 (br s, 1H), 8.89 (t, 1H), 7.92 (d, 1H), 7.83 (dd, 1H), 7.49 (d, 1H), 7.42 (d, 2H), 7.26-7.23 (m, 3H), 7.05-6.98 (m, 4H), 6.60 (d, 1H), 6.42 (d, 1H), 3.60 (q, 2H), 3.24 (t, 2H) and 2.81 (s, 6H). | 5.15 | 522 | A |
| 20 | 3-[5-(4-bromophenyl)-1-phenyl-pyrrol-2-yl]-N-[2-(dimethylamino)ethyl]-4-methoxy-benzamide hydrochloride | A | (DMSO-d$_6$) δ 9.64 (br s, 1H), 8.64 (t, 1H), 7.85-7.81 (m, 2H), 7.39 (d, 2H), 7.23-7.21 (m, 3H), 6.98-6.87 (m, 5H), 6.52 (d, 1H), 6.32 (d, 1H), 3.59 (q, 2H), 3.33 (s, 3H), 3.25 (t, 2H) and 2.83 (s, 6H). | 4.95 | 518 | A |
| 21 | N-[[3-[5-(4-bromophenyl)-1-[2-(trifluoromethyl)phenyl]pyrrol-2-yl]phenyl]methyl]-2-(dimethylamino)acetamide hydrochloride | F | (DMSO-d$_6$) δ 9.76 (br s, 1H), 8.99 (t, 1H), 7.79-7.75 (m, 3H), 7.70-7.67 (m, 1H), 7.39 (d, 2H), 7.14-7.06 (m, 3H), 6.98 (d, 2H), 6.80 (d, 1H), 6.59 (d, 1H), 6.53 (d, 1H), 4.24 (d, 2H), 3.92 (s, 2H) and 2.79 (s, 6H). | 5.02 | 556 | A |
| 22 | N-[2-(dimethylamino)ethyl]-3-[5-(4-isopropylphenyl)-1-[2-(trifluoromethyl)phenyl]pyrrol-2-yl]benzamide hydrochloride | A | (DMSO-d$_6$) δ 10.25 (br s, 1H), 8.85 (br s, 1H), 7.79-7.65 (m, 6H), 7.23 (t, 2H), 7.08-6.97 (m, 5H), 6.65 (d, 1H), 6.52 (d, 1H), 3.61 (br d, 2H), 3.24 (br d, 2H), 2.82 (d, 6H), 2.79-2.77 (m, 1H) and 1.13 (d, 6H). | 5.15 | 520 | A |
| 23 | 3-[5-(4-bromophenyl)-1-[2-(trifluoromethyl)phenyl]pyrrol-2-yl]-N-[2-(methylamino)ethyl]benzamide hydrochloride | A | (DMSO-d$_6$) δ 9.88 (br s, 1H), 8.83 (t, 1H), 7.80-7.77 (m, 4H), 7.71-7.67 (m, 1H), 7.40 (d, 2H), 7.24 (t, 1H), 7.04-6.98 (m, 3H), 6.68 (d, 1H), 6.62 (d, 1H), 3.54 (q, 2H), 3.07 (s, 2H) and 2.57 (s, 3H). | 5.06 | 542 | A |
| 24 | 3-[5-(4-bromophenyl)-1-[2-(trifluoromethyl)phenyl]pyrrol-2-yl]-N-[3-(dimethylamino)propyl]benzamide hydrochloride | A | (DMSO-d$_6$) δ 10.09 (br s, 1H), 8.67 (t, 1H), 7.80-7.63 (m, 6H), 7.40 (d, 2H), 7.24 (t, 1H), 7.04 (d, 1H), 6.99 (d, 2H), 6.65 (d, 1H), 6.62 (d, 1H), 3.31-3.29 (m, 2H), 3.07-3.03 (m, 2H), 2.75 (s, 6H) and 1.92-1.85 (m, 2H). | 5.12 | 570 | A |
| 25 | 3-[5-(4-bromophenyl)-1-(2-hydroxyphenyl)pyrrol-2-yl]-N-[2-(dimethylamino)ethyl]benzamide hydrochloride | A | (DMSO-d$_6$) δ 10.05 (s, 2H), 8.80 (t, 1H), 7.90 (s, 1H), 7.66 (d, 1H), 7.39 (d, 2H), 7.25-7.09 (m, 5H), 6.93-6.90 (m, 2H), 6.74-6.71 (m, 1H), 6.58 (d, 1H), 6.53 (d, 1H), 3.62-3.59 (m, 2H), 3.25-3.24 (m, 2H) and 2.82 (d, 6H). | 4.79 | 506 | A |
| 26 | N-[2-(dimethylamino)ethyl]-4-[5-phenyl-1-[2-(trifluoromethyl)phenyl]pyrrol-2-yl]benzamide hydrochloride | C | (DMSO-d$_6$) δ 9.59 (br s, 1H), 8.67 (t, 1H), 7.82-7.76 (m, 3H), 7.69 (d, 2H), 7.22-7.05 (m, 6H), 6.68 (d, 1H), 6.57 (d, 1H), 3.65 (t, 2H), 3.23-3.16 (m, 2H) and 2.80 (s, 6H). | 4.80 | 478 | A |
| 27 | 4-[5-(4-bromophenyl)-1-[2-(trifluoromethyl)phenyl]pyrrol-2-yl]benzoic acid | C | (DMSO-d$_6$) δ 7.81-7.78 (m, 3H), 7.73-7.69 (m, 3H), 7.40 (d, 2H), 7.14-7.12 (m, 2H), 7.00 (d, 2H), 6.71 (d, 1H) and 6.62 (d, 1H). | 5.93 | 486 | A |
| 28 | 5-[5-(4-bromophenyl)-1-[2-(trifluoromethyl)phenyl]pyrrol-2-yl]-N-[2-(dimethylamino)ethyl]pyridine-2-carboxamide hydrochloride | G | (DMSO-d$_6$) δ 9.87 (br s, 1H), 9.02 (t, 1H), 8.21 (s, 1H), 7.94-7.83 (m, 4H), 7.76-7.67 (m, 2H), 7.43 (d, 2H), 7.02 (d, 2H), 6.88 (d, 1H), 6.69 (d, 1H), 3.60 (d, 2H), 3.23 (d, 2H) and 2.79 (d, 6H). | 4.88 | 557 | A |
| 29 | 6-[5-(4-bromophenyl)-1-[2-(trifluoromethyl)phenyl]pyrrol-2-yl]-N-[2-(dimethylamino)ethyl]pyridine-3-carboxamide hydrochloride | G | (DMSO-d$_6$) δ 10.10 (br s, 1H), 8.88 (t, 1H), 8.52 (d, 1H), 8.14 (dd, 1H), 7.78-7.72 (m, 2H), 7.69-7.62 (m, 3H), 7.41-7.40 (d, 2H), 7.17 (d, 1H), 7.02 (d, 2H), 6.65 (d, 1H), 3.58 (q, 2H), 3.22 (q, 2H) and 2.79 (d, 6H). | 4.92 | 557 | A |
| 30 | 6-[5-(4-bromophenyl)-1-[2-(trifluoromethyl)phenyl]pyrrol-2-yl]pyridine-3-carboxylic acid | G | (DMSO-d$_6$) δ 13.16 (s, 1H), 8.47 (d, 1H), 8.07 (dd, 1H), 7.77-7.72 (m, 2H), 7.68-7.60 (m, 3H), 7.42 (d, 2H), 7.18 (d, 1H), 7.03 (d, 2H) and 6.66 (d, 1H). | 5.82 | 487 | A |

TABLE 3-continued

| Ex. No. | Name | Synthetic Method | $^1$H NMR | LC (RT) | MS (MH$^+$) | LCMS Method |
|---|---|---|---|---|---|---|
| 31 | 4-[5-(4-bromophenyl)-1-[2-(trifluoromethyl)phenyl]pyrrol-2-yl]-N-[3-(dimethylamino)propyl]-2-methoxy-benzamide hydrochloride | A | (DMSO-d$_6$) δ 9.69 (br s, 1H), 8.25 (t, 1H), 7.89-7.81 (m, 3H), 7.72 (t, 1H), 7.59 (d, 1H), 7.41 (d, 2H), 7.01 (d, 2H), 6.84 (d, 1H), 6.73 (d, 1H), 6.62 (d, 1H), 6.60 (s, 1H), 3.56 (s, 3H), 3.30 (q, 2H), 3.03 (t, 2H), 2.75 (s, 6H) and 1.87-1.83 (m, 2H). | 5.09 | 599 | A |
| 32 | 4-[5-(4-bromophenyl)-1-[2-(trifluoromethyl)phenyl]pyrrol-2-yl]-N-[2-(dimethylamino)ethyl]-3-methoxy-benzamide hydrochloride | A | (DMSO-d$_6$) δ 10.12 (br s, 1H), 8.85 (t, 1H), 7.70-7.55 (m, 4H), 7.41-7.36 (m, 4H), 7.10 (d, 1H), 6.96 (dd, 2H), 6.58 (d, 1H), 6.39 (d, 1H), 3.65 (s, 3H), 3.60 (q, 2H), 3.24 (t, 2H) and 2.80 (s, 6H). | 2.31 | 586 | B |
| 33 | 4-[5-(4-chlorophenyl)-1-[2-(trifluoromethyl)phenyl]pyrrol-2-yl]-N-[2-(dimethylamino)ethyl]benzamide hydrochloride | C | (DMSO-d$_6$) δ 10.09 (br s, 1H), 8.76 (t, 1H), 7.86-7.78 (m, 3H), 7.74-7.69 (m, 3H), 7.28 (d, 2H), 7.12 (d, 2H), 7.07 (d, 2H), 6.69 (d, 1H), 6.62 (d, 1H), 3.61-3.56 (m, 2H), 3.22 (br s, 2H) and 2.80 (s, 6H). | 2.26 | 512 | B |
| 34 | 4-[5-(4-bromophenyl)-1-[2-(trifluoromethyl)phenyl]pyrrol-2-yl]-N-[3-(dimethylamino)propyl]benzamide hydrochloride | C | (DMSO-d$_6$) δ 9.85 (br s, 1H), 8.58 (t, 1H), 7.84-7.78 (m, 3H), 7.72-7.70 (m, 1H), 7.66 (d, 2H), 7.40 (d, 2H), 7.11 (d, 2H), 6.99 (d, 2H), 6.68 (d, 1H), 6.61 (d, 1H), 3.30-3.26 (m, 2H), 3.06-3.02 (m, 2H), 2.73 (s, 6H) and 1.87-1.83 (m, 2H). | 5.02 | 571 | A |
| 35 | 3-[4-[5-(4-bromophenyl)-1-[2-(trifluoromethyl)phenyl]pyrrol-2-yl]phenoxy]-N,N-dimethyl-propan-1-amine hydrochloride | E | (DMSO-d$_6$) δ 10.14 (br s, 1H), 7.80-7.75 (m, 3H), 7.68-7.65 (m, 1H), 7.38 (d, 2H), 7.03-6.95 (m, 4H), 6.77 (d, 2H), 6.56 (d, 1H), 6.43 (d, 1H), 3.97 (t, 2H), 3.15 (t, 2H), 2.76 (s, 6H) and 2.11-2.04 (m, 2H). | 5.17 | 543 | A |
| 36 | 4-[5-(4-bromophenyl)-1-[2-(trifluoromethyl)phenyl]pyrrol-2-yl]-3-chloro-N-[2-(dimethylamino)ethyl]benzamide hydrochloride | A | (DMSO-d$_6$) δ 9.89 (br s, 1H), 8.91 (t, 1H), 7.98 (s, 1H), 7.74-7.69 (m, 3H), 7.62-7.60 (m, 2H), 7.41-7.39 (m, 2H), 7.14-7.12 (d, 1H), 6.99 (d, 2H), 6.65 (d, 1H), 6.58 (d, 1H), 3.58 (t, 2H), 3.23 (t, 2H) and 2.80 (s, 6H). | 5.13 | 590 | A |
| 37 | 3-chloro-N-[2-(dimethylamino)ethyl]-4-[5-phenyl-1-[2-(trifluoromethyl)phenyl]pyrrol-2-yl]benzamide hydrochloride | A | (DMSO-d$_6$) δ 9.65 (br s, 1H), 8.85 (t, 1H), 7.96 (d, 1H), 7.74-7.67 (m, 3H), 7.60-7.56 (m, 2H), 7.21-7.11 (m, 4H), 7.05 (d, 2H), 6.58 (dd, 2H), 3.56 (t, 2H), 3.23 (t, 2H) and 2.80 (s, 6H). | 4.90 | 512 | A |
| 38 | 4-[5-(4-bromophenyl)-1-[2-(trifluoromethyl)phenyl]pyrrol-2-yl]-2-chloro-N-[2-(dimethylamino)ethyl]benzamide hydrochloride | A | (DMSO-d$_6$) δ 9.96 (br s, 1H), 8.64 (t, 1H), 7.92-7.90 (m, 1H), 7.86-7.82 (m, 2H), 7.73 (m, 1H), 7.40 (t, 3H), 7.11 (d, 1H), 7.05 (dd, 1H), 7.01 (d, 2H), 6.75 (d, 1H), 6.63 (d, 1H), 3.54 (t, 2H), 3.19 (t, 2H) and 2.80 (s, 6H). | 5.03 | 590 | A |
| 39 | 2-chloro-N-[2-(dimethylamino)ethyl]-4-[5-phenyl-1-[2-(trifluoromethyl)phenyl]pyrrol-2-yl]benzamide hydrochloride | A | (DMSO-d$_6$) δ 10.14 (br s, 1H), 8.66 (t, 1H), 7.90-7.80 (m, 3H), 7.73-7.69 (m, 1H), 7.40 (d, 1H), 7.21-7.16 (m, 3H), 7.10-7.04 (m, 4H), 6.74 (d, 1H), 6.58 (d, 1H), 3.56-3.54 (m, 2H), 3.19-3.15 (m, 2H) and 2.80 (s, 6H). | 4.80 | 512 | A |
| 40 | 4-[5-(4-bromophenyl)-1-[2-[(dimethylamino)methyl]phenyl]pyrrol-2-yl]-N-[2-(dimethylamino)ethyl]benzamide hydrochloride | C | (DMSO-d$_6$) δ 11.22 (br s, 1H), 10.33 (br s, 1H), 8.84 (t, 1H), 8.06 (s, 1H), 7.78-7.77 (m, 3H), 7.57-7.56 (m, 2H), 7.43 (d, 2H), 7.23 (d, 2H), 7.10 (d, 2H), 6.76 (d, 1H), 6.70 (d, 1H), 3.60-3.58 (m, 2H), 3.51 (d, 1H), 3.44 (d, 1H), 3.23-3.22 (m, 2H), 2.79 (s, 6H) and 2.37 (d, 6H). | 4.12 | 545 | A |
| 41 | 4-[5-(4-bromophenyl)-1-[4-(trifluoromethyl)-3-pyridyl]pyrrol-2-yl]-N-[2-(dimethylamino)ethyl]benzamide hydrochloride | C | (DMSO-d$_6$) δ 9.82 (br s, 1H), 9.24 (s, 1H), 8.92 (d, 1H), 8.72 (t, 1H), 7.81 (d, 1H), 7.75 (d, 2H), 7.46 (d, 2H), 7.17 (d, 2H), 7.04 (d, 2H), 6.72 (d, 1H), 6.66 (d, 1H), 3.57-3.54 (m, 2H), 3.24-3.20 (m, 2H) and 2.80 (s, 6H). | 4.84 | 557 | A |
| 42 | N-[2-(dimethylamino)ethyl]-4-[5-(6-fluoro-3-pyridyl)-1-[2-(trifluoromethyl)phenyl]pyrrol-2-yl]benzamide hydrochloride | G | (DMSO-d$_6$) δ 10.03 (br s, 1H), 8.76 (t, 1H), 7.96-7.92 (m, 2H), 7.86-7.80 (m, 2H), 7.75-7.70 (m, 3H), 7.61 (td, 1H), 7.15 (d, 2H), 7.09 (dd, 1H), 6.74 (d, 1H), 6.71-6.70 (d, 1H), 3.58 (q, 2H), 3.22 (t, 2H) and 2.79 (s, 6H). | 4.43 | 497 | A |
| 43 | 4-[5-(2,4-difluorophenyl)-1-[2-(trifluoromethyl)phenyl]pyrrol-2-yl]-N-[2-(dimethylamino)ethyl]benzamide hydrochloride | C | (DMSO-d$_6$) δ 10.48 (br s, 1H), 7.88 (br s, 1H), 7.68 (br s, 2H), 7.59-7.54 (m, 2H), 7.49-7.45 (m, 2H), 7.11 (d, 2H), 7.03-6.97 (m, 1H), 6.76-6.68 (m, 2H), 6.63 (d, 1H), 6.49 (d, 1H), 3.77 (br s, 2H), 3.34 (br s, 2H) and 2.91 (br s, 6H). | 4.78 | 514 | A |
| 44 | 4-[5-(4-bromophenyl)-1-[2-(trifluoromethyl)phenyl]pyrrol-2-yl]-N-[2-(dimethylamino)ethyl]-benzenesulfonamide hydrochloride | K | (DMSO-d$_6$) δ 10.49 (br s, 1H), 8.05 (br s, 1H), 7.84-7.81 (m, 3H), 7.75-7.72 (m, 1H), 7.64 (d, 2H), 7.42 (d, 2H), 7.23 (d, 2H), 7.01 (d, 2H), 6.78 (d, 1H), 6.65 (d, 1H), 3.09 (br s, 4H) and 2.72 (s, 6H). | 4.91 | 592 | A |
| 45 | 2-[[4-[5-(4-bromophenyl)-1-[2-(trifluoromethyl)phenyl]pyrrol-2-yl]phenyl]methoxy]-N,N-dimethyl-ethanamine hydrochloride | H | (DMSO-d$_6$) δ 9.69 (br s, 1H), 7.80-7.76 (m, 3H), 7.69-7.68 (m, 2H), 7.39 (d, 2H), 7.19 (d, 2H), 7.05 (d, 2H), 6.98 (d, 2H), 6.57 (d, 2H), 4.45 (s, 2H), 3.69 (s, 2H), 3.27 (s, 2H) and 2.74 (s, 6H). | 5.03 | 545 | A |
| 46 | N-[4-[5-(4-bromophenyl)-1-[2-(trifluoromethyl)phenyl]pyrrol-2-yl]phenyl]-3-(dimethylamino)propanamide hydrochloride | I | (DMSO-d$_6$) δ 10.30 (s, 1H), 9.87 (br s, 1H), 7.78-7.66 (m, 4H), 7.42-7.37 (m, 4H), 6.70-6.96 (m, 4H), 6.57 (d, 1H), 6.49 (d, 1H), 3.32 (q, 2H), 2.82 (t, 2H) and 2.76 (s, 6H). | 4.97 | 556 | A |
| 47 | 2-[4-[5-(4-bromophenyl)-1-[2-(trifluoromethyl)phenyl]pyrrol-2-yl]phenyl]acetic acid | J | (DMSO-d$_6$) δ 12.29 (s, 1H), 7.82-7.75 (m, 3H), 7.67 (t, 1H), 7.38 (d, 2H), 7.08 (d, 2H), 7.01-6.97 (m, 4H), 6.58 (d, 1H), 6.52 (d, 1H) and 3.48 (s, 2H). | 5.87 | 500 | A |
| 48 | 1-[[4-[5-(4-bromophenyl)-1-[2-(trifluoromethyl)phenyl]pyrrol-2-yl]phenyl]methyl]-4-methyl-piperazine hydrochloride | B | (DMSO-d$_6$) δ 12.23 (br s, 1H), 11.82 (br s, 1H), 7.82-7.78 (m, 3H), 7.72-7.68 (m, 1H), 7.45-7.38 (m, 4H), 7.09 (d, 2H), 6.99 (d, 2H), 6.62 (dd, 2H), 4.19 (s, 2H), 3.37 (br m, 8H) and 2.78 (s, 3H). | 5.02 | 556 | A |

TABLE 3-continued

| Ex. No. | Name | Synthetic Method | ¹H NMR | LC (RT) | MS (MH⁺) | LCMS Method |
|---|---|---|---|---|---|---|
| 49 | 4-[5-(4-chlorophenyl)-1-[4-(trifluoromethyl)-3-pyridyl]pyrrol-2-yl]-N-[2-(dimethylamino)ethyl]-benzamide hydrochloride | C | (DMSO-$d_6$) δ 9.57 (br s, 1H), 9.25 (s, 1H), 8.92 (d, 1H), 8.67 (t, 1H), 7.81 (d, 1H), 7.74 (d, 2H), 7.33 (d, 2H), 7.18 (d, 2H), 7.11 (d, 2H), 6.72 (d, 1H), 6.65 (d, 1H), 3.57 (q, 2H), 3.22 (br s, 2H) and 2.81 (s, 6H). | 4.85 | 513 | A |
| 50 | 4-[5-(4-bromophenyl)-1-[2-(methoxymethyl)phenyl]pyrrol-2-yl]-N-[2-(dimethylamino)ethyl]benzamide hydrochloride | C | (DMSO-$d_6$) δ 9.99 (br s, 1H), 8.73 (t, 1H), 8.72 (d, 2H), 7.46-7.44 (m, 2H), 7.41-7.38 (m, 4H), 7.17 (d, 2H), 7.04 (d, 2H), 6.69 (d, 1H), 6.62 (d, 1H), 3.76 (s, 2H), 3.58 (q, 2H), 3.22 (q, 2H), 3.01 (s, 3H) and 2.80 (s, 6H). | 5.03 | 532 | A |
| 51 | 4-[5-(4-chlorophenyl)-1-[4-(trifluoromethyl)-3-pyridyl]pyrrol-2-yl]-N-[3-(dimethylamino)propyl]benzamide hydrochloride | C | (DMSO-$d_6$) δ 10.12 (br s, 1H), 9.22 (s, 1H), 8.91 (1H, d), 8.62 (br s, 1H), 7.81 (d, 1H), 7.72 (d, 2H), 7.32 (d, 2H), 7.16 (d, 2H), 7.11 (d, 2H), 6.67 (d, 2H), 3.29 (br d, 2H), 3.05 (br s, 2H), 2.73 (d, 6H) and 1.88 (br s, 2H). | 4.84 | 527 | A |
| 52 | 3-[5-(4-bromophenyl)-1-[2-(trifluoromethyl)phenyl]pyrrol-2-yl]-N-[2-(dimethylamino)ethyl]-4-methoxy-benzamide hydrochloride | C | (DMSO-$d_6$) δ 8.67 (br s, 1H), 7.82-7.79 (m, 2H), 7.59-7.56 (m, 2H), 7.50 (t, 2H), 7.30 (d, 2H), 6.97 (d, 2H), 6.90 (d, 1H), 6.54 (d, 1H), 6.36 (d, 1H), 3.74 (q, 2H), 3.63 (s, 3H), 3.37 (t, 2H) and 2.99 (s, 6H). | 4.92 | 588 | A |
| 53 | 5-[5-(4-bromophenyl)-1-[2-(trifluoromethyl)phenyl]pyrrol-2-yl]-N-[2-(dimethylamino)ethyl]-2-methoxy-benzamide hydrochloride | A | (DMSO-$d_6$) δ 9.71 (br s, 1H), 8.43 (t, 1H), 7.78-7.75 (m, 3H), 7.69-7.65 (m, 1H), 7.62 (t, 1H), 7.39-7.37 (m, 2H), 7.10 (dd, 1H), 6.99-6.96 (m, 3H), 6.57 (d, 1H), 6.47 (d, 1H), 3.82 (s, 3H), 3.62-3.57 (m, 2H), 3.20 (t, 2H) and 2.81 (s, 6H). | 5.01 | 586 | A |
| 54 | [3-[5-(4-bromophenyl)-1-[2-(trifluoromethyl)phenyl]pyrrol-2-yl]phenyl]-[(3R)-3-(dimethylamino)pyrrolidin-1-yl]methanone hydrochloride | A | (DMSO-$d_6$) δ 10.68 (br s, 1H), 7.79 (m, 3H), 7.71-7.70 (m, 1H), 7.39 (d, 2H), 7.29 (s, 2H), 7.18-7.14 (m, 2H), 6.98 (d, 2H), 6.60 (s, 2H), 3.86-3.82 (m, 1H), 3.64-3.61 (m, 2H), 3.25-3.22 (m, 1H), 2.79-2.69 (m, 6H) and 2.22-2.16 (m, 2H). | 4.95 | 582 | A |
| 55 | [3-[5-(4-bromophenyl)-1-[2-(trifluoromethyl)phenyl]pyrrol-2-yl]phenyl]-[(3S)-3-(dimethylamino)pyrrolidin-1-yl]methanone hydrochloride | A | (DMSO-$d_6$) δ 10.89 (br s, 1H), 7.81-7.77 (m, 3H), 7.72-7.70 (m, 1H), 7.39 (d, 2H), 7.29-7.14 (m, 4H), 6.98 (d, 2H), 6.61 (s, 2H), 3.85-3.81 (m, 2H), 3.66-3.62 (m, 2H), 3.25-3.18 (m, 1H), 2.80-2.70 (m, 6H) and 2.33-1.99 (m, 2H). | 4.91 | 582 | A |
| 56 | 3-[1-(2-aminophenyl)-5-(4-bromophenyl)pyrrol-2-yl]-N-[2-(dimethylamino)ethyl]benzamide hydrochloride | A | (DMSO-$d_6$) δ 10.19 (br s, 1H), 8.84 (t, 1H), 7.95 (s, 1H), 7.68 (dt, 1H), 7.40 (d, 2H), 7.26-7.15 (m, 4H), 7.08 (td, 1H), 6.91 (dd, 1H), 6.71 (dd, 1H), 6.68 (d, 1H), 6.62 (d, 1H), 6.52 (td, 1H), 3.65-3.60 (m, 2H), 3.27-3.23 (m, 2H) and 2.84 (d, 6H, —CH₃). | 4.83 | 505 | A |
| 57 | 4-[5-(4-cyanophenyl)-1-[2-(trifluoromethyl)phenyl]pyrrol-2-yl]-N-[2-(dimethylamino)ethyl]benzamide hydrochloride | C | (DMSO-$d_6$) δ 10.15 (br s, 1H), 8.78 (d, 1H), 7.89-7.82 (m, 3H), 7.76-7.74 (m, 3H), 7.66 (d, 2H), 7.20 (d, 2H), 7.14 (d, 2H), 6.83 (d, 1H), 6.74 (d, 1H), 3.60-3.57 (m, 2H), 3.23 (s, 2H) and 2.80 (s, 6H). | 4.56 | 503 | A |
| 58 | 4-[5-(4-chlorophenyl)-1-[2-(trifluoromethyl)phenyl]pyrrol-2-yl]-N-[3-(dimethylamino)propyl]benzamide hydrochloride | C | (DMSO-$d_6$) δ 9.73 (br s, 1H), 8.55 (t, 1H), 7.85-7.79 (m, 3H), 7.72-7.65 (m, 3H), 7.28 (d, 2H), 7.12 (d, 2H), 7.06 (d, 2H), 6.69 (d, 1H), 6.62 (d, 1H), 3.31-3.26 (m, 2H), 3.07-3.03 (m, 2H), 2.74 (s, 6H) and 1.90-1.82 (m, 2H). | 4.95 | 526 | A |
| 59 | N-[2-(dimethylamino)ethyl]-4-[5-(4-fluorophenyl)-1-[2-(trifluoromethyl)phenyl]pyrrol-2-yl]benzamide hydrochloride | A | (DMSO-$d_6$) δ 9.52 (br s, 1H), 8.63 (t, 1H), 7.86-7.77 (m, 3H), 7.69 (d, 3H), 7.14-7.04 (m, 6H), 6.69 (d, 1H), 6.56 (d, 1H), 3.59-3.54 (m, 2H), 3.23-3.21 (m, 2H) and 2.81 (d, 6H). | 4.79 | 496 | A |
| 60 | N-[3-(dimethylamino)propyl]-4-[5-(4-fluorophenyl)-1-[2-(trifluoromethyl)phenyl]pyrrol-2-yl]benzamide hydrochloride | A | (DMSO-$d_6$) δ 9.65 (br s, 1H), 8.54 (t, 1H), 7.85-7.77 (m, 3H), 7.71-7.65 (m, 3H), 7.13-7.04 (m, 6H), 6.67 (d, 1H), 6.55 (d, 1H), 3.29 (q, 2H), 3.08-3.03 (m, 2H), 2.75 (d, 6H) and 1.88-1.81 (m, 2H). | 4.79 | 510 | A |
| 61 | 6-[5-(4-chlorophenyl)-1-[2-(trifluoromethyl)phenyl]pyrrol-2-yl]-N-[2-(dimethylamino)ethyl]pyridine-3-carboxamide hydrochloride | G | (DMSO-$d_6$) δ 9.71 (br s, 1H), 8.77 (t, 1H), 8.50 (d, 1H), 8.10 (dd, 1H), 7.77-7.72 (m, 2H), 7.68-7.62 (m, 3H), 7.28 (d, 2H), 7.16 (d, 1H), 7.09 (d, 2H), 6.64 (d, 1H), 3.57 (br d, 2H), 3.22 (br d, 2H) and 2.80 (d, 6H). | 4.85 | 513 | A |
| 62 | 6-[5-(4-chlorophenyl)-1-[2-(trifluoromethyl)phenyl]pyrrol-2-yl]-N-[3-(dimethylamino)propyl]-pyridine-3-carboxamide hydrochloride | G | (DMSO-$d_6$) δ 10.09 (br s, 1H), 8.69 (t, 1H), 8.49 (d, 1H), 8.08 (dd, 1H), 7.78-7.72 (m, 2H), 7.68-7.61 (m, 3H), 7.29-7.27 (m, 2H), 7.16 (d, 1H), 7.09 (d, 2H), 6.64 (d, 1H), 3.28 (q, 2H), 3.07-3.02 (m, 2H), 2.72 (d, 6H) and 1.90-1.83 (m, 2H). | 4.88 | 527 | A |
| 63 | 4-[5-(4-chlorophenyl)-1-[5-isobutyl-2-(trifluoromethyl)phenyl]pyrrol-2-yl]-N-[2-(dimethylamino)ethyl]-benzamide hydrochloride | C | (DMSO-$d_6$) δ 10.01 (br s, 1H), 8.72 (t, 1H), 7.72-7.63 (m, 4H), 7.47 (d, 1H), 7.26 (d, 2H), 7.15 (d, 2H), 7.09 (d, 2H), 6.68 (d, 1H), 6.60 (d, 1H), 3.58 (q, 2H), 3.22 (q, 2H), 2.80 (s, 6H), 2.57 (d, 2H), 1.84-1.81 (m, 1H) and 0.76 (d, 6H). | 5.17 | 568 | A |
| 64 | 4-[5-(4-chlorophenyl)-1-[5-isobutyl-2-(trifluoromethyl)phenyl]pyrrol-2-yl]-N-[3-(dimethylamino)propyl]-benzamide hydrochloride | C | (DMSO-$d_6$) δ 9.47 (br s, 1H), 8.52 (t, 1H), 7.69-7.62 (m, 4H), 7.47 (d, 1H), 7.26 (d, 2H), 7.15-7.07 (m, 4H), 6.68 (d, 1H), 6.60 (d, 1H), 3.28 (t, 2H), 3.05 (t, 2H), 2.76 (s, 6H), 2.58 (d, 2H), 1.84-1.79 (m, 3H) and 0.76 (d, 6H). | 5.28 | 582 | A |
| 65 | 4-[5-(4-bromophenyl)-1-[2-(trifluoromethyl)phenyl]pyrrol-2-yl]benzenesulfonamide | K | (DMSO-$d_6$) δ 7.89-7.79 (m, 3H), 7.73-7.69 (m, 1H), 7.62 (d, 2H), 7.41 (d, 2H), 7.31 (s, 2H), 7.21 (d, 2H), 7.01 (d, 2H), 6.72 (d, 1H), 6.63 (d, 1H). | 5.46 | 521 | A |
| 66 | 4-[5-(6-cyano-3-pyridyl)-1-[2-(trifluoromethyl)phenyl]pyrrol-2-yl]-N-[2-(dimethylamino)ethyl]-benzamide hydrochloride | A | (DMSO-$d_6$) δ 9.94 (br s, 1H), 8.76 (t, 1H), 8.50 (s, 1H), 7.96 (d, 1H), 7.90-7.85 (m, 3H), 7.80-7.74 (m, 3H), 7.46 (dd, 1H), 7.17 (d, 2H), 7.03 (d, 1H), 6.80 (d, 1H), 3.58 (br d, 2H), 3.22 (br s, 2H) and 2.80 (s, 6H). | 4.37 | 504 | A |

TABLE 3-continued

| Ex. No. | Name | Synthetic Method | $^1$H NMR | LC (RT) | MS (MH$^+$) | LCMS Method |
|---|---|---|---|---|---|---|
| 67 | 3-chloro-N-[2-(dimethylamino)-ethyl]-4-[5-phenyl-1-[4-(trifluoromethyl)-3-pyridyl]pyrrol-2-yl]benzamide hydrochloride | A | (DMSO-d$_6$) δ 9.90 (br s, 1H), 9.07 (s, 1H), 8.91 (t, 1H), 8.81 (d, 1H), 7.99 (d, 1H), 7.73 (d, 1H), 7.68 (dd, 1H), 7.27-7.18 (m, 4H), 7.10-7.08 (m, 2H), 6.65-6.63 (m, 2H), 3.61-3.57 (m, 2H), 3.23 (q, 2H) and 2.81 (d, 6H). | 5.00 | 513 | A |
| 68 | 3-chloro-N-[3-(dimethylamino)-propyl]-4-[5-phenyl-1-[4-(trifluoromethyl)-3-pyridyl]pyrrol-2-yl]benzamide hydrochloride | A | (DMSO-d$_6$) δ 9.79 (br s, 1H), 9.06 (s, 1H), 8.81 (d, 1H), 8.75 (t, 1H), 7.92 (d, 1H), 7.73 (d, 1H), 7.63 (dd, 1H), 7.30-7.18 (m, 4H), 7.10-7.08 (m, 2H), 6.64-6.62 (m, 2H), 3.31-3.27 (q, 2H), 3.09-3.03 (m, 2H), 2.75 (d, 6H) and 1.90-1.82 (m, 2H). | 5.00 | 527 | A |
| 69 | 6-[5-(4-chlorophenyl)-1-[4-(trifluoromethyl)-3-pyridyl]pyrrol-2-yl]-N-[2-(dimethylamino)ethyl]-pyridine-3-carboxamide hydrochloride | G | (DMSO-d$_6$) δ 9.94 (br s, 1H), 8.98 (s, 1H) 8.88-8.82 (m, 2H), 8.44 (d, 1H), 8.18 (dd, 1H), 7.90 (d, 1H), 7.79 (d, 1H), 7.33 (d, 2H), 7.25 (d, 1H), 7.14 (d, 2H), 6.68 (d, 1H), 3.60-3.56 (m, 2H), 3.22 (q, 2H) and 2.79 (d, 6H). | 4.70 | 514 | A |
| 70 | 4-[5-(4-chlorophenyl)-1-[2-(trifluoromethyl)phenyl]pyrrol-2-yl]-N-[(3R)-1-methylpyrrolidin-3-yl]benzamide hydrochloride | C | (DMSO-d$_6$) δ 10.71 (br s, 1H), 8.72 (d, 1H), 7.85-7.79 (m, 3H), 7.69 (q, 3H), 7.28 (d, 2H), 7.12 (d, 2H), 7.06 (d, 2H), 6.70 (d, 1H), 6.62 (d, 1H), 4.62-4.50 (br d, 1H), 3.82-3.66 (br d, 1H), 3.30-3.20 (br d, 1H), 3.03 (br d, 1H), 2.83 (br s, 3H), 2.33 (br s, 1H), 2.19 (br d, 1H) and 2.05 (br d, 1H). | 4.88 | 524 | A |
| 71 | 4-[5-(4-chlorophenyl)-1-[2-(trifluoromethyl)phenyl]pyrrol-2-yl]-N-[(3S)-1-methylpyrrolidin-3-yl]benzamide hydrochloride | C | (DMSO-d$_6$) δ 10.84 (br s, 1H), 8.74 (d, 1H), 7.84-7.78 (m, 3H), 7.75-7.69 (m, 3H), 7.27 (d, 2H), 7.12 (d, 2H), 7.06 (d, 2H), 7.06 (d, 1H), 6.62 (d, 1H), 4.64-4.52 (br d, 1H), 3.82-3.67 (br d, 1H), 3.51 (br s, 1H), 3.31 (br d, 1H), 3.06 (br s, 1H), 2.83 (br s, 3H), 2.44 (s, 1H) and 2.00 (d, 1H). | 4.89 | 524 | A |
| 72 | 4-[5-(3-chlorophenyl)-1-[2-(trifluoromethyl)phenyl]pyrrol-2-yl]-N-[2-(dimethylamino)ethyl]-benzamide hydrochloride | C | (DMSO-d$_6$) δ 10.01 (br s, 1H), 8.75 (t, 1H), 7.89-7.80 (m, 3H), 7.74-7.72 (m, 3H), 7.23-7.22 (m, 2H), 7.15-7.13 (m, 2H), 7.06-7.01 (m, 2H), 6.70 (d, 1H), 3.59-3.56 (m, 2H), 3.22 (t, 2H) and 2.80 (s, 6H). | 5.73 | 512 | A |
| 73 | 4-[5-(4-chlorophenyl)-1-[4-(trifluoromethyl)-3-pyridyl]pyrrol-2-yl]-N-[2-(dimethylamino)ethyl]-3-methoxy-benzamide hydrochloride | A | (DMSO-d$_6$) δ 9.93 (s, 1H), 8.85 (d, 2H), 8.77 (d, 1H), 7.70 (d, 1H), 7.45 (dd, 1H), 7.36 (d, 1H), 7.28 (d, 3H), 7.07 (d, 1H), 6.61 (d, 1H), 6.44 (d, 1H), 3.63-3.59 (m, 2H), 3.56 (s, 3H), 3.24 (br d, 2H) and 2.82 (d, 6H). | 5.79 | 543 | A |
| 74 | 4-[5-(4-chlorophenyl)-1-[4-(trifluoromethyl)-3-pyridyl]pyrrol-2-yl]-N-[3-(dimethylamino)propyl]-3-methoxy-benzamide hydrochloride | A | (DMSO-d$_6$) δ 9.90 (s, 1H), 8.85 (s, 1H), 8.77 (d, 1H), 8.68 (br s, 1H), 7.70 (d, 1H), 7.41-7.39 (d, 1H), 7.32-7.24 (m, 4H), 7.06 (d, 1H), 6.61 (d, 1H), 6.43 (d, 1H), 3.56 (s, 3H), 3.30 (d, 2H), 3.06 (t, 2H), 2.75 (s, 6H) and 1.88 (t, 2H). | 5.81 | 557 | A |
| 75 | 4-[5-(5-chloro-2-pyridyl)-1-[2-(trifluoromethyl)phenyl]pyrrol-2-yl]-N-[2-(dimethylamino)ethyl]-benzamide hydrochloride | G | (DMSO-d$_6$) δ 9.85 (br s, 1H), 8.72 (t, 1H), 8.08 (d, 1H), 7.81-7.64 (m, 7H), 7.52 (d, 1H), 7.16 (d, 2H), 7.06 (d, 1H), 6.71 (d, 1H), 3.60 (q, 2H), 3.21 (q, 2H) and 2.80 (d, 6H). | 5.13 | 513 | A |
| 76 | 4-[5-(5-chloro-2-pyridyl)-1-[2-(trifluoromethyl)phenyl]pyrrol-2-yl]-N-[3-(dimethylamino)propyl]-benzamide hydrochloride | G | (DMSO-d$_6$) δ 9.99 (br s, 1H), 8.60 (t, 1H), 8.08 (d, 1H), 7.81-7.73 (m, 3H), 7.66 (t, 4H), 7.52 (d, 1H), 7.14 (d, 2H), 7.06 (d, 1H), 6.70 (d, 1H), 3.28 (q, 2H), 3.07-3.02 (m, 2H), 2.73 (d, 6H) and 1.89-1.82 (m, 2H). | 5.16 | 527 | A |
| 77 | 4-[5-(4-chlorophenyl)-1-[3-(trifluoromethyl)phenyl]pyrrol-2-yl]-N-[2-(dimethylamino)ethyl]-benzamide hydrochloride | C | (DMSO-d$_6$) δ 10.11 (s, 1H), 8.78 (t, 1H), 7.78-7.74 (m, 3H), 7.60 (t, 1H), 7.52 (s, 1H), 7.42 (s, 1H), 7.31 (d, 2H), 7.14 (d, 2H), 7.08 (d, 2H), 6.67 (d, 1H), 6.60 (d, 1H), 3.60 (q, 2H), 3.23 (t, 2H) and 2.80 (s, 6H). | 4.93 | 512 | A |
| 78 | 4-[5-(4-chlorophenyl)-1-[3-(trifluoromethyl)phenyl]pyrrol-2-yl]-N-[3-(dimethylamino)propyl]-benzamide hydrochloride | C | (DMSO-d$_6$) δ 10.26 (s, 1H), 8.63 (t, 1H), 7.76-7.71 (m, 3H), 7.60 (t, 1H), 7.51 (s, 1H), 7.42 (d, 1H), 7.32-7.30 (d, 2H), 7.13 (d, 2H), 7.07 (d, 2H), 6.65 (d, 1H), 6.59 (d, 1H), 3.30 (q, 2H), 3.05 (t, 2H), 2.73 (s, 6H) and 1.92-1.87 (m, 2H). | 4.93 | 526 | A |
| 79 | 4-[5-(4-chlorophenyl)-1-[3-(trifluoromethyl)-2-pyridyl]pyrrol-2-yl]-N-[2-(dimethylamino)ethyl]-benzamide hydrochloride | C | (DMSO-d$_6$) δ 11.77 (s, 1H), 10.00 (br s, 1H), 8.83 (d, 2H), 8.30 (d, 1H), 7.95 (q, 4H), 7.62 (q, 1H), 7.34 (d, 2H), 7.22 (d, 2H), 6.86 (s, 1H), 3.65 (q, 2H), 3.28 (q, 2H) and 2.85 (d, 6H). | 4.85 | 513 | A |
| 80 | 4-[5-(4-chlorophenyl)-1-[3-(trifluoromethyl)-2-pyridyl]pyrrol-2-yl]-N-[3-(dimethylamino)propyl]-benzamide hydrochloride | C | (DMSO-d$_6$) δ 11.77 (s, 1H), 10.32 (br s, 1H), 8.83 (d, 1H), 8.72 (t, 1H), 8.30 (d, 1H), 7.92 (s, 4H), 7.63 (q, 1H), 7.34 (d, 2H), 7.22 (d, 2H), 6.85 (s, 1H), 3.36 (q, 2H), 3.12-3.07 (m, 2H), 2.76 (s, 6H) and 1.98-1.91 (m, 2H). | 4.92 | 527 | A |
| 81 | 4-[5-(4-chlorophenyl)-1-[4-(trifluoromethyl)-3-pyridyl]pyrrol-2-yl]-N-(2-morpholinoethyl)-benzamide hydrochloride | C | (DMSO-d$_6$) δ 10.82 (br s, 1H), 9.24 (s, 1H), 8.92 (d, 1H), 8.86 (t, 1H), 7.82-7.77 (m, 3H), 7.33-7.31 (m, 2H), 7.17 (d, 2H), 7.12-7.10 (m, 2H), 6.72 (d, 1H), 6.65 (d, 1H), 3.97 (d, 2H), 3.80 (t, 2H), 3.66-3.64 (m, 2H), 3.53 (d, 2H), 3.28-3.26 (m, 2H) and 3.13-3.06 (m, 2H). | 5.79 | 555 | A |
| 82 | 4-[4-(4-chlorophenyl)-5-[2-(trifluoromethyl)phenyl]pyrazol-1-yl]-N-[2-(dimethylamino)ethyl]-benzamide hydrochloride | L | (DMSO-d$_6$) δ 9.79 (br s, 1H), 8.81 (s, 1H), 8.31 (s, 1H), 7.85-7.83 (m, 5H), 7.78-7.77 (m, 1H), 7.33 (d, 2H), 7.31 (d, 2H), 7.15 (d, 2H), 3.58 (br d, 2H), 3.23 (br s, 2H) and 2.81 (s, 6H). | 5.04 | 513 | A |
| 83 | 4-[5-(4-chlorophenyl)-1-[2-(trifluoromethyl)phenyl]pyrrol-2-yl]-N-[2-(dimethylamino)ethyl]-N-methyl-benzamide hydrochloride | C | (DMSO-d$_6$) δ 9.79 (br s, 1H), 8.81 (s, 1H), 8.31 (s, 1H), 7.85-7.83 (m, 5H), 7.78-7.77 (m, 1H), 7.33 (d, 2H), 7.31 (d, 2H), 7.15 (d, 2H), 3.58 (br d, 2H), 3.23 (br s, 2H) and 2.81 (s, 6H). | 5.48 | 526 | A |
| 84 | [4-[5-(4-chlorophenyl)-1-[2-(trifluoromethyl)phenyl]pyrrol-2-yl]phenyl]-piperazin-1-yl-methanone hydrochloride | C | (DMSO-d$_6$) δ 9.36 (br s, 2H), 7.81-7.79 (m, 3H), 7.73-7.70 (m, 1H), 7.31-7.26 (m, 4H), 7.10 (d, 2H), 7.06 (d, 2H), 6.66 (d, 1H), 6.61 (d, 1H), 3.65 (br s, 4H) and 3.11 (br s, 4H). | 5.29 | 510 | A |

TABLE 3-continued

| Ex. No. | Name | Synthetic Method | ¹H NMR | LC (RT) | MS (MH⁺) | LCMS Method |
|---|---|---|---|---|---|---|
| 85 | [4-[5-(4-chlorophenyl)-1-[2-(trifluoromethyl)phenyl]pyrrol-2-yl]phenyl]-(4-methylpiperazin-1-yl)methanone hydrochloride | C | (DMSO-d₆) δ 7.75-7.59 (m, 4H), 7.33 (d, 2H), 7.22-7.17 (m, 4H), 7.06 (d, 2H), 6.64 (d, 1H), 6.56 (d, 1H), 3.37 (br s, 4H), 3.06 (br s, 4H) and 2.74 (s, 3H). | 5.41 | 524 | A |
| 86 | 4-[5-(4-chlorophenyl)-1-[2-(trifluoromethyl)phenyl]pyrrol-2-yl]-N-(2-methoxyethyl)benzamide | C | (DMSO-d₆) δ 8.42 (t, 1H), 7.82-7.78 (m, 3H), 7.72-7.64 (m, 3H), 7.27 (d, 2H), 7.11-7.05 (m, 4H), 6.68 (d, 1H), 6.61 (d, 1H), 3.41-3.34 (m, 4H) and 3.24 (s, 3H). | 6.12 | 499 | A |
| 87 | 4-[5-(4-chlorophenyl)-1-[2-(trifluoromethyl)phenyl]pyrrol-2-yl]-N-(2-piperazin-1-ylethyl)benzamide hydrochloride | C | (DMSO-d₆) δ 11.34 (br s, 2H), 9.61 (br s, 2H), 8.73 (s, 1H), 7.83-7.77 (m, 3H), 7.74-7.72 (m, 3H), 7.28 (d, 2H), 7.12 (d, 2H), 7.06 (d, 2H), 6.70 (d, 1H), 6.62 (d, 1H), 3.60 (br s, 3H), 3.41-3.28 (m, 6H) and 3.16 (br s, 3H). | 5.28 | 553 | A |
| 88 | 4-[5-(4-chlorophenyl)-1-[2-(trifluoromethyl)phenyl]pyrrol-2-yl]-N-[2-(4-methylpiperazin-1-yl)ethyl]benzamide hydrochloride | C | (DMSO-d₆) δ 10.85 (br s, 2H), 8.66 (br s, 1H), 7.86-7.79 (m, 3H), 7.73-7.69 (m, 3H), 7.28 (d, 2H), 7.13 (d, 2H), 7.06 (d, 2H), 6.70 (d, 1H), 6.62 (d, 1H), 3.77 (t, 2H), 3.52-3.50 (m, 4H), 3.24 (br s, 6H) and 2.83 (s, 3H). | 5.34 | 567 | A |
| 89 | 4-[5-(4-chlorophenyl)-1-[4-(trifluoromethyl)-3-pyridyl]pyrrol-2-yl]-N-[2-(dimethylamino)ethyl]-3-fluoro-benzamide hydrochloride | C | (DMSO-d₆) δ 9.88 (br s, 1H), 9.08 (s, 1H), 8.88 (s, 1H), 8.86 (d, 1H), 7.78 (d, 1H), 7.67-7.61 (m, 2H), 7.33 (d, 2H), 7.27 (t, 1H), 7.10 (d, 2H), 6.67 (dd, 2H), 3.64-3.57 (m, 2H), 3.24-3.22 (m, 2H) and 2.80 (s, 6H). | 5.04 | 531 | A |
| 90 | 1-[4-[5-(4-chlorophenyl)-1-[2-(trifluoromethyl)phenyl]pyrrol-2-yl]phenyl]-3-[2-(dimethylamino)-ethyl]urea hydrochloride | N | (DMSO-d₆) δ 10.85 (br s, 2H), 8.66 (br s, 1H), 7.86-7.79 (m, 3H), 7.73-7.69 (m, 3H), 7.28 (d, 2H), 7.14-7.12 (d, 2H), 7.06 (d, 2H), 6.70 (d, 1H), 6.62 (d, 1H), 3.77 (t, 2H), 3.52-3.50 (m, 4H), 3.24 (br s, 6H) and 2.83 (s, 3H). | 5.29 | 527 | A |
| 91 | 2-[4-[5-(4-chlorophenyl)-1-[2-(trifluoromethyl)phenyl]pyrrol-2-yl]phenyl]-N-[2-(dimethylamino)-ethyl]acetamide hydrochloride | A | (DMSO-d₆) δ 9.80 (br s, 1H), 8.35 (t, 1H), 7.83-7.76 (m, 3H), 7.68 (t, 1H), 7.26 (d, 2H), 7.10-7.03 (m, 4H), 6.69 (d, 2H), 6.57 (d, 1H), 6.51 (d, 1H), 3.57 (s, 2H), 3.37 (d, 2H), 3.10 (t, 2H) and 2.51 (d, 6H). | 5.36 | 526 | A |
| 92 | 4-[3-(4-chlorophenyl)-4-[2-(trifluoromethyl)phenyl]isoxazol-5-yl]-N-[2-(dimethylamino)ethyl]-benzamide hydrochloride | O | (DMSO-d₆) δ 10.06-9.94 (br d, 2H), 8.96 (dt, 2H), 8.13 (d, 1H), 8.06 (d, 1H), 8.01 (d, 1H), 7.96-7.88 (m, 5H), 7.84-7.76 (m, 4H), 7.67 (t, 1H), 7.54-7.45 (m, 6H), 7.37 (d, 2H), 3.68-3.57 (br m, 4H), 3.30-3.24 (br d, 4H) and 2.83 (br d, 6H). | 4.96 | 514 | A |
| 93 | 4-[3-(4-chlorophenyl)-4-[2-(trifluoromethyl)phenyl]-1H-pyrazol-5-yl]-N-[2-(dimethylamino)ethyl]benzamide hydrochloride | M | (DMSO-d₆) δ 10.03 (br s, 1H), 8.79 (t, 1H), 7.87-7.86 (m, 1H), 7.81-7.77 (m, 3H), 7.72-7.68 (m, 1H), 7.60-7.58 (m, 1H), 7.38-7.32 (m, 4H), 7.29-7.27 (m, 2H), 3.59 (q, 2H), 3.23 (q, 2H) and 2.80 (d, 6H). | 4.81 | 513 | A |
| 94 | N-(2-aminoethyl)-4-[5-(4-chlorophenyl)-1-[2-(trifluoromethyl)-phenyl]pyrrol-2-yl]benzamide hydrochloride | C | (DMSO-d₆) δ 8.69 (br s, 1H), 8.07 (br s, 3H), 7.83-7.72 (m, 6H), 7.28 (d, 2H), 7.12-7.05 (m, 4H), 6.65 (dd, 2H), 3.47 (br s, 2H) and 2.95 (br s, 2H). | 5.40 | 484 | A |
| 95 | 4-[5-(4-chlorophenyl)-1-[2-(trifluoromethyl)phenyl]pyrrol-2-yl]-N-(2-morpholinoethyl)benzamide hydrochloride | C | (DMSO-d₆) δ 10.63 (br s, 1H), 8.79 (s, 1H), 7.86-7.79 (m, 3H), 7.74-7.69 (m, 3H), 7.27 (d, 2H), 7.13 (d, 2H), 7.07 (s, 2H), 6.71 (d, 1H), 6.62 (d, 1H), 3.97 (d, 2H), 3.77 (t, 2H), 3.63 (d, 2H), 3.52 (d, 2H), 3.26 (br s, 2H) and 3.09 (d, 2H). | 5.30 | 554 | A |
| 96 | 4-[5-(4-chlorophenyl)-1-(4-trifluoromethyl-3-pyridyl)pyrrol-2-yl]-N-[2-[[(3S)-tetrahydrofuran-3-yl]amino]ethyl]-benzamide hydrochloride | C | (DMSO-d₆) δ 9.25 (s, 1H), 9.04 (br s, 2H), 8.92 (d, 1H), 8.70 (br s, 1H), 7.81 (d, 1H), 7.76 (d, 2H), 7.32 (d, 2H), 7.17 (d, 2H), 7.11 (d, 2H), 6.72 (d, 1H), 6.65 (d, 1H), 3.91-3.84 (br m, 3H), 3.78-3.76 (br m, 1H), 3.65-3.63 (br m, 1H), 3.55-3.54 (br m, 2H), 3.08 (br s, 2H) and 2.21-2.18 (br m, 2H). | 5.11 | 555 | A |
| 97 | 4-[5-(4-chlorophenyl)-1-[4-fluoro-2-(trifluoromethyl)phenyl]pyrrol-2-yl]-N-[2-(dimethylamino)ethyl]-benzamide hydrochloride | C | (DMSO-d₆) δ 10.03 (br s, 1H), 8.77 (t, 1H), 8.02-7.99 (m, 1H), 7.77-7.70 (m, 4H), 7.31 (dd, 2H), 7.15 (d, 2H), 7.09 (dd, 2H), 6.69 (d, 1H), 6.22 (d, 1H), 3.61-3.57 (m, 2H), 3.22 (t, 2H) and 2.80 (s, 6H). | 5.04 | 530 | A |
| 98 | 4-[5-(4-chlorophenyl)-1-[4-chloro-2-(trifluoromethyl)phenyl]pyrrol-2-yl]-N-[2-(dimethylamino)ethyl]-benzamide hydrochloride | C | (DMSO-d₆) δ 9.97 (br s, 1H), 8.82 (t, 1H), 7.90-7.82 (m, 4H), 7.64 (d, 1H), 7.27 (d, 2H), 7.09 (d, 2H), 6.82 (d, 1H), 6.76 (d, 1H), 6.63 (d, 1H), 3.53-3.50 (m, 2H), 3.20 (t, 2H) and 2.78 (s, 6H). | 5.29 | 546 | A |
| 99 | 5-[5-(4-chlorophenyl)-1-[2-(trifluoromethyl)phenyl]pyrrol-2-yl]-N-[2-(dimethylamino)ethyl]-thiophene-2-carboxamide hydrochloride | A | (DMSO-d₆) δ 9.97 (br s, 1H), 8.82 (t, 1H), 7.90-7.82 (m, 4H), 7.64 (d, 1H), 7.27 (d, 2H), 7.09 (d, 2H), 6.82 (d, 1H), 6.77 (d, 1H), 6.63 (d, 1H), 3.53-3.50 (m, 2H), 3.20 (t, 2H) and 2.78 (s, 6H). | 4.96 | 518 | A |
| 100 | 2-[4-[5-(4-chlorophenyl)-1-[2-(trifluoromethyl)phenyl]pyrrol-2-yl]phenyl]-N-(2-morpholinoethyl)-acetamide hydrochloride | A | (DMSO-d₆) δ 9.97 (br s, 1H), 8.82 (t, 1H), 7.90-7.82 (m, 4H), 7.64 (d, 1H), 7.27 (d, 2H), 7.09 (d, 2H), 6.82 (d, 1H), 6.76 (d, 1H), 6.63 (d, 1H), 3.53-3.50 (m, 2H), 3.19 (t, 2H) and 2.78 (s, 6H). | 8.18 | 568 | A |
| 101 | 2-[4-[5-(4-chlorophenyl)-1-[2-(trifluoromethyl)phenyl]pyrrol-2-yl]phenyl]-N-(2-piperazin-1-ylethyl)acetamide hydrochloride | A | (DMSO-d₆) δ 11.58 (br s, 1H), 9.59 (br s, 2H), 8.38 (s, 1H), 7.83-7.76 (m, 3H), 7.68 (t, 1H), 7.25 (dd, 2H), 7.09 (d, 2H), 7.04 (dd, 2H), 6.99 (d, 2H), 6.57 (d, 1H), 6.51 (d, 1H), 3.73 (br s, 2H), 3.57 (br s, 4H), 3.41 (br s, 2H), 3.38 (br s, 2H) and 3.21 (br s, 4H). | 5.78 | 567 | A |

TABLE 3-continued

| Ex. No. | Name | Synthetic Method | ¹H NMR | LC (RT) | MS (MH⁺) | LCMS Method |
|---|---|---|---|---|---|---|
| 102 | [3-[5-(4-bromophenyl)-1-[2-(trifluoromethyl)phenyl]pyrrol-2-yl]phenyl]-[4-(3-pyridylmethyl)-1-piperidyl]methanone hydrochloride | A | (DMSO-$d_6$) δ 8.79-8.76 (m, 2H), 8.37 (d, 1H), 7.96-7.93 (m, 1H), 7.81-7.76 (m, 3H), 7.70-7.66 (m, 1H), 7.40 (d, 2H), 7.27 (t, 1H), 7.13 (d, 2H), 6.70-6.96 (m, 3H), 6.61 (s, 2H), 4.34 (br s, 1H), 3.18 (br s, 1H), 2.75-2.73 (m, 3H), 1.89-1.82 (m, 1H), 1.59-1.53 (m, 1H), 1.44 (br s, 2H), 1.10 (br s, 1H) and 1.01 (br s, 1H). | 5.75 | 644 | A |
| 103 | 4-[5-(4-chlorophenyl)-1-[2-(trifluoromethyl)phenyl]pyrrol-2-yl]-N-[(2S)-2-(dimethylamino)propyl]benzamide | C | (DMSO-$d_6$) 8.22 (t, 1H), 7.84-7.78 (m, 3H), 7.72-7.70 (m, 1H), 7.63 (d, 2H), 7.27 (d, 2H), 7.11 (d, 2H), 7.06 (d, 2H), 6.68 (d, 1H), 6.61 (d, 1H), 3.30-3.25 (m, 1H), 3.15-3.08 (m, 1H), 2.75-2.73 (m, 1H), 2.18 (s, 6H) and 0.88 (d, 3H). | 4.61 | 526 | A |
| 104 | 4-[4-(4-chlorophenyl)-5-[2-(trifluoromethyl)phenyl]pyrazol-1-yl]-N-(2-morpholinoethyl)-benzamide hydrochloride | L | (DMSO-$d_6$) 10.64 (s, 1H), 8.92 (t, 1H), 8.31 (s, 1H), 7.88-7.84 (m, 5H), 7.78-7.75 (m, 1H), 7.33 (d, 2H), 7.31 (d, 2H), 7.15 (d, 2H), 3.97 (br d, 2H), 3.77 (br t, 2H), 3.65-3.62 (m, 2H), 3.53 (br d, 2H), 3.28 (br d, 2H) and 3.13-3.08 (m, 2H). | 4.14 | 555 | A |
| 105 | 4-[4-(4-chlorophenyl)-5-[2-(trifluoromethyl)phenyl]pyrazol-1-yl]-N-[3-(dimethylamino)propyl]-benzamide hydrochloride | L | (DMSO-$d_6$) 9.91 (s, 1H), 8.68 (t, 1H), 8.30 (s, 1H), 7.87-7.81 (m, 3H), 7.79-7.74 (m, 3H), 7.33-7.30 (m, 4H), 7.15 (dd, 2H), 3.29 (q, 2H), 3.09-3.03 (m, 2H), 2.74 (d, 6H) and 1.91-1.83 (m, 2H). | 4.39 | 527 | A |
| 106 | N-[2-(dimethylamino)ethyl]-4-[4-(4-fluorophenyl)-5-[2-(trifluoromethyl)phenyl]pyrazol-1-yl]benzamide hydrochloride | L | (DMSO-$d_6$) 9.80 (br s, 1H), 8.82 (t, 1H), 8.27 (s, 1H), 7.85-7.83 (m, 5H), 7.78-7.74 (m, 1H), 7.32 (d, 2H), 7.19-7.08 (m, 4H), 3.60-3.56 (m, 2H), 3.23 (d, 2H) and 2.81 (s, 6H). | 3.97 | 497 | C |
| 107 | 2-[4-[5-(4-chlorophenyl)-1-[2-(trifluoromethyl)phenyl]pyrrol-2-yl]phenyl]-N-[2-(dimethylamino)ethyl]-2-methyl-propanamide hydrochloride | J | (DMSO-$d_6$) 10.23 (br s, 1H), 7.81-7.79 (m, 3H), 7.77-7.74 (m, 1H), 7.72-7.69 (m, 1H), 7.25 (dd, 2H), 7.14 (d, 2H), 7.03 (dd, 2H), 7.00 (d, 4H), 6.57 (d, 1H), 6.53 (d, 1H), 3.36 (t, 2H), 3.05 (q, 2H), 2.69 (d, 6H) and 1.40 (s, 6H). | 5.90 | 544 | C |

Synthetic Route A (Illustrated with reference to Example 2)

Example 2

3-[5-(4-Bromophenyl)-1-[2-(trifluoromethyl)phenyl]pyrrol-2-yl]-N-[2-(dimethylamino)ethyl]benzamide hydrochloride

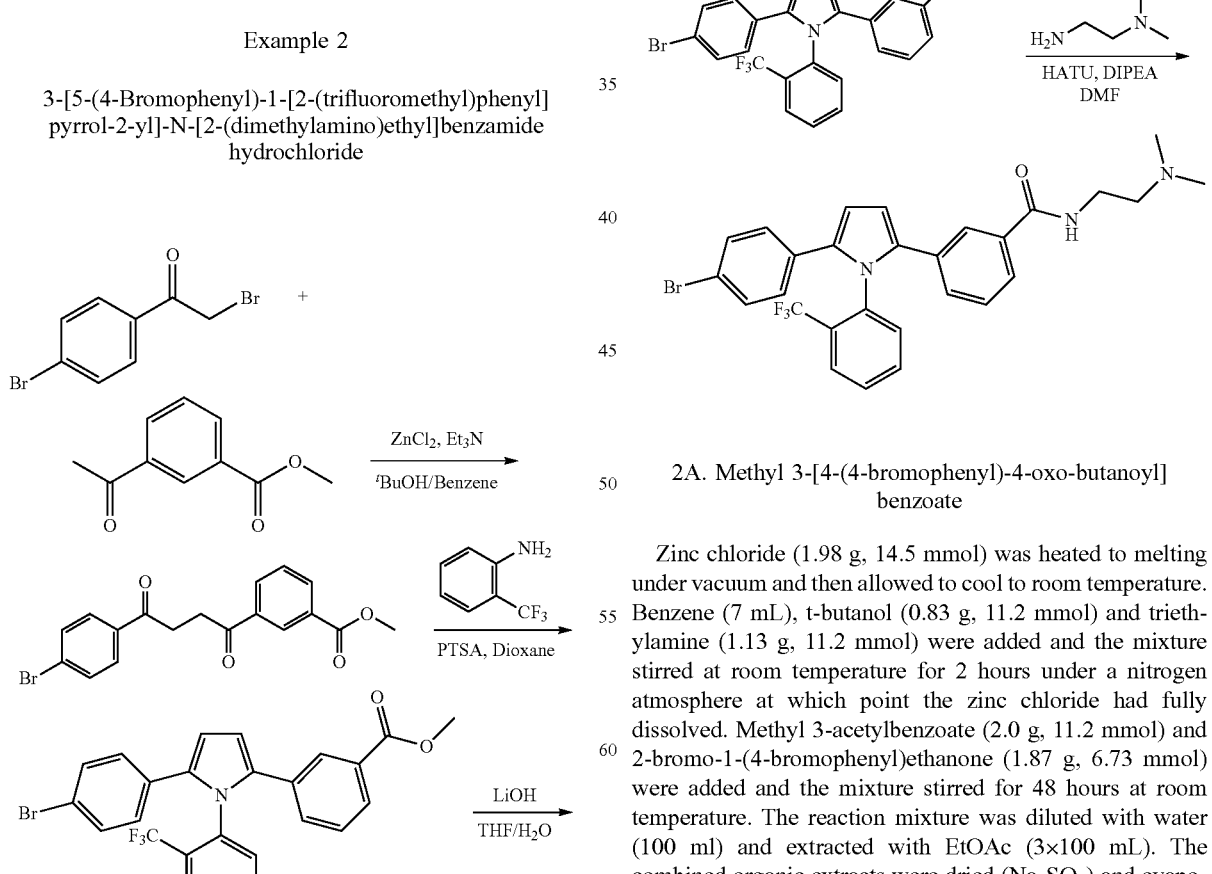

2A. Methyl 3-[4-(4-bromophenyl)-4-oxo-butanoyl]benzoate

Zinc chloride (1.98 g, 14.5 mmol) was heated to melting under vacuum and then allowed to cool to room temperature. Benzene (7 mL), t-butanol (0.83 g, 11.2 mmol) and triethylamine (1.13 g, 11.2 mmol) were added and the mixture stirred at room temperature for 2 hours under a nitrogen atmosphere at which point the zinc chloride had fully dissolved. Methyl 3-acetylbenzoate (2.0 g, 11.2 mmol) and 2-bromo-1-(4-bromophenyl)ethanone (1.87 g, 6.73 mmol) were added and the mixture stirred for 48 hours at room temperature. The reaction mixture was diluted with water (100 ml) and extracted with EtOAc (3×100 mL). The combined organic extracts were dried ($Na_2SO_4$) and evaporated under reduced pressure to leave a residue which was purified by column chromatography on silica gel (60-120 mesh) using 10% EtOAc/hexanes as the eluent to give the title compound (1.3 g, 48%) as a colourless oil.

2B. Methyl 3-[5-(4-bromophenyl)-1-[2-(trifluoromethyl)phenyl]pyrrol-2-yl]benzoate A stirred solution of methyl 3-[4-(4-bromophenyl)-4-oxobutanoyl]benzoate (0.1 g, 0.26 mmol), 2-(trifluoromethyl) aniline (0.043 g, 0.26 mmol) and PTSA (5 mg, 0.02 mmol) in dioxane (1 mL) was heated to 150° C. under microwave irradiation for one hour. The mixture was allowed to cool to room temperature and the solvents evaporated under reduced pressure. The residue was purified by column chromatography on silica gel (60-120 mesh) using 8% EtOAc/hexanes as the eluent to give the title compound (50 mg, 38%) as an off-white solid.

2C. 3-[5-(4-Bromophenyl)-1-[2-(trifluoromethyl)phenyl]pyrrol-2-yl]benzoic acid A mixture of methyl 3-[5-(4-bromophenyl)-1-[2-(trifluoromethyl)phenyl]pyrrol-2-yl]benzoate (50 mg, 0.09 mmol) and lithium hydroxide monohydrate (8 mg, 0.18 mmol) in THF (1 mL) and water (1 mL) was stirred at room temperature for 16 hours. The pH of the mixture was adjusted to 4 with 1 N HCl and then extracted with EtOAc (2×50 mL). The combined organic extracts were dried (Na$_2$SO$_4$) and evaporated under reduced pressure to leave a solid that was triturated with pentane (3×2 mL) and dried to give the title compound (27 mg, 56%) as a beige solid.

2D. 3-[5-(4-Bromophenyl)-1-[2-(trifluoromethyl)phenyl]pyrrol-2-yl]-N-[2-(dimethylamino)ethyl]benzamide hydrochloride HATU (0.175 g, 0.46 mmol) was added to a stirred solution of 3-[5-(4-bromophenyl)-1-[2-(trifluoromethyl)phenyl]pyrrol-2-yl]benzoic acid (0.15 g, 0.30 mmol) in DMF (1 mL) at 0° C. under a nitrogen atmosphere. After stirring for 30 minutes DIPEA (0.16 mL, 0.92 mmol) and N',N'-dimethylethane-1,2-diamine (29 mg, 0.33 mmol) were added and stirring continued for 30 minutes. The mixture was diluted with water (50 mL) and extracted with EtOAc (3×50 mL). The combined organic extracts were washed with brine (20 mL), dried (Na$_2$SO$_4$) and evaporated under reduced pressure to leave a residue which was purified by column chromatography on silica gel (60-120 mesh) using 1% MeOH/DCM as the eluent. The resulting solid was dissolved in dioxane (1 mL) and a 4N HCl solution in dioxane (0.3 mL) was added and the mixture stirred for 16 hours at room temperature. The solvents were evaporated under reduced pressure to leave a solid that was triturated with pentane (3×2 mL) and Et$_2$O (2×2 mL) and then dried to give the title compound (71 mg, 40%) as an off-white solid.

Synthetic Route B (Illustrated with reference to Example 7)

Example 7

1-[3-[5-(4-bromophenyl)-1-[2-(trifluoromethyl)phenyl]pyrrol-2-yl]phenyl]-N,N-dimethyl-methanamine hydrochloride

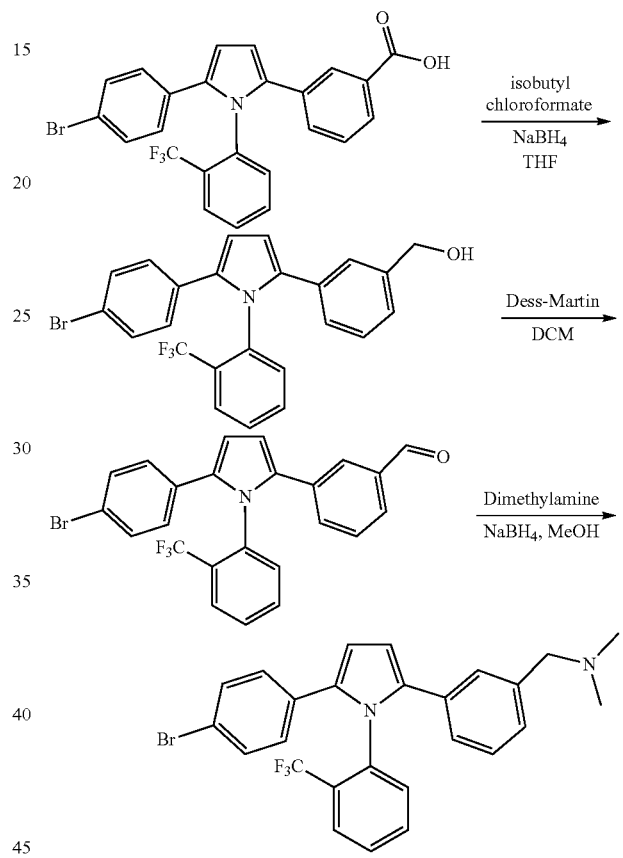

7A. [3-[5-(4-Bromophenyl)-1-[2-(trifluoromethyl)phenyl]pyrrol-2-yl]phenyl]methanol Isobutyl chloroformate (0.6 mL, 4.95 mmol) was added dropwise over 20 minutes to a stirred solution of 3-[5-(4-bromophenyl)-1-[2-(trifluoromethyl)phenyl]pyrrol-2-yl] benzoic acid (Example 2C) (1.5 g, 3.09 mmol) and triethylamine (0.7 mL, 4.95 mmol) in THF (40 mL) at −78° C. under a nitrogen atmosphere. The solution was stirred for one hour then allowed to slowly warm to 0° C. and sodium borohydride (1.3 g, 34 mmol) was added in portions over 10 minutes. Water (20 mL) was added dropwise maintaining the internal temperature at 0° C. and the resulting mixture stirred for 20 minutes. The mixture was filtered, diluted with water (50 mL) and extracted with EtOAc (3×50 mL). The combined organic extracts were washed with brine (20 mL), dried (Na$_2$SO$_4$) and evaporated under reduced pressure to leave the title compound (3.0 g, 100%) which was used without further purification.

7B. 3-[5-(4-Bromophenyl)-1-[2-(trifluoromethyl) phenyl]pyrrol-2-yl]benzaldehyde Dess-Martin periodinane (5.4 g, 12.7 mmol) was added to a solution of [3-[5-(4-bromophenyl)-1-[2-(trifluoromethyl) phenyl]pyrrol-2-yl]phenyl]methanol (3.0 g, 6.4 mmol) in DCM (30 mL) at 0° C. The mixture was stirred for 30 minutes then filtered through celite and the filtrate evaporated under reduced pressure. The residue was purified by column chromatography on silica gel (60-120 mesh) using 1% MeOH/DCM as the eluent to give the title compound (0.64 g, 21% over two steps).

7C. 1-[3-[5-(4-bromophenyl)-1-[2-(trifluoromethyl) phenyl]pyrrol-2-yl]phenyl]-N,N-dimethyl-methanamine hydrochloride Dimethylamine (2M in THF, 1.3 mL, 1.92 mmol) was added dropwise to a stirred solution of 3-[5-(4-bromophenyl)-1-[2-(trifluoromethyl)phenyl]pyrrol-2-yl]benzaldehyde (0.3 g, 0.64 mmol) in MeOH (6 mL) at 0° C. under a nitrogen atmosphere. The solution was stirred for 20 minutes then sodium borohydride (0.05 g, 1.28 mmol) was added in portions over 10 minutes maintaining the internal temperature at 0° C. The mixture was allowed to warm to room temperature and stirred for a further 20 minutes then poured into ice-water (50 mL) and extracted with EtOAc (4×30 mL). The combined organic extracts were dried (Na$_2$SO$_4$) and evaporated under reduced pressure to leave a residue which was purified by column chromatography on silica gel (60-120 mesh) using 3% MeOH/CHCl$_3$ as the eluent. The resulting solid was dissolved in THF (2 mL) and 4N HCl solution in dioxane (0.3 ml) was added and the mixture stirred for 30 minutes at room temperature. The solvents were evaporated under reduced pressure to leave a solid that was triturated with pentane (3×2 mL) and then dried to give the title compound (40 mg, 12%) as an off-white solid.

Synthetic Route C (Illustrated with reference to Example 9)

Example 9

4-[5-(4-Bromophenyl)-1-[2-(trifluoromethyl)phenyl] pyrrol-2-yl]-N-[2-(dimethylamino)ethyl]benzamide hydrochloride

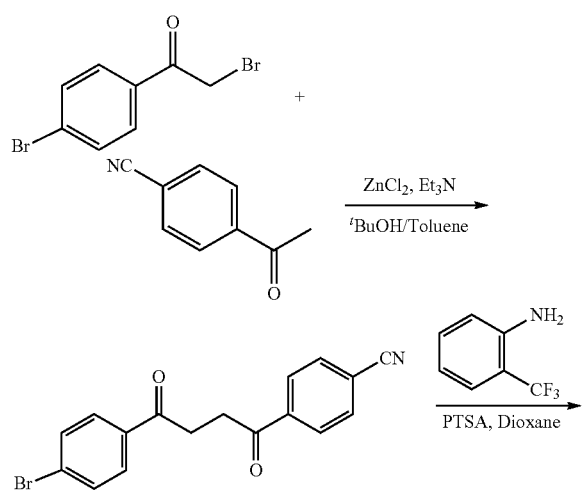

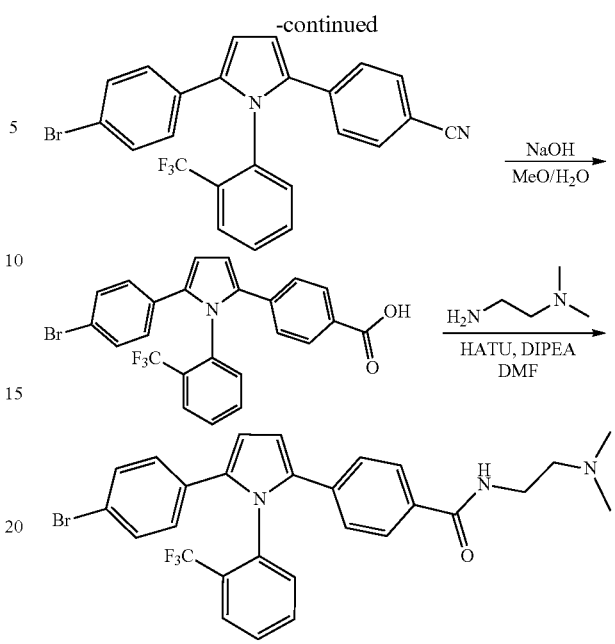

9A. 4-[4-(4-Bromophenyl)-4-oxo-butanoyl]benzonitrile

Zinc chloride (24.4 g, 179 mmol) was heated to melting under vacuum and then allowed to cool to room temperature. Toluene (80 mL), t-butanol (13.2 mL, 138 mmol) and triethylamine (19.3 mL, 138 mmol) were added and the mixture stirred at room temperature for 2 hours under a nitrogen atmosphere at which point the zinc chloride had fully dissolved. 4-Cyanoacetophenone (20.0 g, 138 mmol) and 2-bromo-1-(4-bromophenyl)ethanone (38.1 g, 6.73 mmol) were added and the mixture stirred for 48 hours at room temperature. The reaction mixture was diluted with water (100 ml) and extracted with EtOAc (3×200 mL). The combined organic extracts were dried (Na$_2$SO$_4$) and evaporated under reduced pressure to leave a residue which was purified by column chromatography on silica gel (60-120 mesh) using 8% EtOAc/hexanes as the eluent to give the title compound (8.0 g, 17%) as a colourless oil.

9B. 4-[5-(4-Bromophenyl)-1-[2-(trifluoromethyl) phenyl]pyrrol-2-yl]benzonitrile A stirred solution of 4-[4-(4-bromophenyl)-4-oxo-butanoyl]benzonitrile (6.0 g, 17.6 mmol), 2-(trifluoromethyl) aniline (8.5 g, 52.8 mmol) and PTSA (0.33 g, 1.76 mmol) in dioxane (60 mL) was heated to 150° C. under microwave irradiation for 6 hours. The mixture was allowed to cool to room temperature and the solvents evaporated under reduced pressure. The residue was purified by column chromatography on silica gel (60-120 mesh) using 4% EtOAc/hexanes as the eluent to give the title compound (4.0 g, 49%) as an off-white solid.

9C. 4-[5-(4-Bromophenyl)-1-[2-(trifluoromethyl) phenyl]pyrrol-2-yl]benzoic acid A mixture of 4-[5-(4-bromophenyl)-1-[2-(trifluoromethyl)phenyl]pyrrol-2-yl]benzonitrile (3.44 g, 8.60 mmol) and sodium hydroxide (3.44 g, 86.0 mmol) in methanol (40 mL) and water (4 mL) was stirred at 90° C. for 18 hours. The pH of the mixture was adjusted to 4 with 1N HCl and then extracted with EtOAc (3×50 mL). The combined organic extracts were dried (Na₂SO₄) and evaporated under reduced pressure to leave a solid that was triturated with pentane (3×2 mL) and dried to give the title compound (3.5 g, 84%) as a white solid.

9D. 4-[5-(4-Bromophenyl)-1-[2-(trifluoromethyl) phenyl]pyrrol-2-yl]-N-[2-(dimethylamino)ethyl] benzamide hydrochloride HATU (3.53 g, 9.30 mmol) was added to a stirred solution of 4-[5-(4-bromophenyl)-1-[2-(trifluoromethyl)phenyl]pyrrol-2-yl]benzoic acid (3.0 g, 6.2 mmol) in DMF (30 mL) at 0° C. under a nitrogen atmosphere. After stirring for 30 minutes DIPEA (3.3 mL, 18.6 mmol) and N',N'-dimethyl-ethane-1,2-diamine (0.6 g, 6.8 mmol) were added and stirring continued for 30 minutes. The mixture was diluted with water (300 mL) and extracted with EtOAc (3×100 mL). The combined organic extracts were washed with brine (50 mL), dried (Na₂SO₄) and evaporated under reduced pressure to leave a residue which was purified by column chromatography on silica gel (60-120 mesh) using 4% MeOH/CHCl₃ as the eluent. The resulting solid was dissolved in THF (30 mL) and 4N HCl solution in dioxane (1 mL) was added and the mixture stirred for 30 minutes at room temperature. The solvents were evaporated under reduced pressure to leave a solid that was triturated with Et₂O (3×10 mL) and then dried to give the title compound (2.7 g, 84%) as an off-white solid.

Synthetic Route D (Illustrated with reference to Example 16)

Example 16

N-[3-[5-(4-Bromophenyl)-1-[2-(trifluoromethyl) phenyl]pyrrol-2-yl]phenyl]-N',N'-dimethyl-propane-1,3-diamine hydrochloride

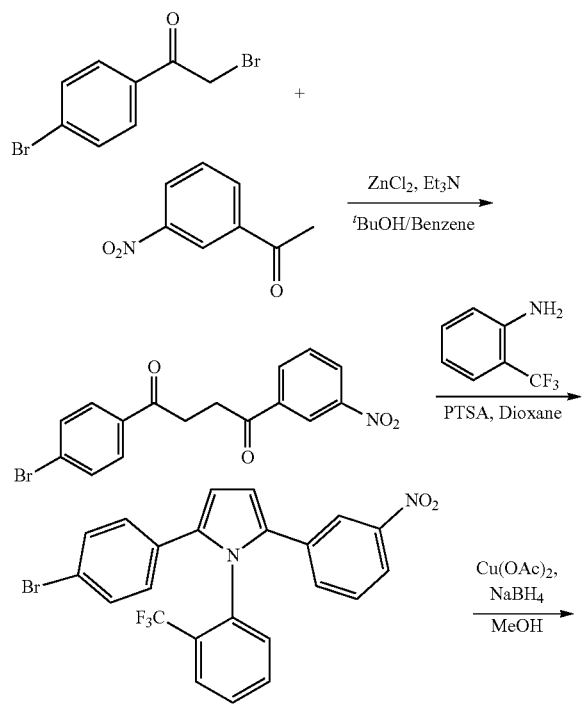

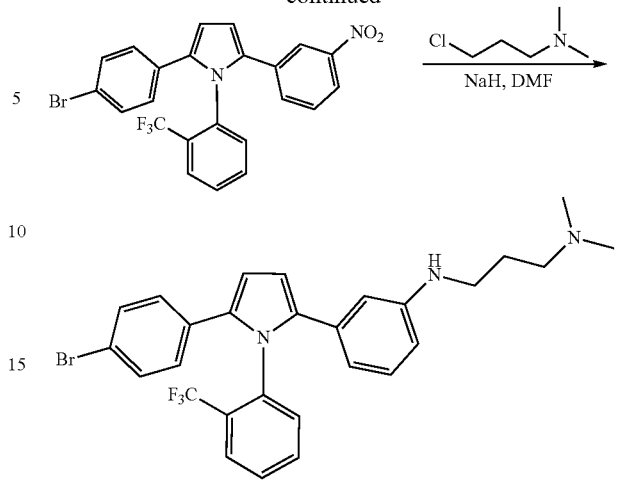

16A. 1-(4-Bromophenyl)-4-(3-nitrophenyl)butane-1,4-dione

Zinc chloride (5.37 g, 39.4 mmol) was heated to melting under vacuum and then allowed to cool to room temperature. Toluene (20 mL), t-butanol (2.9 mL, 30.3 mmol) and triethylamine (4.2 mL, 30.3 mmol) were added and the mixture stirred at room temperature for 2 hours under a nitrogen atmosphere at which point the zinc chloride had fully dissolved. 3-Nitroacetophenone (5.0 g, 30.3 mmol) and 2-bromo-1-(4-bromophenyl)ethanone (8.35 g, 14.0 mmol) were added and the mixture stirred for 24 hours at room temperature. The reaction mixture was diluted with water (50 mL), filtered through celite and extracted with EtOAc (3×100 mL). The combined organic extracts were dried (Na₂SO₄) and evaporated under reduced pressure to leave a residue which was purified by column chromatography on silica gel (60-120 mesh) using 8% EtOAc/hexanes as the eluent to give the title compound (2.1 g, 19%) as a yellow solid.

16B. 2-(4-Bromophenyl)-5-(3-nitrophenyl)-1-[2-(trifluoromethyl)phenyl]pyrrole

A stirred solution of 1-(4-bromophenyl)-4-(3-nitrophenyl)butane-1,4-dione (2.0 g, 5.50 mmol), 2-(trifluoromethyl)aniline (2.66 g, 16.5 mmol) and PTSA (0.11 g, 5.50 mmol) in dioxane (20 mL) was heated to 150° C. under microwave irradiation for 6 hours. The mixture was allowed to cool to room temperature and the solvents evaporated under reduced pressure. The residue was purified by column chromatography on silica gel (60-120 mesh) using 10% EtOAc/hexanes as the eluent to give the title compound (2.2 g, 82%) as an off-white solid.

16C. 3-[5-(4-Bromophenyl)-1-[2-(trifluoromethyl) phenyl]pyrrol-2-yl]aniline

Sodium borohydride (2.04 g, 5.4 mmol) was added in portions over 30 minutes to a stirred solution of 2-(4-bromophenyl)-5-(3-nitrophenyl)-1-[2-(trifluoromethyl)phenyl]pyrrole (2.2 g, 4.50 mmol) and copper (II) acetate (82 mg, 0.45 mmol) in methanol (20 mL) at 0° C. The mixture was allowed to warm to room temperature and stirring continued for one hour. The solvents were evaporated under reduced pressure to leave a residue which was purified by column chromatography on silica gel (60-120 mesh) using 15% EtOAc/hexanes as the eluent to give the title compound (2.0 g, 97%) as an off-white solid.

16D. N-[3-[5-(4-Bromophenyl)-1-[2-(trifluoromethyl)phenyl]pyrrol-2-yl]phenyl]-N',N'-dimethyl-propane-1,3-diamine hydrochloride A solution of 3-[5-(4-bromophenyl)-1-[2-(trifluoromethyl)phenyl]pyrrol-2-yl]aniline (2.0 g, 4.4 mmol) in DMF (10 mL) was added dropwise to a stirred slurry of sodium hydride (60% in oil, 0.53 g, 13.2 mmol) in DMF (10 mL) at room temperature under a nitrogen atmosphere. After stirring for 30 minutes 3-chloro-N,N-dimethylpropan-1-amine hydrochloride (0.75 g, 4.8 mmol) was added and the mixture heated to 80° C. for 3 hours. The solution was allowed to cool to room temperature and then carefully poured into ice-water (100 mL) and extracted with EtOAc (4×50 mL). The combined organic extracts were washed with brine (50 mL), dried ($Na_2SO_4$) and evaporated under reduced pressure to leave a residue which was purified by column chromatography on silica gel (60-120 mesh) using 6% MeOH/$CHCl_3$ as the eluent. The resulting solid was dissolved in THF (30 mL) and 4N HCl solution in dioxane (1 ml) was added and the mixture stirred for 30 minutes at room temperature. The solvents were evaporated under reduced pressure to leave a solid that was triturated with $Et_2O$ (3×10 mL) and then dried to give the title compound (120 mg, 5%) as an off-white solid.

Synthetic Route E (Illustrated with reference to Example 17)

Example 17

3-[3-[5-(4-Bromophenyl)-1-[2-(trifluoromethyl)phenyl]pyrrol-2-yl]phenoxy]-N,N-dimethyl-propan-1-amine hydrochloride

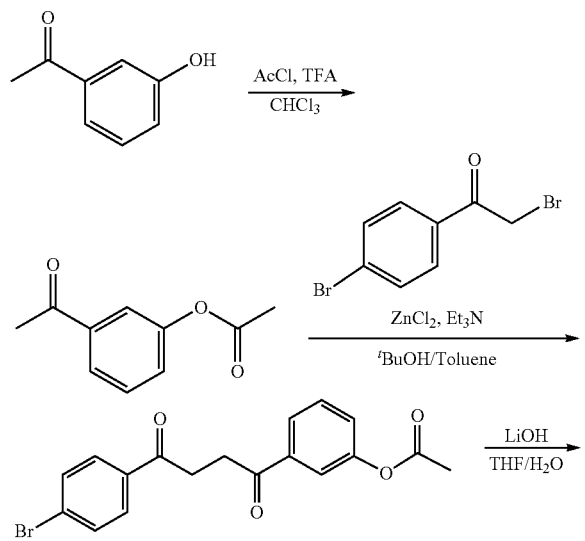

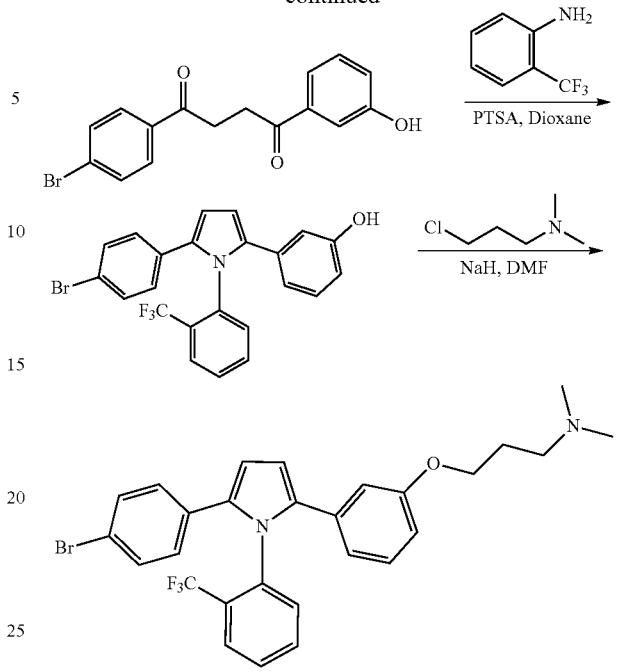

17A. (3-Acetylphenyl) acetate

Acetyl chloride (3.9 mL, 55.0 mmol) was added dropwise to a stirred solution of 3-hydroxyacetophenone (5.0 g, 36.7 mmol) and TFA (1.1 mL, 14.7 mmol) in chloroform (50 mL) under a nitrogen atmosphere. The resulting solution was heated to 80° C. for 20 hours then allowed to cool to room temperature and poured into saturated $NaHCO_3$ solution (50 mL). The mixture was extracted with EtOAc (3×50 mL) then the combined organic extracts were washed with brine (20 mL), dried ($Na_2SO_4$) and evaporated under reduced pressure to leave the title compound (2.8 g, 43%) which was used without further purification.

17B. [3-[4-(4-Bromophenyl)-4-oxo-butanoyl]phenyl]acetate

Zinc chloride (2.48 g, 18.2 mmol) was heated to melting under vacuum and then allowed to cool to room temperature. Toluene (10 mL), t-butanol (1.4 mL, 14.0 mmol) and triethylamine (2.0 mL, 14.0 mmol) were added and the mixture stirred at room temperature for 2 hours under a nitrogen atmosphere at which point the zinc chloride had fully dissolved. (3-Acetylphenyl) acetate (2.5 g, 14.0 mmol) and 2-bromo-1-(4-bromophenyl)ethanone (3.90 g, 14.0 mmol) were added and the mixture stirred for 18 hours at room temperature. The reaction mixture was diluted with water (50 ml), filtered through celite and extracted with EtOAc (3×50 mL). The combined organic extracts were dried ($Na_2SO_4$) and evaporated under reduced pressure to leave a solid that was triturated with pentane (3×10 mL) to give the title compound (2.1 g, 40%) as a beige solid.

17C. 1-(4-Bromophenyl)-4-(3-hydroxyphenyl)butane-1,4-dione

A mixture of methyl [3-[4-(4-bromophenyl)-4-oxo-butanoyl]phenyl] acetate (2.0 mg, 5.40 mmol) and lithium hydroxide monohydrate (0.90 g, 21.6 mmol) in THF (20 mL) and water (20 mL) was stirred at room temperature for 10 minutes. The pH of the mixture was adjusted to 4 with 1N HCl and then extracted with EtOAc (3×50 mL). The combined organic extracts were dried ($Na_2SO_4$) and evaporated under reduced pressure to leave a solid that was triturated with pentane (3×2 mL) and dried to give the title compound (1.50 g, 85%) as a beige solid.

17D. 3-[5-(4-Bromophenyl)-1-[2-(trifluoromethyl)phenyl]pyrrol-2-yl]phenol

A stirred solution of 1-(4-bromophenyl)-4-(3-hydroxyphenyl)butane-1,4-dione (1.0 g, 3.0 mmol), 2-(trifluoromethyl)aniline (1.45 g, 9.0 mmol) and PTSA (0.057 g, 0.30 mmol) in dioxane (10 mL) was heated to 150° C. under microwave irradiation for 2 hours. The mixture was allowed to cool to room temperature and the solvents evaporated under reduced pressure. The residue was purified by column chromatography on silica gel (60-120 mesh) using 10% EtOAc/hexanes as the eluent to give the title compound (0.25 g, 18%) as an off-white solid.

17E. 3-[3-[5-(4-Bromophenyl)-1-[2-(trifluoromethyl)phenyl]pyrrol-2-yl]phenoxy]-N,N-dimethylpropan-1-amine hydrochloride A solution of 3-[5-(4-bromophenyl)-1-[2-(trifluoromethyl)phenyl]pyrrol-2-yl]phenol (0.20 g, 0.44 mmol) in DMF (1 mL) was added dropwise to a stirred slurry of sodium hydride (60% in oil, 0.53 g, 13.2 mmol) in DMF (1 mL) at room temperature under a nitrogen atmosphere. After stirring for 30 minutes 3-chloro-N,N-dimethylpropan-1-amine hydrochloride (0.076 g, 0.48 mmol) was added and the mixture heated to 70° C. for one hour. The solution was allowed to cool to room temperature and then carefully poured into ice-water (20 mL) and extracted with EtOAc (4×30 mL). The combined organic extracts were washed with brine (50 mL), dried ($Na_2SO_4$) and evaporated under reduced pressure to leave a residue which was purified by column chromatography on silica gel (60-120 mesh) using 8% MeOH/$CHCl_3$ as the eluent. The resulting solid was dissolved in THF (5 mL) and 4N HCl solution in dioxane (0.1 ml) was added and the mixture stirred for 30 minutes at room temperature. The solvents were evaporated under reduced pressure to leave a solid that was triturated with $Et_2O$ (3×10 mL) and then dried to give the title compound (150 mg, 64%) as an off-white solid.

Synthetic Route F (Illustrated with reference to Example 21)

Example 21

N-[[3-[5-(4-Bromophenyl)-1-[2-(trifluoromethyl)phenyl]pyrrol-2-yl]phenyl]methyl]-2-(dimethylamino)acetamide hydrochloride

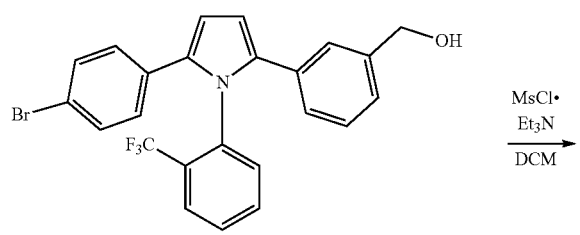

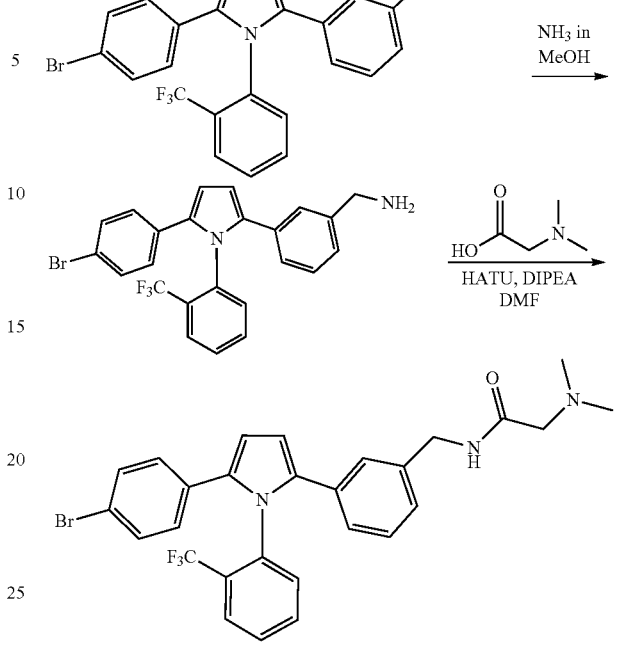

21A. [3-[5-(4-Bromophenyl)-1-[2-(trifluoromethyl)phenyl]pyrrol-2-yl]phenyl]methyl methanesulfonate Methane sulfonyl chloride (0.11 g, 0.96 mmol) was added dropwise to a stirred solution of [3-[5-(4-bromophenyl)-1-[2-(trifluoromethyl)phenyl]pyrrol-2-yl]phenyl]methanol (Example 7B) (0.3 g, 0.64 mmol) and triethylamine (0.13 mL, 0.96 mmol) in THF (3 mL) at 0° C. under a nitrogen atmosphere. The mixture was stirred for 30 minutes then partitioned between saturated $NaHCO_3$ solution (30 mL) and EtOAc (30 mL). The separated aqueous phase was extracted with EtOAc (3×30 mL) and then the combined organic extracts were washed with brine (10 mL), dried ($Na_2SO_4$) and evaporated under reduced pressure to give the title compound (0.62 g, quantitative) which was used without further purification.

21B. [3-[5-(4-Bromophenyl)-1-[2-(trifluoromethyl)phenyl]pyrrol-2-yl]phenyl]methanamine A 9M ammonia in MeOH solution (2 mL) was added to a stirred solution of [3-[5-(4-bromophenyl)-1-[2-(trifluoromethyl)phenyl]pyrrol-2-yl]phenyl]methyl methanesulfonate (0.62 g, 1.1 mmol) in ethanol (6 mL) at −5° C. under a nitrogen atmosphere. The solution was stirred at −5° C. for 2 hours then the solvents were evaporated under reduced pressure. The residue was purified by column chromatography on silica gel (60-120 mesh) using 6% MeOH/$CHCl_3$ as the eluent to give the title compound (0.32 g, 60%) as an off-white solid.

21C. N-[[3-[5-(4-bromophenyl)-1-[2-(trifluoromethyl)phenyl]pyrrol-2-yl]phenyl]methyl]-2-(dimethylamino)acetamide hydrochloride HATU (0.52 g, 1.36 mmol) was added to a stirred solution of N,N-dimethylglycine (70 mg, 0.68 mmol) in DMF (3 mL) at 0° C. under a nitrogen atmosphere. After stirring for 30 minutes DIPEA (0.35 mL, 2.04 mmol) and [3-[5-(4-bromophenyl)-1-[2-(trifluoromethyl)phenyl]pyrrol-2-yl]phenyl]methanamine (0.32 g, 0.68 mmol) were added and stirring continued for 30 minutes. The mixture was diluted with water (30 mL) and extracted with EtOAc (3×30 mL). The combined organic extracts were washed with brine (10 mL), dried (Na$_2$SO$_4$) and evaporated under reduced pressure to leave a residue which was purified by column chromatography on silica gel (60-120 mesh) using 4% MeOH/CHCl$_3$ as the eluent. The resulting solid was dissolved in THF (30 mL) and 4N HCl solution in dioxane (1 mL) was added and the mixture stirred for 30 minutes at room temperature. The solvents were evaporated under reduced pressure to leave a solid that was triturated with Et$_2$O (3×10 mL) and then dried to give the title compound (19 mg, 5%) as an off-white solid.

Synthetic Route G (Illustrated with reference to Example 29)

Example 29

6-[5-(4-Bromophenyl)-1-[2-(trifluoromethyl)phenyl]pyrrol-2-yl]-N-[2-(dimethylamino)ethyl]pyridine-3-carboxamide hydrochloride

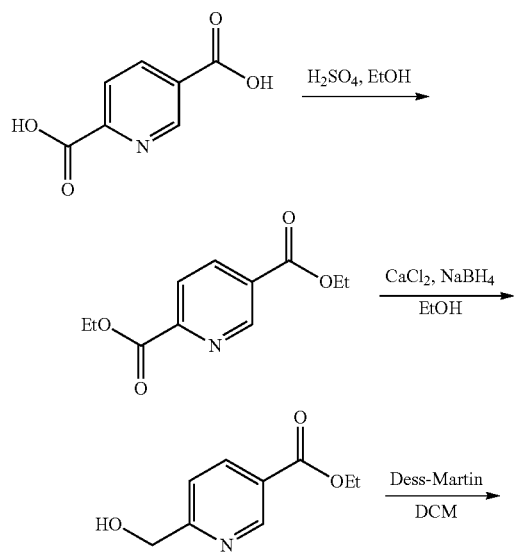

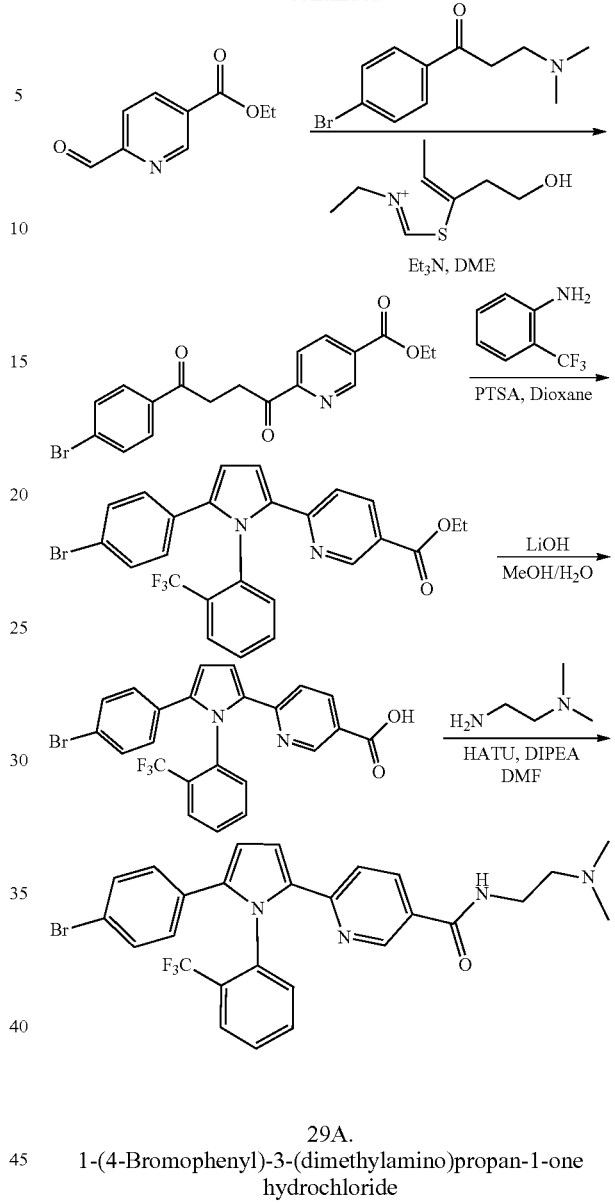

29A. 1-(4-Bromophenyl)-3-(dimethylamino)propan-1-one hydrochloride

A stirred solution of 4-bromoacetophenone (1.0 g, 5.0 mmol), paraformaldehyde (0.15 g, 5.0 mol), N,N-dimethylamine hydrochloride (0.41 g, 5.0 mmol) and concentrated hydrochloric acid (0.5 mL) in absolute ethanol (15 mL) were heated to 90° C. for 4 hours. The solution was allowed to cool to room temperature and the solvents were evaporated under reduced pressure. The residue was triturated with n-pentane (3×20 mL), Et$_2$O (3×10 mL) and dried to give the title compound (1.26 g, 86%) as a white solid.

29B. Diethyl pyridine-2,5-dicarboxylate

Concentrated sulfuric acid (3.9 mL, 71.6 mmol) was added dropwise over 15 minutes to a stirred suspension of 2,5-pyridinedicarboxylic acid (3.0 g, 17.9 mol) in absolute ethanol (10 mL) and the resulting mixture heated to reflux for 18 hours. The solution was allowed to cool to room temperature and the solvents evaporated under reduced pressure. Saturated NaHCO$_3$ solution was added to the residue to adjust the pH to ~8 then the aqueous phase was extracted with EtOAc (4×50 mL). The combined organic extracts were washed with brine (30 mL), dried (Na$_2$SO$_4$) and evaporated under reduced pressure to leave the title compound (3.0 g, 75%) which was used without further purification.

29C. Ethyl 6-(hydroxymethyl)pyridine-3-carboxylate

Sodium borohydride (1.27 g, 33.5 mmol) and anhydrous calcium chloride (2.35 g, 21.2 mmol) was added in several portions over 30 minutes to a stirred solution of diethyl pyridine-2,5-dicarboxylate (3.0 g, 13.4 mmol) in ethanol (12 mL) and THF (6 mL) at 0° C. under a nitrogen atmosphere. The mixture was allowed to warm to room temperature and stirring continued for one hour then poured into saturated NH$_4$Cl solution (150 mL) and extracted with EtOAc (5×50 mL). The combined organic extracts were dried (Na$_2$SO$_4$) and evaporated under reduced pressure to leave a residue which was purified by column chromatography on silica gel (60-120 mesh) using 36% EtOAc/hexanes as the eluent to give the title compound (1.5 g, 62%) as an off-white solid.

29D. Ethyl 6-formylpyridine-3-carboxylate

Dess-Martin periodinane (4.24 g, 10.0 mmol) was added to a solution of ethyl 6-(hydroxymethyl)pyridine-3-carboxylate (1.5 g, 8.3 mmol) in DCM (30 mL) at 0° C. The mixture was stirred for 30 minutes then filtered through celite and the filtrate evaporated under reduced pressure. The residue was purified by column chromatography on silica gel (60-120 mesh) using 9% EtOAc/hexanes as the eluent to give the title compound (0.83 g, 56%).

29E. Ethyl 6-[4-(4-bromophenyl)-4-oxo-butanoyl]pyridine-3-carboxylate

Ethyl 6-formylpyridine-3-carboxylate (0.61 g, 3.4 mmol) and 3-ethyl-5-(2-hydroxyethyl)-4-methylthiazoliumbromide (0.18 g, 0.70 mmol) were added to a stirred solution of 1-(4-bromophenyl)-3-(dimethylamino)propan-1-one hydrochloride (1.0 g, 3.4 mmol) and triethylamine (0.95 mL, 6.8 mmol) in 1,2-dimethoxyethane (15 mL). The resulting solution was heated to 100° C. for 5 hours then allowed to cool to room temperature and diluted with EtOAc (150 mL). The solution was washed with water (3×50 mL), brine (20 mL), dried (Na$_2$SO$_4$) and evaporated under reduced pressure to leave a residue that was purified by column chromatography on silica gel (60-120 mesh) using 12% EtOAc/hexane as the eluent to give the title compound (0.67 g, 44%) as a beige solid.

29F. Ethyl 6-[5-(4-bromophenyl)-1-[2-(trifluoromethyl)phenyl]pyrrol-2-yl]pyridine-3-carboxylate A stirred solution of ethyl 6-[4-(4-bromophenyl)-4-oxo-butanoyl]pyridine-3-carboxylate (0.67 g, 1.7 mmol), 2-(trifluoromethyl)aniline (0.82 g, 5.1 mmol) and PTSA (0.040 g, 0.20 mmol) in dioxane (15 mL) was heated to 170° C. under microwave irradiation for 5 hours. The mixture was allowed to cool to room temperature and the solvents evaporated under reduced pressure. The residue was purified by column chromatography on silica gel (60-120 mesh) using 10% EtOAc/hexanes as the eluent to give the title compound (0.63 g, 71%) as an off-white solid.

29G. 6-[5-(4-Bromophenyl)-1-[2-(trifluoromethyl)phenyl]pyrrol-2-yl]pyridine-3-carboxylic acid A mixture of methyl ethyl 6-[5-(4-bromophenyl)-1-[2-(trifluoromethyl)phenyl]pyrrol-2-yl]pyridine-3-carboxylate (0.63 g, 1.20 mmol) and lithium hydroxide monohydrate (0.20 g, 4.8 mmol) in THF (6 mL) and water (6 mL) was stirred at 90° C. for 3 hours. The cooled solution was diluted with water (60 mL), neutralized with 10% KHSO$_4$ solution and then extracted with EtOAc (3×30 mL). The combined organic extracts were dried (Na$_2$SO$_4$) and evaporated under reduced pressure to leave a solid that was purified by column chromatography on silica gel (60-120 mesh) using 45% EtOAc/hexane as the eluent to give the title compound (0.48 g, 81%) as a white solid.

29H. 6-[5-(4-bromophenyl)-1-[2-(trifluoromethyl)phenyl]pyrrol-2-yl]-N-[2-(dimethylamino)ethyl]pyridine-3-carboxamide hydrochloride HATU (0.21 g, 2.40 mmol) was added to a stirred solution of 6-[5-(4-bromophenyl)-1-[2-(trifluoromethyl)phenyl]pyrrol-2-yl]pyridine-3-carboxylic acid (0.41 g, 0.8 mmol) in DMF (1 mL) at 0° C. under a nitrogen atmosphere. After stirring for 30 minutes DIPEA (0.40 mL, 2.4 mmol) and N',N'-dimethylethane-1,2-diamine (0.21 g, 2.40 mmol) were added and stirring continued for 40 minutes. The mixture was diluted with water (50 mL) and extracted with EtOAc (3×50 mL). The combined organic extracts were washed with brine (20 mL), dried (Na$_2$SO$_4$) and evaporated under reduced pressure to leave a residue which was purified by column chromatography on silica gel (60-120 mesh) using 5% MeOH/CHCl$_3$ as the eluent. The resulting solid was dissolved in dioxane (5 mL) and a 4N HCl solution in dioxane (1.5 mL) was added and the mixture stirred for 30 minutes at room temperature. The solvents were evaporated under reduced pressure to leave a solid that was triturated with pentane (3×2 mL) and Et$_2$O (2×2 mL) and then dried to give the title compound (0.30 g, 72%) as an off-white solid.

Experimental Procedure for Example 33

The compound of Example 33 was made by route C involving the following sequence of reactions:

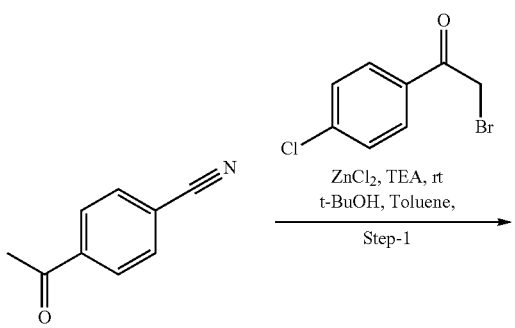

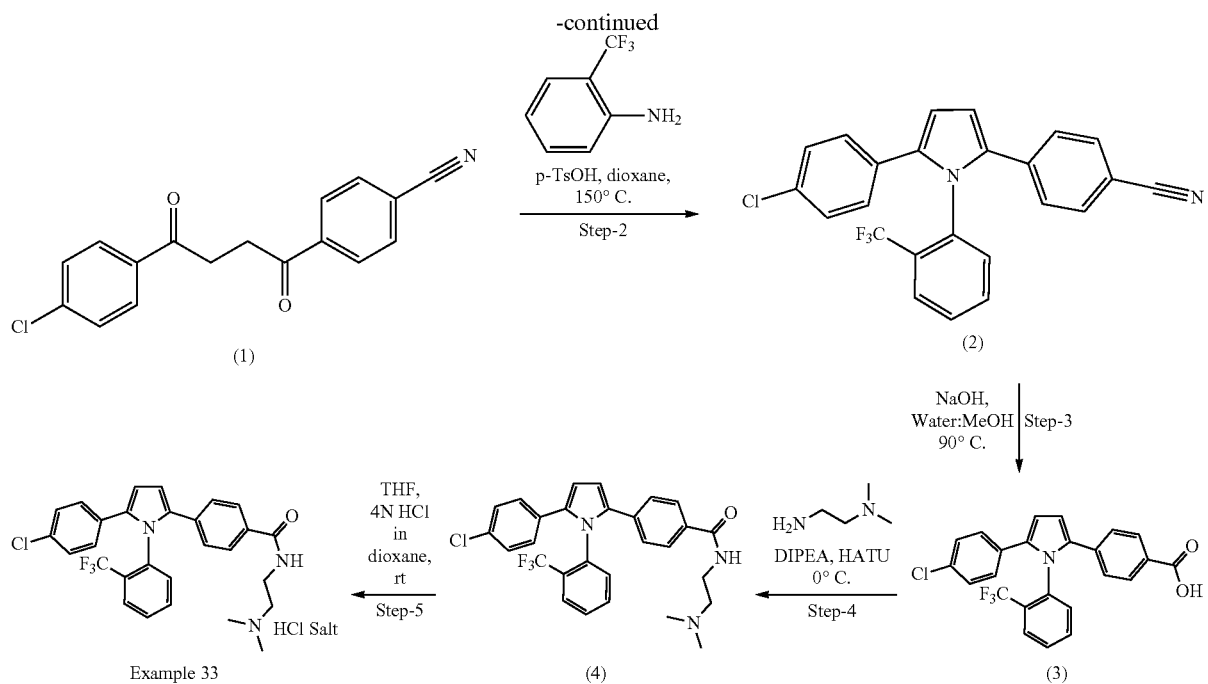

Step 1

4-[4-(4-chlorophenyl)-4-oxo-butanoyl]benzonitrile

Zinc chloride (30.5 g, 0.223 mol) was heated up to melting temperature in a reaction flask in vacuo followed by cooling to room temperature (RT) in vacuo. To this mixture was added toluene (100 mL), tert-butanol (16.5 mL, 0.172 mol) and triethylamine (24 mL, 0.172 mol) under a nitrogen atmosphere. The reaction mixture (RM) was then stirred at the same temperature for 2 h until all the zinc chloride had dissolved. After this, 4-cyanoacetophenone (25 g, 0.172 mol) and 4-chlorophenacylbromide (40.2 g, 0.172 mol) were added at RT and the reaction mixture was stirred at the same temperature for 48 h.

The reaction mixture was diluted with ethyl acetate (1 L) and then washed with water (4×250 mL) followed by brine solution (1×300 mL). The organic layer was separated off and dried over sodium sulphate then filtered. The filtrate was concentrated in vacuo to afford crude title product, which was further purified by triturating with methyl tert-butyl ether to afford the title product. Yield: 31.0 g (61%).

Step 2

4-[5-(4-chlorophenyl)-1-[2-(trifluoromethyl)phenyl]pyrrol-2-yl]benzonitrile

To a solution of 4-[4-(4-chlorophenyl)-4-oxo-butanoyl]benzonitrile (30.0 g, 0.1 mol) and 2-trifluoromethyl aniline (40.64 mL, 0.323 mol) in dioxane (300 mL) was added p-toluene sulfonic acid monohydrate (1.92 g, 0.010 mol) at RT. The reaction mixture was then heated at 150° C. for 16 h.

The reaction mixture was concentrated in vacuo to afford crude product, which was further purified by column chromatography using neutral silica gel. Elution at 5-7% ethyl acetate in hexane afforded the title product. Yield: 19.0 g (45%).

Step 3

4-[5-(4-chlorophenyl)-1-[2-(trifluoromethyl)phenyl]pyrrol-2-yl]benzoic acid

To a solution of 4-[5-(4-chlorophenyl)-1-[2-(trifluoromethyl)phenyl]pyrrol-2-yl]benzonitrile (19 g, 0.045 mol) in methanol (190 mL) was added a solution of sodium hydroxide (18 g, 0.45 mol) in water (95 mL) at RT. The resulting reaction mixture was stirred at 90° C. for 18 h.

The reaction mixture was concentrated in vacuo at 40° C. to afford crude product, which was then acidified using a saturated solution of potassium hydrogen sulphate. The aqueous was extracted with ethyl acetate (3×200 mL). The organics were separated off, combined and washed with brine solution (1×100 mL). The organics were again separated off, dried over sodium sulphate, filtered and then concentrated in vacuo. Further purification by trituration with n-pentane afforded title product. Yield: 15.0 g (75%).

Step 4

4-[5-(4-chlorophenyl)-1-[2-(trifluoromethyl)phenyl]pyrrol-2-yl]-N-[2-(dimethylamino)ethyl]benzamide To a solution of 4-[5-(4-chlorophenyl)-1-[2-(trifluoromethyl)phenyl]pyrrol-2-yl]benzoic acid (15 g, 0.034 mol) in DMF (150 mL) was added N-[(dimethylamino)-1H-1,2,3-triazolo-[4,5-b]pyridin-1-ylmethylene]-N-methylmethanaminium hexafluorophosphate N-oxide (HATU, 19.38 g, 0.051 mol) at 0° C. and the reaction mixture was stirred for 30 minutes at the same temperature. After 30 minutes, N,N'-dimethyl ethylenediamine (4.09 mL, 0.038 mol) and DIPEA (18.26 mL, 0.105 mol) were added at 0° C. and the resulting reaction mixture was stirred at the same temperature for 30 minutes.

The reaction mixture was diluted with ethyl acetate (500 mL), washed with ice-cold water (5×100 mL), followed by brine solution (100 mL) then dried over sodium sulphate.

The organics were filtered and concentrated in vacuo. The crude product was further purified by column chromatography using basic alumina (~100-300 uM), eluting with dichloromethane. Yield: 11.0 g (63%).

Step 5

4-[5-(4-chlorophenyl)-1-[2-(trifluoromethyl)phenyl]pyrrol-2-yl]-N-[2-(dimethylamino)ethyl]benzamide hydrochloride To a solution of 4-[5-(4-chlorophenyl)-1-[2-(trifluoromethyl)phenyl]pyrrol-2-yl]-N-[2-(dimethylamino)ethyl]benzamide (10.5 g, 0.0205 mol) in tetrahydrofuran (100 mL) was added 4N HCl in dioxane (5 mL) at RT. The resulting reaction mixture was then stirred for 30 minutes at RT.

The reaction mixture was concentrated in vacuo then further purified by trituration in n-pentane to afford title product. Yield: 10.5 g (93%).

Synthetic Route H (Illustrated with reference to Example 45)

Example 45

2-[[4-[5-(4-Bromophenyl)-1-[2-(trifluoromethyl)phenyl]pyrrol-2-yl]phenyl]methoxy]-N,N-dimethyl-ethanamine hydrochloride

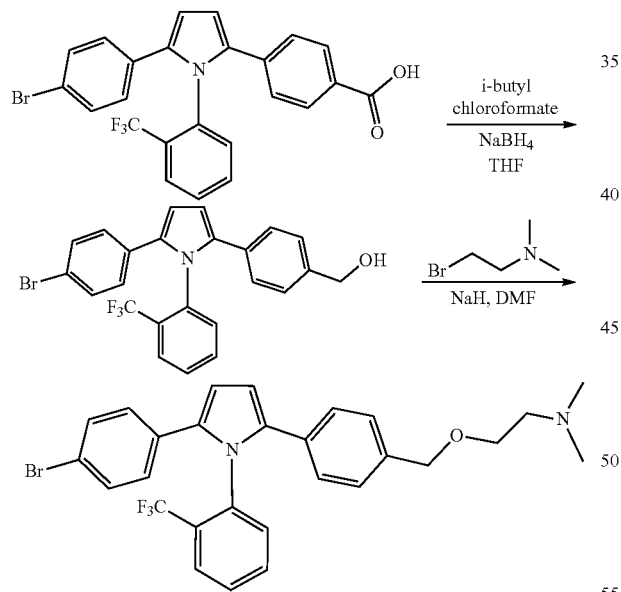

45A. [4-[5-(4-Bromophenyl)-1-[2-(trifluoromethyl)phenyl]pyrrol-2-yl]phenyl]methanol Isobutyl chloroformate (0.6 mL, 4.95 mmol) was added dropwise over 20 minutes to a stirred solution of 4-[5-(4-bromophenyl)-1-[2-(trifluoromethyl)phenyl]pyrrol-2-yl]benzoic acid (Example 9C) (1.5 g, 3.09 mmol) and triethylamine (0.7 mL, 4.95 mmol) in THF (40 mL) at −78° C. under a nitrogen atmosphere. The solution was stirred for one hour then allowed to slowly warm to 0° C. and sodium borohydride (1.3 g, 34 mmol) was added in portions over 10 minutes. Water (20 mL) was added dropwise maintaining in the internal temperature at 0° C. and the resulting mixture stirred for 20 minutes. The mixture was filtered, diluted with water (50 mL) and extracted with EtOAc (3×50 mL). The combined organic extracts were washed with brine (20 mL), dried (Na$_2$SO$_4$) and evaporated under reduced pressure to leave a residue that was purified by column chromatography on silica gel (60-120 mesh) using 17% EtOAc/hexane as the eluent to give the title compound (1.30 g, 89%) as a solid.

45B. 2-[[4-[5-(4-Bromophenyl)-1-[2-(trifluoromethyl)phenyl]pyrrol-2-yl]phenyl]methoxy]-N,N-dimethyl-ethanamine hydrochloride A solution of 3-[5-(4-bromophenyl)-1-[2-(trifluoromethyl)phenyl]pyrrol-2-yl]phenol (0.30 g, 0.64 mmol) in DMF (0.7 mL) was added dropwise to a stirred slurry of sodium hydride (60% in oil, 0.68 g, 0.96 mmol) in DMF (0.5 mL) at room temperature under a nitrogen atmosphere. After stirring for 30 minutes 2-bromo-N,N-dimethyl-ethanamine hydrobromide (0.15 g, 0.64 mmol) was added and the mixture heated to 90° C. for 18 hours. The solution was allowed to cool to room temperature and then carefully poured into ice-water (20 mL) and extracted with EtOAc (3×30 mL). The combined organic extracts were washed with brine (20 mL), dried (Na$_2$SO$_4$) and evaporated under reduced pressure to leave a residue which was purified by column chromatography on silica gel (60-120 mesh) using 8% MeOH/CHCl$_3$ as the eluent. The resulting solid was dissolved in THF (5 mL) and 4N HCl solution in dioxane (0.1 mL) was added and the mixture stirred for 30 minutes at room temperature. The solvents were evaporated under reduced pressure to leave a solid that was triturated with Et$_2$O (3×10 mL) and then dried to give the title compound (58 mg, 16%) as an off-white solid.

Synthetic Route I (Illustrated with reference to Example 46)

Example 46

N-[4-[5-(4-Bromophenyl)-1-[2-(trifluoromethyl)phenyl]pyrrol-2-yl]phenyl]-3-(dimethylamino) propanamide hydrochloride

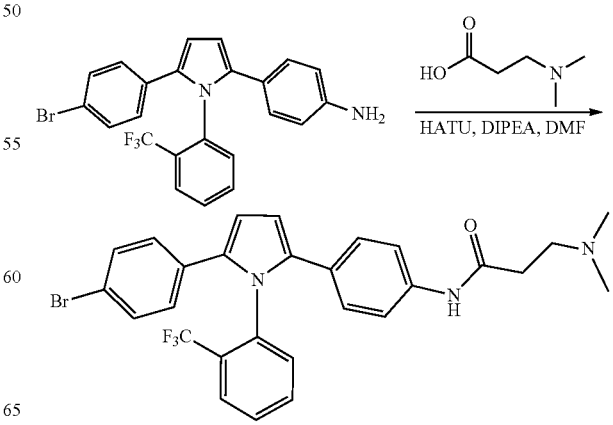

46A. N-[4-[5-(4-Bromophenyl)-1-[2-(trifluoromethyl)phenyl]pyrrol-2-yl]phenyl]-3-(dimethylamino)propanamide hydrochloride HATU (0.67 g, 1.8 mmol) was added to a stirred solution of 3-(dimethylamino)propanoic acid (0.14 g, 0.87 mmol) in DMF (5 mL) at 0° C. under a nitrogen atmosphere. After stirring for 30 minutes DIPEA (0.46 mL, 2.6 mmol) and 3-[5-(4-bromophenyl)-1-[2-(trifluoromethyl)phenyl]pyrrol-2-yl]aniline (prepared in an analogous manner to Example 16C) (0.40 g, 0.87 mmol) were added and stirring continued for 30 minutes. The mixture was diluted with water (30 mL) and extracted with EtOAc (3×40 mL). The combined organic extracts were washed with brine (20 mL), dried ($Na_2SO_4$) and evaporated under reduced pressure to leave a residue which was purified by column chromatography on silica gel (60-120 mesh) using 5% MeOH/$CHCl_3$ as the eluent. The resulting solid was dissolved in dioxane (5 mL) and a 4N HCl solution in dioxane (1.5 mL) was added and the mixture stirred for 30 minutes at room temperature. The solvents were evaporated under reduced pressure to leave a solid that was triturated with pentane (3×2 mL) and $Et_2O$ (2×2 mL) and then dried to give the title compound (0.058 g, 11%) as an off-white solid.

Synthetic Route J (Illustrated with reference to Example 47)

Example 47

2-[4-[5-(4-Bromophenyl)-1-[2-(trifluoromethyl)phenyl]pyrrol-2-yl]phenyl]acetic acid

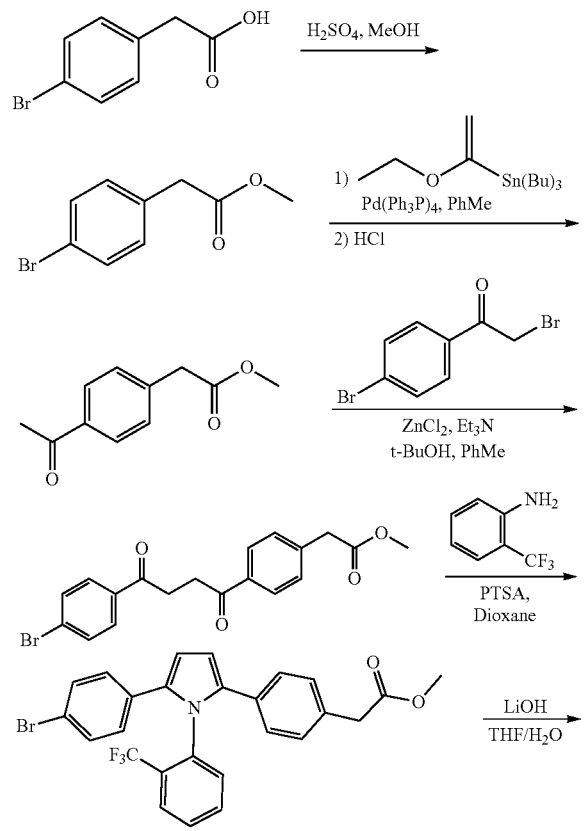

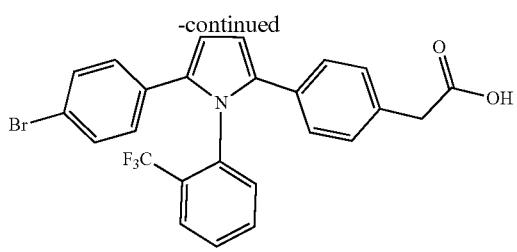

47A. Methyl 2-(4-bromophenyl)acetate

Concentrated sulfuric acid (1.0 mL, 18.4 mmol) was added dropwise over 15 minutes to a stirred solution of 2-(4-bromophenyl)acetic acid (4.0 g, 18.6 mol) in methanol (40 mL) and the resulting mixture heated to reflux for 4 hours. The solution was allowed to cool to room temperature and the solvents evaporated under reduced pressure. Saturated $NaHCO_3$ solution was added to the residue to adjust the pH to ~8, then the aqueous phase was extracted with EtOAc (4×50 mL). The combined organic extracts were washed with brine (30 mL), dried ($Na_2SO_4$) and evaporated under reduced pressure to leave the title compound (3.0 g, 70%) which was used without further purification.

47B. Methyl 2-(4-acetylphenyl)acetate

Nitrogen was bubbled through a solution of methyl 2-(4-bromophenyl)acetate (3.0 g, 13.1 mmol) and tributyl(1-ethoxyvinyl)tin (5.67 g, 15.7 mmol) in toluene (30 mL) for 20 minutes then tetrakis(triphenylphosphine)palladium(0) (0.91 g, 7.9 mmol) was added and the resulting stirred mixture heated to 80° C. for 20 hours. The reaction mixture was allowed to cool to room temperature and 18% aqueous HCl (5 mL) was added and stirring continued for 30 minutes. The mixture was then diluted with water (50 mL), filtered through celite and the filtrate extracted with EtOAc (3×50 mL). The combined organic extracts were washed with brine (20 mL), dried ($Na_2SO_4$) and evaporated under reduced pressure to leave a residue which was purified by column chromatography on silica gel (60-120 mesh) using 20% EtOAc/hexane as the eluent to give the title compound (2.0 g, 79%) as a colourless oil.

47C. Methyl 2-[4-[4-(4-bromophenyl)-4-oxo-butanoyl]phenyl]acetate

Zinc chloride (0.53 g, 3.9 mmol) was heated to melting under vacuum and then allowed to cool to room temperature. Toluene (4 mL), t-butanol (0.25 mL, 2.6 mmol) and triethylamine (0.35 mL, 2.6 mmol) were added and the mixture stirred at room temperature for 2 hours under a nitrogen atmosphere at which point the zinc chloride had fully dissolved. Methyl 2-(4-acetylphenyl)acetate (0.5 g, 2.6 mmol) and 2-bromo-1-(4-bromophenyl)ethanone (0.72 g, 2.6 mmol) were added and the mixture stirred for 18 hours at room temperature. The reaction mixture was diluted with water (20 mL) and extracted with EtOAc (3×20 mL). The combined organic extracts were dried ($Na_2SO_4$) and evaporated under reduced pressure to leave a residue which was purified by trituration with n-pentane (3×10 mL) to give the title compound (0.4 g, 40%) as an off-white solid.

47D. Methyl 2-[4-[5-(4-bromophenyl)-1-[2-(trifluoromethyl)phenyl]pyrrol-2-yl]phenyl]acetate A stirred solution of methyl 2-[4-[4-(4-bromophenyl)-4-oxo-butanoyl]phenyl]acetate (0.40 g, 1.0 mmol), 2-(trifluoromethyl)aniline (0.48 g, 3.0 mmol) and PTSA (0.019 g, 0.10 mmol) in dioxane (4 mL) was heated to 150° C. under microwave irradiation for 4 hours. The mixture was allowed to cool to room temperature and the solvents evaporated under reduced pressure. The residue was purified by column chromatography on silica gel (60-120 mesh) using 7% EtOAc/hexanes as the eluent to give the title compound (0.08 g, 15%) as an off-white solid.

47E. 2-[4-[5-(4-Bromophenyl)-1-[2-(trifluoromethyl)phenyl]pyrrol-2-yl]phenyl]acetic acid A mixture of methyl 2-[4-[5-(4-bromophenyl)-1-[2-(trifluoromethyl)phenyl]pyrrol-2-yl]phenyl]acetate (0.08 g, 0.16 mmol) and lithium hydroxide monohydrate (0.026 g, 0.62 mmol) in THF (1 mL) and water (1 mL) was stirred at 70° C. for 4 hours. The cooled solution was diluted with water (60 mL), neutralized with 10% $KHSO_4$ solution and then extracted with EtOAc (3×10 mL). The combined organic extracts were dried ($Na_2SO_4$) and evaporated under reduced pressure to leave a solid that was purified by triturating with $Et_2O$ (3×2 mL), n-pentane (2×5 mL) and dried to give the title compound (0.05 g, 64%) as a white solid.

Synthetic Route K (Illustrated with reference to Example 44)

Example 44

4-[5-(4-Bromophenyl)-1-[2-(trifluoromethyl)phenyl]pyrrol-2-yl]-N-[2-(dimethylamino)ethyl]benzenesulfonamide hydrochloride

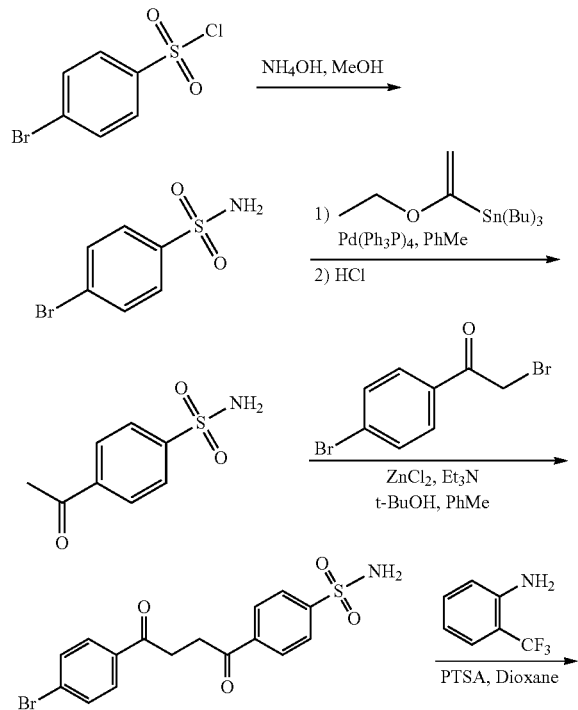

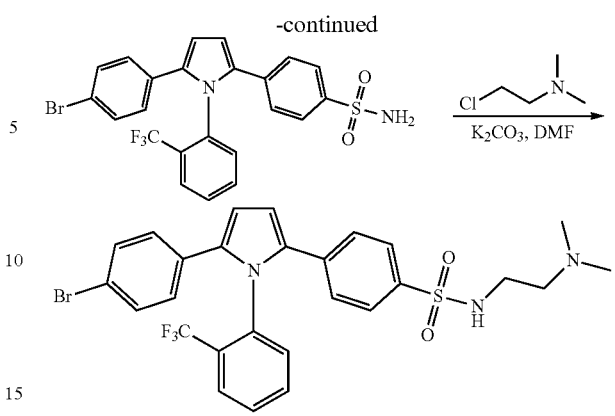

44A. 4-Bromobenzenesulfonamide

Concentrated ammonia solution (12 mL) was added dropwise over 15 minutes to a stirred solution of 4-bromobenzenesulfonyl chloride (6.0 g, 23.6 mmol) in MeOH (60 mL) at room temperature. The mixture was stirred for one hour then concentrated under reduced pressure to leave a solid which was taken up in cold water (50 mL). The solid was collected by filtration, washed with water (2×10 mL) and dried to give the title compound (5.0 g, 85%) as a white solid.

44B. 4-Acetylbenzenesulfonamide

Nitrogen was bubbled through a stirred solution of 4-bromobenzenesulfonamide (4.0 g, 16.0 mmol) and tributyl(1-ethoxyvinyl)tin (6.93 g, 19.2 mmol) in toluene (40 mL) for 20 minutes then tetrakis(triphenylphosphine)palladium(0) (1.1 g, 6.0 mmol) was added and the resulting mixture heated to 100° C. for 5 hours. The reaction mixture was allowed to cool to room temperature and 18% aqueous HCl (5 mL) was added and stirring continued for 30 minutes. The mixture was then diluted with water (50 mL), filtered through celite and the filtrate extracted with EtOAc (3×50 mL). The combined organic extracts were washed with brine (20 mL), dried ($Na_2SO_4$) and evaporated under reduced pressure to leave a residue which was purified by column chromatography on silica gel (60-120 mesh) using 85% EtOAc/hexane as the eluent to give the title compound (2.5 g, 79%) as a white solid.

44C. 4-[4-(4-Bromophenyl)-4-oxo-butanoyl]benzenesulfonamide

Zinc chloride (2.21 g, 16.2 mmol) was heated to melting under vacuum and then allowed to cool to room temperature. THF (25 mL), t-butanol (1.2 mL, 12.5 mmol) and triethylamine (0.35 mL, 12.5 mmol) were added and the mixture stirred at room temperature for 2 hours under a nitrogen atmosphere at which point the zinc chloride had fully dissolved. 4-Acetylbenzenesulfonamide (2.5 g, 12.5 mmol) and 2-bromo-1-(4-bromophenyl)ethanone (3.44 g, 12.5 mmol) were added and the mixture stirred for 48 hours at room temperature. The reaction mixture was diluted with water (50 ml) and extracted with EtOAc (3×80 mL). The combined organic extracts were dried ($Na_2SO_4$) and evaporated under reduced pressure to leave a residue which was purified by column chromatography on silica gel (60-120 mesh) using 2% MeOH/CHCl₃ as the eluent to give the title compound (1.2 g, 24%) as a white solid.

44D. 4-[5-(4-Bromophenyl)-1-[2-(trifluoromethyl)phenyl]pyrrol-2-yl]benzenesulfonamide A stirred solution of 4-[4-(4-bromophenyl)-4-oxo-butanoyl]benzenesulfonamide (1.20 g, 3.0 mmol), 2-(trifluoromethyl)aniline (1.45 g, 9.0 mmol) and PTSA (0.057 g, 0.30 mmol) in dioxane (5 mL) was heated to 150° C. for 8 hours. The mixture was allowed to cool to room temperature and the solvents evaporated under reduced pressure. The residue was purified by column chromatography on silica gel (60-120 mesh) using 50% EtOAc/hexanes as the eluent to give the title compound (0.80 g, 51%) as an off-white solid.

44E. 4-[5-(4-Bromophenyl)-1-[2-(trifluoromethyl)phenyl]pyrrol-2-yl]-N-[2-(dimethylamino)ethyl]benzenesulfonamide hydrochloride A stirred mixture of 4-[5-(4-bromophenyl)-1-[2-(trifluoromethyl)phenyl]pyrrol-2-yl]benzenesulfonamide (0.43 g, 0.82 mmol), potassium carbonate (0.34 g, 2.48 mmol) and 2-chloro-N,N-dimethylethanamine hydrochloride (0.13 g, 0.90 mmol) in anhydrous DMF (5 mL) was heated to 70° C. for 4 hours. The mixture was allowed to cool to room temperature and then poured in to water (50 mL) and extracted with EtOAc (3×50 mL). The combined organic extracts were washed with water (2×15 mL), dried (Na₂SO₄) and evaporated under reduced pressure to leave a residue which was purified by column chromatography on silica gel (60-120 mesh) using 4% MeOH/CHCl₃ as the eluent. The resulting solid was dissolved in THF (10 mL) and a 4N HCl solution in dioxane (0.1 mL) was added and the mixture stirred for 30 minutes at room temperature. The solvents were evaporated under reduced pressure to leave a solid that was triturated with pentane (3×2 mL) and Et₂O (2×2 mL) and then dried to give the title compound (0.13 g, 34%) as an off-white solid.

Synthetic Route L (Illustrated with reference to Example 82)

Example 82

4-[4-(4-Chlorophenyl)-5-[2-(trifluoromethyl)phenyl]pyrazol-1-yl]-N-[2-(dimethylamino)ethyl]-benzamide hydrochloride

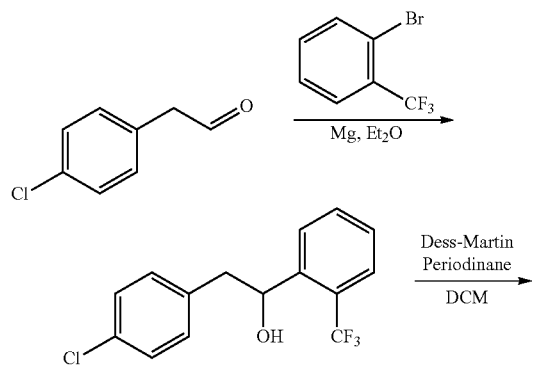

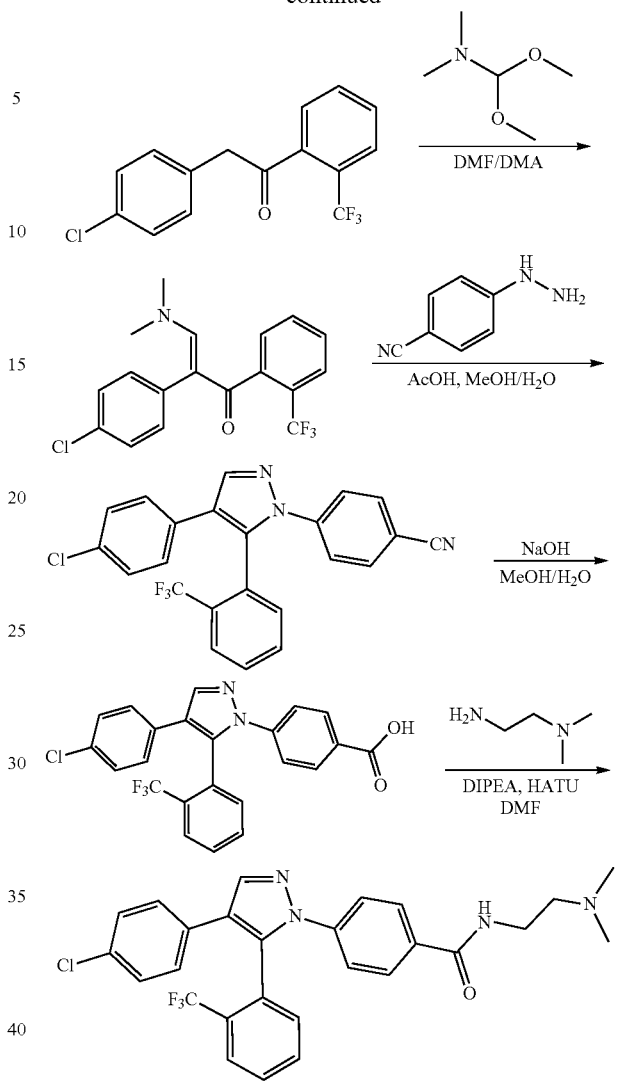

82A. 2-(4-Chlorophenyl)-1-[2-(trifluoromethyl)phenyl]ethanol

A solution of 1-bromo-2-(trifluoromethyl)benzene (2.9 g, 12.9 mmol) in anhydrous THF (5 mL) was added to activated magnesium metal (0.31 g, 12.9 mmol) in a sealed tube under a nitrogen atmosphere. The resulting mixture was stirred vigorously for 3 hours at room temperature. The resulting solution was added to a stirred solution of 2-(4-chlorophenyl)acetaldehyde (1.0 g, 6.4 mmol) in anhydrous THF (25 mL) at 0° C. under a nitrogen atmosphere. The resulting mixture was allowed to warm slowly to room temperature and then heated to reflux for 2 hours. The mixture was allowed to cool to room temperature and then poured in to saturated NH₄Cl solution (100 mL) and extracted with EtOAc (3×200 mL). The combined organic extracts were washed with brine (2×25 mL), dried (Na₂SO₄) and evaporated under reduced pressure to leave a residue which was purified by column chromatography on silica gel (60-120 mesh) using 4% EtOAc/hexanes as the eluent to give the title compound (0.6 g, 31%) as a colourless oil.

82B. 2-(4-Chlorophenyl)-1-[2-(trifluoromethyl)phenyl]ethanone

Dess-Martin periodinane (1.0 g, 2.3 mmol) was added in portions over 10 minutes to a stirred solution of 2-(4-chlorophenyl)-1-[2-(trifluoromethyl)phenyl]ethanol (0.6 g, 1.9 mmol) in DCM (50 mL) and the resulting mixture stirred at room temperature for 3 hours. The mixture was filtered through celite and the filtrate evaporated under reduced pressure to leave a residue which was purified by column chromatography on silica gel (60-120 mesh) using 1% EtOAc/hexanes as the eluent to give the title compound (0.4 g, 67%) as a colourless oil.

82C. (E)-2-(4-Chlorophenyl)-3-(dimethylamino)-1-[2-(trifluoromethyl)phenyl]prop-2-en-1-one A solution of N,N-dimethylformamide dimethyl acetal (0.32 g, 2.68 mmol) in DMF (1 mL) was added dropwise to a stirred solution of 2-(4-chlorophenyl)-1-[2-(trifluoromethyl)phenyl]ethanone (0.4 g, 1.34 mmol) in DMF (4 mL) at room temperature under a nitrogen atmosphere. The mixture was heated to 90° C. for 3 hours then allowed to cool to room temperature and poured in to water (50 mL) and extracted with EtOAc (3×150 mL). The combined organic extracts were washed with brine (2×10 mL), dried ($Na_2SO_4$) and evaporated under reduced pressure to leave a residue which was purified by column chromatography on silica gel (60-120 mesh) using 25% EtOAc/hexanes as the eluent to give the title compound (0.39 g, 82%) as a white solid.

82D. 4-[4-(4-Chlorophenyl)-5-[2-(trifluoromethyl)phenyl]pyrazol-1-yl]benzonitrile A mixture of (E)-2-(4-chlorophenyl)-3-(dimethylamino)-1-[2-(trifluoromethyl)phenyl]prop-2-en-1-one (0.39 g, 1.1 mmol), 4-cyanophenyihydrazine hydrochloride (0.21 g, 1.21 mmol) and sodium carbonate (82 mg, 0.77 mmol) in MeOH (40 mL) and water (80 mL) was stirred at room temperature for 15 minutes. Acetic acid (8 mL) was added dropwise over 10 minutes then the resulting mixture was heated to 140° C. for 8 hours. The cooled solution was neutralized with saturated $Na_2CO_3$ solution and extracted with EtOAc (3×150 mL). The combined organic extracts were washed with brine (2×25 mL), dried ($Na_2SO_4$) and evaporated under reduced pressure to leave a residue which was triturated with $Et_2O$ (3×10 mL) and pentane (3×10 mL) to give the title compound (0.4 g, 79%) as a white solid.

82E. 4-[4-(4-Chlorophenyl)-5-[2-(trifluoromethyl)phenyl]pyrazol-1-yl]benzoic acid A mixture of 4-[4-(4-chlorophenyl)-5-[2-(trifluoromethyl)phenyl]pyrazol-1-yl]benzonitrile (0.40 g, 0.94 mmol) and sodium hydroxide (0.38 g, 9.44 mmol) in methanol (5 mL) and water (5 mL) was stirred at 80° C. for 3 hours. The pH of the mixture was adjusted to 4 with 1 N HCl and the resulting solid collected by filtration. The collected solid was washed with water (2×5 mL) and hexane (2×5 mL) and dried to give the title compound (0.30 g, 77%) as a white solid.

82F. 4-[4-(4-Chlorophenyl)-5-[2-(trifluoromethyl)phenyl]pyrazol-1-yl]-N-[2-(dimethylamino)ethyl]benzamide hydrochloride HATU (0.20 g, 0.53 mmol) was added to a stirred solution of 4-[4-(4-chlorophenyl)-5-[2-(trifluoromethyl)phenyl]pyrazol-1-yl]benzoic acid (0.15 g, 0.35 mmol) in DMF (2 mL) at 0° C. under a nitrogen atmosphere. After stirring for 30 minutes, DIPEA (0.2 mL, 1.01 mmol) and N',N'-dimethylethane-1,2-diamine (37 mg, 0.42 mmol) were added and stirring continued for 90 minutes. The mixture was diluted with water (50 mL) and extracted with EtOAc (3×100 mL). The combined organic extracts were washed with brine (50 mL), dried ($Na_2SO_4$) and evaporated under reduced pressure to leave a residue which was purified by column chromatography on silica gel (60-120 mesh) using 4% MeOH/$CHCl_3$ as the eluent. The resulting solid was dissolved in THF (2 mL) and 4N HCl solution in dioxane (0.1 ml) was added and the mixture stirred for 30 minutes at room temperature. The solvents were evaporated under reduced pressure to leave a solid that was triturated with $Et_2O$ (3×10 mL) and then dried to give the title compound (75 mg, 40%) as an off-white solid.

Synthetic Route M (Illustrated with reference to Example 93)

Example 93

4-[3-(4-chlorophenyl)-4-[2-(trifluoromethyl)phenyl]-1H-pyrazol-5-yl]-N-[2-(dimethylamino)ethyl]benzamide hydrochloride

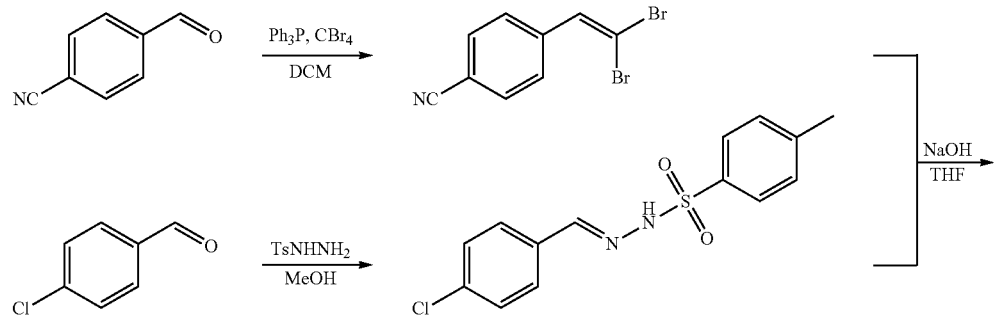

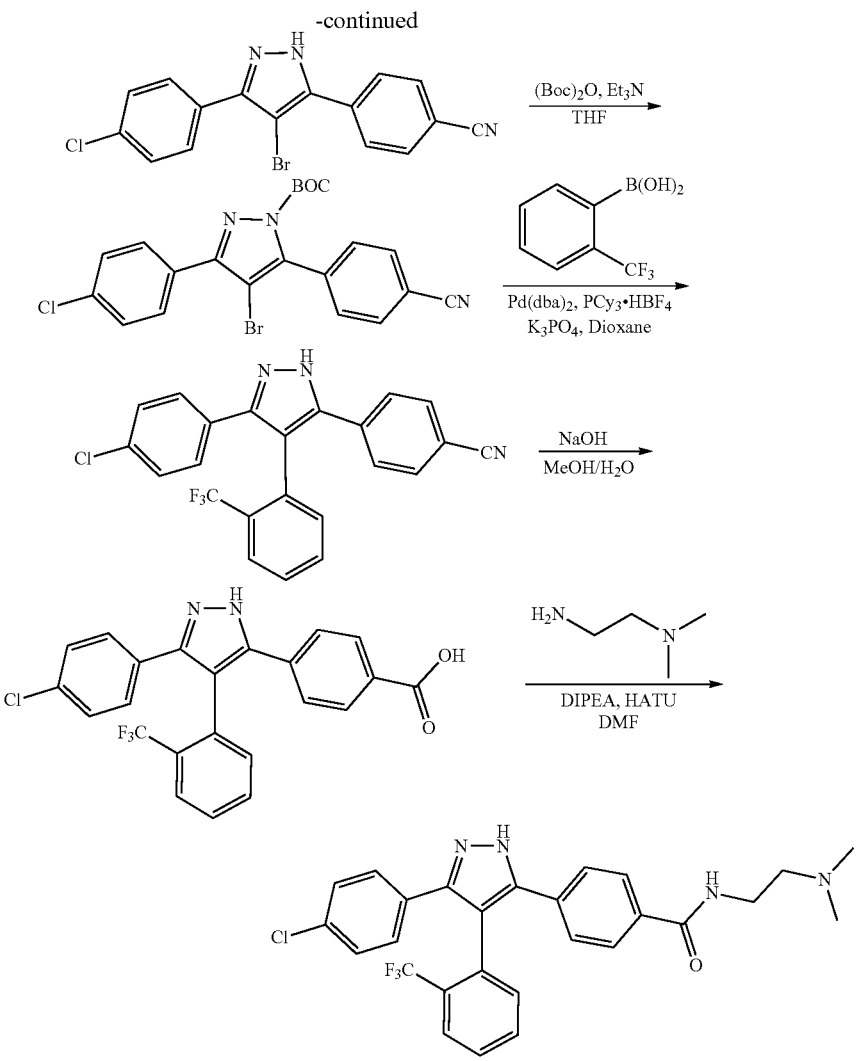

93A. 4-(2,2-Dibromovinyl)benzonitrile

Triphenylphosphine (16.0 g, 60.8 mmol) was added in portions over 15 minutes to a stirred solution of 4-formyl-benzonitrile (2.0 g, 15.2 mmol) and carbon tetrabromide (10.1 g, 30.4 mmol) in DCM (50 mL) at 0° C. under a nitrogen atmosphere. The resulting brown coloured solution was stirred at 0° C. for 2 hours then diluted with EtOAc (100 mL) and poured into water (100 mL). After filtering through a pad of celite the separated aqueous phase was extracted with EtOAc (3×200 mL). The combined organic extracts were washed with brine (2×10 mL), dried ($Na_2SO_4$) and evaporated under reduced pressure to leave a residue which was purified by column chromatography on silica gel (60-120 mesh) using 4% EtOAc/hexanes as the eluent to give the title compound (3.5 g, 81%) as a white solid.

93B. N-[(E)-(4-Chlorophenyl)methyleneamino]-4-methyl-benzenesulfonamide

A stirred solution of 4-chlorobenzaldehyde (3.0 g, 16.1 mmol) and p-toluenesulfonyl hydrazide (2.37 g, 16.9 mmol) in MeOH (20 mL) was heated to 60° C. for two hours. The solution was allowed to cool to room temperature and then the solvents were evaporated under reduced pressure. The resulting solid was recrystallised from MeOH/$H_2O$ to give the title compound (3.5 g, 71%) as a white solid.

93C. 4-[4-Bromo-3-(4-chlorophenyl)-1H-pyrazol-5-yl]benzonitrile

A stirred solution of N-[(E)-(4-chlorophenyl)methyl-eneamino]-4-methyl-benzenesulfonamide (2.0 g, 6.5 mmol), 4-(2,2-dibromovinyl)benzonitrile (1.85 g, 6.5 mmol) and NaOH (0.78 g, 19.5 mmol) in 1,4-dioxane (60 mL) was heated to 70° C. for 17 hours. The cooled reaction mixture was partitioned between saturated potassium bisulfate solution (100 mL) and EtOAc (50 mL). The separated aqueous phase was extracted with EtOAc (3×50 mL) then the combined organic extracts were washed with brine (2×25 mL), dried ($Na_2SO_4$) and evaporated under reduced pressure. The residue was purified by column chromatography on silica gel (60-120 mesh) using 7% EtOAc/hexanes as the eluent to give the title compound (0.5 g, 22%) as an off-white solid.

93D. tert-Butyl 4-bromo-3-(4-chlorophenyl)-5-(4-cyanophenyl)pyrazole-1-carboxylate $(Boc)_2O$ was added to a stirred solution of 4-[4-bromo-3-(4-chlorophenyl)-1H-pyrazol-5-yl]benzonitrile (0.50 g, 1.4 mmol) and triethylamine (0.3 mL, 2.1 mmol) in THF (5 mL) under a nitrogen atmosphere. The solution was stirred for 30 minutes at room temperature then partitioned between saturated potassium bisulfate solution (20 mL) and EtOAc (30 mL). The separated aqueous phase was extracted with EtOAc (3×30 mL) then the combined organic extracts were washed with brine (2×25 mL), dried (Na$_2$SO$_4$) and evaporated under reduced pressure. The residue was purified by column chromatography on silica gel (60-120 mesh) using 7% EtOAc/hexanes as the eluent to give the title compound (0.45 g, 70%) as an off-white solid.

93E. 4-[3-(4-Chlorophenyl)-4-[2-(trifluoromethyl)phenyl]-1H-pyrazol-5-yl]benzonitrile A stirred mixture of tert-butyl 4-bromo-3-(4-chlorophenyl)-5-(4-cyanophenyl)pyrazole-1-carboxylate (0.45 g, 0.97 mmol), (2-(trifluoromethyl)phenyl)boronic acid (0.28 g, 1.46 mmol), tripotassium phosphate (0.62 g, 2.9 mmol) and tricyclohexylphosphine tetrafluoroborate (43 mg, 0.12 mmol) in 1,4-dioxane (13 mL) was degassed with nitrogen for 20 minutes. Bis(dibenzylideneacetone)palladium(0) (55 mg, 0.097 mmol) was added to the solution and the resulting mixture heated to 90° C. for 36 hours under a nitrogen atmosphere. The cooled reaction mixture was partitioned between water (20 mL) and EtOAc (30 mL). The separated aqueous phase was extracted with EtOAc (3×30 mL) then the combined organic extracts were washed with brine (2×25 mL), dried (Na$_2$SO$_4$) and evaporated under reduced pressure. The residue was purified by column chromatography on silica gel (60-120 mesh) using 12% EtOAc/hexanes as the eluent to give the title compound (0.16 g, 39%) as an off-white solid.

93F. 4-[3-(4-Chlorophenyl)-4-[2-(trifluoromethyl)phenyl]-1H-pyrazol-5-yl]benzoic acid A mixture of 4-[3-(4-chlorophenyl)-4-[2-(trifluoromethyl)phenyl]-1H-pyrazol-5-yl]benzonitrile (0.16 g, 0.38 mmol) and sodium hydroxide (0.15 g, 3.78 mmol) in methanol (1.6 mL) and water (0.7 mL) was stirred at 90° C. for 18 hours. The cooled reaction mixture was partitioned between saturated potassium bisulfate solution (10 mL) and EtOAc (10 mL). The separated aqueous phase was extracted with EtOAc (3×10 mL) then the combined organic extracts were washed with brine (2×10 mL), dried (Na$_2$SO$_4$) and evaporated under reduced pressure to give the title compound (0.14 g, 84%) as an off-white solid.

93G. 4-[3-(4-Chlorophenyl)-4-[2-(trifluoromethyl)phenyl]-1H-pyrazol-5-yl]-N-[2-(dimethylamino)ethyl]benzamide hydrochloride HATU (0.17 g, 0.44 mmol) was added to a stirred solution of 4-[3-(4-chlorophenyl)-4-[2-(trifluoromethyl)phenyl]-1H-pyrazol-5-yl]benzoic acid (0.13 g, 0.29 mmol) in DMF (1.3 mL) at 0° C. under a nitrogen atmosphere. After stirring for 30 minutes, DIPEA (0.15 mL, 0.88 mmol) and N',N'-dimethylethane-1,2-diamine (31 mg, 0.35 mmol) were added and stirring continued for 30 minutes. The mixture was diluted with water (20 mL) and extracted with EtOAc (3×50 mL). The combined organic extracts were washed with brine (20 mL), dried (Na$_2$SO$_4$) and evaporated under reduced pressure to leave a residue which was purified by column chromatography on silica gel (60-120 mesh) using 4% MeOH/CHCl$_3$ as the eluent. The resulting solid was dissolved in THF (2 mL) and 4N HCl solution in dioxane (0.1 mL) was added and the mixture stirred for 30 minutes at room temperature. The solvents were evaporated under reduced pressure to leave a solid that was triturated with n-pentane (3×10 mL) and then dried to give the title compound (33 mg, 25%) as an off-white solid.

Synthetic Route N (Illustrated with reference to Example 90)

Example 90

1-[4-[5-(4-Chlorophenyl)-1-[2-(trifluoromethyl)phenyl]pyrrol-2-yl]phenyl]-3-[2-(dimethylamino)-ethyl]urea hydrochloride

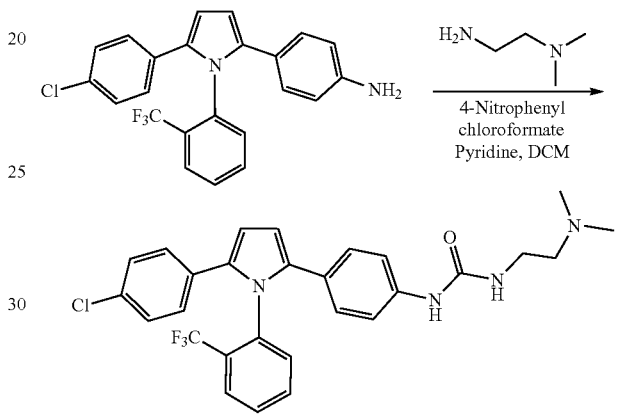

90A. 1-[4-[5-(4-Chlorophenyl)-1-[2-(trifluoromethyl)phenyl]pyrrol-2-yl]phenyl]-3-[2-(dimethylamino)-ethyl]urea hydrochloride A solution of 4-nitrophenylchloroformate (0.16 g, 0.8 mmol) in DCM (5 mL) was added dropwise to a stirred solution of 4-[5-(4-chlorophenyl)-1-[2-(trifluoromethyl)phenyl]pyrrol-2-yl]aniline (0.3 g, 0.72 mmol) (prepared using Method D) and pyridine (63 mg, 0.8 mmol) in DCM (10 mL) at 0° C. under a nitrogen atmosphere. The mixture was stirred at 0° C. for 2 hours then DIPEA (0.18 g, 1.44 mmol) and N,N'-dimethylethelenediamine (63 mg, 0.72 mmol) were added and the mixture allowed to warm to room temperature. Stirring was continued for a further 2 hours then the solvents were evaporated under reduced pressure to leave a residue which was purified by preparative HPLC using (A) 0.1% HCl in water and (B) 100% acetonitrile as mobile phase, using Denali C18 (250×25 mm) 5 um column with the flow rate of 25.0 mL/min and with the following gradient:

| Time (min) | A | B |
|---|---|---|
| 0.01 | 60 | 40 |
| 14.00 | 55 | 45 |
| 14.01 | 0 | 100 |
| 19.00 | 0 | 100 |
| 19.01 | 60 | 40 |
| 20.00 | 60 | 40 |

The title compound (0.07 g, 17%) was obtained as a white solid.

Synthetic Route O (Illustrated with reference to Example 92)

Example 92

4-[3-(4-Chlorophenyl)-4-[2-(trifluoromethyl)phenyl]-1H-pyrazol-5-yl]-N-[2-(dimethylamino)ethyl] benzamide hydrochloride

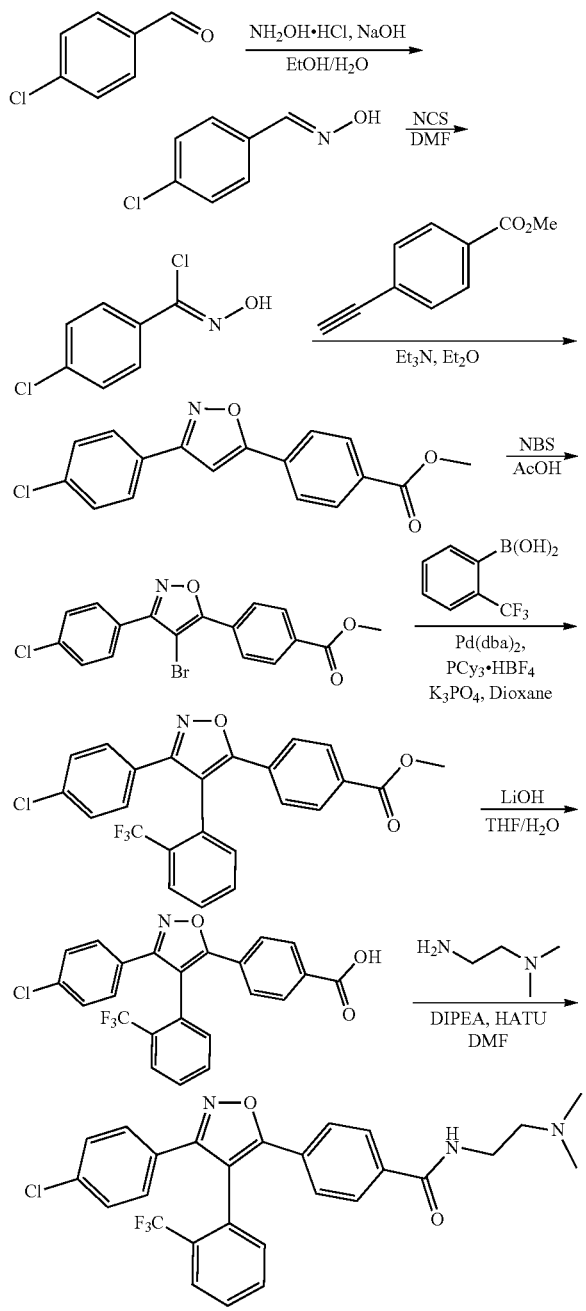

92A. (1E)-4-Chlorobenzaldehyde Oxime

Sodium hydroxide (4.4 g, 110 mmol) was added in portions over 10 minutes to a stirred solution of 4-chlorobenzaldehyde (10 g, 71.1 mmol) and hydroxylamine hydrochloride (10 g, 144 mmol) in EtOH (50 mL) and water (50 mL) and the resulting mixture stirred at room temperature for 18 hours. The solution was neutralized with 2N HCl solution and extracted with EtOAc (3×100 mL). The combined organic extracts were washed with brine (50 mL), dried ($Na_2SO_4$) and evaporated under reduced pressure to give the title compound (10.0 g, 91%) as a white solid.

92B. (1Z)-4-Chloro-N-hydroxy-benzimidoyl chloride

N-Chlorosuccinimide (1.73 g, 12.9 mmol) was added in three portions over 15 minutes to a stirred solution of (1E)-4-chlorobenzaldehyde oxime (2.0 g, 12.9 mmol) in DMF (10 mL) at 0° C. under a nitrogen atmosphere. The solution was allowed to warm to room temperature and stirring continued for 18 hours before partitioning between water (100 mL) and EtOAc (50 mL). The separated aqueous phase was extracted with EtOAc (3×50 mL) then the combined organic extracts were washed with brine (2×25 mL), dried ($Na_2SO_4$) and evaporated under reduced pressure to give the title compound (0.16 g, 39%) as a beige solid.

92C. Methyl 4-[3-(4-chlorophenyl)isoxazol-5-yl] benzoate

A mixture of (1Z)-4-chloro-N-hydroxy-benzimidoyl chloride (1.75 g, 9.2 mmol), methyl 4-ethynylbenzoate (1.47 g, 9.2 mmol) and $Et_3N$ (1.4 mL, 10.1 mmol) in $Et_2O$ (25 mL) was stirred at room temperature under a nitrogen atmosphere for 18 hours. The reaction mixture was partitioned between water (20 mL) and EtOAc (30 mL). The separated aqueous phase was extracted with EtOAc (3×30 mL) then the combined organic extracts were washed with brine (2×25 mL), dried ($Na_2SO_4$) and evaporated under reduced pressure. The residue was purified by column chromatography on silica gel (60-120 mesh) using 85% EtOAc/hexanes as the eluent to give the title compound (1.55 g, 54%) as an off-white solid.

92D. Methyl 4-[4-bromo-3-(4-chlorophenyl)isoxazol-5-yl]benzoate

N-Bromosuccinimide (1.02 g, 5.7 mmol) was added to a stirred solution of methyl 4-[3-(4-chlorophenyl)isoxazol-5-yl]benzoate (1.50 g, 4.7 mmol) in glacial acetic acid (10 mL) and the resulting mixture heated to 110° C. for 3 hours. The cooled reaction mixture was diluted with water (100 mL) and the resulting solid collected by filtration. The obtained solid was further purified by column chromatography on silica gel (60-120 mesh) using 4% EtOAc/hexanes as the eluent to give the title compound (0.84 g, 45%) as a yellow solid.

92E. Methyl 4-[3-(4-chlorophenyl)-4-[2-(trifluoromethyl)phenyl]isoxazol-5-yl]benzoate A stirred mixture of methyl 4-[4-bromo-3-(4-chlorophenyl)isoxazol-5-yl]benzoate (0.80 g, 2.0 mmol), (2-(trifluoromethyl)phenyl)boronic acid (1.92 g, 10.1 mmol), tripotassium phosphate (1.29 g, 6.0 mmol) and tricyclohexylphosphine tetrafluoroborate (75 mg, 0.20 mmol) in 1,4-dioxane (30 mL) was degassed with nitrogen for 30 minutes at room temperature. Bis(dibenzylideneacetone)palladium(0) (60 mg, 0.10 mmol) was added to the solution and the resulting mixture heated to 110° C. for 18 hours under a nitrogen atmosphere. The cooled reaction mixture was partitioned between water (50 mL) and EtOAc (50 mL). The separated aqueous phase was extracted with EtOAc (4×50 mL) then the combined organic extracts were washed with brine (2×25 mL), dried ($Na_2SO_4$) and evaporated under reduced pressure. The residue was purified by column chromatography on silica gel (60-120 mesh) using 5% EtOAc/hexanes as the eluent to give the title compound (0.18 g, 19%) as an off-white solid.

92F. 4-[3-(4-Chlorophenyl)-4-[2-(trifluoromethyl) phenyl]isoxazol-5-yl]benzoic acid A stirred solution of methyl 4-[3-(4-chlorophenyl)-4-[2-(trifluoromethyl)phenyl]isoxazol-5-yl]benzoate (0.17 g, 0.40 mmol) and lithium hydroxide monohydrate (67 mg, 0.16 mmol) in THF (2 mL) and water (2 mL) was heated at 90° C. for 16 hours. The cooled reaction mixture was partitioned between saturated potassium bisulfate solution (20 mL) and EtOAc (30 mL). The separated aqueous phase was extracted with EtOAc (3×30 mL) then the combined organic extracts were washed with brine (2×25 mL), dried ($Na_2SO_4$) and evaporated under reduced pressure to give the title compound (0.16 g, 98%) as an off-white solid.

92G. 4-[3-(4-Chlorophenyl)-4-[2-(trifluoromethyl) phenyl]-1H-pyrazol-5-yl]-N-[2-(dimethylamino) ethyl]benzamide hydrochloride HATU (0.21 g, 0.54 mmol) was added to a stirred solution of 4-[3-(4-chlorophenyl)-4-[2-(trifluoromethyl)phenyl] isoxazol-5-yl]benzoic acid (0.16 g, 0.36 mmol) in DMF (2 mL) at 0° C. under a nitrogen atmosphere. After stirring for 30 minutes, DIPEA (0.2 mL, 1.01 mmol) and N',N'-dimethylethane-1,2-diamine (38 mg, 0.43 mmol) were added and stirring continued for 2 hours. The mixture was diluted with water (50 mL) and extracted with EtOAc (3×100 mL). The combined organic extracts were washed with brine (50 mL), dried ($Na_2SO_4$) and evaporated under reduced pressure to leave a residue which was purified by column chromatography on silica gel (60-120 mesh) using 4% MeOH/$CHCl_3$ as the eluent. The resulting solid was dissolved in THF (2 mL) and 4N HCl solution in dioxane (0.1 mL) was added and the mixture stirred for 30 minutes at room temperature. The solvents were evaporated under reduced pressure to leave a solid that was triturated with n-pentane (3×10 mL) and then dried to give the title compound (35 mg, 18%) as a white solid.

Biological Activity

Example A

Assay to Measure the Effects of Compounds of the Invention on HCT116 Colorectal Cancer Cell Viability The following protocol was used to measure the effects of compounds of the invention on HCT116 cell viability.
1. HCT116 cells were grown in RPM11640 media supplemented with Glutamax and 10% FBS in a 37° C./5% CO2 incubator.
2. Growing culture of HCT116 cells were trypsinised, counted and diluted to give 10,000 cells/mL in an appropriate volume, allowing at least 6 mL of cells per plate.
3. 200 µL of PBS were added to all the outer wells of a flat-bottomed (8×12) 96-well TC plate. 100 µL of media were added only to wells in column 11 of the plates (these wells provided a blank for the cell titre blue assay). Two compounds were assayed on each plate.
4. 100 ul of 10,000 cells/mL HCT116s were plated in rows B-G of each plate.
5. The cells were incubated (37° C. 5% $CO_2$) for 24 hours before treating with compounds.
6. An 8 mM compound stock in DMSO was prepared for all compounds to be tested. 2.5 µL of the compound stock was added to 1000 µL growth medium in a 96-well deep well block and serial dilutions were prepared across the plate by transferring 500 µL into wells containing 500 µL growth medium+0.25% DMSO to give eight concentrations of compound (this ensured a constant amount of DMSO at all concentrations of compound). When making up growth medium+DMSO, an amount of 5 ml was allowed per compound to be diluted.
7. 3 rows of cells were treated with 100 µL/well from each row on the dilution plate so that each cell plate is treated with a single compound. This gave a final volume in all wells of 200 µL and a titration of compound from a final concentration of 10 uM down to 78 nM.
8. The cells were incubated (37° C. 5% $CO_2$) for 72 hours.
9. 5 ul cell titre blue reagent (Promega) were added to all wells except the edge wells (which contain PBS only) and incubated (37° C. 5% $CO_2$) for 2.5-3 hours.
10. Fluorescence was measured on a suitable plate reader using a 530-570 nm filter set for excitation and a 580-620 nm filter set for fluorescence emission.
11. Data were analysed using an appropriate graphing package (such as GraphPad Prism). Data were expressed as the concentration of compound causing a 50% inhibition of cell viability or $GI_{50}$.

From the results obtained by following the above protocol, the $GI_{50}$ values against the HCT116 cell line of each of the compounds of the Examples were determined as shown in Table 4.

TABLE 4

| Example | $GI_{50}$ (µM) | Example | $GI_{50}$ (µM) | Example | $GI_{50}$ (µM) |
|---|---|---|---|---|---|
| 1 | nd | 2 | nd | 3 | nd |
| 4 | nd | 5 | 0.56 | 6 | 0.20 |
| 7 | 1.06 | 8 | 1.85 | 9 | 0.03 |
| 10 | 0.34 | 11 | 0.36 | 12 | 0.29 |
| 13 | 0.66 | 14 | nd | 15 | 2.18 |
| 16 | 2.72 | 17 | nd | 18 | nd |
| 19 | 4.21 | 20 | 3.94 | 21 | 1.06 |
| 22 | 2.75 | 23 | 0.39 | 24 | 0.49 |
| 25 | 3.89 | 26 | 0.12 | 27 | 4.74 |
| 28 | nd | 29 | 0.06 | 30 | 8.44 |
| 31 | 1.45 | 32 | 0.06 | 33 | 0.01 |
| 34 | 0.08 | 35 | 0.22 | 36 | 0.03 |
| 37 | 0.02 | 38 | 0.19 | 39 | 0.35 |
| 40 | 1.03 | 41 | 0.05 | 42 | 0.38 |
| 43 | 0.20 | 44 | 0.51 | 45 | 0.35 |
| 46 | 0.16 | 47 | 1.38 | 48 | 0.41 |
| 49 | 0.05 | 50 | 2.18 | 51 | 0.10 |
| 52 | 0.35 | 53 | 0.56 | 54 | 1.38 |
| 55 | 2.25 | 56 | 2.71 | 57 | 0.06 |
| 58 | 0.03 | 59 | 0.05 | 60 | 0.06 |
| 61 | 0.06 | 62 | 0.12 | 63 | 1.64 |
| 64 | 1.70 | 65 | 1.96 | 66 | 0.89 |
| 67 | 0.07 | 68 | 0.11 | 69 | 0.05 |
| 70 | 0.02 | 71 | 0.02 | 72 | 1.73 |
| 73 | 0.09 | 74 | 0.13 | 75 | 0.15 |
| 76 | 0.24 | 77 | 3.63 | 78 | 2.13 |
| 79 | 3.83 | 80 | 3.92 | 81 | 0.08 |
| 82 | 0.04 | 83 | 0.06 | 84 | 0.19 |

TABLE 4-continued

| Example | GI$_{50}$ (µM) | Example | GI$_{50}$ (µM) | Example | GI$_{50}$ (µM) |
|---|---|---|---|---|---|
| 85 | 0.49 | 86 | 0.34 | 87 | 0.06 |
| 88 | 0.25 | 89 | 1.36 | 90 | 0.50 |
| 91 | 0.01 | 92 | 0.03 | 93 | 0.26 |
| 94 | 0.05 | 95 | 0.08 | 96 | 0.03 |
| 97 | 0.02 | 98 | 0.02 | 99 | 0.04 |
| 100 | 0.13 | 101 | 0.06 | 102 | 0.38 |
| 103 | 0.04 | 104 | 0.15 | 105 | 0.10 |
| 106 | 0.08 | 107 | 0.16 | | |

Example B

Assay to Measure the Effects of Compounds of the Invention on Arresting Cells in Mitosis Inhibiting the ability of PLK1 to bind to its phosphopeptide binding partners through the PBD causes cells to arrest in mitosis. Experimentally, this is measured by assessing the number of cells which are in mitosis at a certain time after treatment with a PLK1-PBD inhibitor by immunofluorescent detection of phosphorylated Histone H3 (pH3), a marker which is only present in mitotic cells. PLK1-PBD inhibitors are expected to cause a dose-dependent increase in pH3-positive cells, which is reported as Mitotic Index (MI)—the percentage of cells which, at a given time, are positive for this mitotic mark. The following protocol has been used to measure MI:

1. Plate HeLa cells at 10,000/well in 100 µL/well in clear flat-bottom 96-well plates and incubate overnight.
2. Immediately prior to treatment, dilute compounds in medium in a 96-well round-bottom plate. Make up all compounds at 5 times final desired concentration on cells, and serially dilute 1:2 across the plate ensuring that there is 100 µL of each concentration (start with 200 µl of the top concentration on the left of the plate). Do not exceed a final concentration on cells of 1% DMSO (i.e. not greater than 5% in the dilution plate), and preferably remain below 0.5%.
3. Treat cells by adding 25 µL from the compound dilution plate to triplicate wells.
4. Incubate cells with compound for 24 hours.
5. After 24 hours, fixation and staining is carried out as follows:
6. Dilute 37% formaldehyde in PBS to give a 12.95% solution by adding 3.5 mL formaldehyde to 6.5 mL of PBS.
7. Add 50 µL of formaldehyde fixation solution directly to each well of cells (which already contain 125 µL medium).
8. Incubate at room temp for 10 minutes.
9. Remove fixative and add 100 µL/well PBS+0.1% Triton X-100 for 10 minutes.
10. Aspirate and add 100 µL/well PBS+1% BSA.
11. Aspirate and add 50 µL/well of primary antibody (anti-PH3 [1:2000]/anti-MPM2 [1:1000]) diluted in PBS+1% BSA. Incubate for 1 hour.
12. Wash×2 with 100 µL/well PBS+1% BSA.
13. Add 50 µL/well of secondary antibody plus Hoechst stain (anti-rabbit Alexafluor 488 [1:500]; anti-mouse Alexafluor 546 [1:500]+Hoechst 33342 [1:2500 final concentration=4 µg/mL]) diluted in PBS+1% BSA. Incubate for 1 hour.
14. Wash twice with 100 µL/well PBS+1% BSA.
15. Aspirate and add 100 µL/well PBS. Plates can be stored at 4° C. in PBS for several weeks before scanning on the Cellomics Arrayscan. Ensure that plates do not dry out.
16. Scan on Cellomics using Target Activation Bioapplication.
17. MI data emerging from the Cellomic Bioapplication can be used to plot MI versus compound concentration, and subsequently used to generate an EC50 value for each compound using an appropriate graphing/curve-fitting package such as GraphPad Prism.

From the results obtained by following the above protocol, the EC$_{50}$ values and the percentage of cells in mitosis against the HeLa cell line was obtained for each of the compounds of the Examples were determined as shown in Table 5.

TABLE 5

| Example | EC$_{50}$ (µM) | % mitotic cells | Example | EC$_{50}$ (µM) | % mitotic cells |
|---|---|---|---|---|---|
| 2 | 0.86 | 86 | 3 | 1.58 | 65 |
| 4 | 0.55 | 65 | 6 | 0.66 | 86 |
| 7 | 2.2 | 75 | 9 | 0.19 | 89 |
| 10 | 0.78 | 62 | 11 | 0.80 | 54 |
| 12 | 0.79 | 62 | 13 | 0.75 | 71 |
| 14 | 0.83 | 68 | 17 | 1.45 | 65 |
| 18 | 1.64 | 67 | 22 | >10 | 5 |
| 23 | 0.74 | 79 | 24 | 0.62 | 77 |

In a separate experiment, the compound of Example 33 was tested in the mitotic arrest assay and was found to have an EC$_{50}$ in the assay of 0.061±0.01 µM.

Example C

Assay to Measure the Effects of Compounds of the Invention on Wild-Type Versus KRAS HeLa Cell Viability Identifying synthetic lethal interactions between targeted small molecule therapies and characterised oncogenic mutations is a goal of modern oncology drug discovery efforts. To this end, PLK1-PBD inhibitors were tested on HeLa cells engineered to inducibly express wild-type or oncogenic KrasG12V transgenes using the FLP-in/T-Rex system (Invitrogen). Cells were plated, and then treated with or without Doxycycline to induce transgene expression, and then treated with serially-diluted PBD inhibitors. After 72 hours of incubation, cell viability was assessed using the Cell Titre Blue reagent (Promega) and a BMG Pherastar plate reader. The effect of PBD inhibition on cell viability with either wild-type or oncogenic G12V KRAS was assessed using the graphing/curve-fitting packages in GraphPad Prism.

From the results obtained by following the above protocol, the GI$_{50}$ values against the wild-type and KRAS G12V HeLa cell line of each of the compounds of the Examples were determined as shown in Table 6.

TABLE 6

| Example | WT GI$_{50}$ (µM) | G12V GI$_{50}$ (µM) | Example | WT GI$_{50}$ (µM) | G12V GI$_{50}$ (µM) |
|---|---|---|---|---|---|
| 2 | 0.18 | 0.05 | 9 | 0.05 | 0.02 |
| 15 | 0.65 | 0.38 | 23 | 0.24 | 0.08 |
| 24 | 0.26 | 0.08 | 25 | 2.51 | 3.58 |
| 26 | 0.12 | 0.07 | 28 | 0.06 | 0.03 |
| 33 | 0.02 | 0.01 | 34 | 0.13 | 0.09 |
| 35 | 0.21 | 0.14 | 36 | 0.12 | 0.06 |
| 37 | 0.05 | 0.02 | 41 | 0.04 | 0.02 |
| 42 | 0.13 | 0.05 | 53 | 0.34 | 0.22 |
| 56 | 2.19 | 2.52 | 57 | 0.05 | 0.03 |
| 58 | 0.03 | 0.02 | 59 | 0.01 | 0.008 |
| 60 | 0.03 | 0.01 | 61 | 0.02 | 0.005 |

TABLE 6-continued

| Example | WT GI$_{50}$ (μM) | G12V GI$_{50}$ (μM) | Example | WT GI$_{50}$ (μM) | G12V GI$_{50}$ (μM) |
|---|---|---|---|---|---|
| 62 | 0.02 | 0.008 | 70 | 0.005 | 0.003 |
| 71 | 0.01 | 0.005 | 82 | 0.03 | 0.01 |
| 87 | 0.02 | 0.008 | 91 | 0.01 | 0.005 |

Example D

Assay to Measure the Effects of Compounds of the Invention on Glioblastoma Cancer Cell Viability The compound of Example 33 was tested for inhibitory activity against the glioblastoma cell lines in Table 7 below.

TABLE 7

| Cell line # | IC$_{50}$(μM) | Cell line # | IC$_{50}$(μM) |
|---|---|---|---|
| 907042 | 0.071 | 949094 | 0.709 |
| 908145 | 0.223 | 909750 | 0.929 |
| 905984 | 0.241 | 907313 | 1.109 |
| 906868 | 0.252 | 909745 | 1.367 |
| 909905 | 0.276 | 946368 | 1.397 |
| 906871 | 0.283 | 946370 | 1.671 |
| 1240170 | 0.363 | 907271 | 2.059 |
| 906746 | 0.430 | 908144 | 2.423 |
| 687586 | 0.489 | 907279 | 27.821 |

Example E

Kinase Selectivity Assay

Compounds of the invention bind to the PBD domain of PLK1 but not to the catalytic domain and should exhibit good selectivity over other kinases. The compound of Example 33 was tested for off-target activity against a panel of fifty five kinases bearing functional or structural similarity to PLK1 at a concentration of 5 μM using the DiscoverX KinomeScreen assay. The results are shown in Table 8 below.

TABLE 8

| Gene Symbol | % Control | Gene Symbol | % Control |
|---|---|---|---|
| AAK1 | 100 | NEK9 | 92 |
| AURKA | 83 | PKMYT1 | 100 |
| AURKB | 95 | PLK1 | 100 |
| AURKC | 85 | PLK2 | 85 |
| BMP2K | 85 | PLK3 | 74 |
| BUB1 | 90 | PLK4 | 90 |
| CAMKK1 | 91 | EIF2AK2 | 90 |
| CAMKK2 | 97 | DSTYK | 75 |
| CDK2 | 89 | ROCK2 | 100 |
| CSNK2A1 | 96 | SBK1 | 61 |
| CSNK2A2 | 92 | SgK110 | 100 |
| EIF2AK1 | 98 | STK16 | 92 |
| ERN1 | 74 | STK35 | 71 |
| GAK | 100 | STK36 | 91 |
| EIF2AK4 | 97 | TBK1 | 80 |
| GSG2 | 77 | TLK1 | 99 |
| CHUK | 100 | TLK2 | 94 |
| IKBKB | 100 | TTK | 83 |
| IKBKE | 75 | ULK1 | 84 |
| NEK1 | 100 | ULK2 | 100 |
| NEK10 | 94 | ULK3 | 88 |
| NEK11 | 100 | WEE1 | 98 |
| NEK2 | 94 | WEE2 | 92 |
| NEK3 | 74 | WNK1 | 97 |
| NEK4 | 100 | WNK2 | 100 |
| NEK5 | 99 | WNK3 | 100 |

TABLE 8-continued

| Gene Symbol | % Control | Gene Symbol | % Control |
|---|---|---|---|
| NEK6 | 99 | WNK4 | 91 |
| NEK7 | 79 | | |

The results demonstrate a lack of activity against the other kinases and hence the specificity of the compound of Example 33 for PLK1-PBD over other kinases.

Example F

Determination of Oral Bioavailability

The oral bioavailability of the compound of Example 33 was determined in mice and compared with the bioavailability following intravenous injection using the following protocol. Male CD-1 mice were dosed with the compound of Example 33, either by i.v. administration (2 mg/kg) or by peroral administration (10 mg/kg) and samples were taken for analysis at 2, 5, 10, 15, 30 min, 1, 2, 4, 8, 16, 24 and 40 hrs (for i.v.) and at 5, 15, 30 min, 1, 2, 4, 8, 16, 24, 48 and 72 hrs. The compound of Example 33 was formulated in 5% DMSO/95% hydroxypropyl-beta-cyclodextrin (20% w/v aqueous) for i.v. and 10% DMSO/90% hydroxypropyl-beta-cyclodextrin (20% w/v aqueous) for p.o. N=3 mice per time point with 15 ul plasma per aliquot. Quantitative bioanalysis was performed and the results are shown in FIG. 1 and in Table 9 below.

TABLE 9

| Parameter | 2 mg/kg IV | Parameter | 10 mg/Kg PO |
|---|---|---|---|
| T½ | 13 hours | T½ | 15 hours |
| Cl | 16 ml/min/kg | Vz | 23 l/kg |
| Vss | 17 l/kg | Cmax | 415 ng/ml |
| Cmax | 873 ng/ml | AUCinf | 9796 ng · hr/ml |
| AUCinf | 2096 ng · hour/ml | F | 93% |

The results demonstrate that the compound of Example 33 is highly absorbed following oral dosing in mice.

Measurements of other pharmacokinetic parameters of the compound of Example 33 demonstrated that it has a kinetic solubility of 32 μM, exhibits negligible (>25 μM) binding to the hERG ion channel, and is stable in human hepatocytes (C$_{Lint}$ 10 μl/min/million cells). It also demonstrates negligible cytochrome P450 inhibition ((1A, 2D6, 2C9, 2C19, 3A4) all >10 uM).

Example G

Determination of Brain Exposure Following Oral Dosing in Mice

Figure 2:
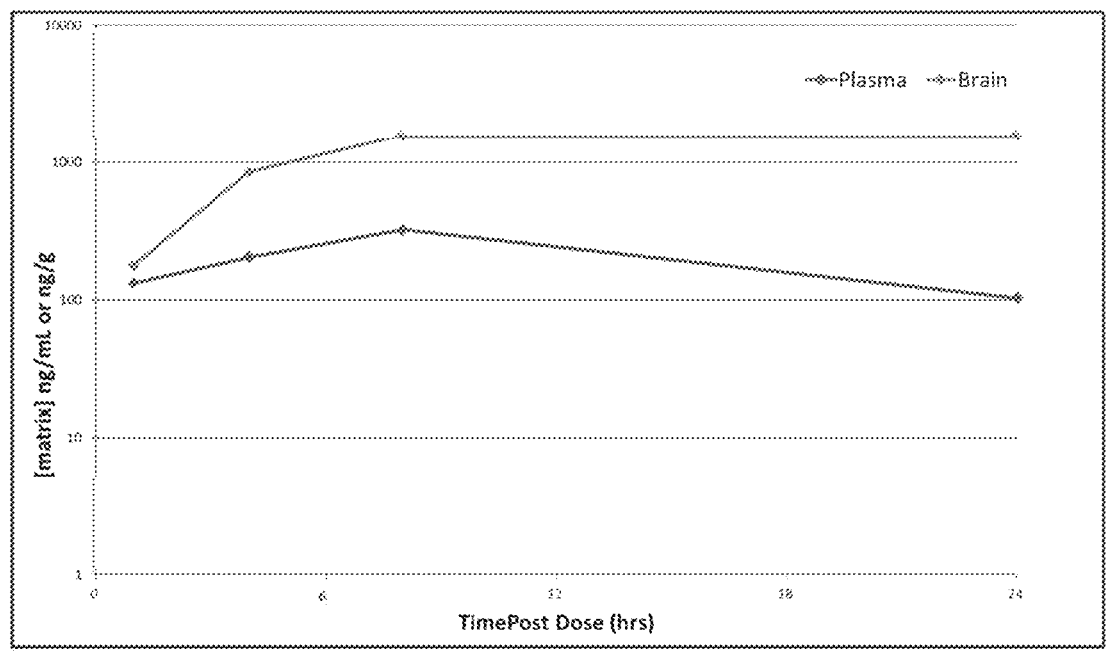
FIG. 2 is a plot of blood plasma and brain concentrations against time following oral dosing to mice of the compound of Example 33. The upper line shows the brain concentrations while the lower line shows the plasma concentrations.

An experiment was carried out on the compound of Example 33 to determine the extent of its brain penetration following oral dosing in mice. The following protocol was used. 15 male CD-1 mice (n=3/time point) were dosed per orally with the compound of Example 33 (10 mg/kg; dose concentration 1 mg/ml; dose volume 10 mL/kg). The compound of Example 33 was formulated in 10% DMSO/90% hydroxypropyl-β-cyclodextrin (20% w/v aqueous). Animals were housed in pre-assigned housing cages until sampling. Appropriate samples were taken at 1, 4, 8 & 24 hour time points and stored immediately at −20° C. Homogenisation and protein precipitation with acetonitrile was carried out for plasma and brain. Analysis was carried out with tandem mass spectrometry using electrospray ionisation. The results of the experiment are shown in FIG. 2 and in Table 10 below.

TABLE 10

| Parameter 10 mg/Kg PO | |
|---|---|
| Tmax (Plasma) | 8.0 hours |
| Tmax (Brain) | 24 hours |
| AUClast (Plasma) | 5031 ng · hr/ml |
| AUClast (Brain) | 31920 ng · hr/ml |

Example H

In Vivo Anti-Cancer Activity in Mice Bearing HCT116 Tumours

Figure 3:
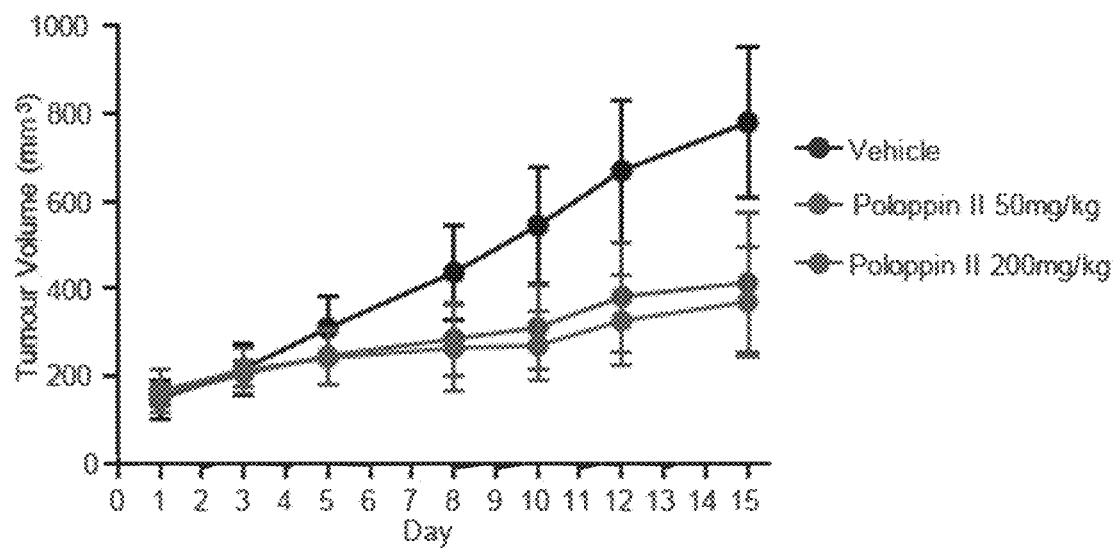
FIG. 3 is a plot of tumour volume against time following the oral dosing of the compound of Example 33 (identified as "Poloppin II" in the Figure) to mice bearing HCT116 tumours. The top line is the vehicle control, the middle line is the 50 mg/kg dose and the lower line is the 200 mg/kg dose.

Mice bearing HCT116 xenograft tumours were give oral dosages of either 50 mg/kg or 200 m/kg on days 1, 3, 7, 10 and 13 and the tumour volumes measured at days 1, 3, 5, 8, 10, 12 and 15. Tumour volumes in a control group of tumour-bearing mice, who had received vehicle only at the same time points were also measured. The results, shown in FIG. 3, demonstrate a pronounced effect on tumour growth (48% T/C).

In a separate experiment, eight mice with established tumours were treated with the compound of Example 33 and euthanised 24 hours after administration of a single dose. The tumours were removed and analysed by Western blotting to reveal a clear induction of phospho-histone H3, indicating a block in mitosis.

Example I

Drug Resistance Studies

The compound 4-[[(7R)-8-cyclopentyl-7-ethyl-5,6,7,8-tetrahydro-5-methyl-6-oxo-2-pteridinyl]amino]-3-methoxy-N-(1-methyl-4-piperidinyl)benzamide, known by the code name B12536, is a PLK1 inhibitor which inhibits the catalytic activity of PLK1 and shows potent anticancer activity. B12536 has progressed into clinical studies in humans with locally advanced or metastatic cancers (Steegmaier et al., Current Biology, 17, 316-322, 2007).

HCT116 cells (a mutant KRAS G-13D expressing cell line) were treated with five times the half maximal growth inhibiting amount of either B12536 or the compound of Example 33. After twenty two days, it was observed that drug-resistant colonies were formed with B12536 but not with the compound of Example 33. This result suggests that inhibiting the C-terminal polo box domain of PLK1, rather than the N-terminal catalytic domain, is less likely to result in the development of drug resistant strains of the cancer.

Pharmaceutical Formulations (i) Tablet Formulation

A tablet composition containing a compound of the formula (1) is prepared by mixing 50 mg of the compound with 197 mg of lactose (BP) as diluent, and 3 mg magnesium stearate as a lubricant and compressing to form a tablet in known manner.

(ii) Capsule Formulation

A capsule formulation is prepared by mixing 100 mg of a compound of the formula (1) with 100 mg lactose and filling the resulting mixture into standard opaque hard gelatin capsules.

(iii) Injectable Formulation I

A parenteral composition for administration by injection can be prepared by dissolving a compound of the formula (1) (e.g. in a salt form) in water containing 10% propylene glycol to give a concentration of active compound of 1.5% by weight. The solution is then sterilised by filtration, filled into an ampoule and sealed.

(iv) Injectable Formulation II

A parenteral composition for injection is prepared by dissolving in water a compound of the formula (1) (e.g. in salt form) (2 mg/ml) and mannitol (50 mg/ml), sterile filtering the solution and filling into sealable 1 ml vials or ampoules.

v) Injectable formulation III

A formulation for i.v. delivery by injection or infusion can be prepared by dissolving the compound of formula (1) (e.g. in a salt form) in water at 20 mg/ml. The vial is then sealed and sterilised by autoclaving.

vi) Injectable Formulation IV

A formulation for i.v. delivery by injection or infusion can be prepared by dissolving the compound of formula (1) (e.g. in a salt form) in water containing a buffer (e.g. 0.2 M acetate pH 4.6) at 20 mg/ml. The vial is then sealed and sterilised by autoclaving.

(vii) Subcutaneous Injection Formulation

A composition for sub-cutaneous administration is prepared by mixing a compound of the formula (1) with pharmaceutical grade corn oil to give a concentration of 5 mg/ml. The composition is sterilised and filled into a suitable container.

viii) Lyophilised Formulation

Aliquots of formulated compound of formula (1) are put into 50 ml vials and lyophilized. During lyophilisation, the compositions are frozen using a one-step freezing protocol at (−45° C.). The temperature is raised to −10° C. for annealing, then lowered to freezing at −45° C., followed by primary drying at +25° C. for approximateley 3400 minutes, followed by a secondary drying with increased steps if temperature to 50° C. The pressure during primary and secondary drying is set at 80 millitor.

EQUIVALENTS

The foregoing examples are presented for the purpose of illustration the invention and should not be construed as imposing any limitation on the scope of the invention. It will readily be apparent that numerous modifications and alterations may be made to the specific embodiments of the invention described above and illustrated in the examples without departing from the principles underlying the invention. All such modifications and alteratoins are intended to be embraced by this application.

The invention claimed is:

1. A method of treating cancer, the method comprising administering to a subject in need thereof a therapeutically effective amount of a compound of formula (3):

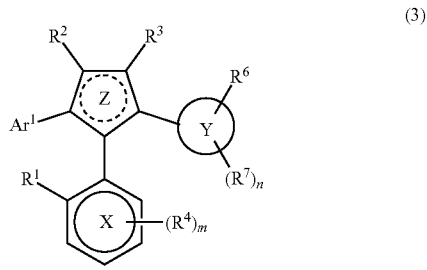

or a pharmaceutically acceptable salt or tautomer thereof, wherein:

Z is selected from a pyrrole, pyrazole or isoxazole ring;
ring X is a benzene or pyridine ring;
ring Y is a benzene, pyridine, thiophene or furan ring;
$Ar^1$ is a benzene, pyridine, thiophene or furan ring optionally substituted with one or more substituent $R^5$;
m is 0, 1 or 2;
n is 0, 1 or 2;
$R^1$ is $CF_3$;
$Hyd^1$ and $Hyd^2$ are the same or different and are $C_{1-4}$ hydrocarbon groups;
$R^2$ is selected from hydrogen and a $C_{1-4}$ hydrocarbon group;
$R^3$ is selected from hydrogen and a $C_{1-4}$ hydrocarbon group;
$R^4$ is selected from:
 fluorine;
 chlorine;
 bromine;
 hydroxyl;
 cyano;
 carboxyl;
 $C(O)O(Hyd^1)$;
 amino;
 $-(Hyd^2)NH$;
 $(Hyd^2)_2N$; and
 a $C_{1-5}$ hydrocarbon group where 0, 1 or 2 of the carbons in the hydrocarbon group are replaced with a heteroatom selected from N, O and S, the hydrocarbon group being optionally substituted with one or more fluorine atoms;
$R^5$ is selected from halogen; $O—Ar^2$; cyano, hydroxy; amino; $Hyd^1-SO_2—$ and a non-aromatic $C_{1-8}$ hydrocarbon group where 0, 1 or 2 but not all of the carbons in the hydrocarbon group are optionally replaced with a heteroatom selected from N, O and S and where the hydrocarbon group is optionally substituted with one or more fluorine atoms;
$Ar^2$ is a phenyl, pyridyl or pyridone group optionally substituted with 1 or 2 substituents selected from halogen; cyano and a $C_{1-4}$ hydrocarbon group optionally substituted with one or more fluorine atoms;
$R^6$ is a group $Q^1-R^a-R^b$;
$Q^1$ is absent or is a $C_{1-3}$ saturated hydrocarbon linker;
$R^a$ is selected from O; C(O); C(O)O; $CONR^c$; $N(R^c)CO$; $N(R^c)CONR^c$, $NR^c$; and $SO_2NR^c$;
$R^b$ is selected from:
 hydrogen;
 a $C_{1-8}$ non-aromatic hydrocarbon group where 0, 1 or 2 of the carbon atoms in the hydrocarbon group are replaced with a heteroatom selected from N and O, the $C_{1-8}$ non-aromatic hydrocarbon group being optionally substituted with one or more substituents selected from fluorine and a group $Cyc^1$; and
 a group $Cyc^1$;
$Cyc^1$ is a non-aromatic 4-7 membered carbocyclic or heterocyclic ring group containing 0, 1 or 2 heteroatom ring members selected from N, O and S and being optionally substituted with one or more substituents selected from hydroxyl; amino; $(Hyd^2)NH$; $(Hyd^2)_2N$; and a $C_{1-5}$ hydrocarbon group where 0, 1 or 2 of the carbons in the hydrocarbon group are replaced with a heteroatom selected from N, O and S, the hydrocarbon group being optionally substituted with one or more fluorine atoms or by a 5- or 6-membered heteroaryl group containing 1 or 2 heteroatom ring members selected from N and O;
$R^c$ is selected from hydrogen and a $C_{1-4}$ non-aromatic hydrocarbon group;
$R^7$ is selected from $R^4$;
with the proviso that when n is 2 and both occurrences of $R^7$ are $—OCH_3$, $R^6$ is not $—NH_2$ or $—NHCH_3$; and
provided that the compound is other than:
(i) a compound wherein $R^6$ is hydroxy, methoxymethyl or unsubstituted or fluoro-substituted $C_{1-8}$ alkoxy;
(ii) a compound wherein the ring Z is an isoxazole ring and $Ar^1$ is an unsubstituted 4-pyridyl group attached to the isoxazole 3-position; and $R^2$ and $R^3$ are both absent; or
(iii) a compound wherein Z is an isoxazole ring and $R^4$ is an azetidin-4-yloxy group wherein the cancer is selected from:
 (a) leukemias, colon cancer, pancreatic cancer and lung cancer; or
 (b) brain cancers,
 (c) gliomas and glioblastomas; or
 (d) lymphomas,
with the proviso that said treating excludes prophylaxis and prevention of recurrence.

2. A method according to claim 1 wherein ring Z is a pyrrole ring.

3. A method according to claim 2 wherein ring X is attached to the nitrogen atom of the pyrrole ring.

4. A method according to claim 1 wherein:
$Q^1$ is absent or is a $CH_2$, $CH_2(CH_3)$ or $C(CH_3)_2$ linker;
$R^a$ is selected from O; C(O); C(O)O; $CONR^c$; $N(R^c)CO$; $N(R^c)CONR^c$, $NR^c$; and $SO_2NR^c$;
$R^b$ is selected from:
 hydrogen;
 a $C_{1-8}$ non-aromatic hydrocarbon group where 0, 1 or 2 of the carbon atoms in the hydrocarbon group are replaced with a heteroatom selected from N and O, the $C_{1-8}$ non-aromatic hydrocarbon group being optionally substituted with a substituent $Cyc^1$; and
 a group $Cyc^1$;
$Cyc^1$ is a non-aromatic 5-6 membered carbocyclic or heterocyclic ring group containing 0, 1 or 2 heteroatom ring members selected from N and O and being optionally substituted with one or more substituents selected from methyl and (dimethyl)amino; and
$R^c$ is selected from hydrogen and methyl.

5. A method according to claim 1 wherein $R^6$ is selected from groups A to AM in the table below:

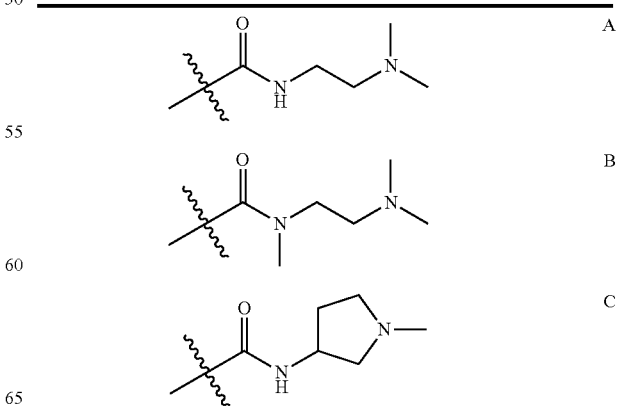

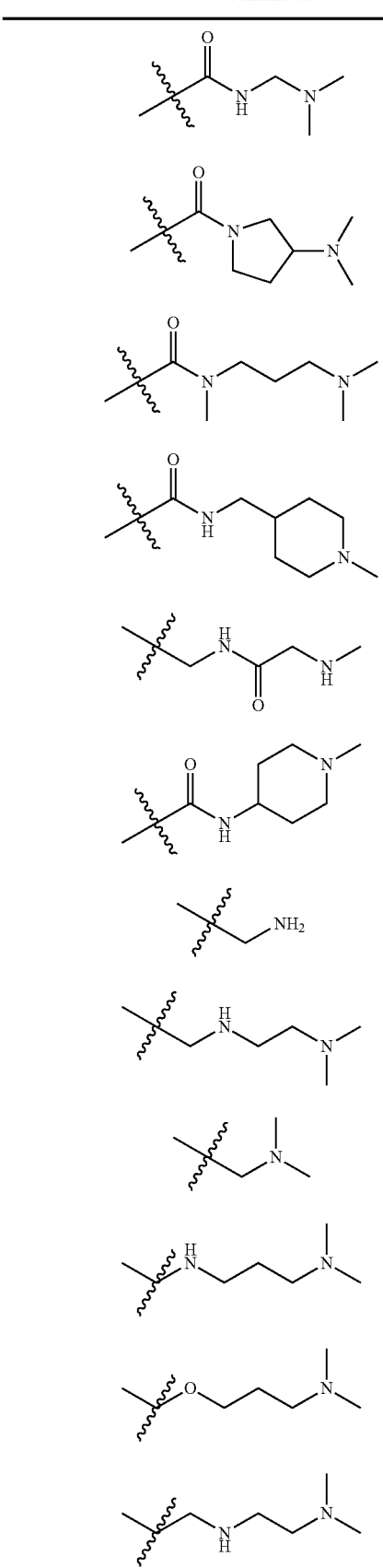
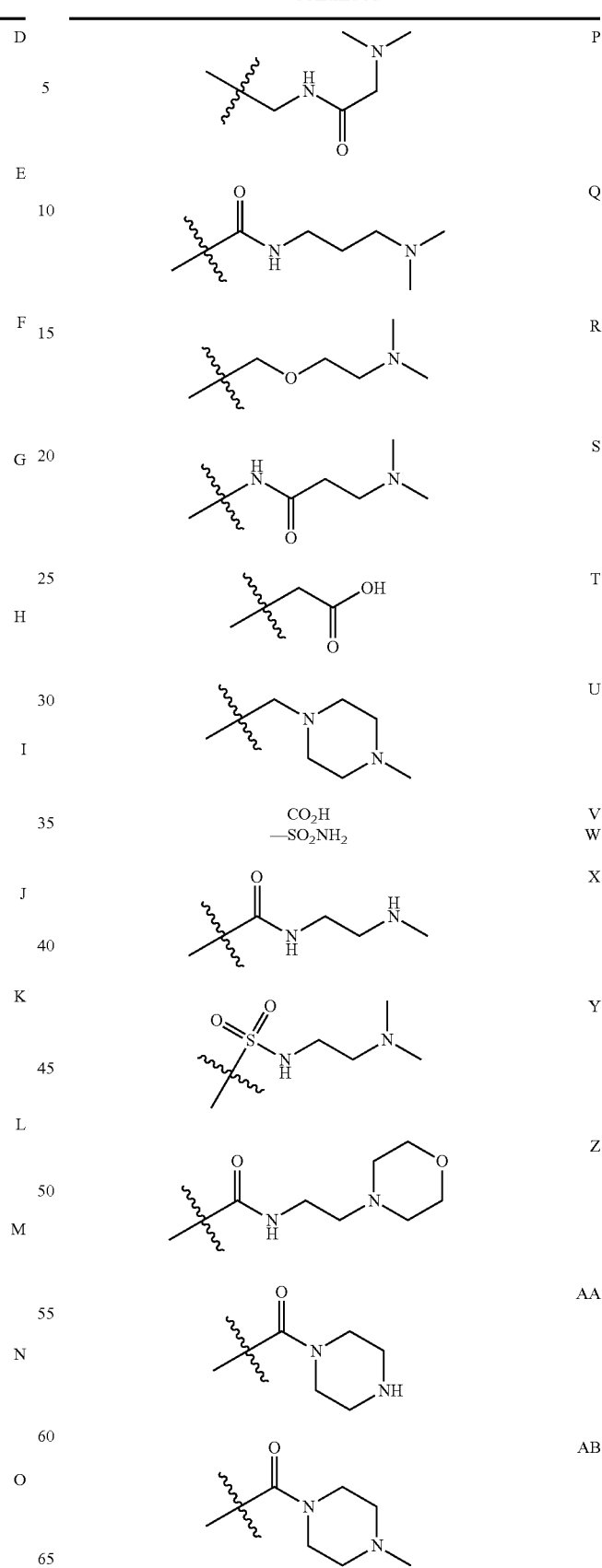

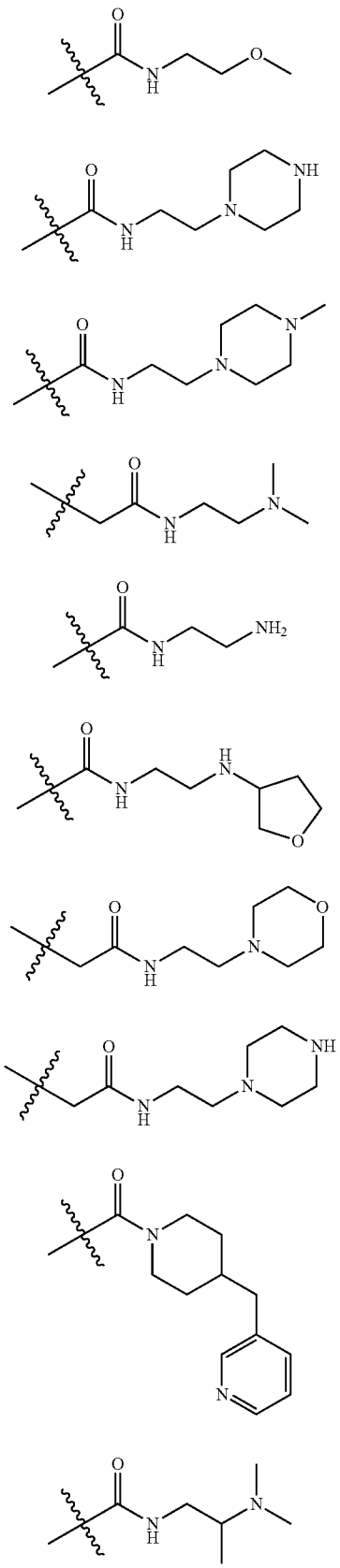

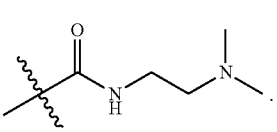 [SMILES: *C(=O)NCCN(C)C]

6. A method according to claim 1 wherein $R^a$ is $CONR^c$.

7. A method according to claim 1 wherein $R^6$ is a group:

8. A method according to claim 1 wherein ring X is a benzene ring.

9. A method according to claim 1 wherein ring Y is a benzene ring.

10. A method according to claim 1 wherein $Ar^1$ is an optionally substituted benzene ring.

11. A method according to claim 10 wherein the benzene ring is monosubstituted with a bromine or chlorine atom.

12. A method according to claim 1 wherein $R^2$ and $R^3$ are both hydrogen.

13. A method according to claim 1 wherein m is 0 and/or n is 0.

14. A method according to claim 1 wherein the compound is selected from
  3-[5-(4-bromophenyl)-1-[2-(trifluoromethyl)phenyl]pyrrol-2-yl]benzoic acid;
  3-[5-(4-bromophenyl)-1-[2-(trifluoromethyl)phenyl]pyrrol-2-yl]-N-[2-(dimethylamino) ethyl]benzamide;
  N-[2-(dimethylamino)ethyl]-3-[5-phenyl-1-[2-(trifluoromethyl) phenyl]pyrrol-2-yl]benzamide;
  3-[5-(4-bromophenyl)-1-[4-chloro-2-(trifluoromethyl) phenyl] pyrrol-2-yl]-N-[2-(dimethylamino) ethyl]benzamide;
  N-[2-(dimethylamino)ethyl]-3-[5-(4-fluorophenyl)-1-[2-(trifluoromethyl) phenyl]pyrrol-2-yl]benzamide;
  3-[5-(4-bromophenyl)-1-[4-(trifluoromethyl)-3-pyridyl]pyrrol-2-yl]-N-[2-(dimethylamino)ethyl]benzamide;
  1-[3-[5-(4-bromophenyl)-1-[2-(trifluoromethyl)phenyl]pyrrol-2-yl]phenyl]-N,N-dimethyl-methanamine;
  4-[5-(4-bromophenyl)-1-[2-(trifluoromethyl)phenyl]pyrrol-2-yl]-N-[2-(dimethylamino)ethyl] benzamide;
  3-[5-(4-bromophenyl)-1-[2-(trifluoromethyl)phenyl]pyrrol-2-yl]-N-[(1-methyl-4-piperidyl)methyl] benzamide;
  3-[5-(4-bromophenyl)-1-[2-(trifluoromethyl)phenyl]pyrrol-2-yl]-N-(1-methyl-4-piperidyl)benzamide;
  3-[5-(4-bromophenyl)-1-[2-(trifluoromethyl)phenyl]pyrrol-2-yl]-N-[2-(dimethylamino)ethyl]-N-methyl-benzamide;
  3-[5-(4-bromophenyl)-1-[2-(trifluoromethyl)phenyl]pyrrol-2-yl]-N-[(3R)-1-methylpyrrolidin-3-yl]benzamide;
  3-[5-(4-bromophenyl)-1-[2-(trifluoromethyl)phenyl]pyrrol-2-yl]-N-[(3 S)-1-methylpyrrolidin-3-yl]benzamide;
  3-[5-(4-bromophenyl)-1-[2-(trifluoromethyl)phenyl]pyrrol-2-yl]-4-chloro-N-[2-(dimethylamino)-ethyl]benzamide;
  N-[3-[5-(4-bromophenyl)-1-[2-(trifluoromethyl)phenyl]pyrrol-2-yl]phenyl]-N',N'-dimethyl-propane-1,3-diamine;

3-[3-[5-(4-bromophenyl)-1-[2-(trifluoromethyl)phenyl]pyrrol-2-yl]phenoxy]-N,N-dimethyl-propan-1-amine;

N-[[3-[5-(4-bromophenyl)-1-[2-(trifluoromethyl)phenyl]pyrrol-2-yl]phenyl]methyl]-N',N'-dimethyl-ethane-1,2-diamine;

N-[[3-[5-(4-bromophenyl)-1-[2-(trifluoromethyl)phenyl]pyrrol-2-yl]phenyl]methyl]-2-(dimethylamino)acetamide;

N-[2-(dimethylamino)ethyl]-3-[5-(4-isopropylphenyl)-1-[2-(trifluoromethyl)phenyl]pyrrol-2-yl]benzamide;

3-[5-(4-bromophenyl)-1-[2-(trifluoromethyl)phenyl]pyrrol-2-yl]-N-[2-(methylamino)ethyl] benzamide;

3-[5-(4-bromophenyl)-1-[2-(trifluoromethyl)phenyl]pyrrol-2-yl]-N-[3-(dimethylamino)propyl] benzamide;

3-[5-(4-bromophenyl)-1-(2-hydroxyphenyl)pyrrol-2-yl]-N-[2-(dimethyl amino)ethyl]benzamide;

N-[2-(dimethylamino)ethyl]-4-[5-phenyl-1-[2-(trifluoromethyl) phenyl]pyrrol-2-yl]benzamide;

4-[5-(4-bromophenyl)-1-[2-(trifluoromethyl)phenyl]pyrrol-2-yl]benzoic acid

5-[5-(4-bromophenyl)-1-[2-(trifluoromethyl)phenyl]pyrrol-2-yl]-N-[2-(dimethylamino)ethyl] pyridine-2-carboxamide;

6-[5-(4-bromophenyl)-1-[2-(trifluoromethyl)phenyl]pyrrol-2-yl]-N-[2-(dimethylamino)ethyl] pyridine-3-carboxamide;

6-[5-(4-bromophenyl)-1-[2-(trifluoromethyl)phenyl]pyrrol-2-yl]pyridine-3-carboxylic acid;

4-[5-(4-bromophenyl)-1-[2-(trifluoromethyl)phenyl]pyrrol-2-yl]-N-[3-(dimethylamino)propyl]-2-methoxy-benzamide;

4-[5-(4-bromophenyl)-1-[2-(trifluoromethyl)phenyl]pyrrol-2-yl]-N-[2-(dimethylamino)ethyl]-3-methoxy-benzamide;

4-[5-(4-chlorophenyl)-1-[2-(trifluoromethyl)phenyl]pyrrol-2-yl]-N-[2-(dimethylamino)ethyl] benzamide;

4-[5-(4-bromophenyl)-1-[2-(trifluoromethyl)phenyl]pyrrol-2-yl]-N-[3-(dimethylamino)propyl] benzamide;

3-[4-[5-(4-bromophenyl)-1-[2-(trifluoromethyl)phenyl]pyrrol-2-yl]phenoxy]-N,N-dimethyl-propan-1-amine;

4-[5-(4-bromophenyl)-1-[2-(trifluoromethyl)phenyl]pyrrol-2-yl]-3-chloro-N-[2-(dimethylamino) ethyl]benzamide;

3-chloro-N-[2-(dimethyl amino) ethyl]-4-[5-phenyl-1-[2-(trifluoromethyl)phenyl]pyrrol-2-yl]benzamide;

4-[5-(4-bromophenyl)-1-[2-(trifluoromethyl)phenyl]pyrrol-2-yl]-2-chloro-N-[2-(dimethylamino)ethyl]benzamide;

2-chloro-N-[2-(dimethyl amino) ethyl]-4-[5-phenyl-1-[2-(trifluoromethyl)phenyl]pyrrol-2-yl]benzamide;

4-[5-(4-bromophenyl)-1-[4-(trifluoromethyl)-3-pyridyl]pyrrol-2-yl]-N-[2-(dimethylamino)ethyl] benzamide;

N-[2-(dimethylamino)ethyl]-4-[5-(6-fluoro-3-pyridyl)-1-[2-(trifluoromethyl)phenyl]pyrrol-2-yl]benzamide;

4-[5-(2,4-difluorophenyl)-1-[2-(trifluoromethyl)phenyl]pyrrol-2-yl]-N-[2-(dimethylamino)ethyl] benzamide;

4-[5-(4-bromophenyl)-1-[2-(trifluoromethyl)phenyl]pyrrol-2-yl]-N-[2-(dimethylamino)ethyl]-benzenesulfonamide;

2-[[4-[5-(4-bromophenyl)-1-[2-(trifluoromethyl)phenyl]pyrrol-2-yl]phenyl]methoxy]-N,N-dimethyl-ethanamine;

N-[5-[5-(4-bromophenyl)-1-[2-(trifluoromethyl)phenyl]pyrrol-2-yl]phenyl]-3-(dimethylamino) propanamide;

2-[4-[5-(4-bromophenyl)-1-[2-(trifluoromethyl)phenyl]pyrrol-2-yl]phenyl]acetic acid;

1-[[4-[5-(4-bromophenyl)-1-[2-(trifluoromethyl)phenyl]pyrrol-2-yl]phenyl]methyl]-4-methyl-piperazine;

4-[5-(4-chlorophenyl)-1-[4-(trifluoromethyl)-3-pyridyl]pyrrol-2-yl]-N-[2-(dimethylamino)ethyl]-benzamide;

4-[5-(4-bromophenyl)-1-[2-(methoxymethyl)phenyl]pyrrol-2-yl]-N-[2-(dimethylamino)ethyl] benzamide;

4-[5-(4-chlorophenyl)-1-[4-(trifluoromethyl)-3-pyridyl]pyrrol-2-yl]-N-[3-(dimethylamino)-propyl]benzamide;

3-[5-(4-bromophenyl)-1-[2-(trifluoromethyl)phenyl]pyrrol-2-yl]-N-[2-(dimethylamino)ethyl]-4-methoxy-benzamide;

5-[5-(4-bromophenyl)-1-[2-(trifluoromethyl)phenyl]pyrrol-2-yl]-N-[2-(dimethylamino)ethyl]-2-methoxy-benzamide;

[3-[5-(4-bromophenyl)-1-[2-(trifluoromethyl)phenyl]pyrrol-2-yl]phenyl]-[(3R)-3-(dimethylamino) pyrrolidin-1-yl]methanone;

[3-[5-(4-bromophenyl)-1-[2-(trifluoromethyl)phenyl]pyrrol-2-yl]phenyl]-[(3S)-3-(dimethylamino) pyrrolidin-1-yl]methanone;

4-[5-(4-cyanophenyl)-1-[2-(trifluoromethyl)phenyl]pyrrol-2-yl]-N-[2-(dimethylamino)ethyl] benzamide;

4-[5-(4-chlorophenyl)-1-[2-(trifluoromethyl)phenyl]pyrrol-2-yl]-N-[3-(dimethylamino)propyl] benzamide;

N-[2-(dimethylamino)ethyl]-4-[5-(4-fluorophenyl)-1-[2-(trifluoromethyl) phenyl]pyrrol-2-yl]benzamide;

N-[3-(dimethylamino)propyl]-4-[5-(4-fluorophenyl)-1-[2-(trifluoromethyl)phenyl]pyrrol-2-yl]benzamide;

6-[5-(4-chlorophenyl)-1-[2-(trifluoromethyl)phenyl]pyrrol-2-yl]-N-[2-(dimethylamino)ethyl]pyridine-3-carboxamide;

6-[5-(4-chlorophenyl)-1-[2-(trifluoromethyl)phenyl]pyrrol-2-yl]-N-[3-(dimethylamino)propyl]-pyridine-3-carboxamide;

4-[5-(4-chlorophenyl)-1-[5-isobutyl-2-(trifluoromethyl)phenyl]pyrrol-2-yl]-N-[2-(dimethylamino)ethyl]-benzamide;

4-[5-(4-chlorophenyl)-1-isobutyl-2-(trifluoromethyl)phenyl]pyrrol-2-yl]-N-[3-(dimethylamino)propyl]-benzamide;

4-[5-(4-bromophenyl)-1-[2-(trifluoromethyl)phenyl]pyrrol-2-yl]benzenesulfonamide;

4-[5-(6-cyano-3-pyridyl)-1-[2-(trifluoromethyl)phenyl]pyrrol-2-yl]-N-[2-(dimethylamino)ethyl]-benzamide;

3-chloro-N-[2-(dimethylamino)-ethyl]-4-[5-phenyl-1-[4-(trifluoromethyl)-3-pyridyl]pyrrol-2-yl]benzamide;

3-chloro-N-[3-(dimethylamino)-propyl]-4-[5-phenyl-1-[4-(trifluoromethyl)-3-pyridyl]pyrrol-2-yl]benzamide;

6-[5-(4-chlorophenyl)-1-[4-(trifluoromethyl)-3-pyridyl]pyrrol-2-yl]-N-[2-(dimethylamino)ethyl]-pyridine-3-carboxamide;

4-[5-(4-chlorophenyl)-1-[2-(trifluoromethyl)phenyl]pyrrol-2-yl]-N-[(3R)-1-methylpyrrolidin-3-yl]benzamide;

4-[5-(4-chlorophenyl)-1-[2-(trifluoromethyl)phenyl]pyrrol-2-yl]-N-[(3S)-1-methylpyrrolidin-3-yl]benzamide;

4-[5-(3-chlorophenyl)-1-[2-(trifluoromethyl)phenyl]pyrrol-2-yl]-N-[2-(dimethylamino)ethyl]-benzamide;

4-[5-(4-chlorophenyl)-1-[4-(trifluoromethyl)-3-pyridyl]pyrrol-2-yl]-N-[2-(dimethylamino)ethyl]-3-methoxy-benzamide;

4-[5-(4-chlorophenyl)-1-[4-(trifluoromethyl)-3-pyridyl]pyrrol-2-yl]-N-[3-(dimethylamino)propyl]-3-methoxy-benzamide;

4-[5-(5-chloro-2-pyridyl)-1-[2-(trifluoromethyl)phenyl]pyrrol-2-yl]-N-[2-(dimethylamino)ethyl]-benzamide;

4-[5-(5-chloro-2-pyridyl)-1-[2-(trifluoromethyl)phenyl]pyrrol-2-yl]-N-[3-(dimethylamino)propyl]-benzamide;

4-[5-(4-chlorophenyl)-1-[3-(trifluoromethyl)phenyl]pyrrol-2-yl]-N-[2-(dimethylamino)ethyl]-benzamide;
4-[5-(4-chlorophenyl)-1-[3-(trifluoromethyl)phenyl]pyrrol-2-yl]-N-[3-(dimethylamino)propyl]-benzamide;
4-[5-(4-chlorophenyl)-1-(trifluoromethyl)-2-pyridyl]pyrrol-2-yl]-N-[2-(dimethylamino)ethyl]-benzamide;
4-[5-(4-chlorophenyl)-1-[3(trifluoromethyl)-2-pyridyl]pyrrol-2-yl]-N-[3-(dimethylamino)propyl]-benzamide;
4-[5-(4-chlorophenyl)-1-[4-(trifluoromethyl)-3-pyridyl]pyrrol-2-yl]-N-(2-morpholinoethyl)-benzamide;
4-[4-(4-(4-chlorophenyl)-5-[2-(trifluoromethyl)phenyl]pyrazol-1-yl]-N-[2-(dimethylamino)ethyl]-benzamide;
4-[5-(4-chlorophenyl)-1-[2-(trifluoromethyl)phenyl]pyrrol-2-yl]-N-[2-(dimethylamino)ethyl]-N-methyl-benzamide;
[4-[5-(4-chlorophenyl)-1-[2-(trifluoromethyl)phenyl]pyrrol-2-yl]phenyl]-piperazin-1-yl-methanone;
[4-[5-(4-chlorophenyl)-1-[2-(trifluoromethyl)phenyl]pyrrol-2-yl]phenyl]-(4-methylpiperazin-1-yl)methanone;
4-[5-(4-chlorophenyl)-1-[2-(trifluoromethyl)phenyl]pyrrol-2-yl]-N-(2-methoxyethyl)benzamide;
4-[5-(4-chlorophenyl)-1-[2-(trifluoromethyl)phenyl]pyrrol-2-yl]-N-(2-piperazin-1-ylethyl)benzamide;
4-[5-(4-chlorophenyl)-1-[2-(trifluoromethyl)phenyl]pyrrol-2-yl]-N-[2-(4-methylpiperazin-1-yl)ethyl]benzamide;
4-[5-(4-chlorophenyl)-1-[4-(trifluoromethyl)-3-pyridyl]pyrrol-2-yl]-N-[2-(dimethylamino)ethyl]-3-fluoro-benzamide;
1-[4-[5-(4-chlorophenyl)-1-[2-(trifluoromethyl)phenyl]pyrrol-2-yl]phenyl]-3-[2-(dimethylamino)-ethyl]urea;
2-[4-[5-(4-chlorophenyl)-1-[2-(trifluoromethyl)phenyl]pyrrol-2-yl]phenyl]-N-[2-(dimethylamino)-ethyl]acetamide;
4-[3-(4-chlorophenyl)-4-[2-(trifluoromethyl)phenyl]isoxazol-5-yl]-N-[2-(dimethylamino)ethyl]-benzamide;
4-[3-(4-chlorophenyl)-4-[2-(trifluoromethyl)phenyl]-1H-pyrazol-5-yl]-N-[2-(dimethylamino)ethyl] benzamide;
N-(2-aminoethyl)-4-[5-(4-chlorophenyl)-1-[2-(trifluoromethyl)-phenyl]pyrrol-2-yl]benzamide;
4-[5-(4-chlorophenyl)-1-[2-(trifluoromethyl)phenyl]pyrrol-2-yl]-N-(2-morpholinoethyl)benzamide;
4-[5-(4-chlorophenyl)-1-[4-fluoro-2-(trifluoromethyl)phenyl]pyrrol-2-yl]-N-[2-(dimethylamino)ethyl]-benzamide;
4-[5-(4-chlorophenyl)-1-[4-chloro-2-(trifluoromethyl)phenyl]pyrrol-2-yl]-N-[2-(dimethylamino)ethyl]-benzamide;
5-[5-(4-chlorophenyl)-1-[2-(trifluoromethyl)phenyl]pyrrol-2-yl]-N-[2-(dimethylamino)ethyl]-thiophene-2-carboxamide;
2-[4-[5-(4-chlorophenyl)-1-[2-(trifluoromethyl)phenyl]pyrrol-2-yl]phenyl]-N-(2-morpholinoethyl)-acetamide;
2-[4-[5-(4-chlorophenyl)-1-[2-(trifluoromethyl)phenyl]pyrrol-2-yl]phenyl]-N-(2-piperazin-1-ylethyl)acetamide;
[3-[5-(4-bromophenyl)-1-[2-(trifluoromethyl)phenyl]pyrrol-2-yl]phenyl]-[4-(3-pyridylmethyl)-1-piperidyl]methanone;
4-[4-(4-chlorophenyl)-5-[2-(trifluoromethyl)phenyl]pyrazol-1-yl]-N-(2-morpholinoethyl)-benzamide;
4-[4-(4-chlorophenyl)-5-[2-(trifluoromethyl)phenyl]pyrazol-1-yl]-N-[3-(dimethylamino)propyl]-benzamide;
N-[2-(dimethylamino)ethyl]-4-[4-(4-fluorophenyl)-5-[2-(trifluoromethyl)phenyl]pyrazol-1-yl]benzamide;
2-[4-[5-(4-chlorophenyl)-1-[2-(trifluoromethyl)phenyl]pyrrol-2-yl]phenyl]-N-[2-(dimethylamino)ethyl]-2-methyl-propanamide;
4-[5-(4-chlorophenyl)-1-(4-trifluoromethyl-3-pyridyl)pyrrol-2-yl]-N-[2-[[(3S)-tetrahydrofuran-3-yl]amino]ethyl]-benzamide;
4-[5-(4-chlorophenyl)-1-[2-(trifluoromethyl)phenyl]pyrrol-2-yl]-N-[(2S)-2-(dimethylamino)propyl]benzamide, or a pharmaceutically acceptable salt or tautomer thereof.

15. A method according to claim 1 wherein the compound is 4-[5-(4-chlorophenyl)-1-[2-(trifluoromethyl)-phenyl]pyrrol-2-yl]-N-[2 (dimethylamino)ethyl]benzamide or a pharmaceutically acceptable salt thereof.

16. A method according to claim 1 wherein the cancer is a KRAS mutant cancer.

17. A method for the treatment of a disease state or condition characterised by the presence of a mutated form of KRAS, which method comprises administering a therapeutically effective amount of a compound to a patient who has been screened and has been determined as suffering from a disease or condition which would be susceptible to treatment with a compound having activity against KRAS, wherein the compound is a compound of formula (3):

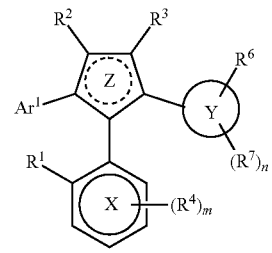

(3)

or a pharmaceutically acceptable salt or tautomer thereof, wherein:
Z is selected from a pyrrole, pyrazole or isoxazole ring;
ring X is a benzene or pyridine ring;
ring Y is a benzene, pyridine, thiophene or furan ring;
$Ar^1$ is a benzene, pyridine, thiophene or furan ring optionally substituted with one or more substituent $R^5$;
m is 0, 1 or 2;
n is 0, 1 or 2;
$R^1$ is $CF_3$;
$Hyd^1$ and $Hyd^2$ are the same or different and are $C_{1-4}$ hydrocarbon groups;
$R^2$ is selected from hydrogen and a $C_{1-4}$ hydrocarbon group;
$R^3$ is selected from hydrogen and a $C_{1-4}$ hydrocarbon group;
$R^4$ is selected from:
fluorine;
chlorine;
bromine;
hydroxyl;
cyano;
carboxyl;
$C(O)O(Hyd^1)$;
amino;
$-(Hyd^2)NH$;
$(Hyd^2)_2N$; and a C$_{1-5}$ hydrocarbon group where 0, 1 or 2 of the carbons in the hydrocarbon group are replaced with a heteroatom selected from N, O and S, the hydrocarbon group being optionally substituted with one or more fluorine atoms;

R$^5$ is selected from halogen; O—Ar$^2$; cyano, hydroxy; amino; Hyd$^1$-SO$_2$— and a non-aromatic C$_{1-8}$ hydrocarbon group where 0, 1 or 2 but not all of the carbons in the hydrocarbon group are optionally replaced with a heteroatom selected from N, O and S and where the hydrocarbon group is optionally substituted with one or more fluorine atoms:

Ar$^2$ is a phenyl, pyridyl or pyridone group optionally substituted with 1 or 2 substituents selected from halogen; cyano and a C$_{1-4}$ hydrocarbon group optionally substituted with one or more fluorine atoms;

R$^6$ is a group Q$^1$-R$^a$—R$^b$;

Q$^1$ is absent or is a C$_{1-3}$ saturated hydrocarbon linker;

R$^a$ is selected from O; C(O); C(O)O; CONR$^c$; N(R$^c$) CONR$^c$, NR$^c$; and SO$_2$NR$^c$;

R$^b$ is selected from:
  hydrogen;
  a C$_{1-8}$ non-aromatic hydrocarbon group where 0, 1 or 2 of the carbon atoms in the hydrocarbon group are replaced with a heteroatom selected from N and O, the C$_{1-8}$ non-aromatic hydrocarbon group being optionally substituted with one or more substituents selected from fluorine and a group Cyc$^1$; and
  a group Cyc$^1$;

Cyc$^1$ is a non-aromatic 4-7 membered carbocyclic or heterocyclic ring group containing 0, 1 or 2 heteroatom ring members selected from N, O and S and being optionally substituted with one or more substituents selected from hydroxyl; amino; (Hyd$^2$)NH; (Hyd$^2$)$_2$N; and a C$_{1-5}$ hydrocarbon group where 0, 1 or 2 of the carbons in the hydrocarbon group are replaced with a heteroatom selected from N, O and S, the hydrocarbon group being optionally substituted with one or more fluorine atoms or by a 5- or 6-membered heteroaryl group containing 1 or 2 heteroatom ring members selected from N and O;

R$^c$ is selected from hydrogen and a C$_{1-4}$ non-aromatic hydrocarbon group;

R$^7$ is selected from R$^4$;

with the proviso that when n is 2 and both occurrences of R$^7$ are —OCH$_3$, R$^6$ is not —NH$_2$ or —NHCH$_3$; and provided that the compound is other than:
(i) a compound wherein R$^6$ is hydroxy, methoxymethyl or unsubstituted or fluoro-substituted C$_{1-8}$ alkoxy;
(ii) a compound wherein the ring Z is an isoxazole ring and Ar$^1$ is an unsubstituted 4-pyridyl group attached to the isoxazole 3-position; and R$^2$ and R$^3$ are both absent or
(iii) a compound wherein Z is an isoxazole ring and R$^4$ is an azetidin-4-yloxy group with the proviso that said treatment excludes prophylaxis and prevention of recurrence.

18. A method for the treatment of a subject suffering from a cancer in a patient who has been screened and has been determined as suffering from a cancer which is characterised by elevated levels of PLK1 kinase; which method comprises administering to the subject a therapeutically effective amount of a compound of formula (3):

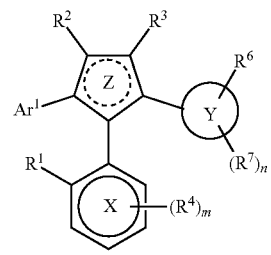

(3)

or a pharmaceutically acceptable salt or tautomer thereof, wherein:

Z is selected from a pyrrole, pyrazole or isoxazole ring;
ring X is a benzene or pyridine ring;
ring Y is a benzene, pyridine, thiophene or furan ring;
Ar$^1$ is a benzene, pyridine, thiophene or furan ring optionally substituted with one or more substituent R$^5$;
m is 0, 1 or 2;
n is 0, 1 or 2;
R$^1$ is CF$_3$;
Hyd$^1$ and Hyd$^2$ are the same or different and are C$_{1-4}$ hydrocarbon groups;
R$^2$ is selected from hydrogen and a C$_{1-4}$ hydrocarbon group;
R$^3$ is selected from hydrogen and a C$_{1-4}$ hydrocarbon group;
R$^4$ is selected from:
  fluorine;
  chlorine;
  bromine;
  hydroxyl;
  cyano;
  carboxyl;
  C(O)O(Hyd$^1$);
  amino;
  -(Hyd$^2$)NH;
  (Hyd$^2$)$_2$N; and
  a C$_{1-5}$ hydrocarbon group where 0, 1 or 2 of the carbons in the hydrocarbon group are replaced with a heteroatom selected from N, O and S, the hydrocarbon group being optionally substituted with one or more fluorine atoms;

R$^5$ is selected from halogen; O—Ar$^2$; cyano, hydroxy; amino; Hyd$^1$-SO$_2$— and a non-aromatic C$_{1-8}$ hydrocarbon group where 0, 1 or 2 but not all of the carbons in the hydrocarbon group are optionally replaced with a heteroatom selected from N, O and S and where the hydrocarbon group is optionally substituted with one or more fluorine atoms;

Ar$^2$ is a phenyl, pyridyl or pyridone group optionally substituted with 1 or 2 substituents selected from halogen; cyano and a C$_{1-4}$ hydrocarbon group optionally substituted with one or more fluorine atoms;

R$^6$ is a group Q$^1$-R$^a$—R$^b$;

Q$^1$ is absent or is a C$_{1-3}$ saturated hydrocarbon linker;

R$^a$ is selected from O; C(O); C(O)O; CONR$^c$; N(R$^c$)CO; N(R$^c$)CONR$^c$, NR$^c$; and SO$_2$NR$^c$;

R$^b$ is selected from:
  hydrogen;
  a C$_{1-8}$ non-aromatic hydrocarbon group where 0, 1 or 2 of the carbon atoms in the hydrocarbon group are replaced with a heteroatom selected from N and O, the C$_{1-8}$ non-aromatic hydrocarbon group being optionally substituted with one or more substituents selected from fluorine and a group $Cyc^1$; and
a group $Cyc^1$;

$Cyc^1$ is a non-aromatic 4-7 membered carbocyclic or heterocyclic ring group containing 0, 1 or 2 heteroatom ring members selected from N, O and S and being optionally substituted with one or more substituents selected from hydroxyl; amino; $(Hyd^2)NH$; $(Hyd^2)_2N$; and a $C_{1-5}$ hydrocarbon group where 0, 1 or 2 of the carbons in the hydrocarbon group are replaced with a heteroatom selected from N, O and S, the hydrocarbon group being optionally substituted with one or more fluorine atoms or by a 5- or 6-membered heteroaryl group containing 1 or 2 heteroatom ring members selected from N and O;

$R^c$ is selected from hydrogen and a $C_{1-4}$ non-aromatic hydrocarbon group;

$R^7$ is selected from $R^4$;

with the proviso that when n is 2 and both occurrences of $R^7$ are —$OCH_3$, $R^6$ is not —$NH_2$ or —$NHCH_3$; and provided that the compound is other than:

(i) a compound wherein $R^6$ is hydroxy, methoxymethyl or unsubstituted or fluoro-substituted $C_{1-8}$ alkoxy;

(ii) a compound wherein the ring Z is an isoxazole ring and $Ar^1$ is an unsubstituted 4-pyridyl group attached to the isoxazole 3-position, and $R^2$ and $R^3$ are both absent or (iii) a compound wherein Z is an isoxazole ring and $R^4$ is an azetidin-4-yloxy group wherein the cancer is selected from:

(a) leukemias, colon cancer, pancreatic cancer and lung cancer, or (b) brain cancers, (c) gliomas and glioblastomas, or (d) lymphomas, with the proviso that said treatment excludes prophylaxis and prevention of recurrence.

19. A method according to claim 17 wherein the compound is 4-[5-(4-chlorophenyl)-1-[2-(trifluoromethyl)-phenyl]pyrrol-2-yl]-N-[2 (dimethylamino)ethyl]benzamide or a pharmaceutically acceptable salt thereof.

20. A method according to claim 18 wherein the compound is 4-[5-(4-chlorophenyl)-1-[2-(trifluoromethyl)-phenyl]pyrrol-2-yl]-N-[2 (dimethylamino)ethyl]benzamide or a pharmaceutically acceptable salt thereof.

* * * * *

UNITED STATES PATENT AND TRADEMARK OFFICE
CERTIFICATE OF CORRECTION

PATENT NO. : 11,884,656 B2
APPLICATION NO. : 17/453959
DATED : January 30, 2024
INVENTOR(S) : Boyle et al.

It is certified that error appears in the above-identified patent and that said Letters Patent is hereby corrected as shown below:

In the Claims

Column 143, Line 64: Claim 14, Delete "N-[5-[5-(4-bromophenyl)-" and insert -- N-[4-[5-(4-bromophenyl)- --

Column 145, Line 5: Claim 14, Delete "4-[5-(4-chlorophenyl)-1-(trifluoromethyl)-2" and insert -- 4-[5-(4-chlorophenyl)-1-[3-(trifluoromethyl)-2 --

Column 145 Line 11: Claim 14, Delete "4-[4-(4-(4-chlorophenyl)-5-" and insert -- 4-[4-(4-chlorophenyl)-5- --

Column 147 Lines 20-21: Claim 17, Delete "O; C(O); C(O)O; CONR$^c$; N(R$^c$) CONR$^c$, NR$^c$" and insert -- O; C(O); C(O)O; CONR$^c$; N(R$^c$)CO; N(R$^c$)CONR$^c$, NR$^c$ --

Signed and Sealed this
Nineteenth Day of March, 2024

*Katherine Kelly Vidal*
*Director of the United States Patent and Trademark Office*